(12) United States Patent
Sawa et al.

(10) Patent No.: US 9,102,637 B2
(45) Date of Patent: Aug. 11, 2015

(54) BICYCLIC THIAZOLE COMPOUNDS

(71) Applicants: CARNA BIOSCIENCES INC., Kobe, Hyogo (JP); NATIONAL CANCER CENTER, Tokyo (JP)

(72) Inventors: Masaaki Sawa, Ibaraki (JP); Hideki Moriyama, Kobe (JP); Tesshi Yamada, Tokyo (JP); Miki Shitashige, Tokyo (JP); Yusuke Kawase, Ashiya (JP); Yuko Uno, Kobe (JP)

(73) Assignees: CARNA BIOSCIENCES, INC., Kobe-shi (JP); NATIONAL CANCER CENTER, Tokyo (JP)

( * ) Notice: Subject to any disclaimer, the term of this patent is extended or adjusted under 35 U.S.C. 154(b) by 0 days.

(21) Appl. No.: 14/403,071

(22) PCT Filed: May 22, 2013

(86) PCT No.: PCT/JP2013/064960
§ 371 (c)(1),
(2) Date: Nov. 21, 2014

(87) PCT Pub. No.: WO2013/176293
PCT Pub. Date: Nov. 28, 2013

(65) Prior Publication Data
US 2015/0133656 A1    May 14, 2015

Related U.S. Application Data

(63) Continuation of application No. 13/479,396, filed as application No. PCT/JP2013/064960 on May 22, 2013, now abandoned.

(51) Int. Cl.
| | | |
|---|---|---|
| *C07D 277/56* | (2006.01) | |
| *C07D 417/14* | (2006.01) | |
| *C07D 417/12* | (2006.01) | |

(52) U.S. Cl.
CPC ............ *C07D 277/56* (2013.01); *C07D 417/12* (2013.01); *C07D 417/14* (2013.01)

(58) Field of Classification Search
CPC ... C07D 277/56; C07D 417/14; C07D 417/12
See application file for complete search history.

(56) References Cited

U.S. PATENT DOCUMENTS

2010/0137386 A1* 6/2010 Yamada et al. ............... 514/371
2013/0317218 A1  11/2013 Sawa et al.

FOREIGN PATENT DOCUMENTS

| WO | 2009/104413 A1 | 8/2009 |
| WO | 2010/064111 A1 | 6/2010 |

OTHER PUBLICATIONS

International Search Report dated Jul. 22, 2013, issued in corresponding application No. PCT/JP2013/064960.
Shitashige, Miki et al., "Traf2- and Nck-Interacting Kinase is Essential for Wnt Signaling and Colorectal Cancer Growth," Cancer Research, Jun. 15, 2010, vol. 70, No. 12, pp. 5024-5033, cited in specification.
Shitashige, Miki et al., "Regulation of Wnt Signaling by the Nuclear Pore Complex," Gastroenterology, 2008, vol. 134, No. 7, pp. 1961-1971, cited in specification.
Cook, A.H. et al., "Azole Series. XXIII. New synthesis of 6-aminopurines," Journal of the Chemical Society, 1949, pp. 3001-3007, cited in specification.
Zhong, Boyu et al., "Novel route to the synthesis of 4-quinolyl isothiocyanates," Tetrahedron Letters, Jan. 23, 2006, vol. 47, pp. 2161-2164, cited in specification.
Golankiewicz, Bozenna et al., "Reaction of Acylaminocyanoesters With 2.4-Bis(4-Methoxyphenyl)-1,3,2,4-Dithiadiphosphetane 2,4-Disulfide Leading to Substituted Aminothiazoles, Crystal Structure of 5-Aminothiazole-4-Carboxylic Acid Ethyl Ester," Tetrahedron, Aug. 12, 1985, vol. 41, No. 24, pp. 5989-5994, cited in specification.
U.S. Appl. No. 12/790,084, filed on May 28, 2010, which is now abandoned.
U.S. Appl. No. 13/031,980, filed on Feb. 22, 2011, which is now abandoned.
U.S. Appl. No. 13/151,726, filed on Jun. 2, 2011, which is now abandoned.

* cited by examiner

*Primary Examiner* — Matthew Coughlin
(74) *Attorney, Agent, or Firm* — Westerman, Hattori, Daniels & Adrian, LLP

(57) ABSTRACT

The present invention relates to novel bicyclic thiazole compounds that inhibit Traf2- and Nck-interacting kinase (TNIK), and as such are useful as TNIK inhibitors administered to cancer patients, especially to solid cancer patients such as colorectal cancer, pancreatic cancer, non-small cell lung cancer, prostate cancer or breast cancer. The bicyclic thiazole compounds are showed by a next formula (I). (wherein $R^1$, $R^2$, $R^3$ and Q are as defined in the specification), or a pharmaceutically acceptable salt thereof.

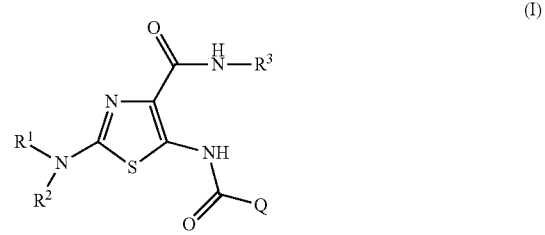

4 Claims, No Drawings

BICYCLIC THIAZOLE COMPOUNDS

FIELD OF THE INVENTION

The present invention relates to novel bicyclic thiazole compounds that inhibit Traf2- and Nck-interacting kinase (TNIK), and as such are useful as TNIK inhibitors administered to cancer patients, especially to solid cancer patients such as colorectal cancer, pancreatic cancer, non-small cell lung cancer, prostate cancer or breast cancer.

BACKGROUND OF THE INVENTION

Wnt proteins constitute a large family of secreted glycoproteins that activate signal transduction pathways to control a wide variety of cellular processes such as determination of cell fate, proliferation, migration, and polarity. Wnt proteins are capable of signaling through several pathways, the best-characterized being the canonical pathway through β-catenin (Wnt/β-catenin signaling). Deregulation of Wnt/β-catenin signaling is frequently found in many human cancers like colorectal cancer, pancreatic cancer, non-small cell lung cancer, prostate cancer, breast cancer, and many others.

TNIK is known as one of STE20 family kinases that activates the c-Jun N-terminal kinase pathway and regulates the cytoskeleton. Recently, TNIK was identified as one of 70 proteins immunoprecipitated commonly with anti-TCF4 (T-cell factor-4) and anti-β-catenin antibodies in two colorectal cancer cell lines DLD1 and HCT-116 (Shitashige M, et al., Gastroenterology 2008, 134:1961-71). Recent studies has been shown that TNIK plays critical roles in canonical Wnt signaling pathway, and therefore TNIK can be a promising target to ablate aberrant Wnt signaling in tumors (Shitashige M, et al., Cancer Res; 70(12); 5024-33 (2010)). Namely, small interfering RNA targeting TNIK inhibited the proliferation of colorectal cancer cells and the growth of tumors produced by injecting colorectal cancer cells s.c. into immunodeficient mice.

Evaluation methods for utility of the present invention which is the screening of an anti-cancer agent have already been described in WO 2009/104413 filed by the present inventors. WO 2010/64111 filed by the present inventors discloses novel aminothiazole derivatives as potent TNIK inhibitors and the effects of TNIK inhibitors on the transcriptional activity of the β-catenin and TCF4 complex. However, it has not been disclosed that thiazole compounds having bicyclic structures of the present invention are useful as TNIK inhibitors until now.

SUMMARY OF THE INVENTION

This invention provides novel bicyclic thiazole compounds that inhibit TNIK, and as such are useful as TNIK inhibitors administered to cancer patients, especially to solid cancer patients such as colorectal cancer, pancreatic cancer, non-small cell lung cancer, prostate cancer or breast cancer.

DETAILED DESCRIPTION OF THE INVENTION

In accordance with the present invention, we have discovered novel bicyclic thiazole TNIK inhibitors that will provide effective treatments for disorders such as those described herein and those apparent to one skilled in the art.

The present invention provides compounds that have the formula (I):

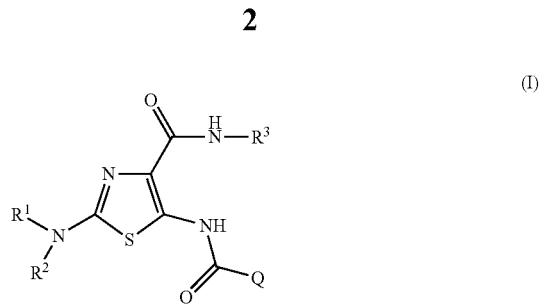

(wherein,
$R^1$ is

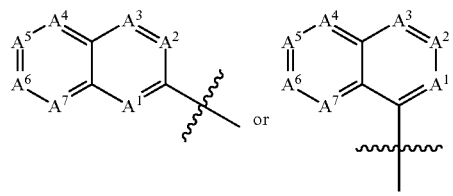

wherein each of $A^1, A^2, A^3, A^4, A^5, A^6, A^7$ is, independently C—Z or N, $R^2$ is a hydrogen atom, a substituted or unsubstituted alkyl group, $R^3$ is a hydrogen atom, a substituted or unsubstituted alkyl group, a hydroxyl group, a substituted or unsubstituted alkoxy group, Q is

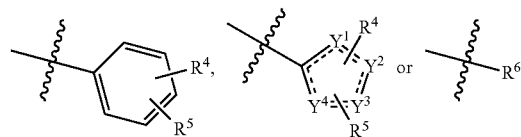

wherein each of $Y^1, Y^2, Y^3$ and $Y^4$ is, independently represent a nitrogen atom optionally substituted with hydrogen atom or lower alkyl group, sulfur atom, oxygen atom or carbon atom, Z, $R^4$ and $R^5$ independently represent a hydrogen atom, a halogen atom, a substituted or unsubstituted alkyl group, a substituted or unsubstituted alkenyl group, a substituted or unsubstituted alkynyl group, a hydroxyl group, a substituted or unsubstituted alkoxy group, a substituted or unsubstituted amino group, a carboxyl group, a ester group, a formyl group, a substituted carbonyl group, a substituted carbamoyl group, a substituted or unsubstituted urea group, a substituted or unsubstituted aromatic group, a substituted or unsubstituted heterocyclic group, a substituted or unsubstituted heteroaromatic group, a substituted or unsubstituted acylamino group, a substituted or unsubstituted arylcarbonylamino group, a thiol group, a substituted or unsubstituted thioalkyl group, a sulfonic acid group, a substituted sulfone group, a substituted or unsubstituted sulfonamide group, a cyano group, a nitro group, or neighboring $R^4$ and $R^5$ may be combined to form a 5- to 7-membered ring forming an alicyclic or heterocyclic bicyclic fused ring respectively, wherein the 5- to 7-membered ring may optionally have a substituent $R^6$ is a substituted or unsubstituted alkyl group, a substituted or unsubstituted alkenyl group, a substituted or unsubstituted alkynyl group, a substituted or unsubstituted alkoxy group, a substituted or unsubstituted amino group, a substituted or unsubstituted heterocyclic group) or a pharmaceutically acceptable salt thereof.

The substituent as used herein includes, for example, a halogen atom (such as F, Cl, Br), a substituted or unsubstituted alkyl group (such as a substituted or unsubstituted C1-C6 alkyl group, a substituted or unsubstituted C3-C7 cycloalkyl group, a substituted or unsubstituted aralkyl group, wherein the substituent includes, for example, hydroxyl group, dimethylamino group, morpholino group, 4-methylpiperazin-1-yl group and piperazin-1-yl group.), a substituted or unsubstituted alkenyl group (such as a substituted or unsubstituted C2-C6 alkenyl group, for example, vinyl, allyl, isopropenyl, butenyl, isobutenyl, etc.), a substituted or unsubstituted alkynyl group (such as a substituted or unsubstituted C2-C6 alkynyl group, for example, ethynyl, 2-propynyl, propargyl, etc), a substituted or unsubstituted alkoxy group (such as a substituted or unsubstituted C1-C6 alkoxy group), a substituted or unsubstituted amino group (such as amino group, morpholino group or 4-methylpiperazin-1-yl group), a substituted or unsubstituted acylamino group (such as a substituted or unsubstituted C1-C4 acylamino group), a substituted or unsubstituted arylcarbonylamino group (such as phenylcarbonylamino group or pyridylcarbonylamino group), a ester group (such as a substituted or unsubstituted C1-C4 alkylester group), a substituted carbonyl group (such as acetyl group, benzoyl group), a substituted carbamoyl group (such as a substituted or unsubstituted C1-C4 carbamoyl group), a substituted or unsubstituted urea group (such as a substituted or unsubstituted C1-C4 urea group), a substituted or unsubstituted aromatic group (such as a substituted or unsubstituted phenyl group), a substituted or unsubstituted heterocyclic group (such as a substituted or unsubstituted morpholino group, piperazinyl group or pyrrolidino group), a substituted or unsubstituted heteroaromatic group (such as a substituted or unsubstituted pyridino group), a substituted or unsubstituted thioalkyl group (such as a substituted or unsubstituted C1-C4 thioalkyl group), a substituted sulfone group (such as a substituted or unsubstituted C1-C4 alkylsulfone group), a substituted or unsubstituted sulfonamide group (such as a substituted or unsubstituted C1-C4 alkylsulfonamide group).

The following general reaction schemes detail the synthetic approaches to the bicyclic thiazole compounds disclosed herein. Compounds of formula (I) disclosed herein can be prepared as shown in Schemes 1-7 and as illustrated in the Examples by using standard synthetic methods and the starting materials, which are either commercially available or can be synthesized from commercially available precursors using synthetic methods known in the art, or variations thereof as appreciated by those skilled in the art.

Although these schemes often indicate exact structures, those skilled in the art will appreciate that the methods apply widely to analogous compounds of formula (I), by being given appropriate consideration to protection and deprotection or reactive functional groups by methods standard to the art of organic chemistry. For example, hydroxy groups, in order to prevent unwanted side reactions, generally need to be converted to ethers or esters during chemical reactions at other sites in the molecule. The hydroxyl protecting group is readily removed to provide the free hydroxy group. Amino groups and carboxylic acid groups are similarly derivatized to protect them against unwanted side reactions. Typical protecting groups and methods for attaching and cleaving them are described fully by T. W. Greene, Protective Groups in Organic Synthesis 3rd Edition, John Wiley and Sons, Inc., New York (1999).

Each variable in the following schemes refers to any group consistent with the description of the compounds provided herein. Tautomers and solvates (e.g., hydrates) of the compounds of formula (I) are also within the scope of the invention.

Any compound of any formula disclosed herein can be obtained using procedures provided in the reaction Schemes, as well as procedures provided in the Examples, by selecting suitable starting materials and following analogous procedures. Thus, any compound of any formula disclosed or exemplified herein, can be obtained by using the appropriate starting materials and appropriate reagents, with the desired substitutions, and following procedures analogous to those described herein.

Compounds of formula (I) wherein $R^2$ is a hydrogen atom, are generally synthesized by the formation of the amide from 5-aminothiazole intermediate (II) and an acid chloride (III-a), as shown in Scheme 1:

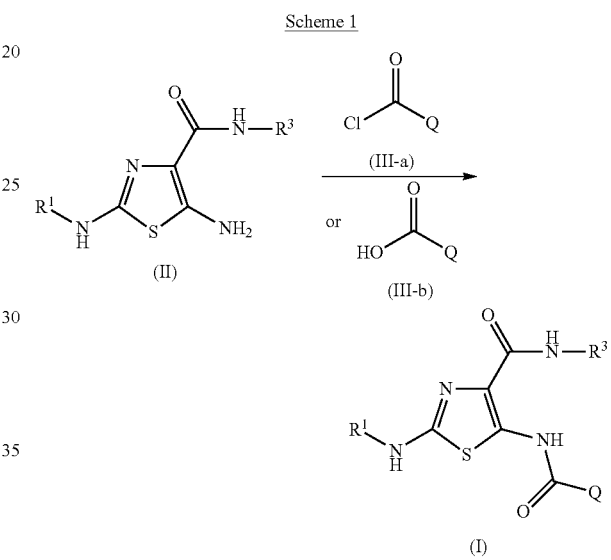

wherein $R^1$, $R^3$, and Q are the same as defined in the formula (I).

The same type of amide-coupling reaction may be done with a carboxylic acid (III-b) under general amide coupling conditions such as 1-ethyl-3-(3-dimethylaminopropyl) carbodiimide hydrochloride (EDC), hydroxybenzotriazole (HOBT) and a base such as diisopropylethylamine or triethylamine to afford the compounds of formula (I) wherein $R^2$ is a hydrogen atom.

In another approach, compounds of formula (I) may be prepared from the ester intermediate (IV) by a direct aminolysis with amines, as shown in Scheme 2:

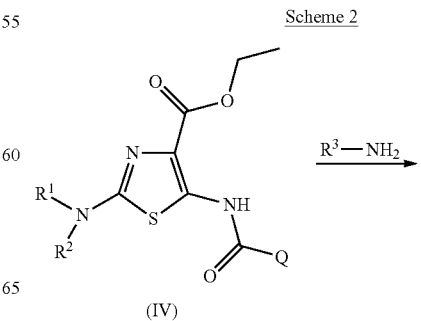

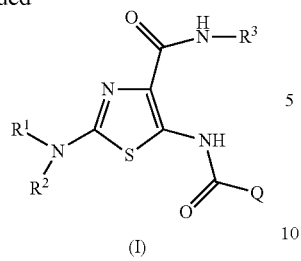

(I)

wherein R$^1$, R$^2$, R$^3$, and Q are the same as defined in the formula (I).

The aminolysis reaction is carried out by using a neat amine solution or an amine in an alcohol solution in presence of a solvent such as THF, or dioxane. The reaction is stirred and heated in a sealed tube at a temperature from 80° C. to 150° C., for 1-24 hours, preferably under microwave irradiation at 80° C. for 150 minutes using a microwave synthesizer.

An alternative route as shown in Scheme 3, compounds of formula (I) can be made by N-alkylation of compound of formula (I) having R$^2$ being hydrogen using well-known synthetic route such as reductive alkylation or alkylation with alkyl halides in case the functionalization of the molecule is compatible with this type of reactions.

Scheme 3

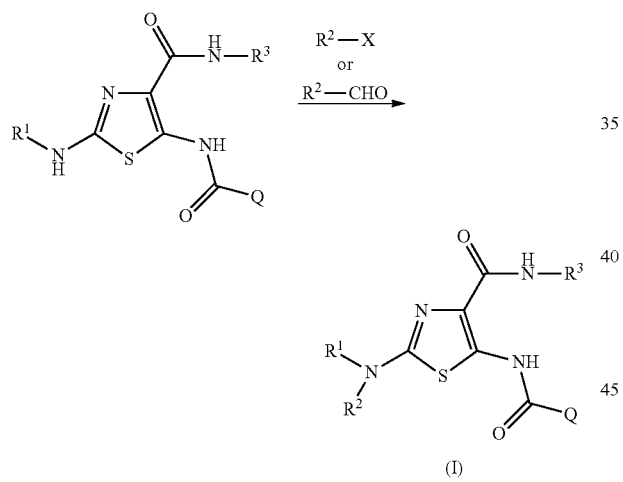

(I)

wherein R$^1$, R$^2$, R$^3$, and Q are the same as defined in the formula (I) and X is a halogen selected from Cl, Br and I.

The compounds represented by the formula (II) in Scheme 1, which are used as starting materials of the amide-coupling reaction, may be prepared in a similar manner as described by Cook et al. (J. Chem. Soc. 1949, 3001). For example, the compounds represented by the formula (II) may be prepared by the Scheme 4 below:

Scheme 4

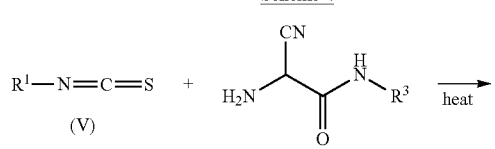

(V)

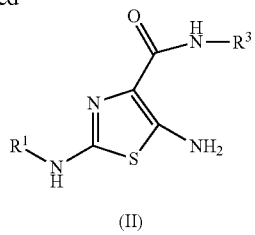

(II)

wehrein R$^1$ and R$^3$ are the same as defined in the formula (I).

Thus, a mixture of isothiocyanate (V) and 2-amino-2-cyano-N-alkylacetamide is stirred in a suitable solvent such as ethyl acetate or ethanol, and heated to reflux condition for 0.5-2 hours to give the compounds represented by the formula (II).

The isothiocyanate (V) may be commercially available, or may be prepared from the corresponding amine by the methods well known in the field of organic synthesis, such as a thiophosgene treatment. The isothiocyanate (V) also can be prepared from the corresponding halides with silver (I) thiocyanate in a similar manner as described by Zhong et al. (Tetrahedron Letters, 47(13), 2161-2164 (2006)).

The ester intermediate (IV) may be prepared via a palladium-catalyzed reaction with an amine (VII) and 2-halogenothiazole compound (VI), as shown in Scheme 5:

Scheme 5

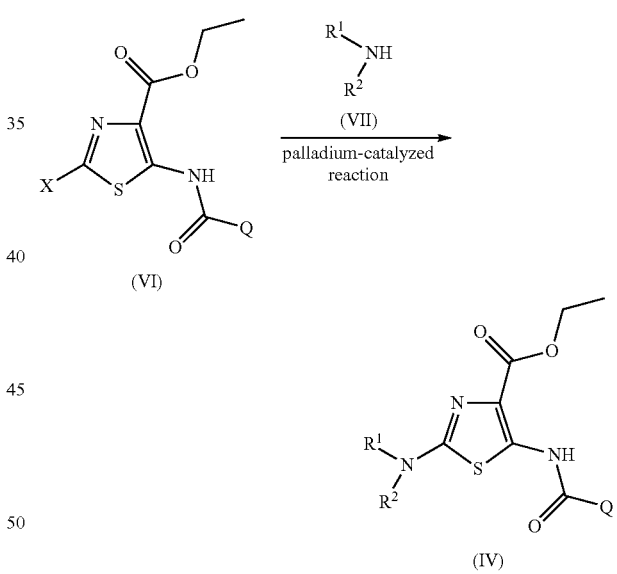

(IV)

wherein R$^1$, R$^2$, and Q are the same as defined in the formula (I) and X is a halogen selected from Cl, Br and I.

These Buchwald/Hartwig type reactions are well-known to those skilled in the art and are performed in inert solvents such as toluene, THF or dioxane and involve a palladium catalyst such as tris(dibenzylideneacetone)dipalladium (0), tetrakis(triphenylphosphine)palladium (0), palladium (II) acetate, and a base such as sodium, potassium or cesium carbonate, and a ligand such as 4,5-Bis(diphenylphosphino)-9,9-dimethylxanthene (XANTPHOS). The same type of palladium-coupling reaction may be done with a corresponding halogeno-aromatic/heteroaromatic compound and a corresponding 2-aminothiazole analog to give the same desired aminothiazole intermediates (IV).

The compound represented by the formula (VI) may be prepared by the Scheme 6 below:

Scheme 6

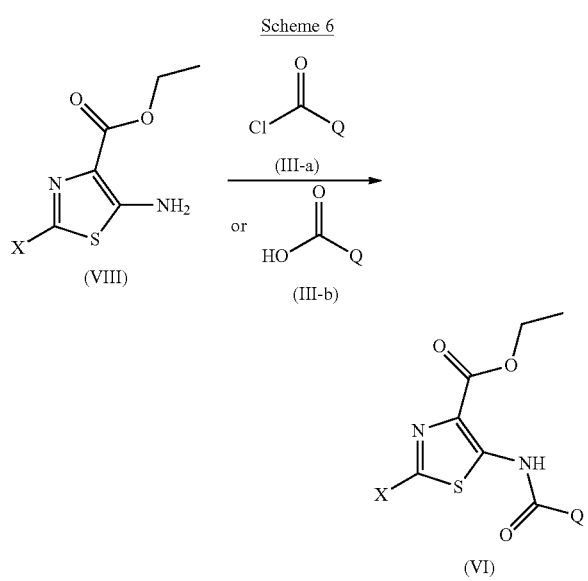

wherein Q are the same as defined in the formula (I) and X is a halogen selected from Cl, Br and I.

Thus, the compound represented by the formula (VI) may be synthesized by the formation of the amide from 5-aminothiazole intermediate (VIII) and an acid chloride (III-a). The same type of amide-coupling reaction may be done with a carbxylic acid (III-b) under general amide coupling conditions such as EDC, HOBT and a base such as diisopropyl-ethylamine, or triethylamine.

The compound represented by the formula (VIII) may be prepared from 5-aminothiazole-4-carboxylic acid ethyl ester by the Scheme 7 below:

Scheme 7

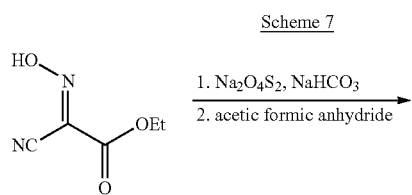

1. Na$_2$O$_4$S$_2$, NaHCO$_3$
2. acetic formic anhydride

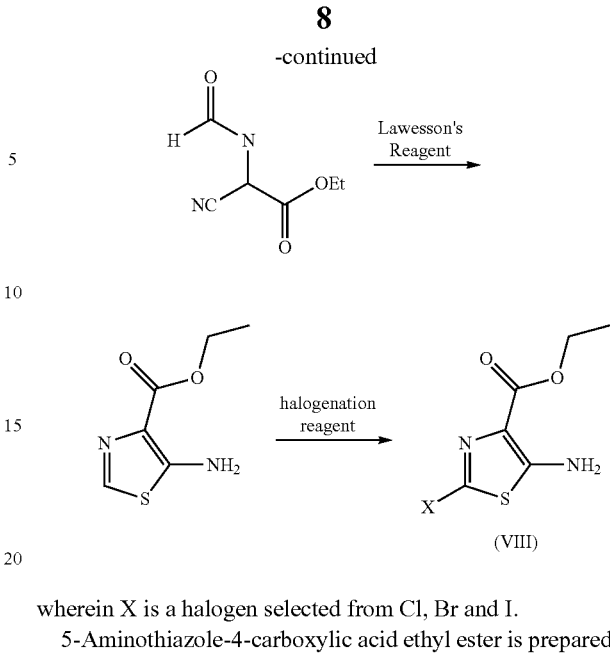

wherein X is a halogen selected from Cl, Br and I.

5-Aminothiazole-4-carboxylic acid ethyl ester is prepared according to the procedure described by Golankiewicz et al. (Tetrahedron, 41 (24), 5989-5994 (1985)). Thus, commercially available ethyl cyano (hydroxyimino)acetate is treated with sodium dithionate in sat. sodium bicarbonate aqueous solution to give ethyl 2-amino-2-cyanoacetate, which is then converted to the corresponding formamide with acetic formic anhydride. Subsequently, the obtained ethyl 2-cyano-2-formamidoacetate is treated with Lawesson's reagent, followed by treating with a halogenation reagent such as NCS, NBS to give the desired product.

The invention is further defined in the following Examples. It should be understood that these Examples are given by way of illustration only. From the above discussion and this Example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

Specific examples of the compounds represented by the formula (I) are given in Table 1 below:

TABLE 1

| Example number | Structure | Name |
|---|---|---|
| 1 | ![structure] | 5-(4-acetamidobenzamido)-2-(naphthalen-1-yl-amino)thiazole-4-carboxamide |

TABLE 1-continued

| Example number | Structure | Name |
|---|---|---|
| 2 | 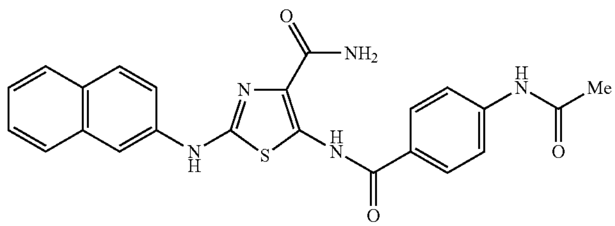 [SMILES: CC(=O)Nc1ccc(C(=O)Nc2sc(Nc3ccc4ccccc4c3)nc2C(N)=O)cc1] | 5-(4-acetamidobenzamido)-2-(naphthalen-2-yl-amino)thiazole-4-carboxamide |
| 3 | 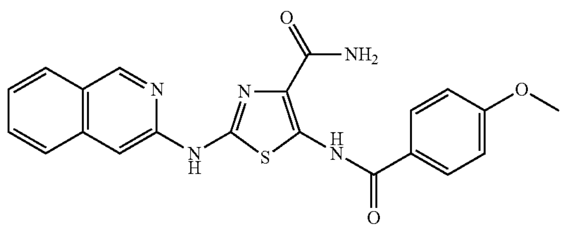 [SMILES: COc1ccc(C(=O)Nc2sc(Nc3cc4ccccc4cn3)nc2C(N)=O)cc1] | 2-(isoquinolin-3-ylamino)-5-(4-methoxybenz-amido)thiazole-4-carboxamide |
| 4 | 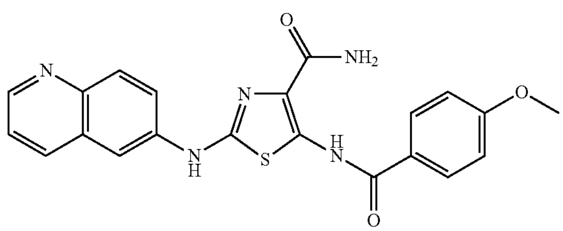 [SMILES: COc1ccc(C(=O)Nc2sc(Nc3ccc4ncccc4c3)nc2C(N)=O)cc1] | 5-(4-methoxybenzamido)-2-(quinolin-6-ylamino)thiazole-4-carboxamide |
| 5 | 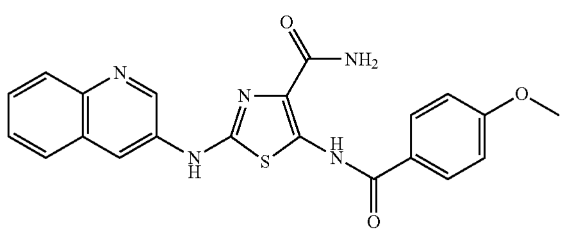 [SMILES: COc1ccc(C(=O)Nc2sc(Nc3cnc4ccccc4c3)nc2C(N)=O)cc1] | 5-(4-methoxybenzamido)-2-(quinolin-3-ylamino)thiazole-4-carboxamide |
| 6 | 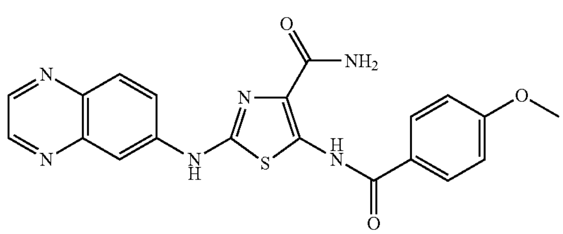 [SMILES: COc1ccc(C(=O)Nc2sc(Nc3ccc4nccnc4c3)nc2C(N)=O)cc1] | 5-(4-methoxybenzamido)-2-(quinoxalin-6-yl-amino)thiazole-4-carboxamide |
| 7 | 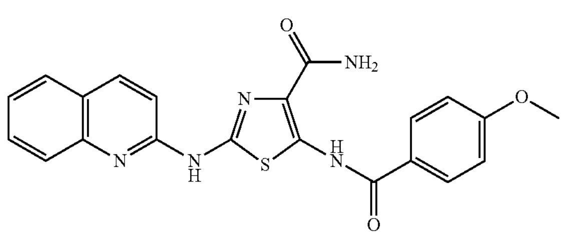 [SMILES: COc1ccc(C(=O)Nc2sc(Nc3ccc4ccccc4n3)nc2C(N)=O)cc1] | 5-(4-methoxybenzamido)-2-(quinolin-2-ylamino)thiazole-4-carboxamide |

| Example number | Structure | Name |
|---|---|---|
| 8 | 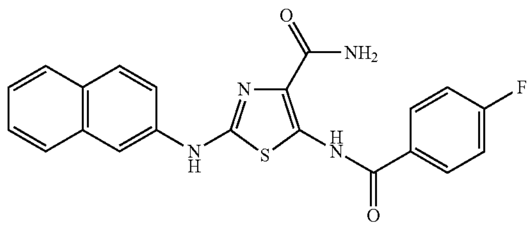 [SMILES: NC(=O)c1nc(Nc2ccc3ccccc3c2)sc1NC(=O)c1ccc(F)cc1] | 5-(4-fluorobenzamido)-2-(naphthalen-2-ylamino)thiazole-4-carboxamide |
| 9 | 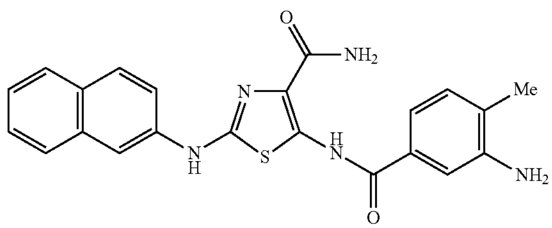 [SMILES: Cc1ccc(C(=O)Nc2sc(Nc3ccc4ccccc4c3)nc2C(N)=O)cc1N] | 5-(3-amino-4-methylbenzamido)-2-(naphthalen-2-ylamino)thiazole-4-carboxamide |
| 10 | 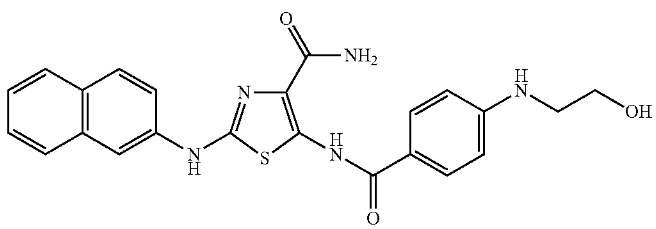 [SMILES: NC(=O)c1nc(Nc2ccc3ccccc3c2)sc1NC(=O)c1ccc(NCCO)cc1] | 5-[4-(2-hydroxyethylamino)benzamido]-2-(naphthalen-2-ylamino)thiazole-4-carboxamide |
| 11 | 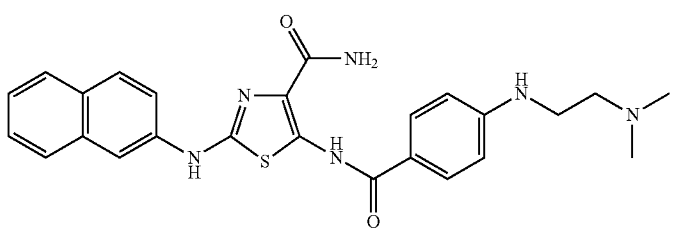 [SMILES: CN(C)CCNc1ccc(C(=O)Nc2sc(Nc3ccc4ccccc4c3)nc2C(N)=O)cc1] | 5-{4-[2-(dimethylamino)ethylamino]benzamido}-2-(naphthalen-2-ylamino)thiazole-4-carboxamide |
| 12 | 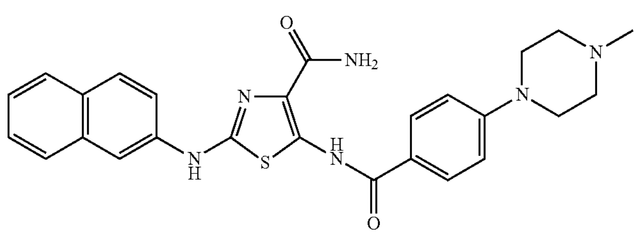 [SMILES: CN1CCN(c2ccc(C(=O)Nc3sc(Nc4ccc5ccccc5c4)nc3C(N)=O)cc2)CC1] | 5-[4-(4-methylpiperazin-1-yl)benzamido]-2-(naphthalen-2-ylamino)thiazole-4-carboxamide |
| 13 | 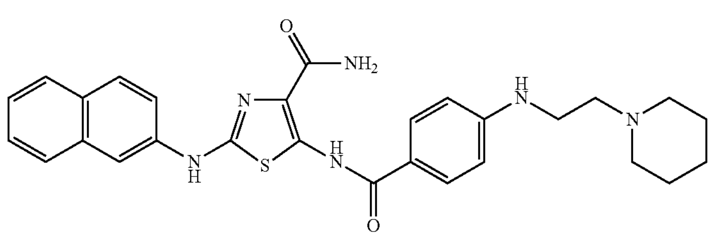 [SMILES: NC(=O)c1nc(Nc2ccc3ccccc3c2)sc1NC(=O)c1ccc(NCCN2CCCCC2)cc1] | 2-(naphthalen-2-ylamino)-5-{4-[2-(piperidin-1-yl)ethylamino]benzamido}thiazole-4-carboxamide |

TABLE 1-continued

| Example number | Structure | Name |
|---|---|---|
| 14 | 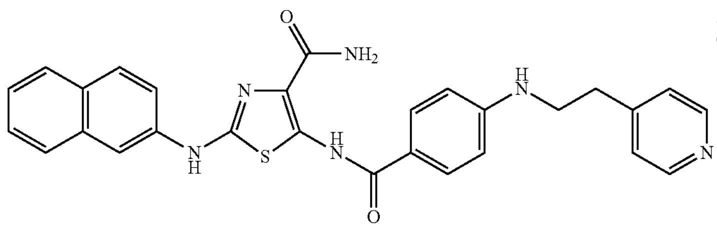 [SMILES: NC(=O)c1nc(Nc2ccc3ccccc3c2)sc1NC(=O)c1ccc(NCCc2ccncc2)cc1] | 2-(naphthalen-2-ylamino)-5-{4-[2-(pyridin-4-yl)ethylamino]benzamido}thiazole-4-carboxamide |
| 15 | 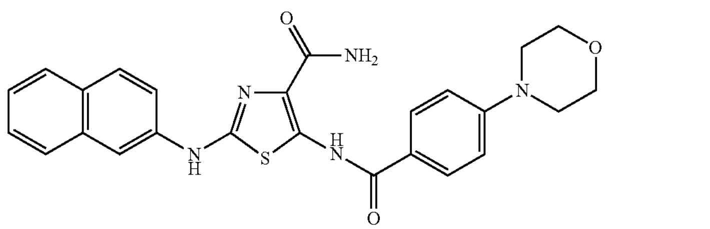 [SMILES: NC(=O)c1nc(Nc2ccc3ccccc3c2)sc1NC(=O)c1ccc(N2CCOCC2)cc1] | 5-(4-morpholinobenzamido)-2-(naphthalen-2-ylamino)thiazole-4-carboxamide |
| 16 | 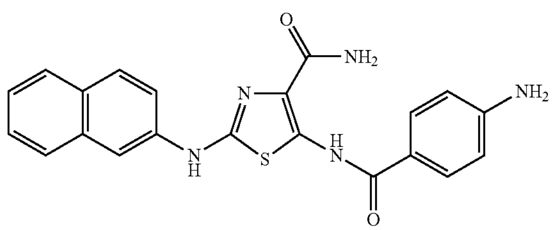 [SMILES: NC(=O)c1nc(Nc2ccc3ccccc3c2)sc1NC(=O)c1ccc(N)cc1] | 5-(4-aminobenzamido)-2-(naphthalen-2-ylamino)thiazole-4-carboxamide |
| 17 | 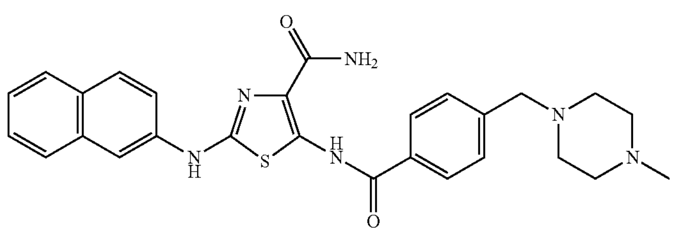 [SMILES: CN1CCN(Cc2ccc(C(=O)Nc3sc(Nc4ccc5ccccc5c4)nc3C(N)=O)cc2)CC1] | 5-{4-[(4-methylpiperazin-1-yl)methyl]benzamido}-2-(naphthalen-2-ylamino)thiazole-4-carboxamide |
| 18 | 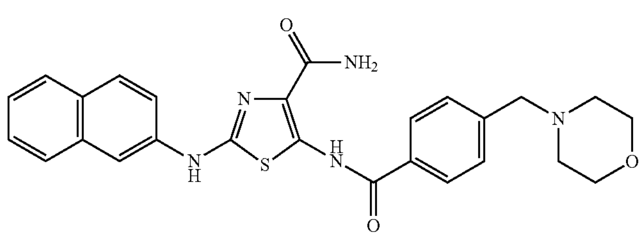 [SMILES: NC(=O)c1nc(Nc2ccc3ccccc3c2)sc1NC(=O)c1ccc(CN2CCOCC2)cc1] | 5-[4-(morpholinomethyl)benzamido]-2-(naphthalen-2-ylamino)thiazole-4-carboxamide |
| 19 | 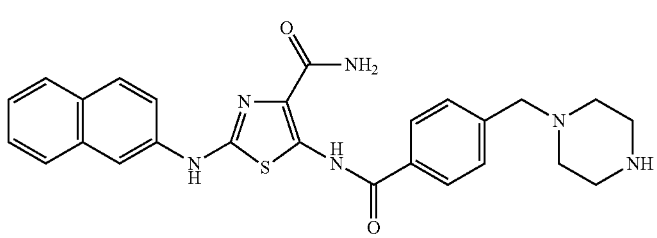 [SMILES: NC(=O)c1nc(Nc2ccc3ccccc3c2)sc1NC(=O)c1ccc(CN2CCNCC2)cc1] | 2-(naphthalen-2-ylamino)-5-[4-(piperazin-1-ylmethyl)benzamido]thiazole-4-carboxamide |

TABLE 1-continued

| Example number | Structure | Name |
|---|---|---|
| 20 | 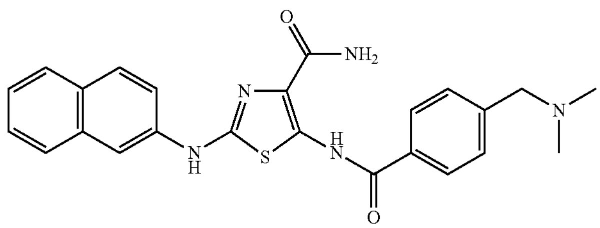 [SMILES: CN(C)Cc1ccc(C(=O)Nc2sc(Nc3ccc4ccccc4c3)nc2C(N)=O)cc1] | 5-{4-[(dimethylamino)methyl]benzamido}-2-(naphthalen-2-ylamino)thiazole-4-carboxamide |
| 21 | 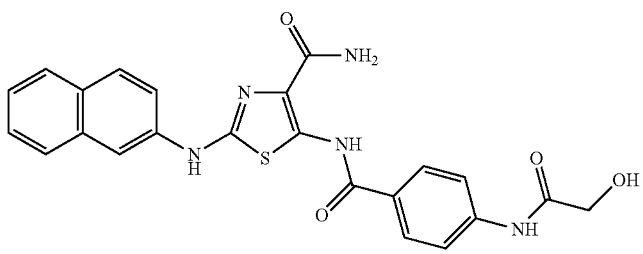 [SMILES: NC(=O)c1nc(Nc2ccc3ccccc3c2)sc1NC(=O)c1ccc(NC(=O)CO)cc1] | 5-[4-(2-hydroxyacetamido)benzamido]-2-(naphthalen-2-ylamino)thiazole-4-carboxamide |
| 22 | 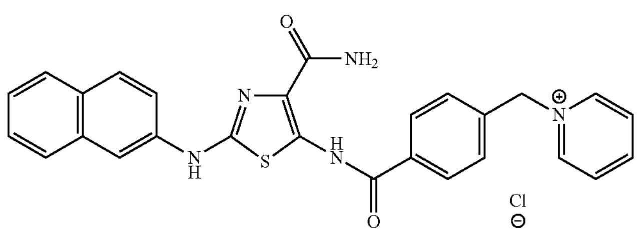 [SMILES: NC(=O)c1nc(Nc2ccc3ccccc3c2)sc1NC(=O)c1ccc(C[n+]2ccccc2)cc1 ; [Cl-]] | 1-{4-[4-carbamoyl-2-(naphthalen-2-ylamino)thiazol-5-ylcarbamoyl]benzyl}pyridinium chloride |
| 23 | 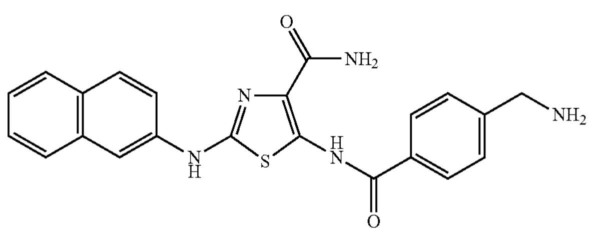 [SMILES: NCc1ccc(C(=O)Nc2sc(Nc3ccc4ccccc4c3)nc2C(N)=O)cc1] | 5-(4-aminomethylbenzamido)-2-(naphthalen-2-ylamino)thiazole-4-carboxamide |
| 24 | 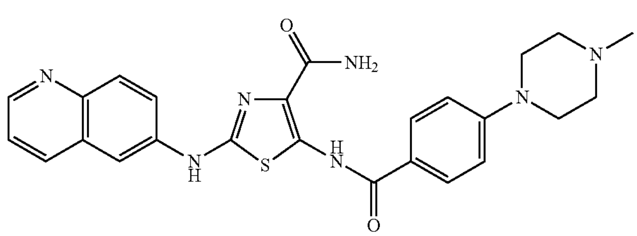 [SMILES: CN1CCN(c2ccc(C(=O)Nc3sc(Nc4ccc5ncccc5c4)nc3C(N)=O)cc2)CC1] | 5-[4-(4-methylpiperazin-1-yl)benzamido]-2-(quinolin-6-ylamino)thiazole-4-carboxamide |
| 25 | 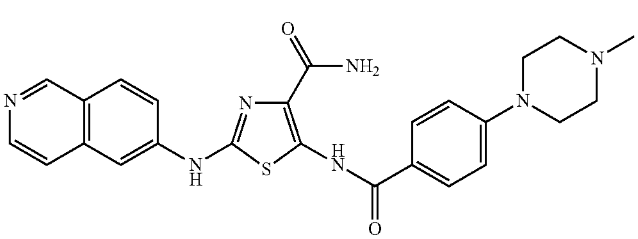 [SMILES: CN1CCN(c2ccc(C(=O)Nc3sc(Nc4ccc5cnccc5c4)nc3C(N)=O)cc2)CC1] | 2-(isoquinolin-6-ylamino)-5-[4-(4-methylpiperazin-1-yl)benzamido]thiazole-4-carboxamide |

TABLE 1-continued

| Example number | Structure | Name |
|---|---|---|
| 26 | 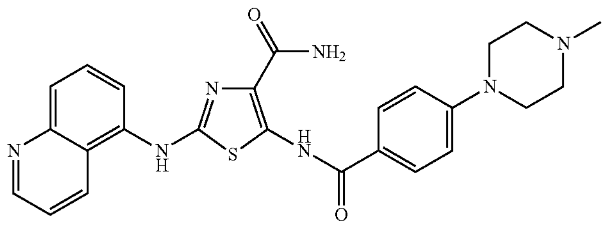 [SMILES: CN1CCN(c2ccc(C(=O)Nc3sc(Nc4cccc5ncccc45)nc3C(N)=O)cc2)CC1] | 5-[4-(4-methylpiperazin-1-yl)benzamido]-2-(quinolin-5-ylamino)thiazole-4-carboxamide |
| 27 | 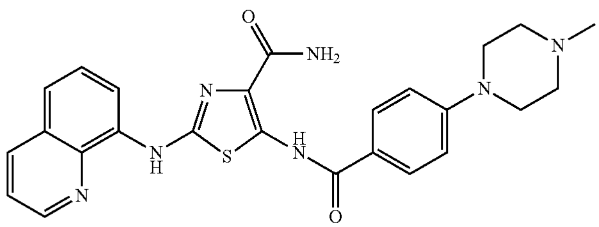 [SMILES: CN1CCN(c2ccc(C(=O)Nc3sc(Nc4cccc5cccnc45)nc3C(N)=O)cc2)CC1] | 5-[4-(4-methylpiperazin-1-yl)benzamido]-2-(quinolin-8-ylamino)thiazole-4-carboxamide |
| 28 | 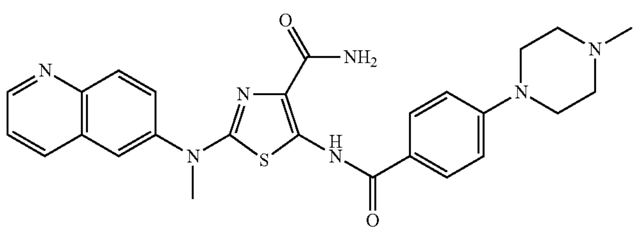 [SMILES: CN1CCN(c2ccc(C(=O)Nc3sc(N(C)c4ccc5ncccc5c4)nc3C(N)=O)cc2)CC1] | 2-[methyl(quinolin-6-yl)amino]-5-[4-(4-methyl-piperazin-1-yl)benzamido)thiazole-4-carboxamide |
| 29 | 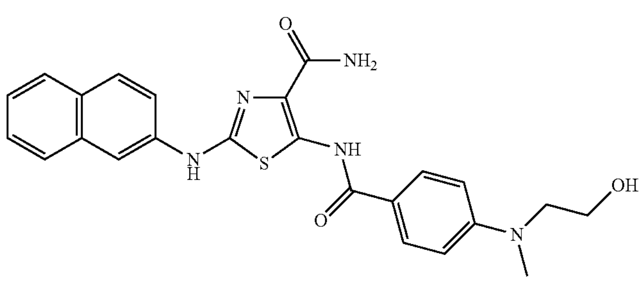 [SMILES: CN(CCO)c1ccc(C(=O)Nc2sc(Nc3ccc4ccccc4c3)nc2C(N)=O)cc1] | 5-{4-[(2-hydroxyethyl)methylamino]benzamido}-2-(naphthalen-2-ylamino)thiazole-4-carboxamide |
| 30 | 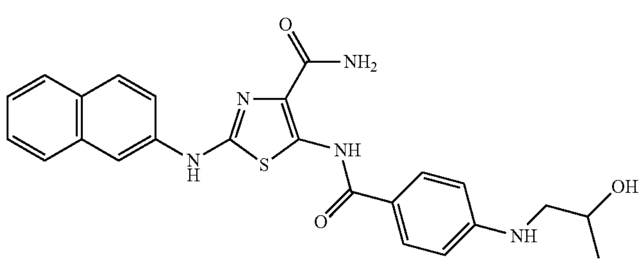 [SMILES: CC(O)CNc1ccc(C(=O)Nc2sc(Nc3ccc4ccccc4c3)nc2C(N)=O)cc1] | 5-{4-[(2-hydroxypropyl)amino]benzamido}-2-(naphthalen-2-ylamino)thiazole-4-carboxamide |
| 31 | 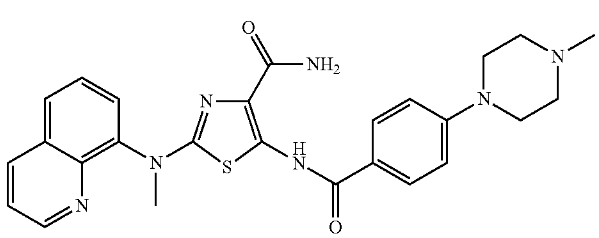 [SMILES: CN1CCN(c2ccc(C(=O)Nc3sc(N(C)c4cccc5cccnc45)nc3C(N)=O)cc2)CC1] | 2-[methyl(quinolin-8-yl)amino]-5-[4-(4-methyl-piperazin-1-yl)benzamido]thiazole-4-carboxamide |

TABLE 1-continued

| Example number | Structure | Name |
|---|---|---|
| 32 | 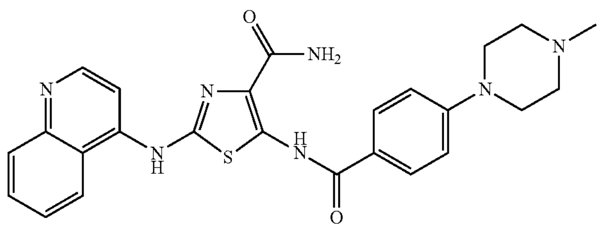 [SMILES: CN1CCN(c2ccc(C(=O)Nc3sc(Nc4ccnc5ccccc45)nc3C(N)=O)cc2)CC1] | 5-[4-(4-methylpiperazin-1-yl)benzamido]-2-(quinolin-4-ylamino)thiazole-4-carboxamide |
| 33 | 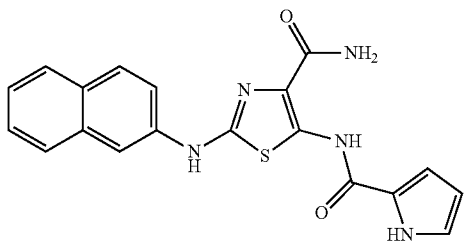 [SMILES: NC(=O)c1nc(Nc2ccc3ccccc3c2)sc1NC(=O)c1ccc[nH]1] | 2-(naphthalen-2-ylamino)-5-(1H-pyrrole-2-carboxamido)thiazole-4-carboxamide |
| 34 | 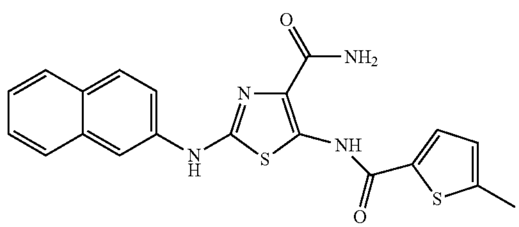 [SMILES: Cc1ccc(C(=O)Nc2sc(Nc3ccc4ccccc4c3)nc2C(N)=O)s1] | 5-(5-methylthiophene-2-carboxamido)-2-(naphthalen-2-ylamino)thiazole-4-carboxamide |
| 35 | 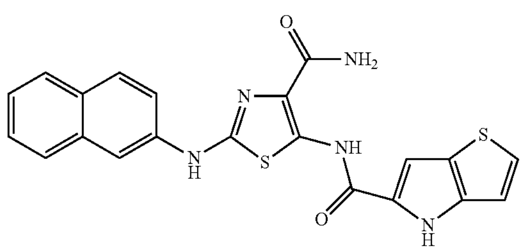 [SMILES: NC(=O)c1nc(Nc2ccc3ccccc3c2)sc1NC(=O)c1cc2sccc2[nH]1] | N-[4-carbamoyl-2-(naphthalen-2-ylamino)thiazol-5-yl]-4H-thieno[3,2-b]pyrrole-5-carboxamide |
| 36 | 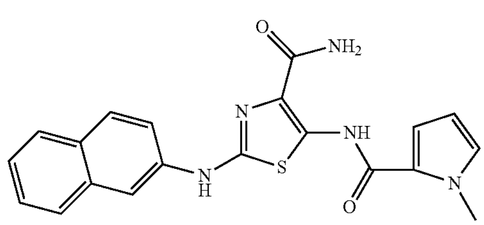 [SMILES: Cn1cccc1C(=O)Nc1sc(Nc2ccc3ccccc3c2)nc1C(N)=O] | 5-(1-methyl-1H-pyrrole-2-carboxamido)-2-(naphthalen-2-ylamino)thiazole-4-carboxamide |
| 37 | 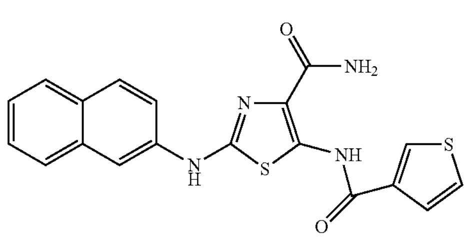 [SMILES: NC(=O)c1nc(Nc2ccc3ccccc3c2)sc1NC(=O)c1ccsc1] | 2-(naphthalen-2-ylamino)-5-(thiophene-3-carboxamido)thiazole-4-carboxamide |

TABLE 1-continued

| Example number | Structure | Name |
|---|---|---|
| 38 | 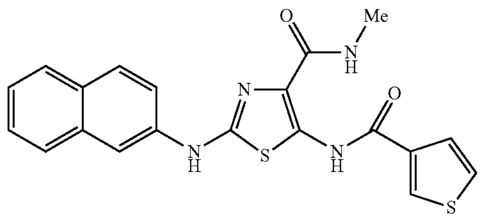 [SMILES: CNC(=O)c1nc(Nc2ccc3ccccc3c2)sc1NC(=O)c1ccsc1] | N-methyl-2-(naphthalen-2-ylamino)-5-(thiophene-3-carboxamido)thiazole-4-carboxamide |
| 39 | 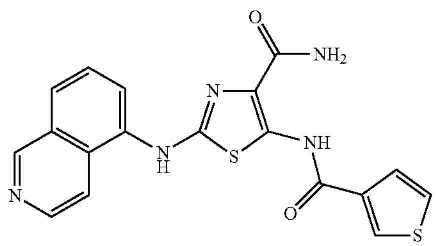 [SMILES: NC(=O)c1nc(Nc2cccc3cnccc23)sc1NC(=O)c1ccsc1] | 2-(isoquinolin-5-ylamino)-5-(thiophene-3-carboxamido)thiazole-4-carboxamide |
| 40 | 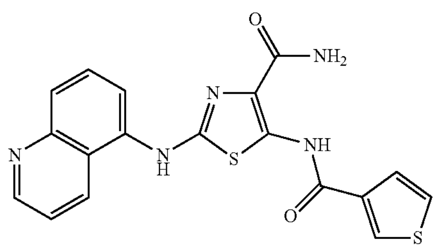 [SMILES: NC(=O)c1nc(Nc2cccc3ncccc23)sc1NC(=O)c1ccsc1] | 2-(quinolin-5-ylamino)-5-(thiophene-3-carboxamido)thiazole-4-carboxamide |
| 41 | 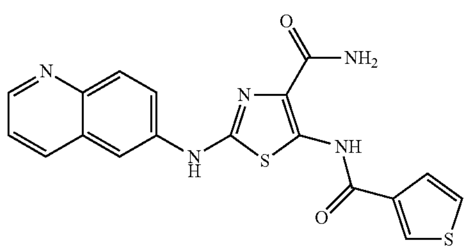 [SMILES: NC(=O)c1nc(Nc2ccc3ncccc3c2)sc1NC(=O)c1ccsc1] | 2-(quinolin-6-ylamino)-5-(thiophene-3-carboxamido)thiazole-4-carboxamide |
| 42 | 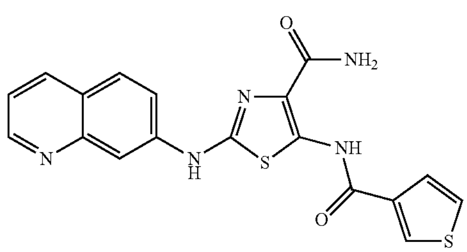 [SMILES: NC(=O)c1nc(Nc2ccc3cccnc3c2)sc1NC(=O)c1ccsc1] | 2-(quinolin-7-ylamino)-5-(thiophene-3-carboxamido)thiazole-4-carboxamide |
| 43 | 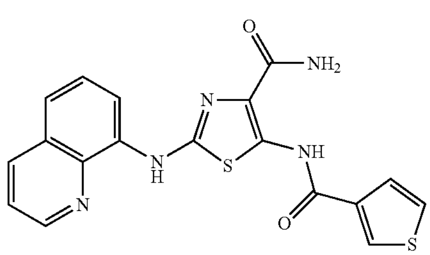 [SMILES: NC(=O)c1nc(Nc2cccc3cccnc23)sc1NC(=O)c1ccsc1] | 2-(quinolin-8-ylamino)-5-(thiophene-3-carboxamido)thiazole-4-carboxamide |

TABLE 1-continued

| Example number | Structure | Name |
|---|---|---|
| 44 | 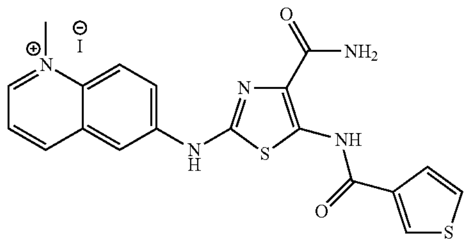 [SMILES: C[n+]1cccc2cc(Nc3nc(C(N)=O)c(NC(=O)c4ccsc4)s3)ccc21 ; [I-]] | 6-{[4-carbamoyl-5-(thiophene-3-carboxamido)thiazol-2-yl]amino}-1-methylquinolin-1-ium iodide |
| 45 | 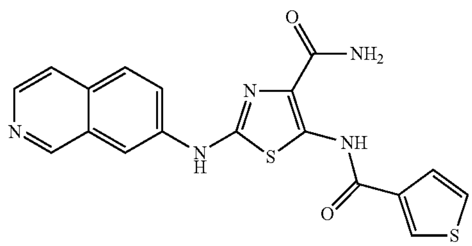 [SMILES: NC(=O)c1nc(Nc2ccc3ccncc3c2)sc1NC(=O)c1ccsc1] | 2-(isoquinolin-7-ylamino)-5-(thiophene-3-carboxamido)thiazole-4-carboxamide |
| 46 | 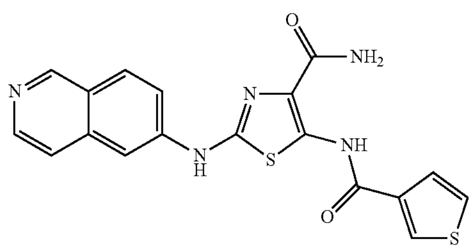 [SMILES: NC(=O)c1nc(Nc2ccc3cnccc3c2)sc1NC(=O)c1ccsc1] | 2-(isoquinolin-6-ylamino)-5-(thiophene-3-carboxamido)thiazole-4-carboxamide |
| 47 | 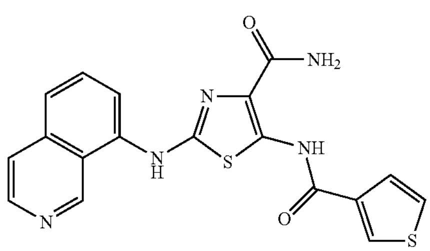 [SMILES: NC(=O)c1nc(Nc2cccc3ccncc23)sc1NC(=O)c1ccsc1] | 2-(isoquinolin-8-ylamino)-5-(thiophene-3-carboxamido)thiazole-4-carboxamide |
| 48 | 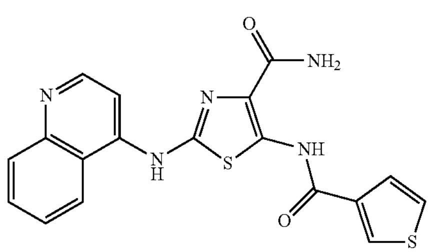 [SMILES: NC(=O)c1nc(Nc2ccnc3ccccc23)sc1NC(=O)c1ccsc1] | 2-(quinolin-4-ylamino)-5-(thiophene-3-carboxamido)thiazole-4-carboxamide |
| 49 | 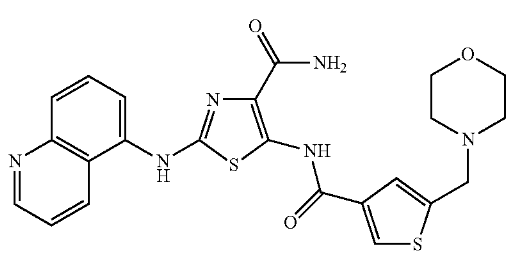 [SMILES: NC(=O)c1nc(Nc2cccc3ncccc23)sc1NC(=O)c1csc(CN2CCOCC2)c1] | 5-[5-(morpholinomethyl)thiophene-3-carboxamido]-2-(quinolin-5-ylamino)thiazole-4-carboxamide |

TABLE 1-continued

| Example number | Structure | Name |
|---|---|---|
| 50 | 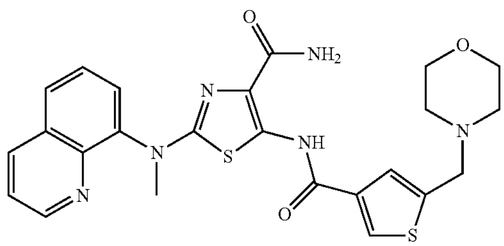 [SMILES: CN(c1nc(C(N)=O)c(NC(=O)c2csc(CN3CCOCC3)c2)s1)c1cccc2cccnc12] | 2-[methyl(quinolin-8-yl)amino]-5-[5-(morpholinomethyl)thiophene-3-carboxamido]thiazole-4-carboxamide |
| 51 | 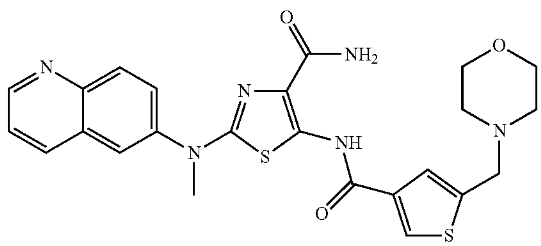 [SMILES: CN(c1ccc2ncccc2c1)c1nc(C(N)=O)c(NC(=O)c2csc(CN3CCOCC3)c2)s1] | 2-[methyl(quinolin-6-yl)amino]-5-[5-(morpholinomethyl)thiophene-3-carboxamidoithiazole-4-carboxamide |
| 52 | 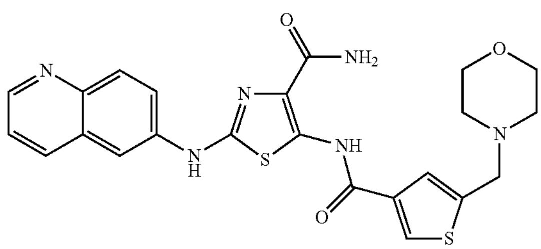 | 5-[5-(morpholinomethyl)thiophene-3-carboxamido]-2-(quinolin-6-ylamino)thiazole-4-carboxamide |
| 53 | 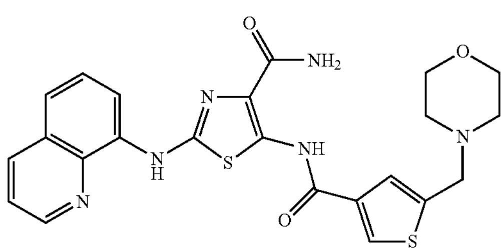 | 5-[5-(morpholinomethyl)thiophene-3-carboxamido]-2-(quinolin-8-ylamino)thiazole-4-carboxamide |
| 54 | 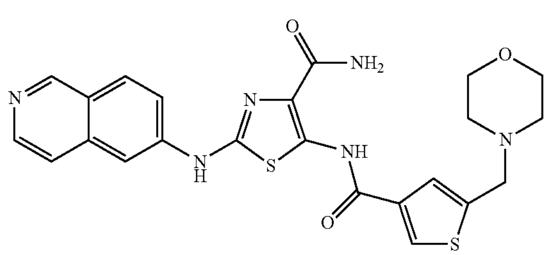 [SMILES: NC(=O)c1nc(Nc2ccc3cnccc3c2)sc1NC(=O)c1csc(CN2CCOCC2)c1] | 2-(isoquinolin-6-ylamino)-5-[5-(morpholinomethyl)thiophene-3-carboxamido]thiazole-4-carboxamide |
| 55 | 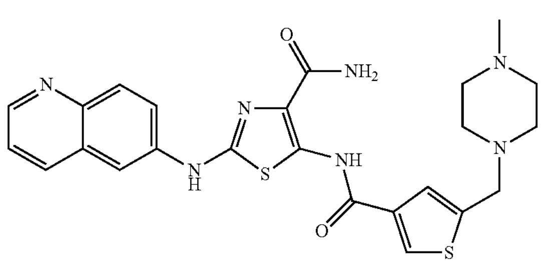 [SMILES: CN1CCN(Cc2cc(C(=O)Nc3sc(Nc4ccc5ncccc5c4)nc3C(N)=O)cs2)CC1] | 5-{5-[(4-methylpiperazin-1-yl)methyl]thiophene-3-carboxamido}-2-(quinolin-6-ylamino)thiazole-4-carboxamide |

TABLE 1-continued

| Example number | Structure | Name |
|---|---|---|
| 56 | 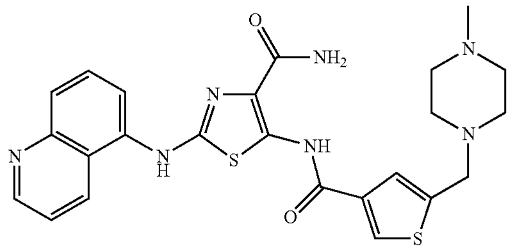 [SMILES: CN1CCN(Cc2cc(C(=O)Nc3sc(Nc4cccc5ncccc45)nc3C(N)=O)cs2)CC1] | 5-{5-[(4-methylpiperazin-1-yl)methyl]thiophene-3-carboxamido}-2-(quinolin-5-ylamino)thiazole-4-carboxamide |
| 57 | 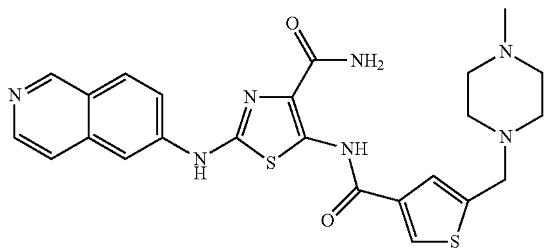 [SMILES: CN1CCN(Cc2cc(C(=O)Nc3sc(Nc4ccc5cnccc5c4)nc3C(N)=O)cs2)CC1] | 2-(isoquinolin-6-ylamino)-5-{5-[(4-methylpiperazin-1-yl)methyl]thiophene-3-carboxamido}thiazole-4-carboxamide |
| 58 | 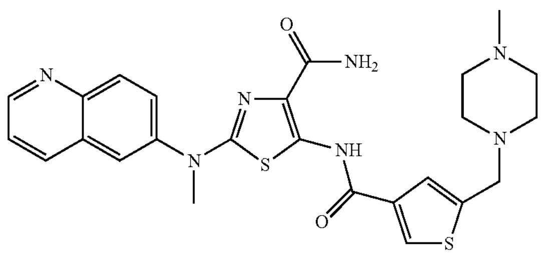 | 2-[methyl(quinolin-6-yl)amino]-5-{5-[(4-methyl-piperazin-1-yl)methyl]thiophene-3-carboxamido}thiazole-4-carboxamide |
| 59 | 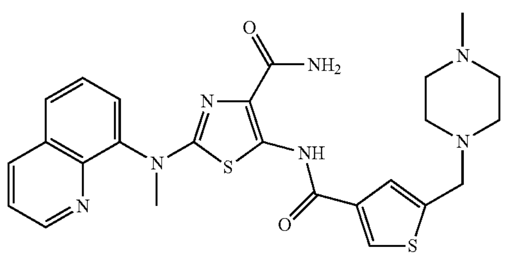 [SMILES: CN1CCN(Cc2cc(C(=O)Nc3sc(N(C)c4cccc5cccnc45)nc3C(N)=O)cs2)CC1] | 2-[methyl(quinolin-8-yl)amino]-5-{5-[(4-methyl-piperazin-1-yl)methyl]thiophene-3-carboxamido}thiazole-4-carboxamide |
| 60 | 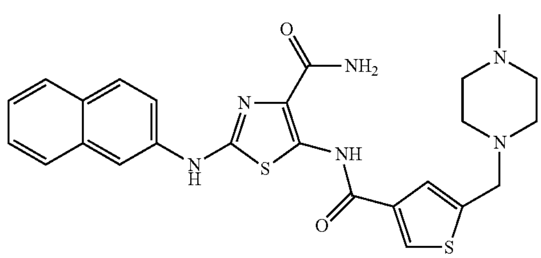 | 5-{5-[(4-methylpiperazin-1-yl)methyl]thiophene-3-carboxamido}-2-(naphthalen-2-ylamino)thiazole-4-carboxamide |
| 61 | 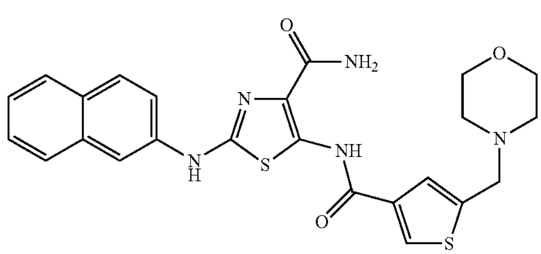 [SMILES: NC(=O)c1nc(Nc2ccc3ccccc3c2)sc1NC(=O)c1csc(CN2CCOCC2)c1] | 5-[5-(morpholinomethyl)thiophene-3-carboxamido]-2-(naphthalen-2-ylamino)thiazole-4-carboxamide |

TABLE 1-continued

| Example number | Structure | Name |
|---|---|---|
| 62 | 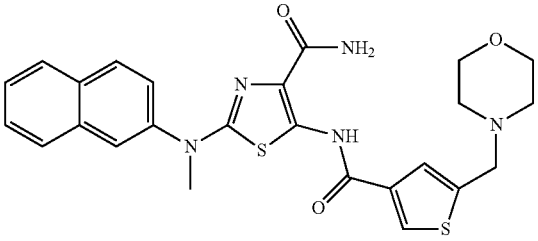 | 2-[methyl(naphthalen-2-yl)amino]-5-[5-(morpholinomethyl)thiophene-3-carboxamido]thiazole-4-carboxamide |
| 63 | 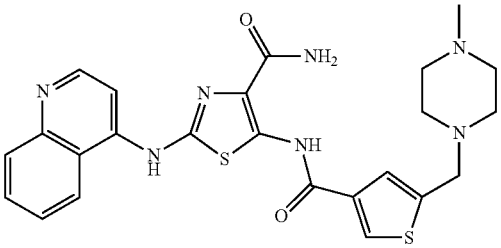 [SMILES: CN1CCN(Cc2cc(C(=O)Nc3sc(Nc4ccnc5ccccc45)nc3C(N)=O)cs2)CC1] | 5-{5-[(4-methylpiperazin-1-yl)methyl]thiophene-3-carboxamido}-2-(quinolin-4-ylamino)thiazole-4-carboxamide |
| 64 | 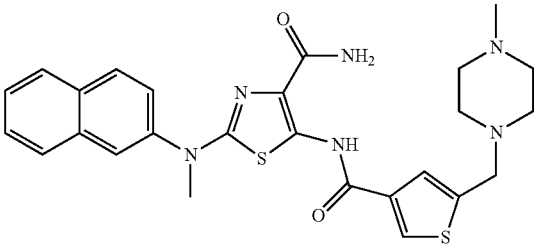 [SMILES: CN1CCN(Cc2cc(C(=O)Nc3sc(N(C)c4ccc5ccccc5c4)nc3C(N)=O)cs2)CC1] | 2-[methyl(naphthalen-2-yl)amino]-5-{5-[(4-methylpiperazin-1-yl)methyl]thiophene-3-carboxamido}thiazole-4-carboxamide |
| 65 | 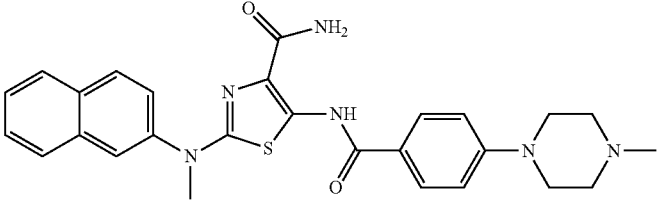 [SMILES: CN1CCN(c2ccc(C(=O)Nc3sc(N(C)c4ccc5ccccc5c4)nc3C(N)=O)cc2)CC1] | 2-[methyl(naphthalen-2-yl)amino]-5-[4-(4-methylpiperazin-1-yl)benzamido]thiazole-4-carboxamide |
| 66 | 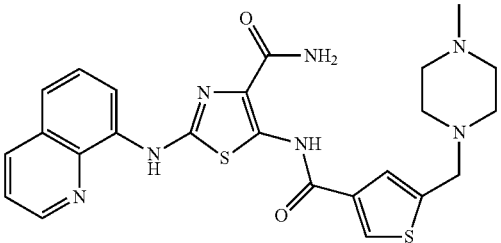 [SMILES: CN1CCN(Cc2cc(C(=O)Nc3sc(Nc4cccc5cccnc45)nc3C(N)=O)cs2)CC1] | 5-{5-[(4-methylpiperazin-1-yl)methyl]thiophene-3-carboxamido}-2-(quinolin-8-ylamino)thiazole-4-carboxamide |
| 67 | 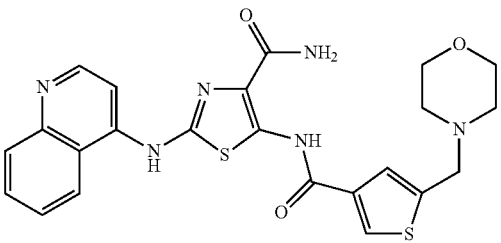 [SMILES: NC(=O)c1nc(Nc2ccnc3ccccc23)sc1NC(=O)c1csc(CN2CCOCC2)c1] | 5-[5-morpholinomethyl)thiophene-3-carboxamido]-2-(quinolin-4-ylamino)thiazole-4-carboxamide |

TABLE 1-continued

| Example number | Structure | Name |
|---|---|---|
| 68 | 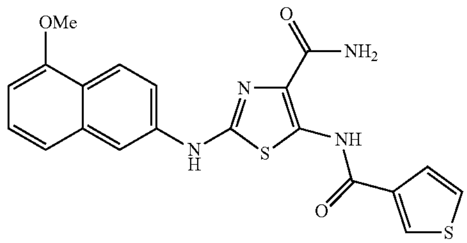 [SMILES: COc1cccc2cc(Nc3nc(C(N)=O)c(NC(=O)c4ccsc4)s3)ccc12] | 2-[(5-methoxynaphthalen-2-yl)amino]-5-(thiophene-3-carboxamido)thiazole-4-carboxamide |
| 69 | 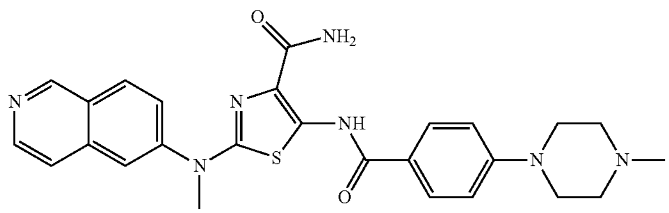 [SMILES: CN1CCN(c2ccc(C(=O)Nc3sc(N(C)c4ccc5cnccc5c4)nc3C(N)=O)cc2)CC1] | 2-[isoquinolin-6-yl(methyl)amino]-5-[4-(4-methylpiperazin-1-yl)benzamido]thiazole-4-carboxamide |
| 70 | 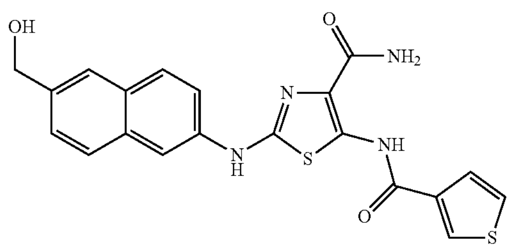 [SMILES: NC(=O)c1nc(Nc2ccc3cc(CO)ccc3c2)sc1NC(=O)c1ccsc1] | 2-{[6-(hydroxymethyl)naphthalen-2-yl]amino}-5-(thiophene-3-carboxamido)thiazole-4-carboxamide |
| 71 | 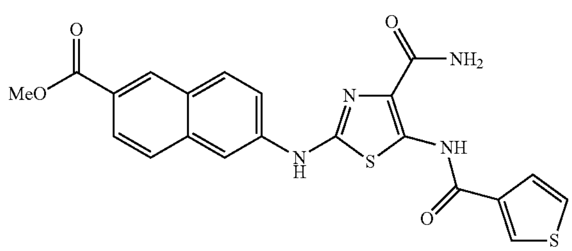 [SMILES: COC(=O)c1ccc2cc(Nc3nc(C(N)=O)c(NC(=O)c4ccsc4)s3)ccc2c1] | methyl 6-{[4-carbamoyl-5-(thiophene-3-carboxamido)thiazol-2-yl]amino}-2-naphthoate |
| 72 | 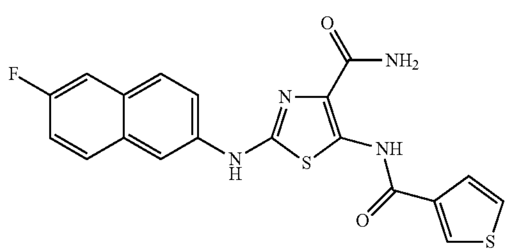 [SMILES: NC(=O)c1nc(Nc2ccc3cc(F)ccc3c2)sc1NC(=O)c1ccsc1] | 2-{(6-fluoronaphthalen-2-yl)amino]-5-(thiophene-3-carboxamido)thiazole-4-carboxamide |
| 73 | 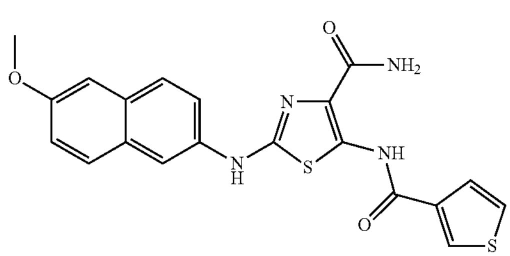 [SMILES: COc1ccc2cc(Nc3nc(C(N)=O)c(NC(=O)c4ccsc4)s3)ccc2c1] | 2-[(6-methoxynaphthalen-2-yl)amino]-5-(thiophene-3-carboxamido)thiazole-4-carboxamide |

TABLE 1-continued

| Example number | Structure | Name |
|---|---|---|
| 74 | 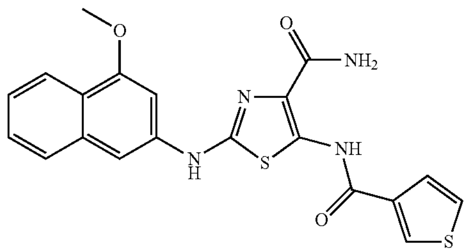 [SMILES: COc1cc(Nc2nc(C(N)=O)c(NC(=O)c3ccsc3)s2)cc2ccccc12] | 2-[(4-methoxynaphthalen-2-yl)amino]-5-(thiophene-3-carboxamido)thiazole-4-carboxamide |
| 75 | 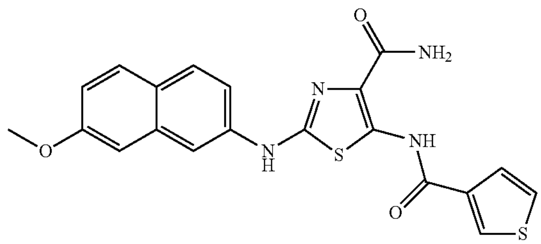 [SMILES: COc1ccc2ccc(Nc3nc(C(N)=O)c(NC(=O)c4ccsc4)s3)cc2c1] | 2-[(7-methoxynaphthalen-2-yl)amino]-5-(thiophene-3-carboxamido)thiazole-4-carboxamide |
| 76 | 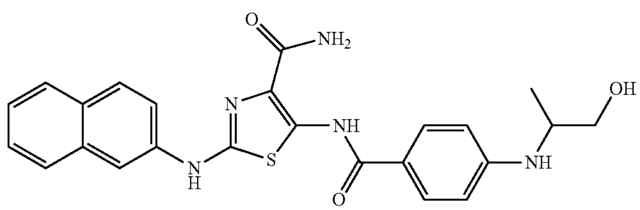 [SMILES: CC(CO)Nc1ccc(C(=O)Nc2sc(Nc3ccc4ccccc4c3)nc2C(N)=O)cc1] | 5-{4-[(1-hydroxypropan-2-yl)amino]benzamido}-2-(naphthalen-2-ylamino)thiazole-4-carboxamide |
| 77 | 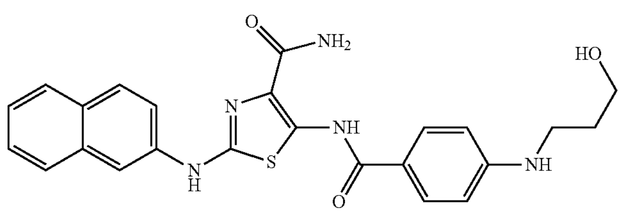 [SMILES: NC(=O)c1nc(Nc2ccc3ccccc3c2)sc1NC(=O)c1ccc(NCCCO)cc1] | 5-{4-[(3-hydroxypropyl)amino]benzamido}-2-(naphthalen-2-ylamino)thiazole-4-carboxamide |
| 78 | 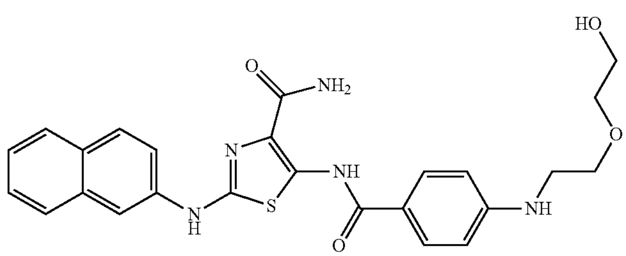 [SMILES: NC(=O)c1nc(Nc2ccc3ccccc3c2)sc1NC(=O)c1ccc(NCCOCCO)cc1] | 5-(4-{[2-(2-hydroxyethoxy)ethyl]amino}benzamido)-2-(naphthalen-2-ylamino)thiazole-4-carboxamide |
| 79 | 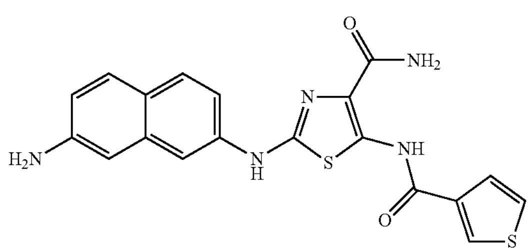 [SMILES: NC(=O)c1nc(Nc2ccc3ccc(N)cc3c2)sc1NC(=O)c1ccsc1] | 2-[(7-aminonaphthalen-2-yl)amino]-5-(thiophene-3-carboxamido)thiazole-4-carboxamide |

TABLE 1-continued

| Example number | Structure | Name |
|---|---|---|
| 80 | 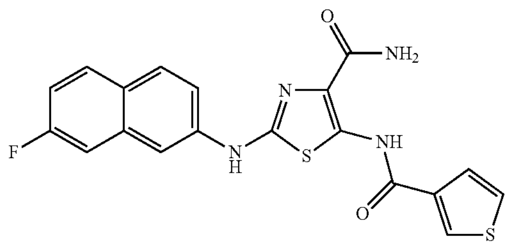 [SMILES: NC(=O)c1nc(Nc2ccc3ccc(F)cc3c2)sc1NC(=O)c1ccsc1] | 2-[(7-fluoronaphthalen-2-yl)amino]-5-(thiophene-3-carboxamido)thiazole-4-carboxamide |
| 81 | 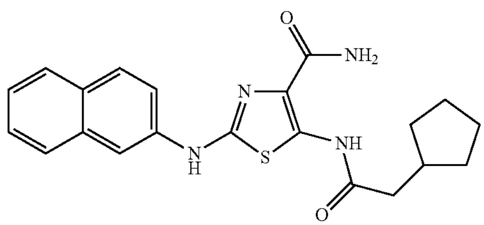 [SMILES: NC(=O)c1nc(Nc2ccc3ccccc3c2)sc1NC(=O)CC1CCCC1] | 5-(2-cyclopentylacetamido)-2-(naphthalen-2-yl-amino)thiazole-4-carboxamide |
| 82 | 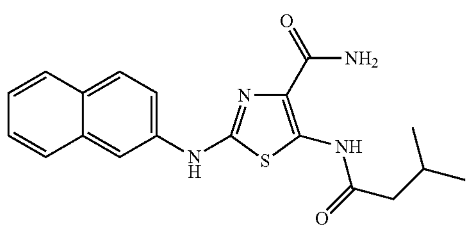 [SMILES: CC(C)CC(=O)Nc1sc(Nc2ccc3ccccc3c2)nc1C(N)=O] | 5-(3-methylbutanamido)-2-(naphthalen-2-ylamino)thiazole-4-carboxamide |
| 83 | 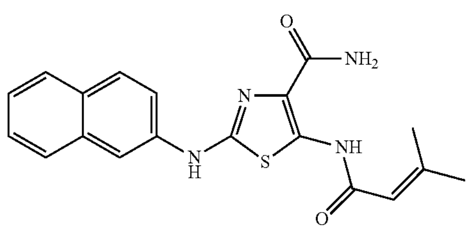 [SMILES: CC(C)=CC(=O)Nc1sc(Nc2ccc3ccccc3c2)nc1C(N)=O] | 5-(3-methylbut-2-enamido)-2-(naphthalen-2-yl-amino)thiazole-4-carboxamide |
| 84 | 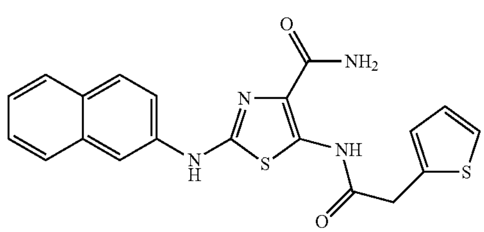 [SMILES: NC(=O)c1nc(Nc2ccc3ccccc3c2)sc1NC(=O)Cc1cccs1] | 2-(naphthalen-2-ylamino)-5-[2-(thiophen-2-yl)acetamido]thiazole-4-carboxamide |
| 85 | 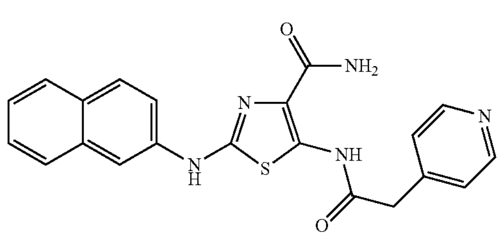 [SMILES: NC(=O)c1nc(Nc2ccc3ccccc3c2)sc1NC(=O)Cc1ccncc1] | 2-(naphthalen-2-ylamino)-5-[2-(pyridin-4-yl)acetamido]thiazole-4-carboxamide |

TABLE 1-continued

| Example number | Structure | Name |
|---|---|---|
| 86 | 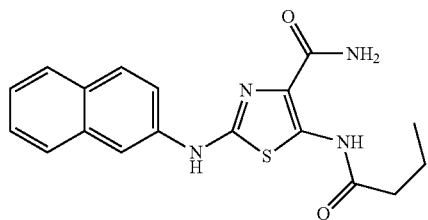 [SMILES: CCCC(=O)Nc1sc(Nc2ccc3ccccc3c2)nc1C(N)=O] | 5-butyramido-2-(naphthalen-2-ylamino)thiazole-4-carboxamide |
| 87 | 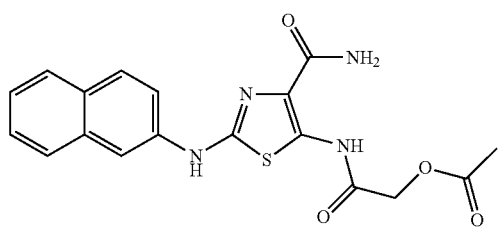 [SMILES: CC(=O)OCC(=O)Nc1sc(Nc2ccc3ccccc3c2)nc1C(N)=O] | 2-{[4-carbamoyl-2-(naphthalen-2-ylamino)thiazol-5-yl]amino}-2-oxoethyl acetate |
| 88 | 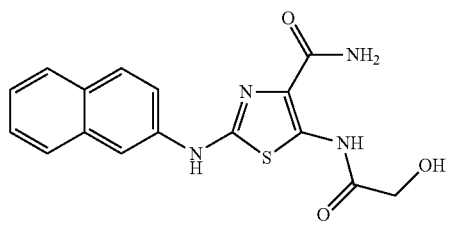 [SMILES: NC(=O)c1nc(Nc2ccc3ccccc3c2)sc1NC(=O)CO] | 5-(2-hydroxyacetamido)-2-(naphthalen-2-ylamino)thiazole-4-carboxamide |
| 89 | 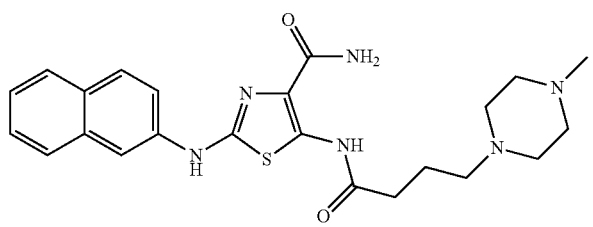 [SMILES: CN1CCN(CCCC(=O)Nc2sc(Nc3ccc4ccccc4c3)nc2C(N)=O)CC1] | 5-[4-(4-methylpiperazin-1-yl)butanamido]-2-(naphthalen-2-ylamino)thiazole-4-carboxamide |
| 90 | 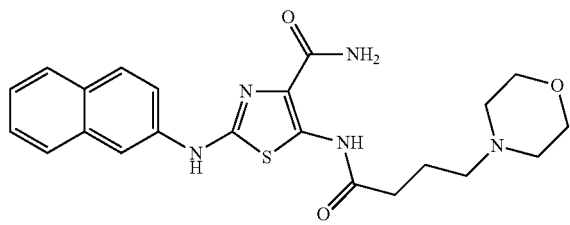 [SMILES: NC(=O)c1nc(Nc2ccc3ccccc3c2)sc1NC(=O)CCCN1CCOCC1] | 5-(4-morpholinobutanamido)-2-(naphthalen-2-ylamino)thiazole-4-carboxamide |
| 91 | 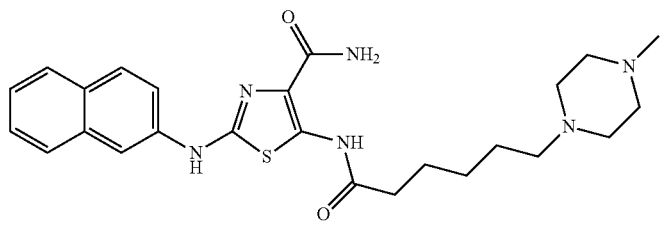 [SMILES: CN1CCN(CCCCCC(=O)Nc2sc(Nc3ccc4ccccc4c3)nc2C(N)=O)CC1] | 5-[6-(4-methylpiperazin-1-yl)hexanamido]-2-(naphthalen-2-ylamino)thiazole-4-carboxamide |

TABLE 1-continued

| Example number | Structure | Name |
|---|---|---|
| 92 | 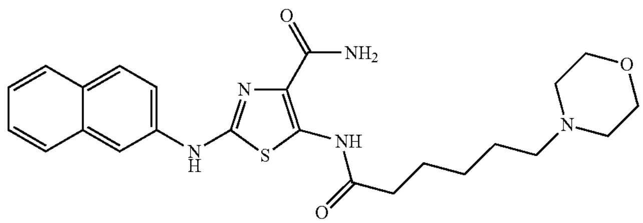 [SMILES: NC(=O)c1nc(Nc2ccc3ccccc3c2)sc1NC(=O)CCCCCN1CCOCC1] | 5-(6-morpholinohexanamido)-2-(naphthalen-2-yl-amino)thiazole-4-carboxamide |
| 93 | 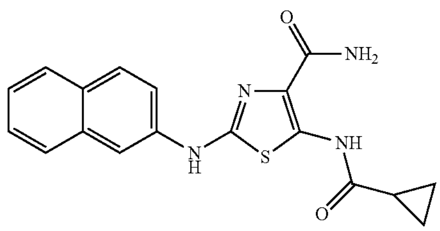 [SMILES: NC(=O)c1nc(Nc2ccc3ccccc3c2)sc1NC(=O)C1CC1] | 5-(cyclopropanecarboxamido)-2-(naphthalen-2-yl-amino)thiazole-4-carboxamide |
| 94 | 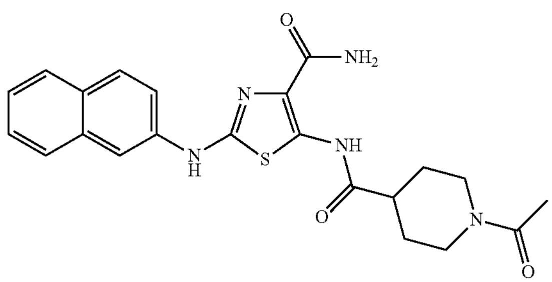 [SMILES: CC(=O)N1CCC(C(=O)Nc2sc(Nc3ccc4ccccc4c3)nc2C(N)=O)CC1] | 5-(1-acetylpiperidine-4-carboxamido)-2-(naphthalen-2-ylamino)thiazole-4-carboxamide |
| 95 | 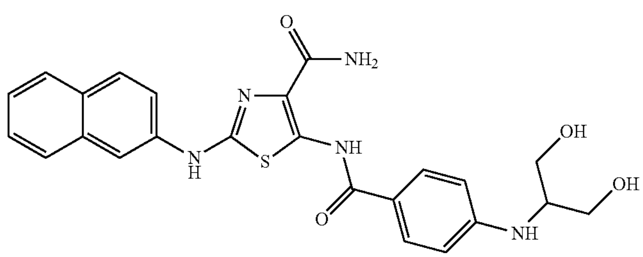 [SMILES: NC(=O)c1nc(Nc2ccc3ccccc3c2)sc1NC(=O)c1ccc(NC(CO)CO)cc1] | 5-{4-[(1,3-dihydroxypropan-2-yl)amino]benzamido}-2-(naphthalen-2-ylamino)thiazole-4-carboxamide |
| 96 | 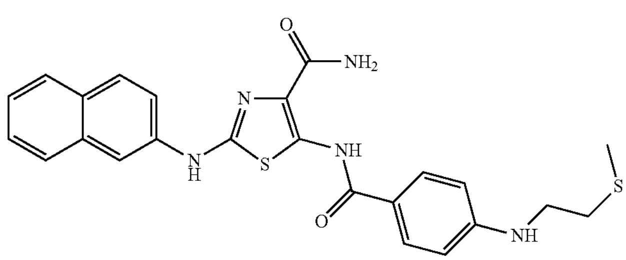 [SMILES: CSCCNc1ccc(C(=O)Nc2sc(Nc3ccc4ccccc4c3)nc2C(N)=O)cc1] | 5-(4-{[2-(methylthio)ethyl]amino}benzamido)-2-(naphthalen-2-ylamino)thiazole-4-carboxamide |
| 97 | 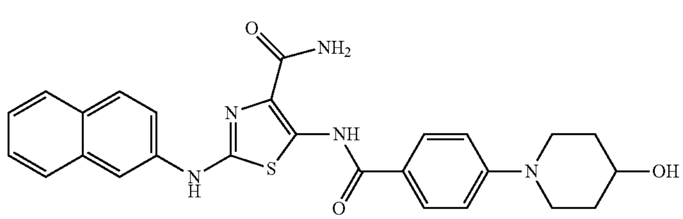 [SMILES: NC(=O)c1nc(Nc2ccc3ccccc3c2)sc1NC(=O)c1ccc(N2CCC(O)CC2)cc1] | 5-[4-(4-hydroxypiperidin-1-yl)benzamido]-2-(naphthalen-2-ylamino)thiazole-4-carboxamide |

TABLE 1-continued

| Example number | Structure | Name |
|---|---|---|
| 98 | 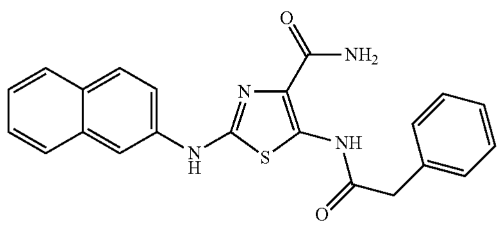 [SMILES: NC(=O)c1nc(Nc2ccc3ccccc3c2)sc1NC(=O)Cc1ccccc1] | 2-(naphthalen-2-ylamino)-5-(2-phenylacetamido)thiazole-4-carboxamide |
| 99 | 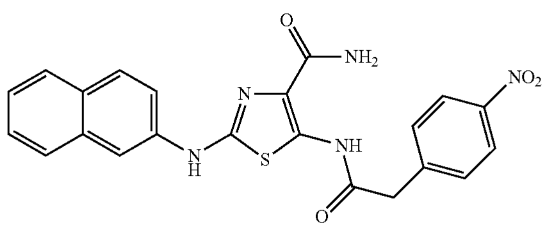 [SMILES: NC(=O)c1nc(Nc2ccc3ccccc3c2)sc1NC(=O)Cc1ccc([N+](=O)[O-])cc1] | 2-(naphthalen-2-ylamino)-5-[2-(4-nitrophenyl)acetamido]thiazole-4-carboxamide |
| 100 | 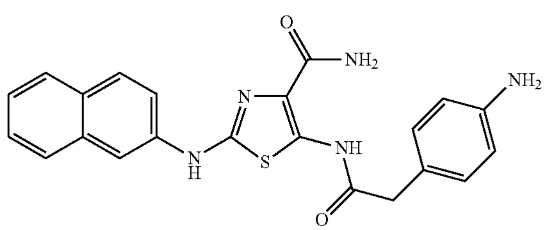 [SMILES: NC(=O)c1nc(Nc2ccc3ccccc3c2)sc1NC(=O)Cc1ccc(N)cc1] | 5-[2-(4-aminophenyl)acetamido]-2-(naphthalen-2-ylamino)thiazole-4-carboxamide |
| 101 | 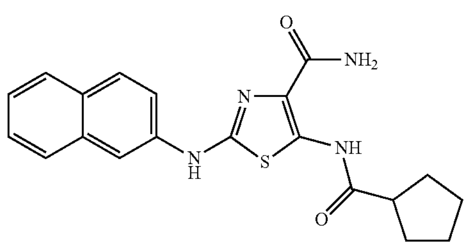 [SMILES: NC(=O)c1nc(Nc2ccc3ccccc3c2)sc1NC(=O)C1CCCC1] | 5-(cyclopentanecarboxamido)-2-(naphthalen-2-ylamino)thiazole-4-carboxamide |
| 102 | 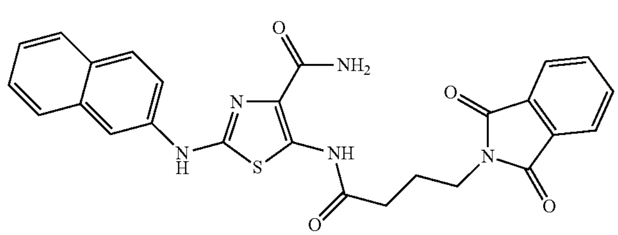 [SMILES: NC(=O)c1nc(Nc2ccc3ccccc3c2)sc1NC(=O)CCCN1C(=O)c2ccccc2C1=O] | 2-(naphthalen-2-ylamino)-5-(4-phthalimidobutanamido)thiazole-4-carboxamide |
| 103 | 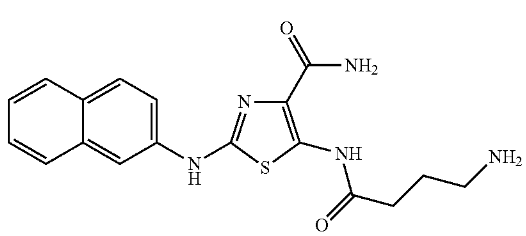 [SMILES: NCCCC(=O)Nc1sc(Nc2ccc3ccccc3c2)nc1C(N)=O] | 5-(4-aminobutanamido)-2-(naphthalen-2-ylamino)thiazole-4-carboxamide |

TABLE 1-continued

| Example number | Structure | Name |
|---|---|---|
| 104 | 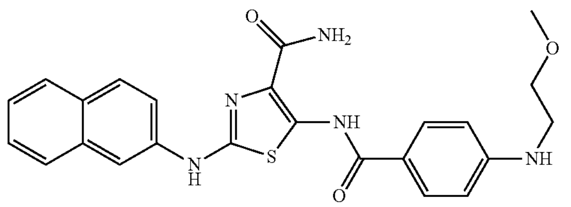 [SMILES: COCCNc1ccc(C(=O)Nc2sc(Nc3ccc4ccccc4c3)nc2C(N)=O)cc1] | 5-{4-[(2-methoxyethyl)amino]benzamido}-2-(naphthalen-2-ylamino)thiazole-4-carboxamide |
| 105 | 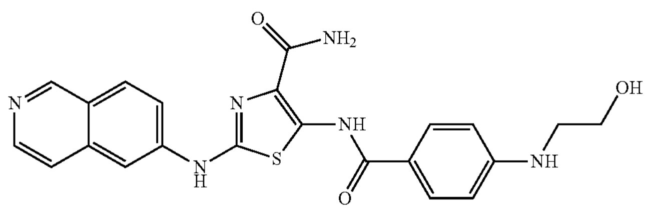 [SMILES: NC(=O)c1nc(Nc2ccc3cnccc3c2)sc1NC(=O)c1ccc(NCCO)cc1] | 5-{4-[(2-hydroxyethyl)amino]benzamido}-2-(isoquinolin-6-ylamino)thiazole-4-carboxamide |
| 106 | 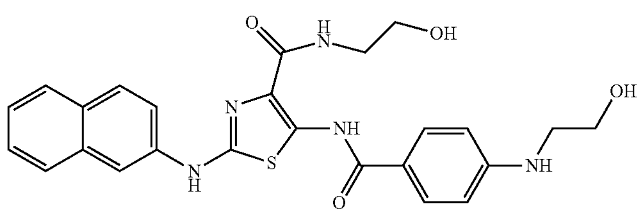 [SMILES: O=C(Nc1sc(Nc2ccc3ccccc3c2)nc1C(=O)NCCO)c1ccc(NCCO)cc1] | N-(2-hydroxyethyl)-5-{4-[(2-hydroxyethyl)amino]benzamido}-2-(naphthalen-2-ylamino)thiazole-4-carboxamide |
| 107 | 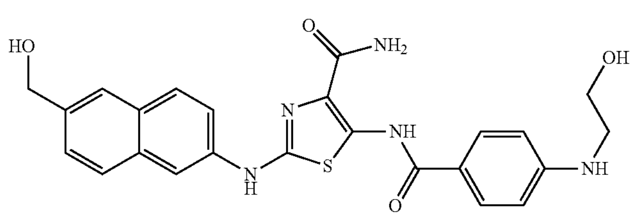 [SMILES: NC(=O)c1nc(Nc2ccc3cc(CO)ccc3c2)sc1NC(=O)c1ccc(NCCO)cc1] | 5-{4-[(2-hydroxyethyl)amino]benzamido}-2-{[6-(hydroxymethyl)naphthalen-2-yl]amino}thiazole-4-carboxamide |
| 108 | 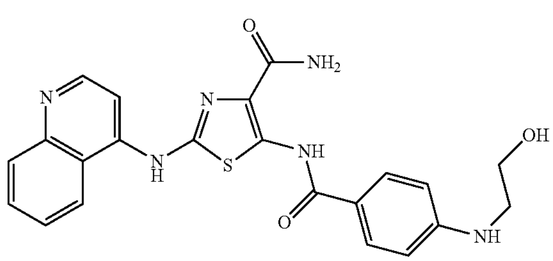 [SMILES: NC(=O)c1nc(Nc2ccnc3ccccc23)sc1NC(=O)c1ccc(NCCO)cc1] | 5-{4-[(2-hydroxyethyl)amino]benzamido}-2-(quinolin-4-ylamino)thiazole-4-carboxamide |
| 109 | 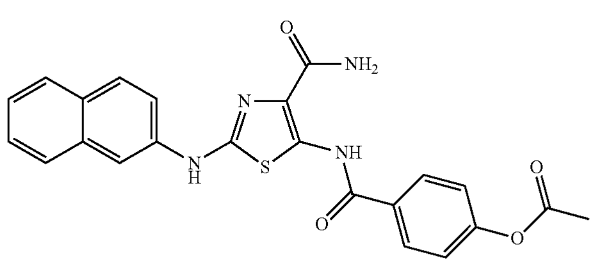 [SMILES: CC(=O)Oc1ccc(C(=O)Nc2sc(Nc3ccc4ccccc4c3)nc2C(N)=O)cc1] | 4-{[4-carbamoyl-2-(naphthalen-2-ylamino)thiazol-5-yl]carbamoyl}phenyl acetate |

TABLE 1-continued

| Example number | Structure | Name |
|---|---|---|
| 110 | 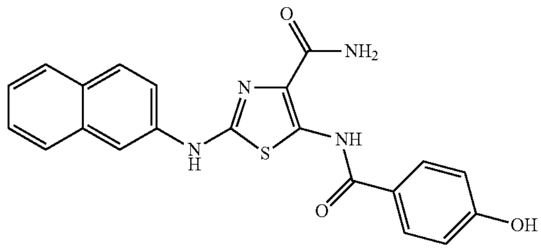 [SMILES: NC(=O)c1nc(Nc2ccc3ccccc3c2)sc1NC(=O)c1ccc(O)cc1] | 5-(4-hydroxybenzamido)-2-(naphthalen-2-ylamino)thiazole-4-carboxamide |
| 111 | 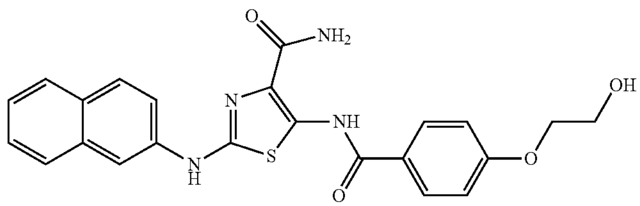 | 5-[4-(2-hydroxyethoxy)benzamido]-2-(naphthalen-2-ylamino)thiazole-4-carboxamide |
| 112 | 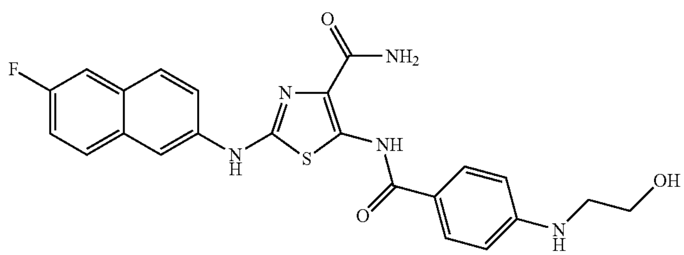 [SMILES: NC(=O)c1nc(Nc2ccc3cc(F)ccc3c2)sc1NC(=O)c1ccc(NCCO)cc1] | 2-[(6-fluoronaphthalen-2-yl)amino]-5-{4-[(2-hydroxyethyl)amino]benzamido}thiazole-4-carboxamide |
| 113 | 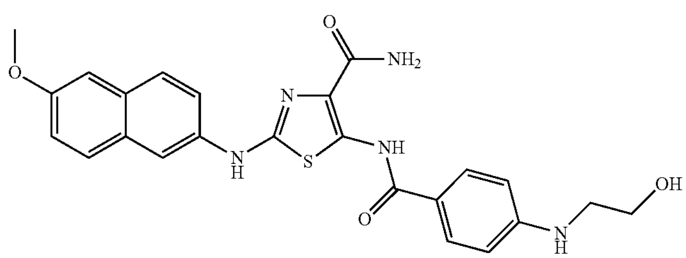 [SMILES: COc1ccc2cc(Nc3nc(C(N)=O)c(NC(=O)c4ccc(NCCO)cc4)s3)ccc2c1] | 5-{4-[(2-hydroxyethyl)amino]benzamido}-2-[(6-methoxynaphthalen-2-yl)amino]thiazole-4-carboxamide |
| 114 | 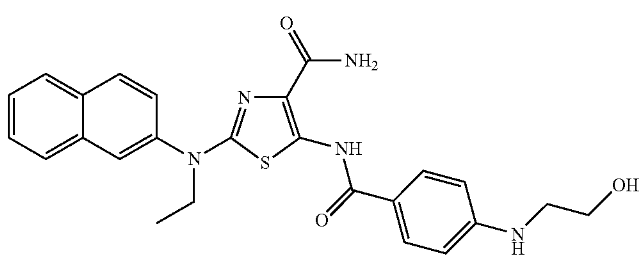 [SMILES: CCN(c1ccc2ccccc2c1)c1nc(C(N)=O)c(NC(=O)c2ccc(NCCO)cc2)s1] | 2-[ethyl(naphthalen-2-yl)amino]-5-{4-[(2-hydroxyethyl)amino]benzamido}thiazole-4-carboxamide |
| 115 | 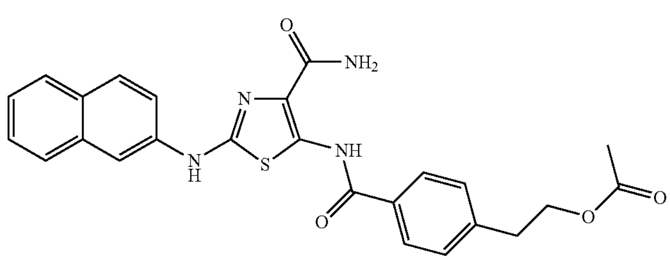 [SMILES: CC(=O)OCCc1ccc(C(=O)Nc2sc(Nc3ccc4ccccc4c3)nc2C(N)=O)cc1] | 4-{[4-carbamoyl-2-(naphthalen-2-ylamino)thiazol-5-yl]carbamoyl}phenethyl acetate |

TABLE 1-continued

| Example number | Structure | Name |
|---|---|---|
| 116 | 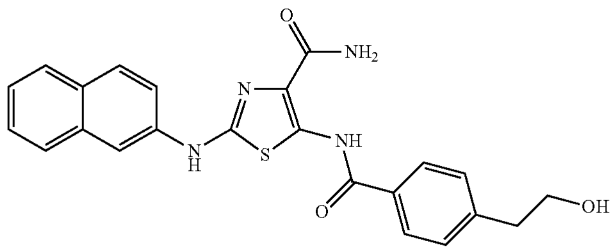 [SMILES: NC(=O)c1nc(Nc2ccc3ccccc3c2)sc1NC(=O)c1ccc(CCO)cc1] | 5-[4-(2-hydroxyethyl)benzamido]-2-(naphthalen-2-ylamino)thiazole-4-carboxamide |
| 117 | 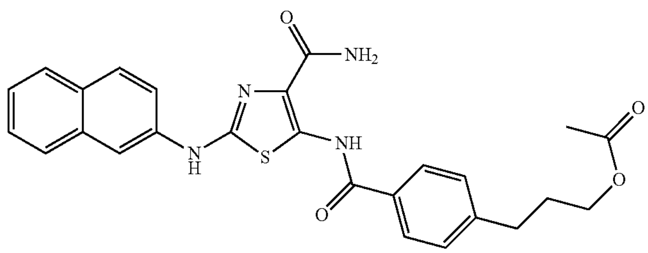 [SMILES: CC(=O)OCCCc1ccc(C(=O)Nc2sc(Nc3ccc4ccccc4c3)nc2C(N)=O)cc1] | 3-(4-{[4-carbamoyl-2-(naphthalen-2-ylamino)thiazol-5-yl]carbamoyl}phenyl)propyl acetate |
| 118 | 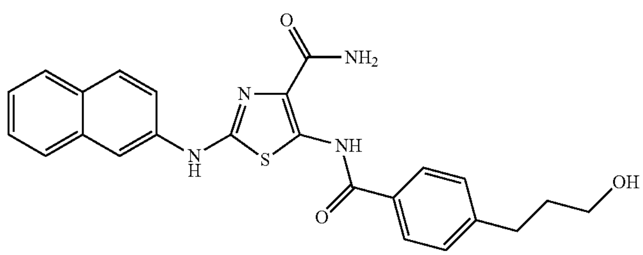 [SMILES: NC(=O)c1nc(Nc2ccc3ccccc3c2)sc1NC(=O)c1ccc(CCCO)cc1] | 5-[4-(3-hydroxypropyl)benzamido]-2-(naphthalen-2-ylamino)thiazole-4-carboxamide |
| 119 | 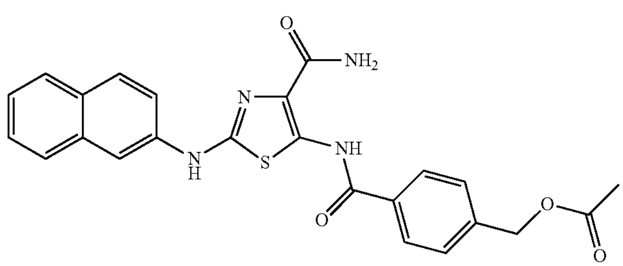 [SMILES: CC(=O)OCc1ccc(C(=O)Nc2sc(Nc3ccc4ccccc4c3)nc2C(N)=O)cc1] | 4-{[4-carbamoyl-2-(naphthalen-2-ylamino)thiazol-5-yl]carbamoyl}benzyl acetate |
| 120 | 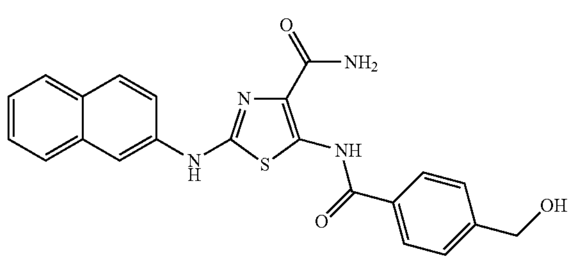 [SMILES: NC(=O)c1nc(Nc2ccc3ccccc3c2)sc1NC(=O)c1ccc(CO)cc1] | 5-[4-(hydroxymethyl)benzamido]-2-(naphthalen-2-ylamino)thiazole-4-carboxamide |

TABLE 1-continued

| Example number | Structure | Name |
|---|---|---|
| 121 | 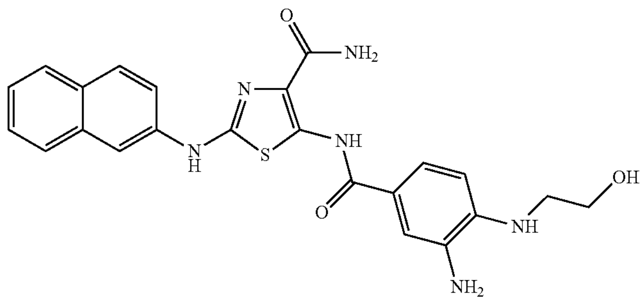 [SMILES: NC(=O)c1nc(Nc2ccc3ccccc3c2)sc1NC(=O)c1ccc(NCCO)c(N)c1] | 5-{3-amino-4-[(2-hydroxyethyl)amino]benzamido}-2-(naphthalen-2-ylamino)thiazole-4-carboxamide |
| 122 | 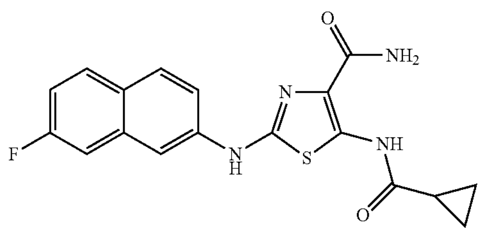 [SMILES: NC(=O)c1nc(Nc2ccc3ccc(F)cc3c2)sc1NC(=O)C1CC1] | 5-(cyclopropanecarboxamido)-2-[(7-fluoronaphthalen-2-yl)amino]thiazole-4-carboxamide |
| 123 | 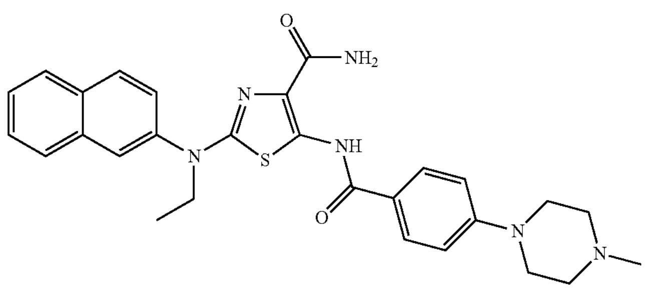 [SMILES: CCN(c1ccc2ccccc2c1)c1nc(C(N)=O)c(NC(=O)c2ccc(N3CCN(C)CC3)cc2)s1] | 2-[ethyl(naphthalen-2-yl)amino]-5-[4-(4-methylpiperazin-1-yl)benzamido]thiazole-4-carboxamide |
| 124 | 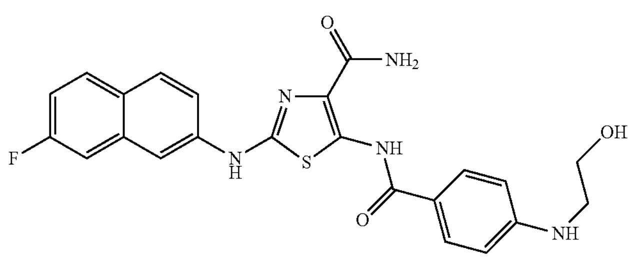 [SMILES: NC(=O)c1nc(Nc2ccc3ccc(F)cc3c2)sc1NC(=O)c1ccc(NCCO)cc1] | 2-[(7-fluoronaphthalen-2-yl)amino]-5-{4-[(2-hydroxyethyl)amino]benzamido}thiazole-4-carboxamide |
| 125 | 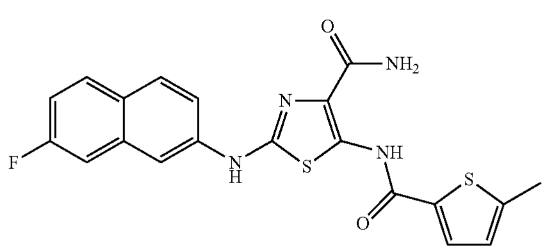 [SMILES: Cc1ccc(C(=O)Nc2sc(Nc3ccc4ccc(F)cc4c3)nc2C(N)=O)s1] | 2-[(7-fluoronaphthalen-2-yl)amino]-5-(5-methylthiophene-2-carboxamido)thiazole-4-carboxamide |

TABLE 1-continued

| Example number | Structure | Name |
|---|---|---|
| 126 | 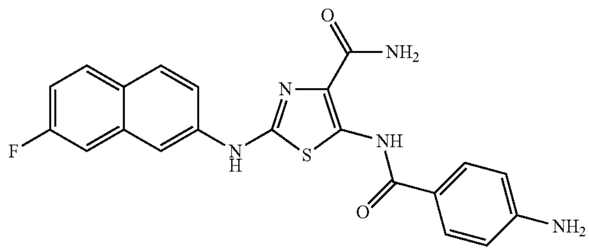 [SMILES: NC(=O)c1nc(Nc2ccc3ccc(F)cc3c2)sc1NC(=O)c1ccc(N)cc1] | 5-(4-aminobenzamido)-2-[(7-fluoronaphthalen-2-yl)amino]thiazole-4-carboxamide |
| 127 | 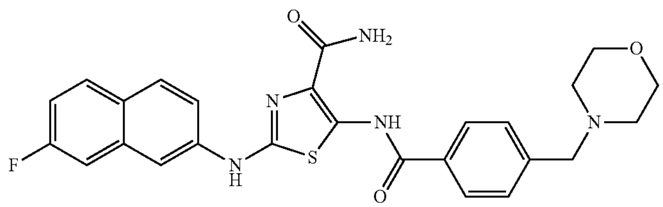 [SMILES: NC(=O)c1nc(Nc2ccc3ccc(F)cc3c2)sc1NC(=O)c1ccc(CN2CCOCC2)cc1] | 2-[(7-fluoronaphthalen-2-yl)amino]-5-[4-(morpholinomethyl)benzamido]thiazole-4-carboxamide |
| 128 | 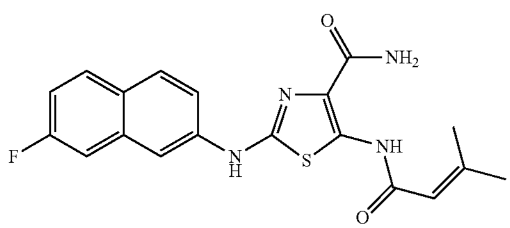 [SMILES: CC(C)=CC(=O)Nc1sc(Nc2ccc3ccc(F)cc3c2)nc1C(N)=O] | 2-[(7-fluoronaphthalen-2-yl)amino]-5-(3-methylbut-2-enamido)thiazole-4-carboxamide |
| 129 | 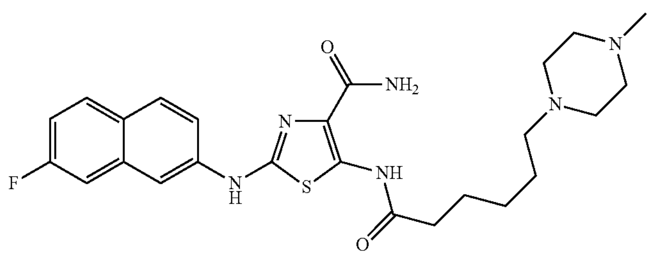 [SMILES: CN1CCN(CCCCCC(=O)Nc2sc(Nc3ccc4ccc(F)cc4c3)nc2C(N)=O)CC1] | 2-[(7-fluoronaphthalen-2-yl)amino]-5-[6-(4-methylpiperazin-1-yl)hexanamido]thiazole-4-carboxamide |
| 130 | 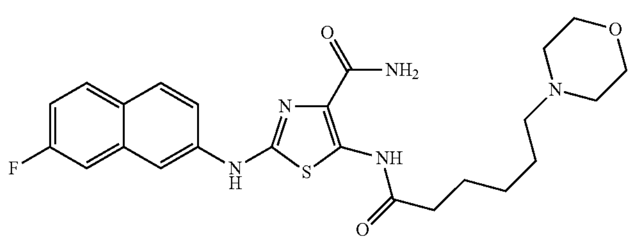 [SMILES: NC(=O)c1nc(Nc2ccc3ccc(F)cc3c2)sc1NC(=O)CCCCCN1CCOCC1] | 2-[(7-fluoronaphthalen-2-yl)amino]-5-(6-morpholinohexanamido)thiazole-4-carboxamide |
| 131 | 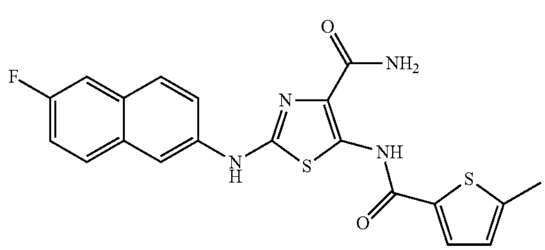 [SMILES: Cc1ccc(C(=O)Nc2sc(Nc3ccc4cc(F)ccc4c3)nc2C(N)=O)s1] | 2-[(6-fluoronaphthalen-2-yl)amino]-5-(5-methylthiophene-2-carboxamido)thiazole-4-carboxamide |

TABLE 1-continued

| Example number | Structure | Name |
|---|---|---|
| 132 | 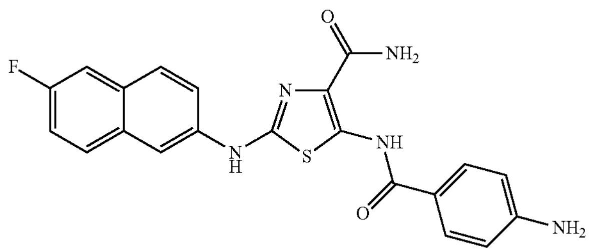 [SMILES: NC(=O)c1nc(Nc2ccc3cc(F)ccc3c2)sc1NC(=O)c1ccc(N)cc1] | 5-(4-aminobenzamido)-2-[(6-fluoronaphthalen-2-yl)amino]thiazole-4-carboxamide |
| 133 | 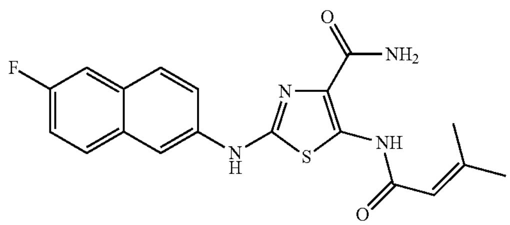 [SMILES: CC(C)=CC(=O)Nc1sc(Nc2ccc3cc(F)ccc3c2)nc1C(N)=O] | 2-[(6-fluoronaphthalen-2-yl)amino]-5-(3-methylbut-2-enamido)thiazole-4-carboxamide |
| 134 | 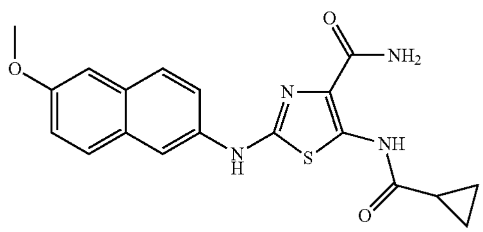 [SMILES: COc1ccc2cc(Nc3nc(C(N)=O)c(NC(=O)C4CC4)s3)ccc2c1] | 5-(cyclopropanecarboxamido)-2-[(6-methoxynaphthalen-2-yl)amino]thiazole-4-carboxamide |
| 135 | 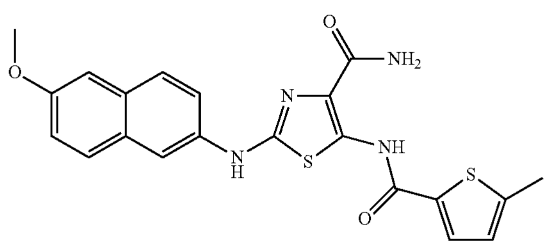 [SMILES: COc1ccc2cc(Nc3nc(C(N)=O)c(NC(=O)c4ccc(C)s4)s3)ccc2c1] | 2-[(6-methoxynaphthalen-2-yl)amino]-5-(5-methylthiophene-2-carboxamido)thiazole-4-carboxamide |
| 136 | 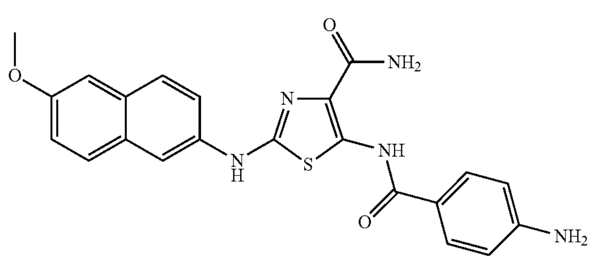 [SMILES: COc1ccc2cc(Nc3nc(C(N)=O)c(NC(=O)c4ccc(N)cc4)s3)ccc2c1] | 5-(4-aminobenzamido)-2-[(6-methoxynaphthalen-2-yl)amino]thiazole-4-carboxamide |
| 137 | 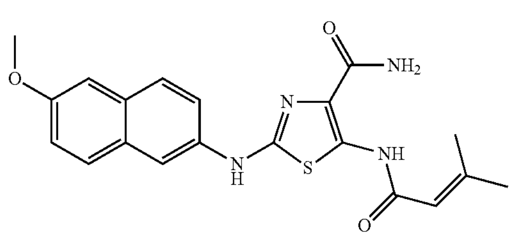 [SMILES: COc1ccc2cc(Nc3nc(C(N)=O)c(NC(=O)C=C(C)C)s3)ccc2c1] | 2-[(6-methoxynaphthalen-2-yl)amino]-5-(3-methylbut-2-enamido)thiazole-4-carboxamide |

TABLE 1-continued

| Example number | Structure | Name |
|---|---|---|
| 138 | 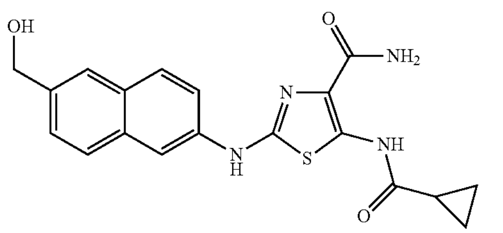 [SMILES: NC(=O)c1nc(Nc2ccc3cc(CO)ccc3c2)sc1NC(=O)C1CC1] | 5-(cyclopropanecarboxamido)-2-{[6-(hydroxymethyl)naphthalen-2-yl]amino}thiazole-4-carboxamide |
| 139 | 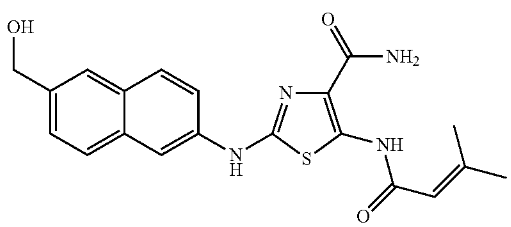 [SMILES: CC(C)=CC(=O)Nc1sc(Nc2ccc3cc(CO)ccc3c2)nc1C(N)=O] | 2-{[6-(hydroxymethyl)naphthalen-2-yl]amino}-5-(3-methylbut-2-enamido)thiazole-4-carboxamide |
| 140 | 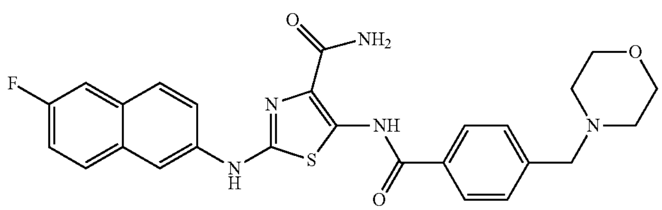 [SMILES: NC(=O)c1nc(Nc2ccc3cc(F)ccc3c2)sc1NC(=O)c1ccc(CN2CCOCC2)cc1] | 2-[(6-fluoronaphthalen-2-yl)amino]-5-(4-(morpholinomethyl)benzamido)thiazole-4-carboxamide |
| 141 | 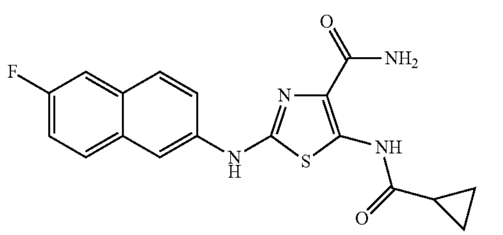 [SMILES: NC(=O)c1nc(Nc2ccc3cc(F)ccc3c2)sc1NC(=O)C1CC1] | 5-(cyclopropanecarboxamido)-2-[(6-fluoronaphthalen-2-yl)amino]thiazole-4-carboxamide |
| 142 | 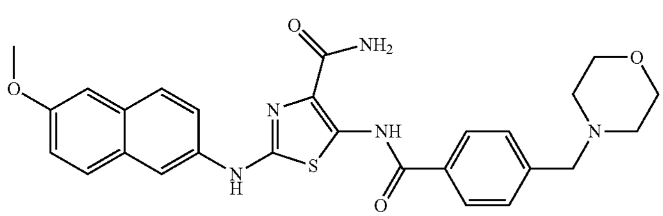 [SMILES: COc1ccc2cc(Nc3nc(C(N)=O)c(NC(=O)c4ccc(CN5CCOCC5)cc4)s3)ccc2c1] | 2-[(6-methoxynaphthalen-2-yl)amino]-5-[4-(morpholinomethyl)benzamido]thiazole-4-carboxamide |
| 143 | 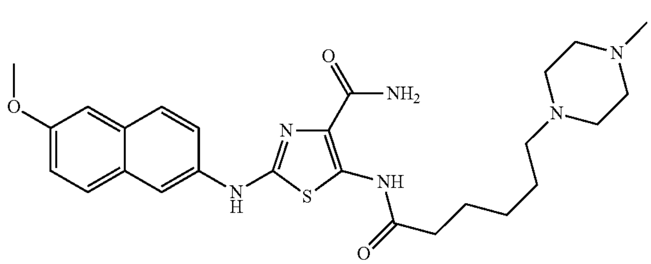 [SMILES: COc1ccc2cc(Nc3nc(C(N)=O)c(NC(=O)CCCCCN4CCN(C)CC4)s3)ccc2c1] | 2-[(6-methoxynaphthalen-2-yl)amino]-5-[6-(4-methylpiperazin-1-yl)hexanamido]thiazole-4-carboxamide |

TABLE 1-continued

| Example number | Structure | Name |
|---|---|---|
| 144 | 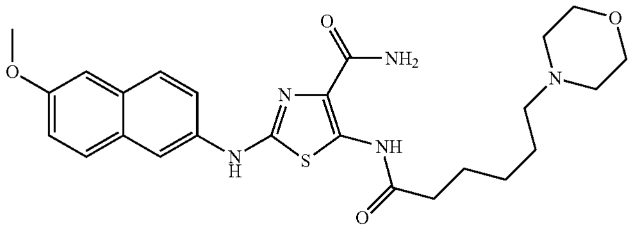 [SMILES: COc1ccc2cc(Nc3nc(C(N)=O)c(NC(=O)CCCCCN4CCOCC4)s3)ccc2c1] | 2-[(6-methoxynaphthalen-2-yl)amino]-5-(6-morpholinohexanamido)thiazole-4-carboxamide |
| 145 | 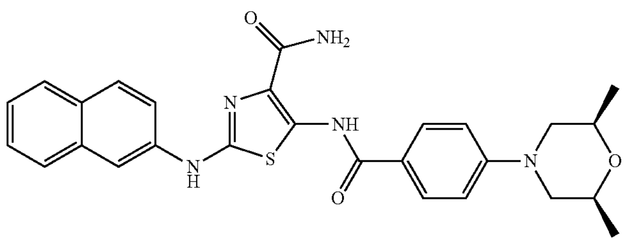 [SMILES: C[C@@H]1CN(c2ccc(C(=O)Nc3sc(Nc4ccc5ccccc5c4)nc3C(N)=O)cc2)C[C@H](C)O1] | 5-[4-(cis-2,6-dimethylmorpholino)benzamido]-2-(naphthalen-2-ylamino)thiazole-4-carboxamide |
| 146 | 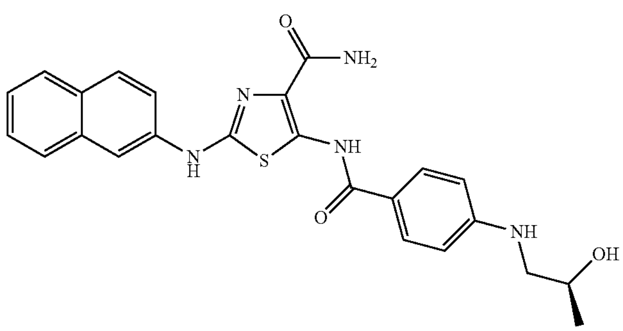 [SMILES: C[C@H](O)CNc1ccc(C(=O)Nc2sc(Nc3ccc4ccccc4c3)nc2C(N)=O)cc1] | (S)-5-{4-[(2-hydroxypropyl)amino]benzamido}-2-(naphthalen-2-ylamino)thiazole-4-carboxamide |
| 147 | 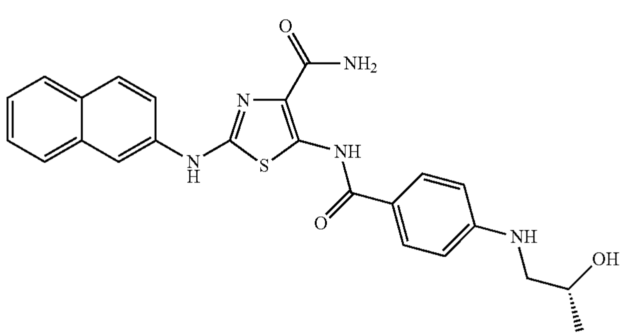 [SMILES: C[C@@H](O)CNc1ccc(C(=O)Nc2sc(Nc3ccc4ccccc4c3)nc2C(N)=O)cc1] | (R)-5-{4-[(2-hydroxypropyl)amino]benzamido}-2-(naphthalen-2-ylamino)thiazole-4-carboxamide |
| 148 | 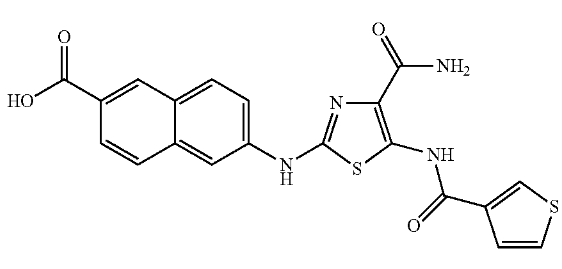 [SMILES: NC(=O)c1nc(Nc2ccc3cc(C(=O)O)ccc3c2)sc1NC(=O)c1ccsc1] | 6-{[4-carbamoyl-5-(thiophene-3-carboxamido)thiazol-2-yl]amino}-2-naphthoic acid |

TABLE 1-continued

| Example number | Structure | Name |
|---|---|---|
| 149 | 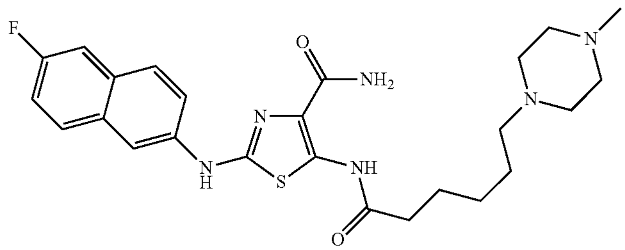 [SMILES: CN1CCN(CCCCCC(=O)Nc2sc(Nc3ccc4cc(F)ccc4c3)nc2C(N)=O)CC1] | 2-[(6-fluoronaphthalen-2-y)amino]-5-[6-(4-methylpiperazin-1-yl)hexanamido]thiazole-4-carboxamide |
| 150 | 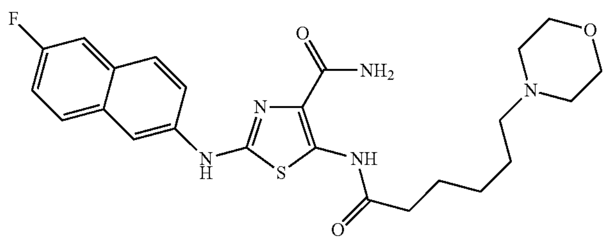 [SMILES: NC(=O)c1nc(Nc2ccc3cc(F)ccc3c2)sc1NC(=O)CCCCCN1CCOCC1] | 2-[(6-fluoronaphthalen-2-yl)amino]-5-(6-morpholinohexanamido)thiazole-4-carboxamide |
| 151 | 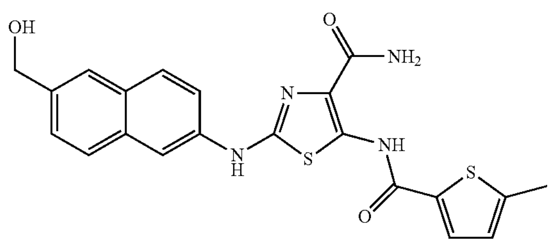 [SMILES: Cc1ccc(C(=O)Nc2sc(Nc3ccc4cc(CO)ccc4c3)nc2C(N)=O)s1] | 2-{[6-(hydroxymethyl)naphthalen-2-yl]amino}-5-(5-methylthiophene-2-carboxamido)thiazole-4-carboxamide |
| 152 | 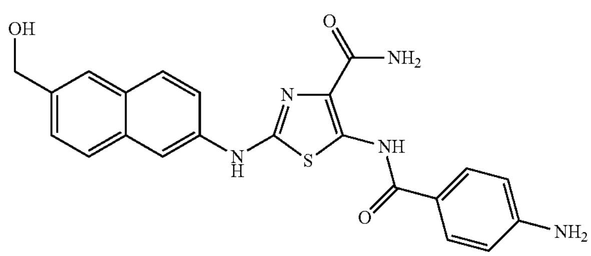 [SMILES: NC(=O)c1nc(Nc2ccc3cc(CO)ccc3c2)sc1NC(=O)c1ccc(N)cc1] | 5-(4-aminobenzamido)-2-{[6-(hydroxymethyl)naphthalen-2-yl]amino}thiazole-4-carboxamide |
| 153 | 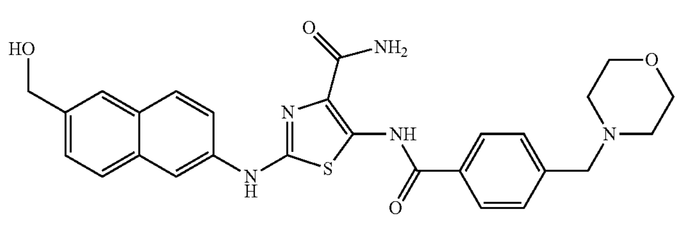 [SMILES: NC(=O)c1nc(Nc2ccc3cc(CO)ccc3c2)sc1NC(=O)c1ccc(CN2CCOCC2)cc1] | 2-{[6-(hydroxymethyl)naphthalen-2-yl]amino}-5-(4-(morpholinomethyl)benzamido)thiazole-4-carboxamide |
| 154 | 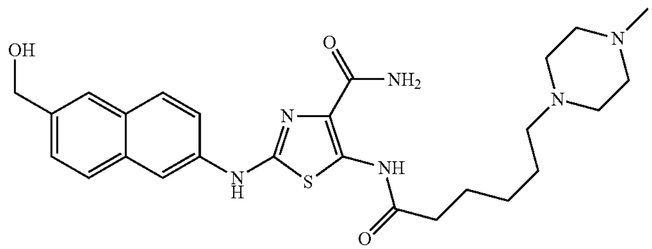 [SMILES: CN1CCN(CCCCCC(=O)Nc2sc(Nc3ccc4cc(CO)ccc4c3)nc2C(N)=O)CC1] | 2-{[6-(hydroxymethyl)naphthalen-2-yl]amino}-5-[6-(4-methylpiperazin-1-yl)hexanamido]thiazole-4-carboxamide |

TABLE 1-continued

| Example number | Structure | Name |
|---|---|---|
| 155 | 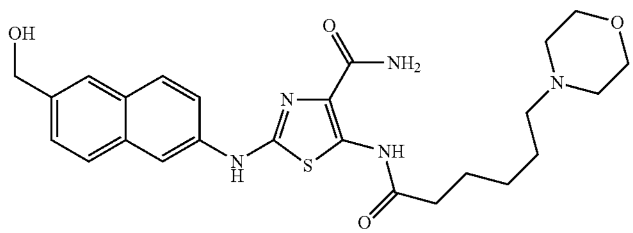 [SMILES: NC(=O)c1nc(Nc2ccc3cc(CO)ccc3c2)sc1NC(=O)CCCCCN1CCOCC1] | 2-{[6-(hydroxymethyl)naphthalen-2-yl]amino}-5-(6-morpholinohexanamido)thiazole-4-carboxamide |
| 156 | 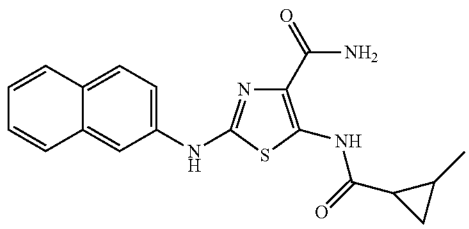 [SMILES: CC1CC1C(=O)Nc1sc(Nc2ccc3ccccc3c2)nc1C(N)=O] | 5-(2-methylcyclopropanecarboxamido)-2-(naphthalen-2-ylamino)thiazole-4-carboxamide |
| 157 | 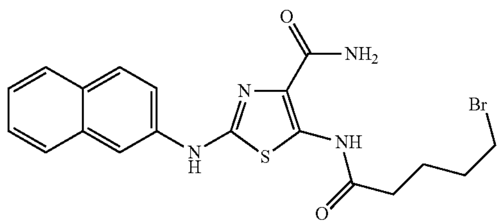 [SMILES: NC(=O)c1nc(Nc2ccc3ccccc3c2)sc1NC(=O)CCCCBr] | 5-(5-bromopentanamido)-2-(naphthalen-2-ylamino)thiazole-4-carboxamide |
| 158 | 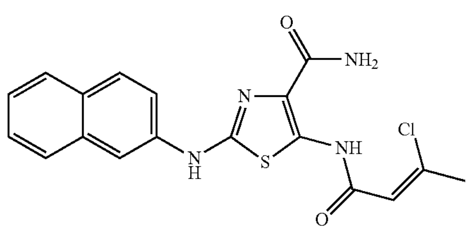 [SMILES: C/C(Cl)=C/C(=O)Nc1sc(Nc2ccc3ccccc3c2)nc1C(N)=O] | (Z)-5-(3-chlorobut-2-enamido)-2-(naphthalen-2-ylamino)thiazole-4-carboxamide |
| 159 | 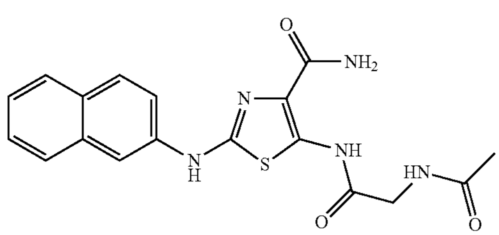 [SMILES: CC(=O)NCC(=O)Nc1sc(Nc2ccc3ccccc3c2)nc1C(N)=O] | 5-(2-acetamidoacetamido)-2-(naphthalen-2-ylamino)thiazole-4-carboxamide |
| 160 | 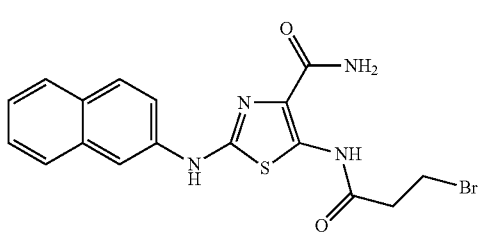 [SMILES: NC(=O)c1nc(Nc2ccc3ccccc3c2)sc1NC(=O)CCBr] | 5-(3-bromopropanamido)-2-(naphthalen-2-ylamino)thiazole-4-carboxamide |

TABLE 1-continued

| Example number | Structure | Name |
|---|---|---|
| 161 | 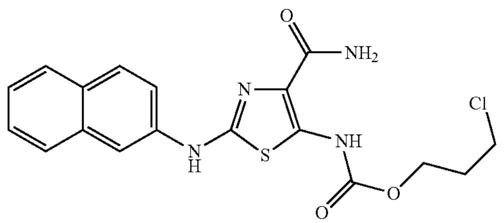 [SMILES: NC(=O)c1nc(Nc2ccc3ccccc3c2)sc1NC(=O)OCCCCl] | 3-chloropropyl [4-carbamoyl-2-(naphthalen-2-ylamino)thiazol-5-yl]carbamate |
| 162 | 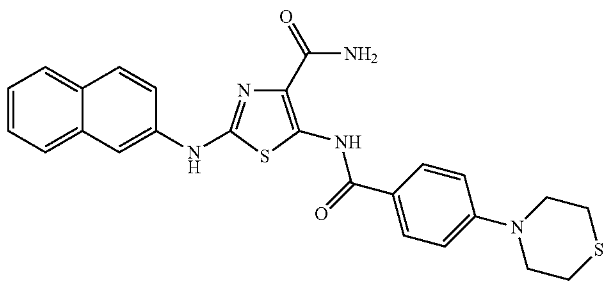 [SMILES: NC(=O)c1nc(Nc2ccc3ccccc3c2)sc1NC(=O)c1ccc(N2CCSCC2)cc1] | 2-(naphthalen-2-ylamino)-5-(4-thiomorpholino-benzamido)thiazole-4-carboxamide |
| 163 | 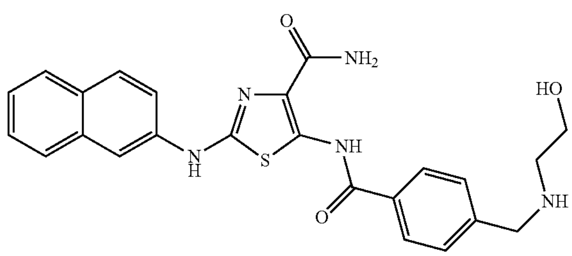 [SMILES: NC(=O)c1nc(Nc2ccc3ccccc3c2)sc1NC(=O)c1ccc(CNCCO)cc1] | 5-(4-{[(2-hydroxyethyl)amino]methyl}benzamido)-2-(naphthalen-2-ylamino)thiazole-4-carboxamide |
| 164 | 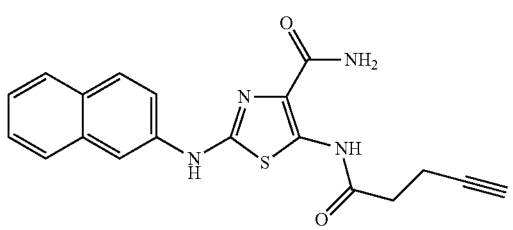 [SMILES: C#CCCC(=O)Nc1sc(Nc2ccc3ccccc3c2)nc1C(N)=O] | 2-(naphthalen-2-ylamino)-5-(pent-4-ynamido)thiazole-4-carboxamide |
| 165 | 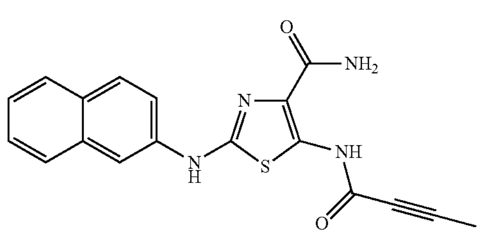 [SMILES: CC#CC(=O)Nc1sc(Nc2ccc3ccccc3c2)nc1C(N)=O] | 5-(but-2-ynamido)-2-(naphthalen-2-ylamino)thiazole-4-carboxamide |
| 166 | 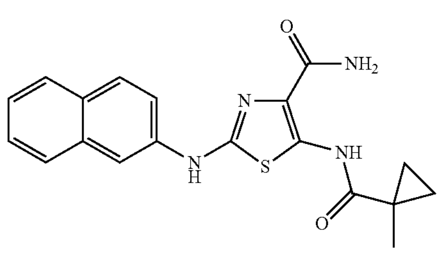 [SMILES: CC1(C(=O)Nc2sc(Nc3ccc4ccccc4c3)nc2C(N)=O)CC1] | 5-(1-methylcyclopropanecarboxamido)-2-(naphthalen-2-ylamino)thiazole-4-carboxamide |

TABLE 1-continued

| Example number | Structure | Name |
|---|---|---|
| 167 | 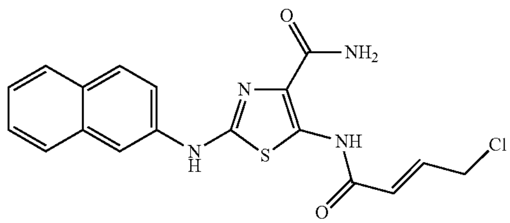 [SMILES: NC(=O)c1nc(Nc2ccc3ccccc3c2)sc1NC(=O)/C=C/CCl] | (E)-5-(4-chlorobut-2-enamido)-2-(naphthalen-2-ylamino)thiazole-4-carboxamide |
| 168 | 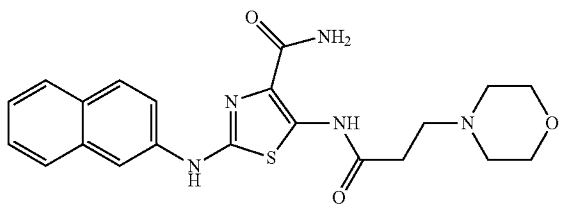 [SMILES: NC(=O)c1nc(Nc2ccc3ccccc3c2)sc1NC(=O)CCN1CCOCC1] | 5-(3-morpholinopropanamido)-2-(naphthalen-2-ylamino)thiazole-4-carboxamide |
| 169 | 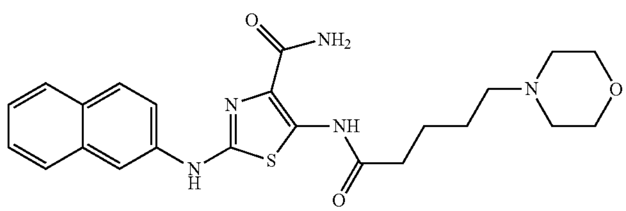 | 5-(5-morpholinopentanamido)-2-(naphthalen-2-ylamino)thiazole-4-carboxamide |
| 170 | 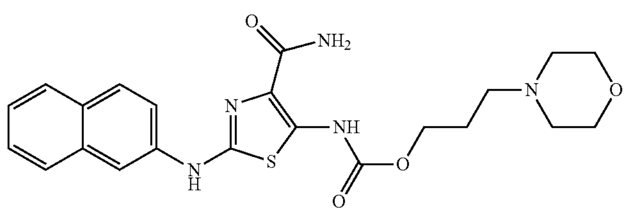 [SMILES: NC(=O)c1nc(Nc2ccc3ccccc3c2)sc1NC(=O)OCCCN1CCOCC1] | 3-morpholinopropyl (4-carbamoyl-2-(naphthalen-2-ylamino)thiazol-5-yl)carbamate |
| 171 | 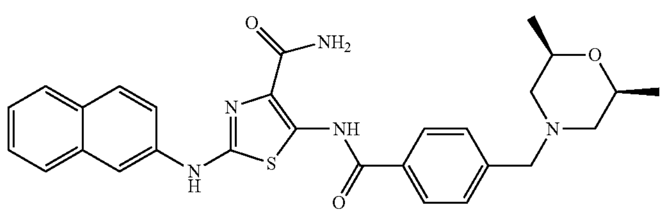 [SMILES: C[C@@H]1CN(Cc2ccc(C(=O)Nc3sc(Nc4ccc5ccccc5c4)nc3C(N)=O)cc2)C[C@H](C)O1] | 5-{4-[(cis-2,6-dimethylmorpholino)methyl]benzamido}-2-(naphthalen-2-ylamino)thiazole-4-carboxamide |
| 172 | 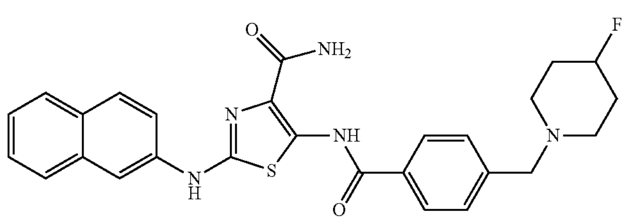 [SMILES: NC(=O)c1nc(Nc2ccc3ccccc3c2)sc1NC(=O)c1ccc(CN2CCC(F)CC2)cc1] | 5-{4-[(4-fluoropiperidin-1-yl)methyl]benzamido}-2-(naphthalen-2-ylamino)thiazole-4-carboxamide |
| 173 | 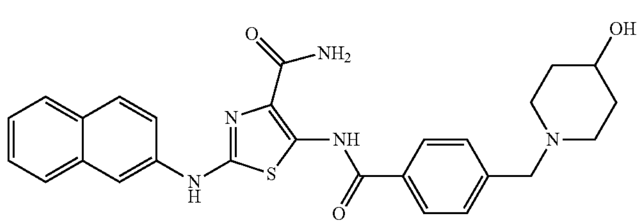 [SMILES: NC(=O)c1nc(Nc2ccc3ccccc3c2)sc1NC(=O)c1ccc(CN2CCC(O)CC2)cc1] | 5-{4-[(4-hydroxypiperidin-1-yl)methyl]benzamido}-2-(naphthalen-2-ylamino)thiazole-4-carboxamide |

TABLE 1-continued

| Example number | Structure | Name |
|---|---|---|
| 174 | 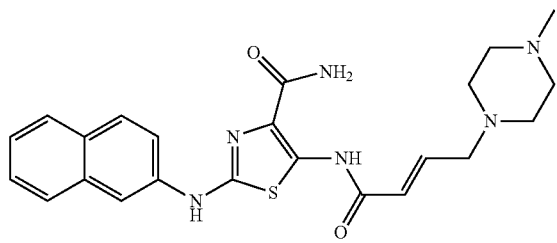 [SMILES: CN1CCN(C/C=C/C(=O)Nc2sc(Nc3ccc4ccccc4c3)nc2C(N)=O)CC1] | (E)-5-(4-(4-methylpiperazin-1-yl)but-2-enamido)-2-(naphthalen-2-ylamino)thiazole-4-carboxamide |
| 175 | 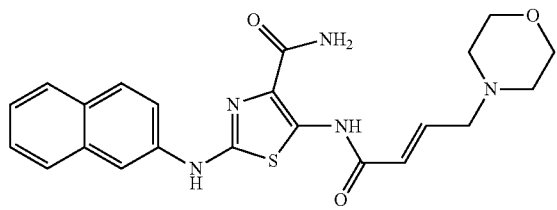 [SMILES: NC(=O)c1nc(Nc2ccc3ccccc3c2)sc1NC(=O)/C=C/CN1CCOCC1] | (E)-5-(4-morpholinobut-2-enamido)-2-(naphthalen-2-ylamino)thiazole-4-carboxamide |
| 176 | 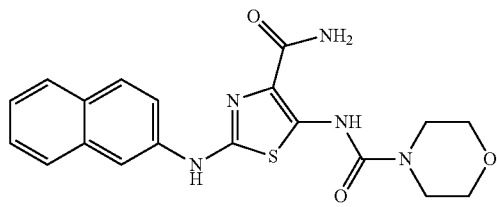 [SMILES: NC(=O)c1nc(Nc2ccc3ccccc3c2)sc1NC(=O)N1CCOCC1] | N-[4-carbamoyl-2-(naphthalen-2-ylamino)thiazol-5-yl]morpholine-4-carboxamide |
| 177 | 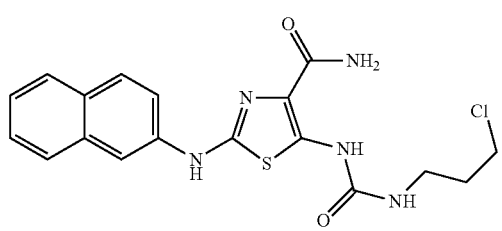 [SMILES: NC(=O)c1nc(Nc2ccc3ccccc3c2)sc1NC(=O)NCCCCl] | 5-[3-(3-chloropropyl)ureido]-2-(naphthalen-2-ylamino)thiazole-4-carboxamide |
| 178 | 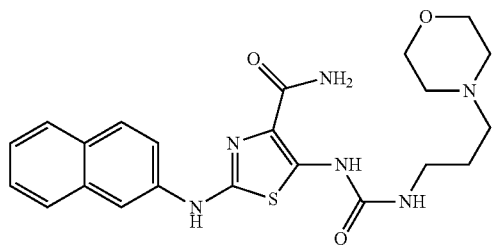 [SMILES: NC(=O)c1nc(Nc2ccc3ccccc3c2)sc1NC(=O)NCCCN1CCOCC1] | 5-[3-(3-morpholinopropyl)ureido]-2-(naphthalen-2-ylamino)thiazole-4-carboxamide |
| 179 | 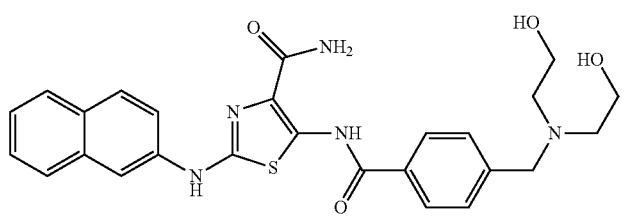 [SMILES: NC(=O)c1nc(Nc2ccc3ccccc3c2)sc1NC(=O)c1ccc(CN(CCO)CCO)cc1] | 5-(4-{[bis(2-hydroxyethyl)amino]methyl}benzamido)-2-(naphthalen-2-ylamino)thiazole-4-carboxamide |

TABLE 1-continued

| Example number | Structure | Name |
|---|---|---|
| 180 | 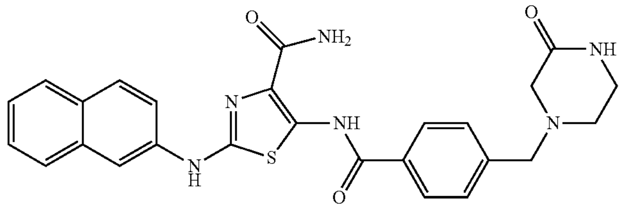 [SMILES: NC(=O)c1nc(Nc2ccc3ccccc3c2)sc1NC(=O)c1ccc(CN2CCNC(=O)C2)cc1] | 2-(naphthalen-2-ylamino)-5-{4-[(3-oxopiperazin-1-yl)methyl]benzamido}thiazole-4-carboxamide |
| 181 | 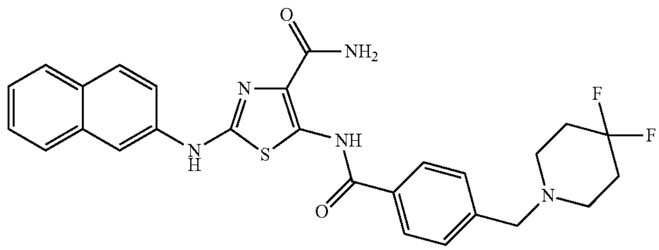 [SMILES: NC(=O)c1nc(Nc2ccc3ccccc3c2)sc1NC(=O)c1ccc(CN2CCC(F)(F)CC2)cc1] | 5-{4-[(4,4-difluoropiperidin-1-yl)methyl]benzamido}-2-(naphthalen-2-ylamino)thiazole-4-carboxamide |
| 182 | 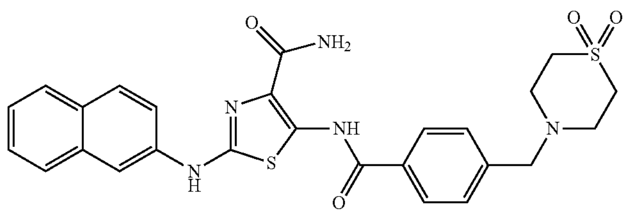 [SMILES: NC(=O)c1nc(Nc2ccc3ccccc3c2)sc1NC(=O)c1ccc(CN2CCS(=O)(=O)CC2)cc1] | 5-(4-[(1,1-dioxidothiomorpholino)methyl]benzamido)-2-(naphthalen-2-ylamino)thiazole-4-carboxamide |
| 183 | 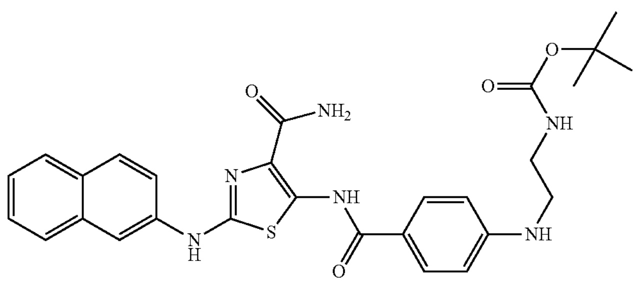 [SMILES: CC(C)(C)OC(=O)NCCNc1ccc(C(=O)Nc2sc(Nc3ccc4ccccc4c3)nc2C(N)=O)cc1] | tert-butyl {2-[(4-{[4-carbamoyl-2-(naphthalen-2-ylamino)thiazol-5-yl]carbamoyl}phenyl)amino]ethyl}carbamate |
| 184 | 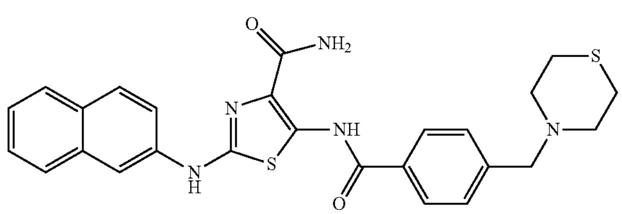 [SMILES: NC(=O)c1nc(Nc2ccc3ccccc3c2)sc1NC(=O)c1ccc(CN2CCSCC2)cc1] | 2-(naphthalen-2-ylamino)-5-[4-(thiomorpholinomethyl)benzamido]thiazole-4-carboxamide |
| 185 | 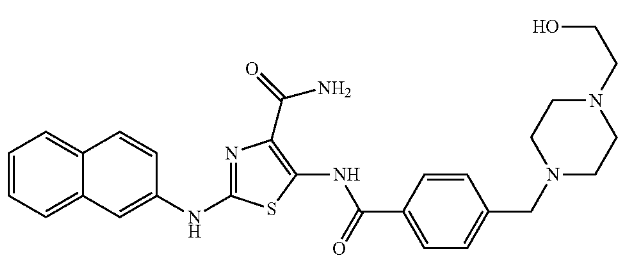 [SMILES: NC(=O)c1nc(Nc2ccc3ccccc3c2)sc1NC(=O)c1ccc(CN2CCN(CCO)CC2)cc1] | 5-(4-{[4-(2-hydroxyethyl)piperazin-1-yl]methyl}benzamido)-2-(naphthalen-2-ylamino)thiazole-4-carboxamide |

TABLE 1-continued

| Example number | Structure | Name |
|---|---|---|
| 186 | 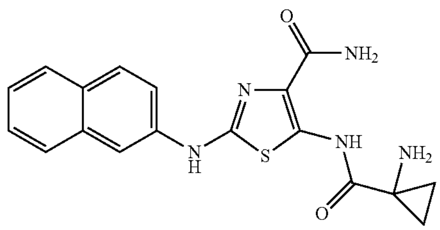 [SMILES: NC(=O)c1nc(Nc2ccc3ccccc3c2)sc1NC(=O)C1(N)CC1] | 5-(1-aminocyclopropanecarboxamido)-2-(naphthalen-2-ylamino)thiazole-4-carboxamide |
| 187 | 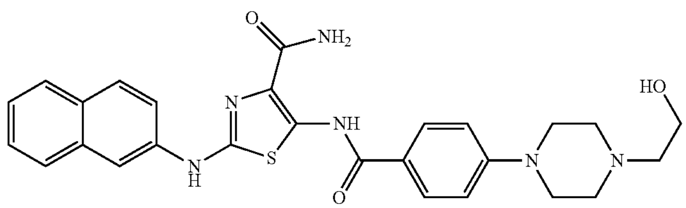 [SMILES: NC(=O)c1nc(Nc2ccc3ccccc3c2)sc1NC(=O)c1ccc(N2CCN(CCO)CC2)cc1] | 5-{4-[4-(2-hydroxyethyl)piperazin-1-yl]benzamido}-2-(naphthalen-2-ylamino)thiazole-4-carboxamide |
| 188 | 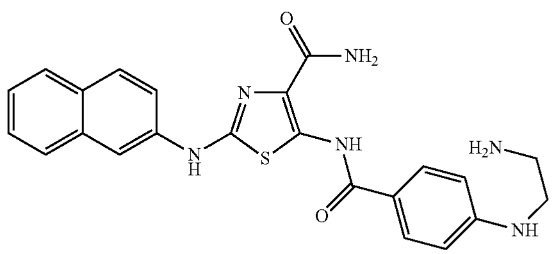 [SMILES: NCCNc1ccc(C(=O)Nc2sc(Nc3ccc4ccccc4c3)nc2C(N)=O)cc1] | 5-{4-[(2-aminoethyl)amino]benzamido}-2-(naphthalen-2-ylamino)thiazole-4-carboxamide |
| 189 | 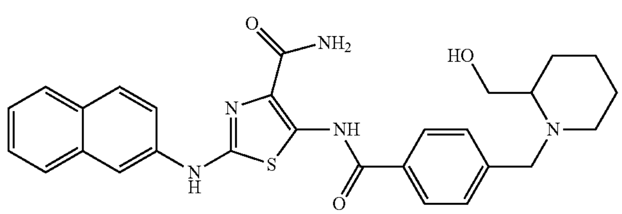 [SMILES: NC(=O)c1nc(Nc2ccc3ccccc3c2)sc1NC(=O)c1ccc(CN2CCCCC2CO)cc1] | 5-(4-{[2-(hydroxymethyl)piperidin-1-yl]methyl}benzamido)-2-(naphthalen-2-ylamino)thiazole-4-carboxamide |
| 190 | 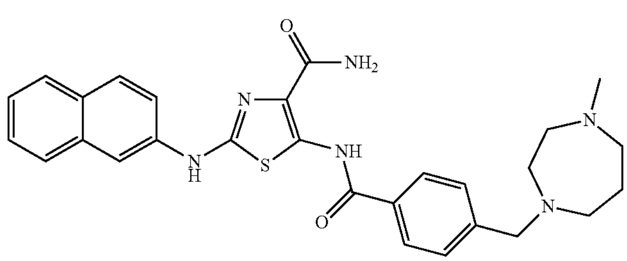 [SMILES: CN1CCCN(Cc2ccc(C(=O)Nc3sc(Nc4ccc5ccccc5c4)nc3C(N)=O)cc2)CC1] | 5-{4-[(4-methyl-1,4-diazepan-1-yl)methyl]benzamido}-2-(naphthalen-2-ylamino)thiazole-4-carboxamide |
| 191 | 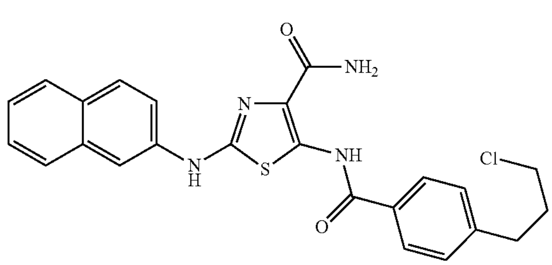 [SMILES: NC(=O)c1nc(Nc2ccc3ccccc3c2)sc1NC(=O)c1ccc(CCCCl)cc1] | 5-[4-(3-chloropropyl)benzamido]-2-(naphthalen-2-ylamino)thiazole-4-carboxamide |

TABLE 1-continued

| Example number | Structure | Name |
|---|---|---|
| 192 | 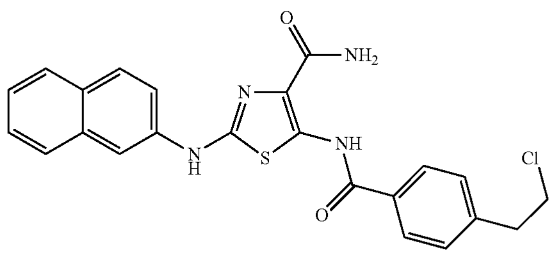 [SMILES: NC(=O)c1nc(Nc2ccc3ccccc3c2)sc1NC(=O)c1ccc(CCCl)cc1] | 5-[4-(2-chloroethyl)benzamido]-2-(naphthalen-2-ylamino)thiazole-4-carboxamide |
| 193 | 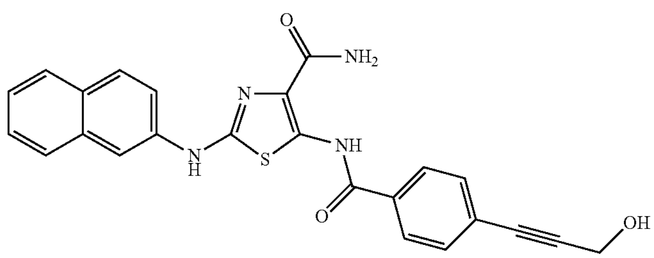 [SMILES: NC(=O)c1nc(Nc2ccc3ccccc3c2)sc1NC(=O)c1ccc(C#CCO)cc1] | 5-[4-(3-hydroxyprop-1-yn-1-yl)benzamido]-2-(naphthalen-2-ylamino)thiazole-4-carboxamide |
| 194 | 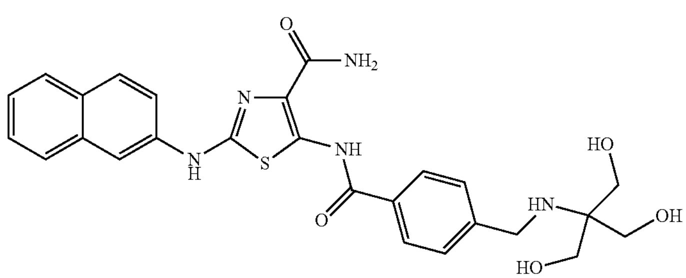 [SMILES: NC(=O)c1nc(Nc2ccc3ccccc3c2)sc1NC(=O)c1ccc(CNC(CO)(CO)CO)cc1] | 5-[4-({[1,3-dihydroxy-2-(hydroxymethyl)propan-2-yl]amino}methyl)benzamido]-2-(naphthalen-2-ylamino)thiazole-4-carboxamide |
| 195 | 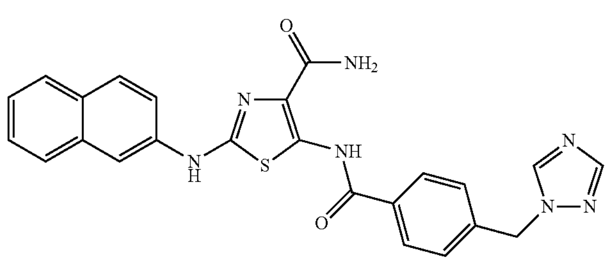 [SMILES: NC(=O)c1nc(Nc2ccc3ccccc3c2)sc1NC(=O)c1ccc(Cn2cncn2)cc1] | 5-{4-[(1H-1,2,4-triazol-1-yl)methyl]benzamido}-2-(naphthalen-2-ylamino)thiazole-4-carboxamide |
| 196 | 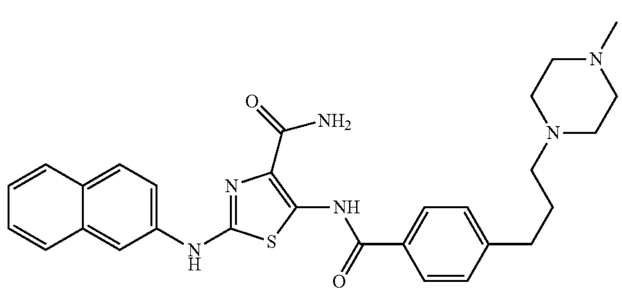 [SMILES: CN1CCN(CCCc2ccc(C(=O)Nc3sc(Nc4ccc5ccccc5c4)nc3C(N)=O)cc2)CC1] | 5-{4-[3-(4-methylpiperazin-1-yl)propyl]benzamido}-2-(naphthalen-2-ylamino)thiazole-4-carboxamide |

TABLE 1-continued

| Example number | Structure | Name |
|---|---|---|
| 197 | 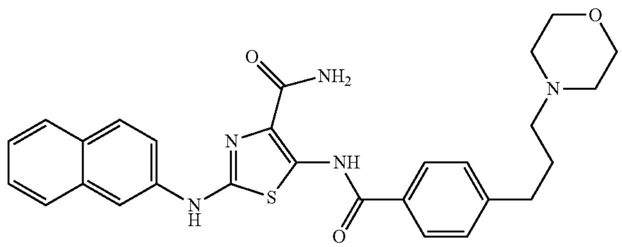 [SMILES: NC(=O)c1nc(Nc2ccc3ccccc3c2)sc1NC(=O)c1ccc(CCCN2CCOCC2)cc1] | 5-[4-(3-morpholinopropyl)benzamido]-2-(naphthalen-2-ylamino)thiazole-4-carboxamide |
| 198 | 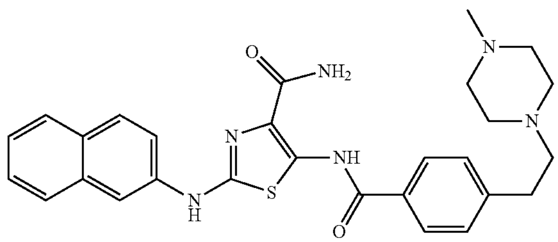 [SMILES: CN1CCN(CCc2ccc(C(=O)Nc3sc(Nc4ccc5ccccc5c4)nc3C(N)=O)cc2)CC1] | 5-{4-[2-(4-methylpiperazin-1-yl)ethyl]benzamido}-2-(naphthalen-2-ylamino)thiazole-4-carboxamide |
| 199 | 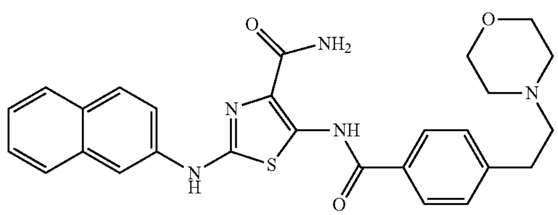 [SMILES: NC(=O)c1nc(Nc2ccc3ccccc3c2)sc1NC(=O)c1ccc(CCN2CCOCC2)cc1] | 5-[4-(2-morpholinoethyl)benzamido]-2-(naphthalen-2-ylamino)thiazole-4-carboxamide |
| 200 | 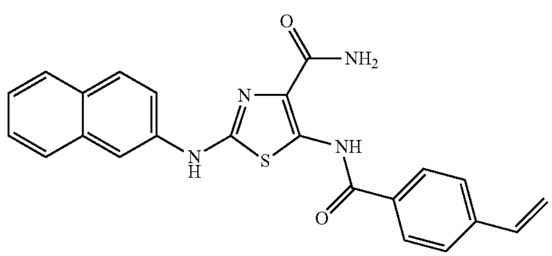 [SMILES: C=Cc1ccc(C(=O)Nc2sc(Nc3ccc4ccccc4c3)nc2C(N)=O)cc1] | 2-(naphthalen-2-ylamino)-5-(4-vinylbenzamido)thiazole-4-carboxamide |
| 201 | 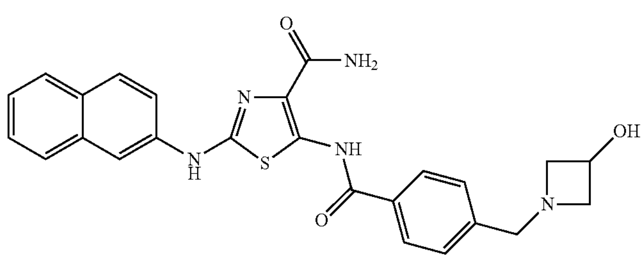 [SMILES: NC(=O)c1nc(Nc2ccc3ccccc3c2)sc1NC(=O)c1ccc(CN2CC(O)C2)cc1] | 5-{4-[(3-hydroxyazetidin-1-yl)methyl]benzamido}-2-(naphthalen-2-ylamino)thiazole-4-carboxamide |
| 202 | 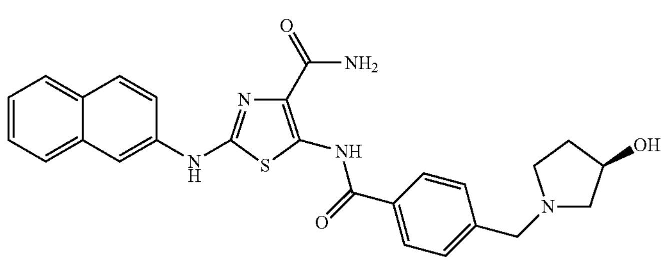 [SMILES: NC(=O)c1nc(Nc2ccc3ccccc3c2)sc1NC(=O)c1ccc(CN2CC[C@@H](O)C2)cc1] | (R)-5-{4-[(3-hydroxypyrrolidin-1-yl)methyl]benzamido}-2-(naphthalen-2-ylamino)thiazole-4-carboxamide |

TABLE 1-continued

| Example number | Structure | Name |
|---|---|---|
| 203 | 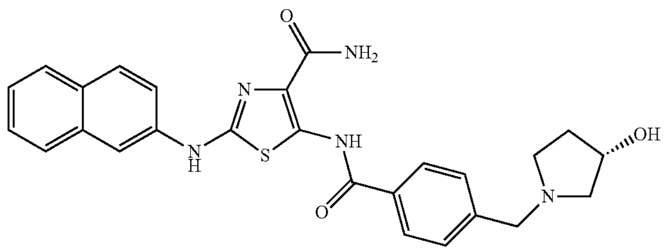 [SMILES: NC(=O)c1nc(Nc2ccc3ccccc3c2)sc1NC(=O)c1ccc(CN2CC[C@H](O)C2)cc1] | (S)-5-{4-[(3-hydroxypyrrolidin-1-yl)methyl]benzamido}-2-(naphthalen-2-ylamino)thiazole-4-carboxamide |
| 204 | 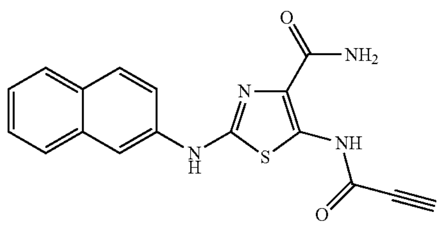 [SMILES: C#CC(=O)Nc1sc(Nc2ccc3ccccc3c2)nc1C(N)=O] | 2-(naphthalen-2-ylamino)-5-propiolamidothiazole-4-carboxamide |
| 205 | 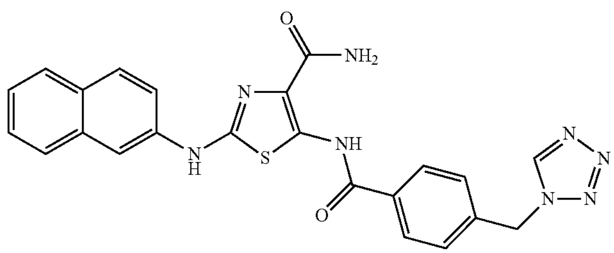 [SMILES: NC(=O)c1nc(Nc2ccc3ccccc3c2)sc1NC(=O)c1ccc(Cn2cnnn2)cc1] | 5-(4-[(1H-tetrazol-1-yl)methyl)benzamido]-2-(naphthalen-2-ylamino)thiazole-4-carboxamide |
| 206 | 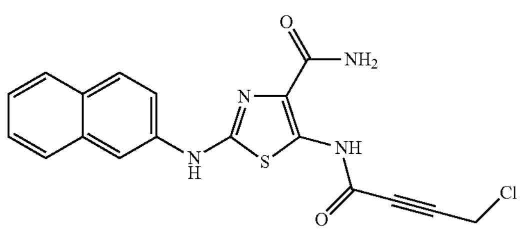 [SMILES: NC(=O)c1nc(Nc2ccc3ccccc3c2)sc1NC(=O)C#CCCl] | 5-(4-chlorobut-2-ynamido)-2-(naphthalen-2-yl-amino)thiazole-4-carboxamide |
| 207 | 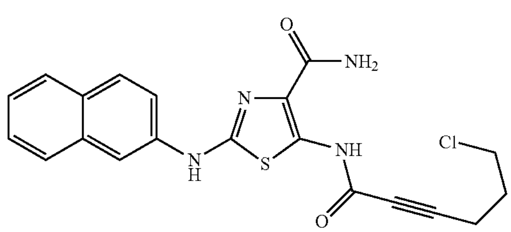 [SMILES: NC(=O)c1nc(Nc2ccc3ccccc3c2)sc1NC(=O)C#CCCCCl] | 5-(6-chlorohex-2-ynamido)-2-(naphthalen-2-yl-amino)thiazole-4-carboxamide |
| 208 | 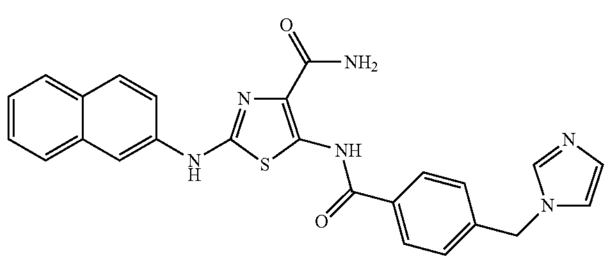 [SMILES: NC(=O)c1nc(Nc2ccc3ccccc3c2)sc1NC(=O)c1ccc(Cn2ccnc2)cc1] | 5-{4-[(1H-imidazol-1-yl)methyl]benzamido}-2-(naphthalen-2-ylamino)thiazole-4-carboxamide |

TABLE 1-continued

| Example number | Structure | Name |
|---|---|---|
| 209 | 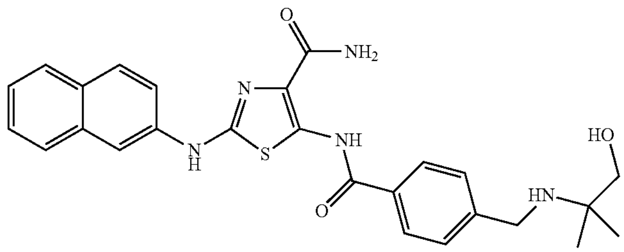 [SMILES: CC(C)(CO)NCc1ccc(C(=O)Nc2sc(Nc3ccc4ccccc4c3)nc2C(N)=O)cc1] | 5-(4-{[(1-hydroxy-2-methylpropan-2-yl)amino]methyl}benzamido)-2-(naphthalen-2-ylamino)thiazole-4-carboxamide |
| 210 | 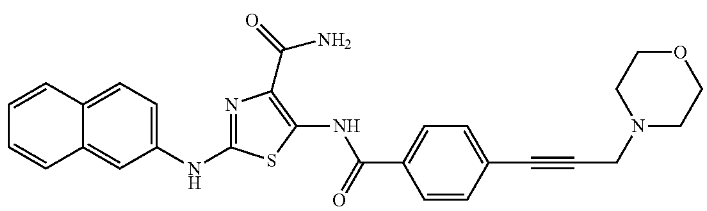 [SMILES: CN1CCN(CC#Cc2ccc(C(=O)Nc3sc(Nc4ccc5ccccc5c4)nc3C(N)=O)cc2)CC1] | 5-[4-(3-morpholinoprop-1-yn-1-yl)benzamido]-2-(naphthalen-2-ylamino)thiazole-4-carboxamide |
| 211 | 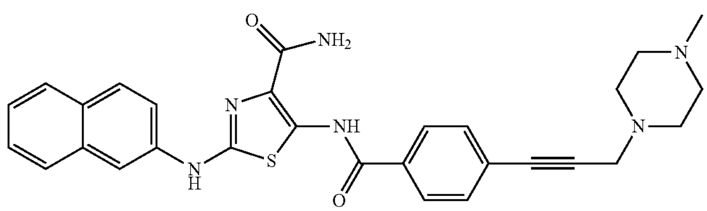 | 5-{4-[3-(4-methylpiperazin-1-yl)prop-1-yn-1-yl]benzamido}-2-(naphthalen-2-ylamino)thiazole-4-carboxamide |
| 212 | 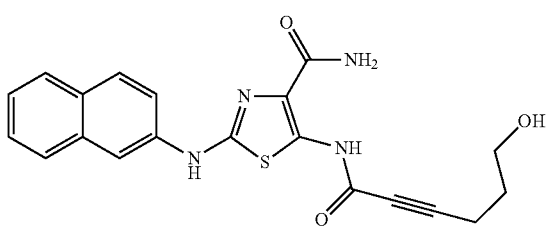 [SMILES: NC(=O)c1nc(Nc2ccc3ccccc3c2)sc1NC(=O)C#CCCCO] | 5-(6-hydroxyhex-2-ynamido)-2-(naphthalen-2-ylamino)thiazole-4-carboxamide |
| 213 | 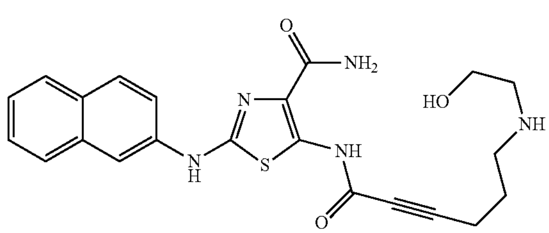 [SMILES: NC(=O)c1nc(Nc2ccc3ccccc3c2)sc1NC(=O)C#CCCCNCCO] | 5-{6-[(2-hydroxyethyl)amino]hex-2-ynamido}-2-(naphthalen-2-ylamino)thiazole-4-carboxamide |
| 214 | 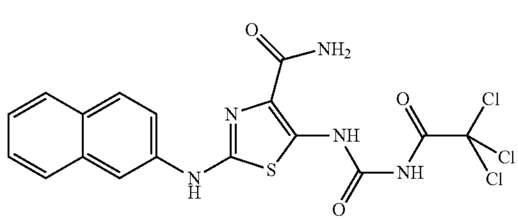 [SMILES: NC(=O)c1nc(Nc2ccc3ccccc3c2)sc1NC(=O)NC(=O)C(Cl)(Cl)Cl] | 2-(naphthalen-2-ylamino)-5-[3-(2,2,2-trichloroacetyl)ureido]thiazole-4-carboxamide |

TABLE 1-continued

| Example number | Structure | Name |
|---|---|---|
| 215 | 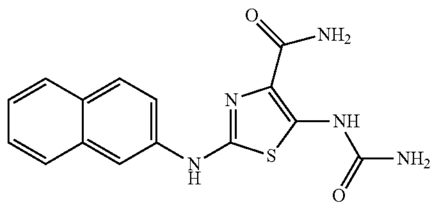 [SMILES: NC(=O)Nc1sc(Nc2ccc3ccccc3c2)nc1C(N)=O] | 2-(naphthalen-2-ylamino)-5-ureidothiazole-4-carboxamide |
| 216 | 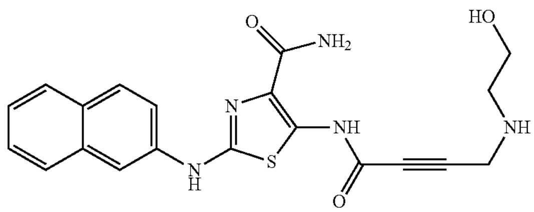 [SMILES: NC(=O)c1nc(Nc2ccc3ccccc3c2)sc1NC(=O)C#CCNCCO] | 5-{4-[(2-hydroxyethyl)amino]but-2-ynamido}-2-(naphthalen-2-ylamino)thiazole-4-carboxamide |
| 217 | 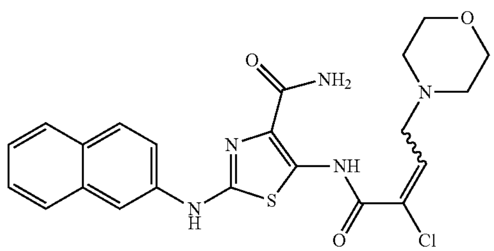 [SMILES: NC(=O)c1nc(Nc2ccc3ccccc3c2)sc1NC(=O)C(Cl)=CCN1CCOCC1] | 5-(2-chloro-4-morpholinobut-2-enamido)-2-(naphthalen-2-ylamino)thiazole-4-carboxamide |
| 218 | 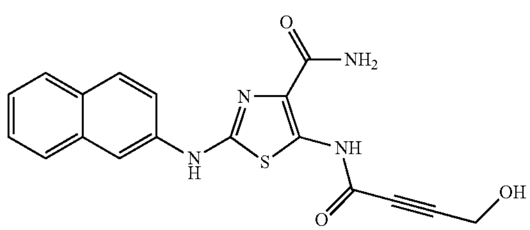 [SMILES: NC(=O)c1nc(Nc2ccc3ccccc3c2)sc1NC(=O)C#CCO] | 5-(4-hydroxybut-2-ynamido)-2-(naphthalen-2-ylamino)thiazole-4-carboxamide |
| 219 | 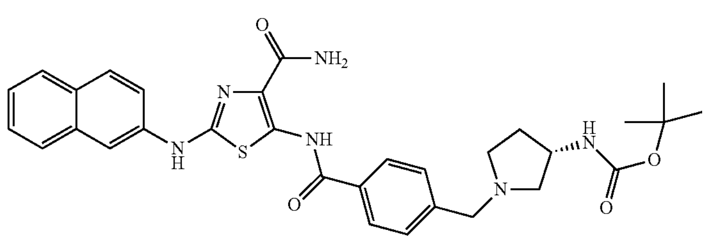 [SMILES: CC(C)(C)OC(=O)N[C@H]1CCN(Cc2ccc(C(=O)Nc3sc(Nc4ccc5ccccc5c4)nc3C(N)=O)cc2)C1] | (S)-tert-butyl [1-(4-{[4-carbamoyl-2-(naphthalen-2-ylamino)thiazol-5-yl]carbamoyl}benzyl)pyrrolidin-3-yl]carbamate |
| 220 | 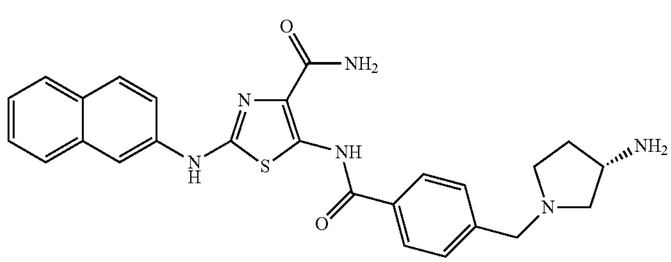 [SMILES: NC(=O)c1nc(Nc2ccc3ccccc3c2)sc1NC(=O)c1ccc(CN2CC[C@H](N)C2)cc1] | (S)-5-{4-[(3-aminopyrrolidin-1-yl)methyl]benzamido}-2-(naphthalen-2-ylamino)thiazole-4-carboxamide |

TABLE 1-continued

| Example number | Structure | Name |
|---|---|---|
| 221 | 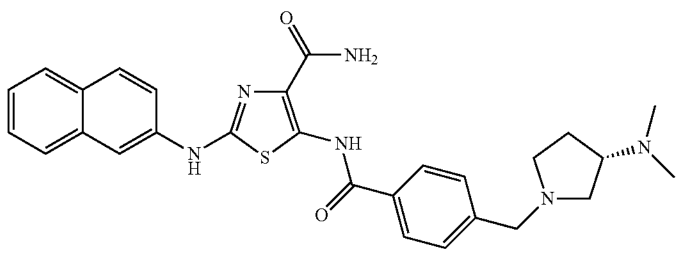 [SMILES: CN(C)[C@H]1CCN(Cc2ccc(C(=O)Nc3sc(Nc4ccc5ccccc5c4)nc3C(N)=O)cc2)C1] | (S)-5-(4-{[3-(dimethylamino)pyrrolidin-1-yl]methyl}benzamido)-2-(naphthalen-2-ylamino)thiazole-4-carboxamide |
| 222 | 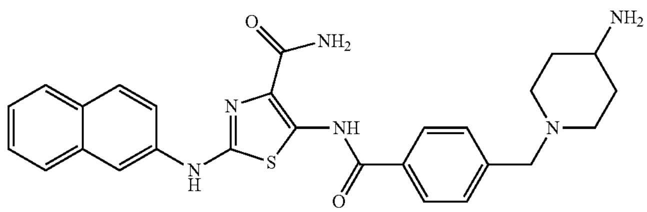 [SMILES: NC(=O)c1nc(Nc2ccc3ccccc3c2)sc1NC(=O)c1ccc(CN2CCC(N)CC2)cc1] | 5-{4-[(4-aminopiperidin-1-yl)methyl]benzamido}-2-(naphthalen-2-ylamino)thiazole-4-carboxamide |
| 223 | 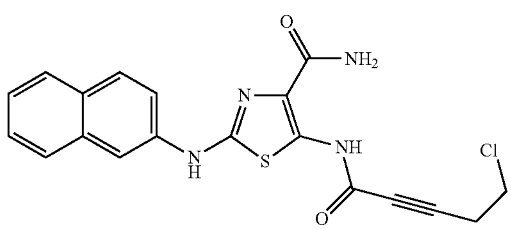 [SMILES: NC(=O)c1nc(Nc2ccc3ccccc3c2)sc1NC(=O)C#CCCCl] | 5-(5-chloropent-2-ynamido)-2-(naphthalen-2-ylamino)thiazole-4-carboxamide |
| 224 | 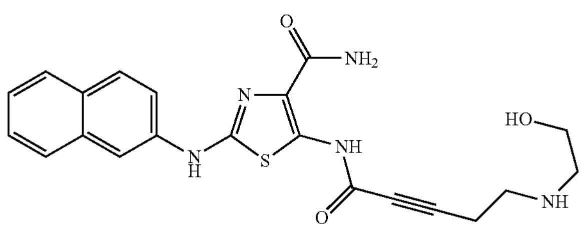 [SMILES: NC(=O)c1nc(Nc2ccc3ccccc3c2)sc1NC(=O)C#CCCNCCO] | 5-{5-[(2-hydroxyethyl)amino]pent-2-ynamido}-2-(naphthalen-2-ylamino)thiazole-4-carboxamide |
| 225 | 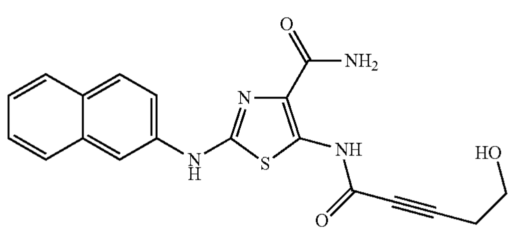 | 5-(5-hydroxypent-2-ynamido)-2-(naphthalen-2-ylamino)thiazole-4-carboxamide |
| 226 | 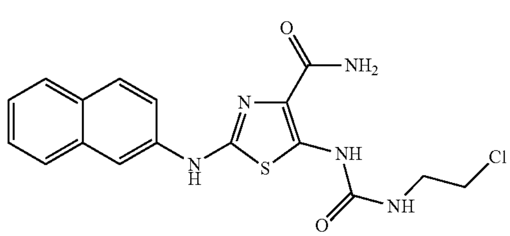 [SMILES: NC(=O)c1nc(Nc2ccc3ccccc3c2)sc1NC(=O)NCCCl] | 5-[3-(2-chloroethyl)ureido]-2-(naphthalen-2-ylamino)thiazole-4-carboxamide |

TABLE 1-continued

| Example number | Structure | Name |
|---|---|---|
| 227 | 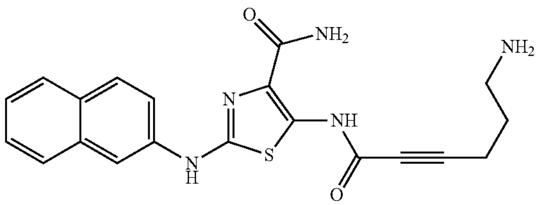 [SMILES: NCCCC#CC(=O)Nc1sc(Nc2ccc3ccccc3c2)nc1C(N)=O] | 5-(6-aminohex-2-ynamido)-2-(naphthalen-2-yl-amino)thiazole-4-carboxamide |
| 228 | 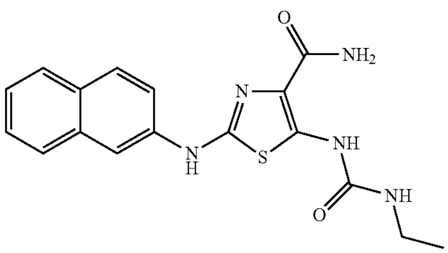 [SMILES: CCNC(=O)Nc1sc(Nc2ccc3ccccc3c2)nc1C(N)=O] | 5-(3-ethylureido)-2-(naphthalen-2-ylamino)thiazole-4-carboxamide |
| 229 | 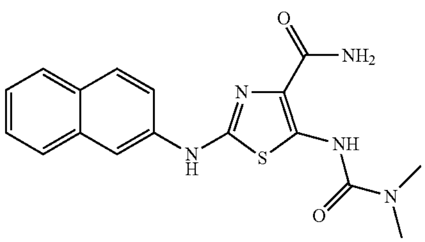 [SMILES: CN(C)C(=O)Nc1sc(Nc2ccc3ccccc3c2)nc1C(N)=O] | 5-(3,3-dimethylureido)-2-(naphthalen-2-ylamino)thiazole-4-carboxamide |
| 230 | 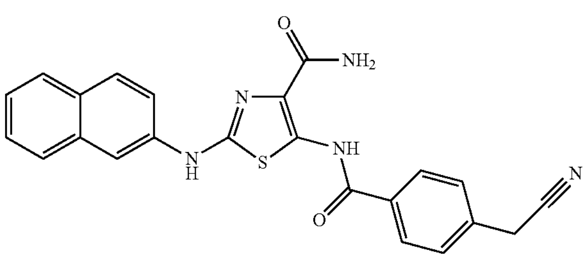 [SMILES: N#CCc1ccc(C(=O)Nc2sc(Nc3ccc4ccccc4c3)nc2C(N)=O)cc1] | 5-[4-(cyanomethyl)benzamido]-2-(naphthalen-2-ylamino)thiazole-4-carboxamide |
| 231 | 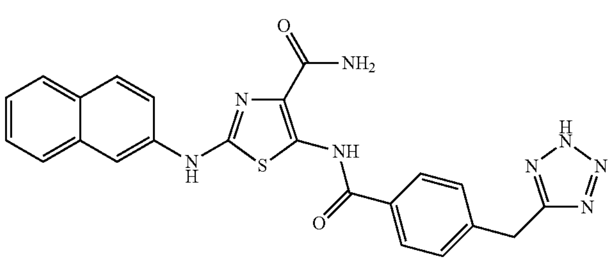 [SMILES: NC(=O)c1nc(Nc2ccc3ccccc3c2)sc1NC(=O)c1ccc(Cc2nn[nH]n2)cc1] | 5-{4-[(2H-tetrazol-5-yl)methyl]benzamido}-2-(naphthalen-2-ylamino)thiazole-4-carboxamide |
| 232 | 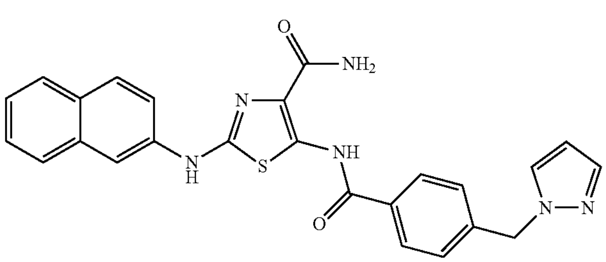 [SMILES: NC(=O)c1nc(Nc2ccc3ccccc3c2)sc1NC(=O)c1ccc(Cn2cccn2)cc1] | 5-{4-[(1H-pyrazol-1-yl)methyl]benzamido}-2-(naphthalen-2-ylamino)thiazole-4-carboxamide |

TABLE 1-continued

| Example number | Structure | Name |
|---|---|---|
| 233 | 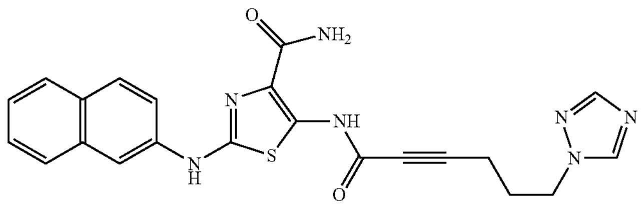 [SMILES: NC(=O)c1nc(Nc2ccc3ccccc3c2)sc1NC(=O)C#CCCCn1cncn1] | 5-[6-(1H-1,2,4-triazol-1-yl)hex-2-ynamido]-2-(naphthalen-2-ylamino)thiazole-4-carboxamide |
| 234 | 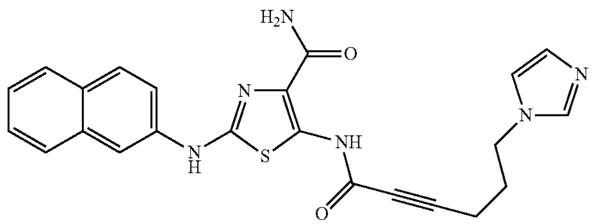 [SMILES: NC(=O)c1nc(Nc2ccc3ccccc3c2)sc1NC(=O)C#CCCCn1ccnc1] | 5-[6-(1H-imidazol-1-yl)hex-2-ynamido]-2-(naphthalen-2-ylamino)thiazole-4-carboxamide |
| 235 | 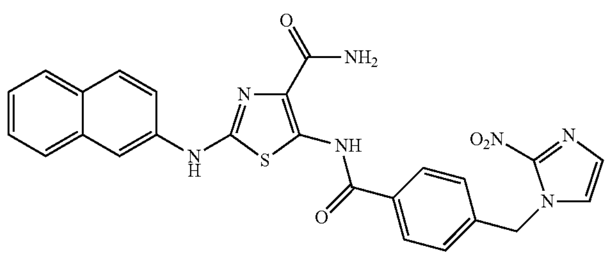 [SMILES: NC(=O)c1nc(Nc2ccc3ccccc3c2)sc1NC(=O)c1ccc(Cn2ccnc2[N+](=O)[O-])cc1] | 2-(naphthalen-2-ylamino)-5-{4-[(2-nitro-1H-imidazol-1-yl)methyl]benzamido}thiazole-4-carboxamide |
| 236 | 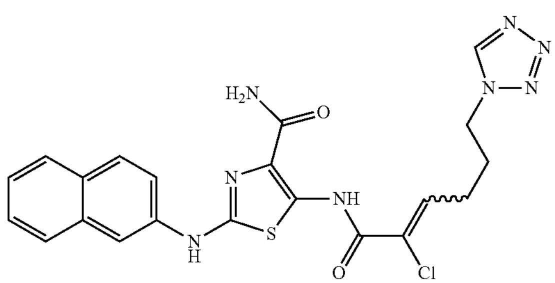 [SMILES: NC(=O)c1nc(Nc2ccc3ccccc3c2)sc1NC(=O)C(Cl)=CCCCn1cnnn1] | 5-[2-chloro-6-(1H-tetrazol-1-yl)hex-2-enamido]-2-(naphthalen-2-ylamino)thiazole-4-carboxamide |
| 237 | 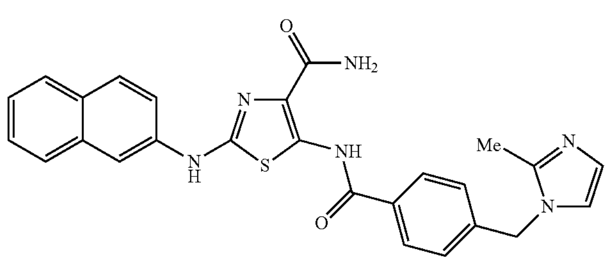 [SMILES: Cc1nccn1Cc1ccc(C(=O)Nc2sc(Nc3ccc4ccccc4c3)nc2C(N)=O)cc1] | 5-{4-[(2-methyl-1H-imidazol-1-yl)methyl]benzamido}-2-(naphthalen-2-ylamino)thiazole-4-carboxamide |
| 238 | 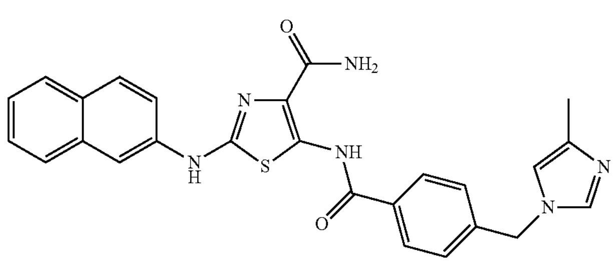 [SMILES: Cc1cn(Cc2ccc(C(=O)Nc3sc(Nc4ccc5ccccc5c4)nc3C(N)=O)cc2)cn1] | 5-{4-[(4-methyl-1H-imidazol-1-yl)methyl]benzamido}-2-(naphthalen-2-ylamino)thiazole-4-carboxamide |

TABLE 1-continued

| Example number | Structure | Name |
|---|---|---|
| 239 | 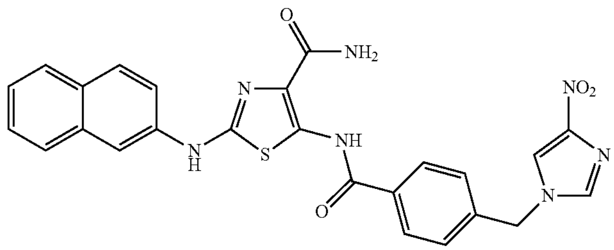 | 2-(naphthalen-2-ylamino)-5-{4-[(4-nitro-1H-imidazol-1-yl)methyl]benzamido}thiazole-4-carboxamide |
| 240 | 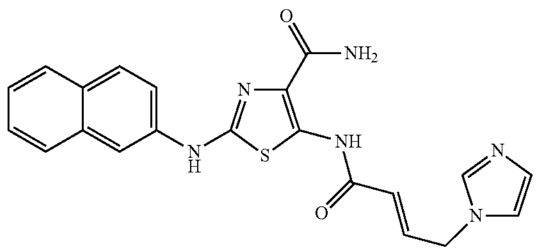 [SMILES: NC(=O)c1nc(Nc2ccc3ccccc3c2)sc1NC(=O)/C=C/Cn1ccnc1] | (E)-5-[4-(1H-imidazol-1-yl)but-2-enamido]-2-(naphthalen-2-ylamino)thiazole-4-carboxamide |
| 241 | 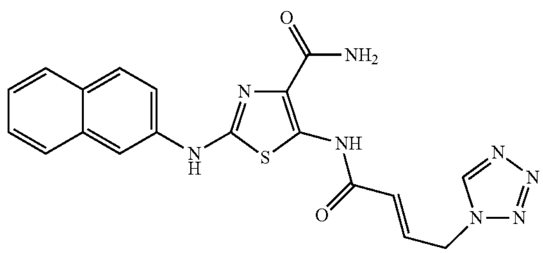 [SMILES: NC(=O)c1nc(Nc2ccc3ccccc3c2)sc1NC(=O)/C=C/Cn1cnnn1] | (E)-5-[4-(1H-tetrazol-1-yl)but-2-enamido]-2-(naphthalen-2-ylamino)thiazole-4-carboxamide |
| 242 | 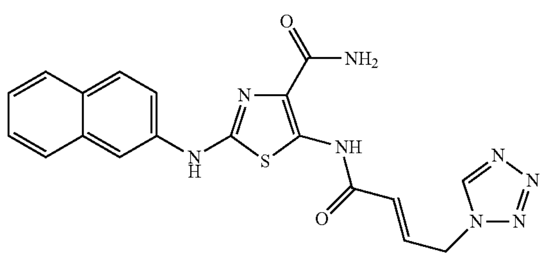 [SMILES: NC(=O)c1nc(Nc2ccc3ccccc3c2)sc1NC(=O)/C=C/Cn1cnnn1] | (E)-5-[4-(1H-tetrazol-1-yl)but-2-enamido]-2-(naphthalen-2-ylamino)thiazole-4-carboxamide |
| 243 | 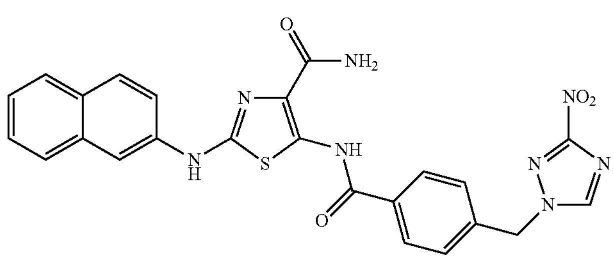 [SMILES: NC(=O)c1nc(Nc2ccc3ccccc3c2)sc1NC(=O)c1ccc(Cn2cnc([N+](=O)[O-])n2)cc1] | 2-(naphthalen-2-ylamino)-5-{4-[(3-nitro-1H-1,2,4-triazol-1-yl)methyl]benzamido}thiazole-4-carboxamide |
| 244 | 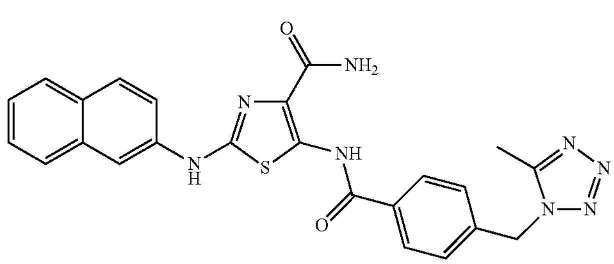 [SMILES: Cc1nnnn1Cc1ccc(C(=O)Nc2sc(Nc3ccc4ccccc4c3)nc2C(N)=O)cc1] | 5-{4-[(5-methyl-1H-tetrazol-1-yl)methyl]benzamido}-2-(naphthalen-2-ylamino)thiazole-4-carboxamide |

TABLE 1-continued

| Example number | Structure | Name |
|---|---|---|
| 245 | 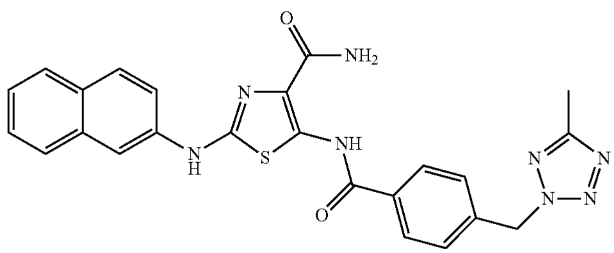 [SMILES: Cc1nnn(Cc2ccc(C(=O)Nc3sc(Nc4ccc5ccccc5c4)nc3C(N)=O)cc2)n1] | 5-{4-[(5-methyl-2H-tetrazol-2-yl)methyl]benzamido}-2-(naphthalen-2-ylamino)thiazole-4-carboxamide |
| 246 | 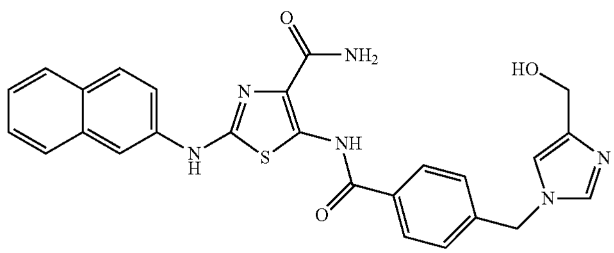 [SMILES: NC(=O)c1nc(Nc2ccc3ccccc3c2)sc1NC(=O)c1ccc(Cn2cnc(CO)c2)cc1] | 5-{4-[(4-(hydroxymethyl)-1H-imidazol-1-yl)methyl]benzamido}-2-(naphthalen-2-ylamino)thiazole-4-carboxamide |
| 247 | 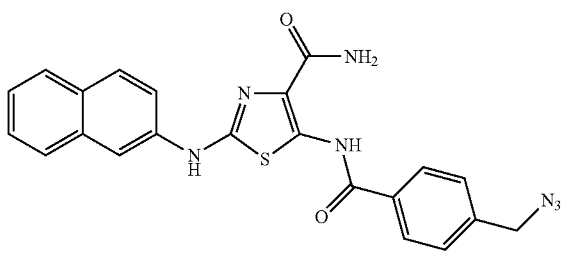 [SMILES: [N-]=[N+]=NCc1ccc(C(=O)Nc2sc(Nc3ccc4ccccc4c3)nc2C(N)=O)cc1] | 5-[4-(azidomethyl)benzamido]-2-(naphthalen-2-ylamino)thiazole-4-carboxamide |
| 248 | 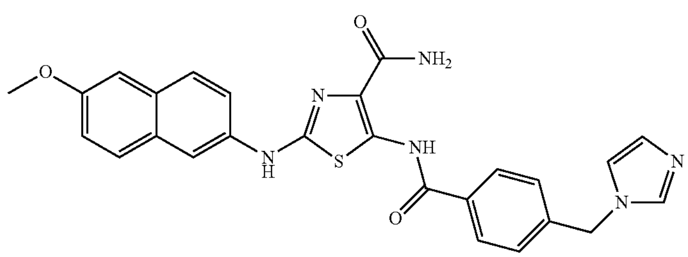 [SMILES: COc1ccc2cc(Nc3nc(C(N)=O)c(NC(=O)c4ccc(Cn5ccnc5)cc4)s3)ccc2c1] | 5-{4-[(1H-imidazol-1-yl)methyl]benzamido}-2-[(6-methoxynaphthalen-2-yl)amino]thiazole-4-carboxamide |
| 249 | 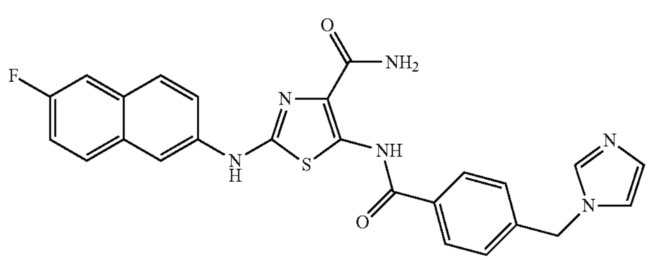 [SMILES: NC(=O)c1nc(Nc2ccc3cc(F)ccc3c2)sc1NC(=O)c1ccc(Cn2ccnc2)cc1] | 5-{4-[(1H-imidazol-1-yl)methyl]benzamido}-2-[(6-fluoronaphthalen-2-yl)amino]thiazole-4-carboxamide |
| 250 | 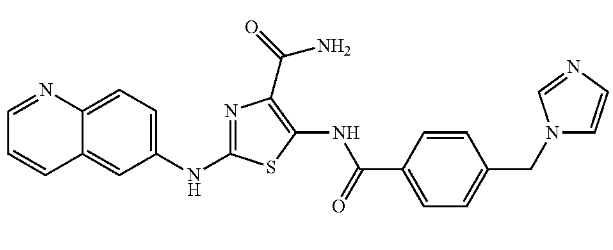 [SMILES: NC(=O)c1nc(Nc2ccc3ncccc3c2)sc1NC(=O)c1ccc(Cn2ccnc2)cc1] | 5-{4-[(1H-imidazol-1-yl)methyl]benzamido}-2-(quinolin-6-ylamino)thiazole-4-carboxamide |

TABLE 1-continued

| Example number | Structure | Name |
|---|---|---|
| 251 | 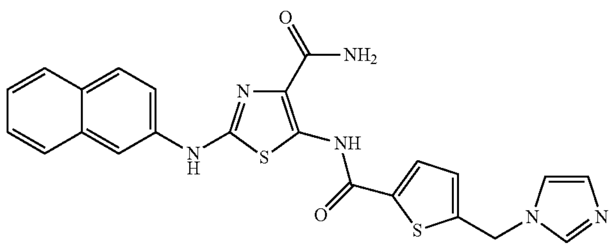 [SMILES: NC(=O)c1nc(Nc2ccc3ccccc3c2)sc1NC(=O)c1ccc(Cn2ccnc2)s1] | 5-{5-[(1H-imidazol-1-yl)methyl]thiophene-2-carboxamido}-2-(naphthalen-2-ylamino)thiazole-4-carboxamide |
| 252 | 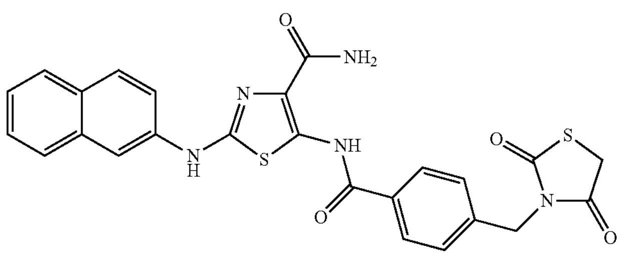 [SMILES: NC(=O)c1nc(Nc2ccc3ccccc3c2)sc1NC(=O)c1ccc(CN2C(=O)CSC2=O)cc1] | 5-{4-[(2,4-dioxothiazolidin-3-yl)methyl]benzamido}-2-(naphthalen-2-ylamino)thiazole-4-carboxamide |
| 253 | 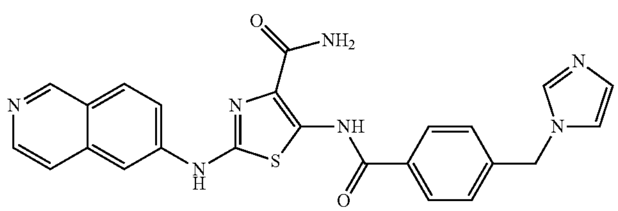 [SMILES: NC(=O)c1nc(Nc2ccc3cnccc3c2)sc1NC(=O)c1ccc(Cn2ccnc2)cc1] | 5-{4-[(1H-imidazol-1-yl)methyl]benzamido}-2-(isoquinolin-6-ylamino)thiazole-4-carboxamide |
| 254 | 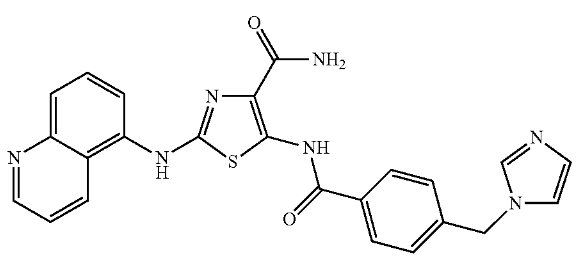 [SMILES: NC(=O)c1nc(Nc2cccc3ncccc23)sc1NC(=O)c1ccc(Cn2ccnc2)cc1] | 5-{4-[(1H-imidazol-1-yl)methyl]benzamido}-2-(quinolin-5-ylamino)thiazole-4-carboxamide |
| 255 | 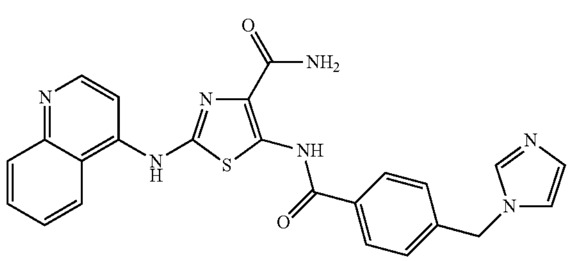 [SMILES: NC(=O)c1nc(Nc2ccnc3ccccc23)sc1NC(=O)c1ccc(Cn2ccnc2)cc1] | 5-{4-[(1H-imidazol-1-yl)methyl]benzamido}-2-(quinolin-4-ylamino)thiazole-4-carboxamide |
| 256 | 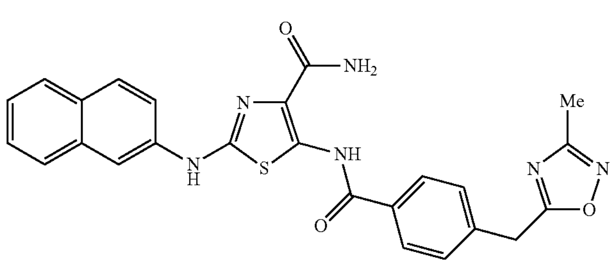 [SMILES: Cc1noc(Cc2ccc(C(=O)Nc3sc(Nc4ccc5ccccc5c4)nc3C(N)=O)cc2)n1] | 5-{4-[(3-methyl-1,2,4-oxadiazol-5-yl)methyl]benzamido}-2-(naphthalen-2-ylamino)thiazole-4-carboxamide |

TABLE 1-continued

| Example number | Structure | Name |
|---|---|---|
| 257 | 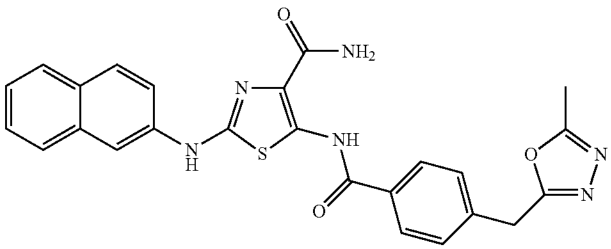 [SMILES: Cc1nnc(Cc2ccc(C(=O)Nc3sc(Nc4ccc5ccccc5c4)nc3C(N)=O)cc2)o1] | 5-{4-[(5-methyl-1,3,4-oxadiazol-2-yl)methyl]benzamido}-2-(naphthalen-2-ylamino)thiazole-4-carboxamide |
| 258 | 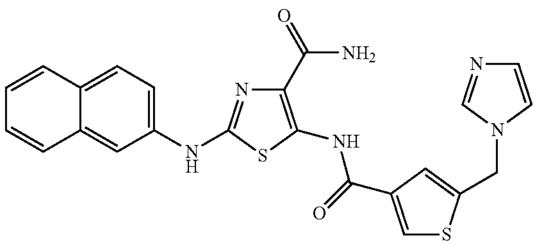 [SMILES: NC(=O)c1nc(Nc2ccc3ccccc3c2)sc1NC(=O)c1csc(Cn2ccnc2)c1] | 5-{5-[(1H-imidazol-1-yl)methyl]thiophene-3-carboxamido}-2-(naphthalen-2-ylamino)thiazole-4-carboxamide |
| 259 | 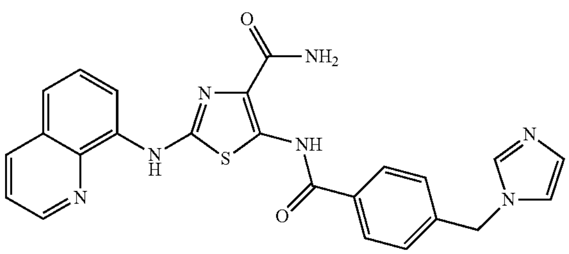 [SMILES: NC(=O)c1nc(Nc2cccc3cccnc23)sc1NC(=O)c1ccc(Cn2ccnc2)cc1] | 5-{4-[(1H-imidazol-1-yl)methyl]benzamido}-2-(quinolin-8-ylamino)thiazole-4-carboxamide |
| 260 | 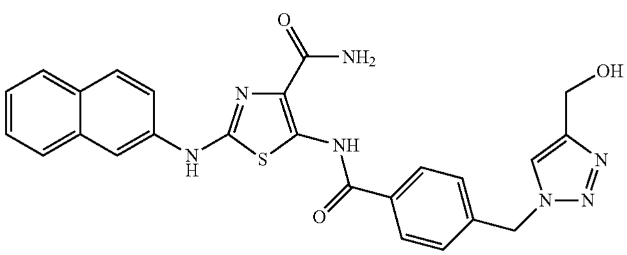 [SMILES: NC(=O)c1nc(Nc2ccc3ccccc3c2)sc1NC(=O)c1ccc(Cn2cc(CO)nn2)cc1] | 5-{4-[(4-(hydroxymethyl)-1H-1,2,3-triazol-1-yl)methyl]benzamido}-2-(naphthalen-2-ylamino)thiazole-4-carboxamide |
| 261 | 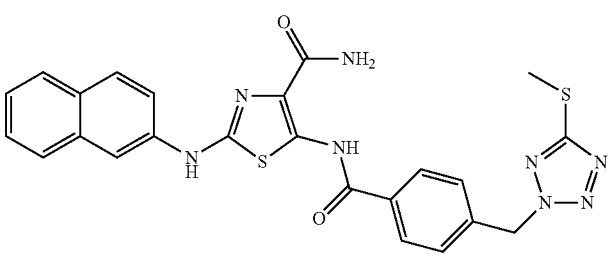 [SMILES: CSc1nnn(Cc2ccc(C(=O)Nc3sc(Nc4ccc5ccccc5c4)nc3C(N)=O)cc2)n1] | 5-(4-{[5-(methylthio)-2H-tetrazol-2-yl]methyl}benzamido)-2-(naphthalen-2-ylamino)thiazole-4-carboxamide |
| 262 | 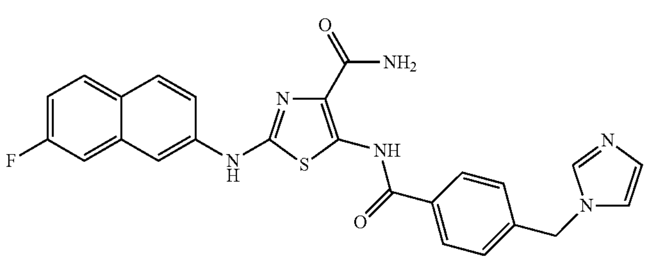 [SMILES: NC(=O)c1nc(Nc2ccc3ccc(F)cc3c2)sc1NC(=O)c1ccc(Cn2ccnc2)cc1] | 5-{4-[(1H-imidazol-1-yl)methyl]benzamido}-2-[(7-fluoronaphthalen-2-yl)amino]thiazole-4-carboxamide |

TABLE 1-continued

| Example number | Structure | Name |
|---|---|---|
| 263 | 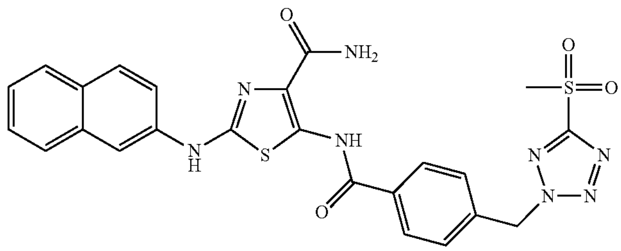 [SMILES: CS(=O)(=O)c1nnn(Cc2ccc(C(=O)Nc3sc(Nc4ccc5ccccc5c4)nc3C(N)=O)cc2)n1] | 5-(4-{[5-(methylsulfonyl)-2H-tetrazol-2-yl]methyl}benzamido)-2-(naphthalen-2-ylamino)thiazole-4-carboxamide |
| 264 | 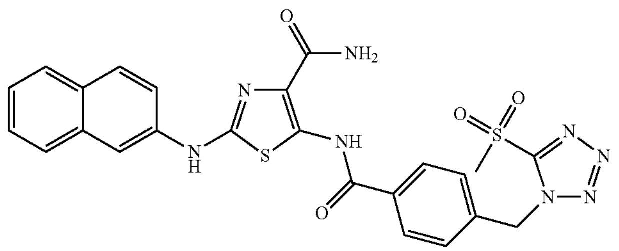 [SMILES: CS(=O)(=O)c1nnnn1Cc1ccc(C(=O)Nc2sc(Nc3ccc4ccccc4c3)nc2C(N)=O)cc1] | 5-(4-{[5-(methylsulfonyl)-1H-tetrazol-1-yl]methyl}benzamido)-2-(naphthalen-2-ylamino)thiazole-4-carboxamide |
| 265 | 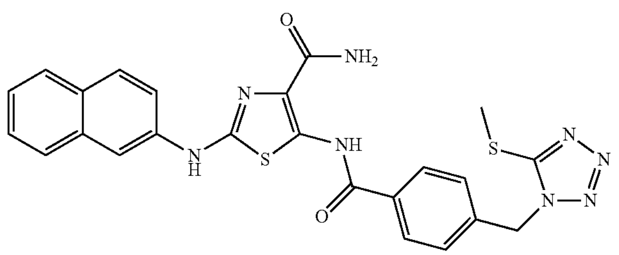 [SMILES: CSc1nnnn1Cc1ccc(C(=O)Nc2sc(Nc3ccc4ccccc4c3)nc2C(N)=O)cc1] | 5-(4{[5-(methylthio)-1H-tetrazol-1-yl]methyl}benzamido)-2-(naphthalen-2-ylamino)thiazole-4-carboxamide |

In accordance with the present invention, the bicyclic thiazole compounds (I) or a pharmaceutically acceptable salt thereof show the TNIK inhibitory effects (Test Example1) and a remarkable antiproliferative activity (Test Example2).

Therefore, the bicyclic thiazole compounds may be used as a pharmaceutical composition (for example an anti-tumor agent) in the form of a conventional pharmaceutical preparation for an oral or parenteral administration such as intravenous drip injection.

The preparation for oral administration includes solid preparations such as tablets, granules, powders, capsules, and liquid preparations such as syrups. These preparations can be prepared by a conventional method. The solid preparations can be prepared by using conventional pharmaceutical carriers, such as lactose, starch such as cornstarch, crystalline cellulose such as microcrystalline cellulose, hydroxypropyl cellulose, calcium carboxymethylcellulose, talc, magnesium stearate, etc. Capsules can be prepared by capsulating the granules or powders thus prepared. Syrups can be prepared by dissolving or suspending the bicyclic thiazole compounds in an aqueous solution containing sucrose, carboxymethylcellulose, etc.

The preparation for parenteral administration includes injections such as intravenous drip injection. The injection preparation can also be prepared by a conventional method, and optionally may be incorporated in isotonic agents (e.g. mannitol, sodium chloride, glucose, sorbitol, glycerol, xylitol, fructose, maltose, mannose), stabilizers (e.g. sodium sulfite, albumin), preservatives (e.g. benzyl alcohol, methyl p-hydroxybenzoate).

The bicyclic thiazole compounds are effective for the treatment of tumors, especially solid tumors such as colorectal cancer, pancreatic cancer, non-small cell lung cancer, prostate cancer or breast cancer.

The dose of the bicyclic thiazole compounds may vary according to the severity of the diseases, ages and body weights of the patients, dosage forms and the like, but is usually in the range of 1 mg-1,000 mg per day in an adult, which may be administered once or by dividing into two or three times by the oral or parenteral route.

Test Example

Test Example 1

Preparation of Recombinant Human TNIK (N-Terminal Segment):

A cDNA encoding the N-terminal segment (TNIK_N, residues 1-314) containing the kinase domain of human TNIK (NM_015028.1) was amplified from cDNA mixture synthesized from human tissue (Biochain) by PCR using the following primers.

Forward primer, 40 nucleotides including a EheI site (described as SEQ ID NO.1 in "Preparation of recombinant human TNIK (N-terminal segment)" of WO 2010/064111 (P.29))

Reverse primer, 42 nucleotides including a NotI site (described as SEQ ID NO.2 in "Preparation of recombinant human TNIK (N-terminal segement)" of WO 2010/064111 (P.29)).

The cDNA was subcloned into baculovirus transfer vector pFastBac_GSTb that includes protease cleavage site and glutathione S-transferase purification tag (GST-tag). The plasmid was purified and the insertion of the pFastBac_GSTb-TNIK_N was confirmed by DNA sequencing. Then E. coli DH10Bac competent cells were transformed with the plasmid to prepare the recombinant bacmid according to the instructions for the Bac-to-Bac™ baculovirus expression systems (Invitrogen). The Sf9 cells were transfected with the recombinant bacmid containing pFastBac_GSTb-TNIK_N using Cellfectin Reagent (Invitrogen) in SF-900II serum free media (Invitrogen). The viral supernatant was collected from the medium 72 h after transfection. The virus was amplified three times by infecting actively growing Sf9 or Sf21 cells in Grace's insect media (Invitrogen) supplemented with 10% FCS and an antibiotic-antimycotic reagent (Invitrogen) for 72 h at 27° C. in T-flask or roller bottles. The titer of amplified TNIK_N virus was estimated at $2.36 \times 10^8$ pfu/ml by using BacPAK™ Baculovirus Rapid Titer kit (Clontech).

Log-phase Sf21 cells ($2 \times 10^6$ cells/ml) in the Grace's insect media were infected with the recombinant baculovirus at MOI of 3.0 and incubated in roller bottles (250 ml media per bottle) for 72 h at 27° C., after which, the cells were collected by centrifugation, and the cell pellet washed with cold PBS and kept at −80° C. until purification. The following purification procedures were carried out at 4° C. The frozen cells were thawed on ice and lysed in lysis buffer (50 mM Tris-HCl, pH 7.5, 150 mM NaCl, 1% Nonidet P-40, 5 mM DTT, 0.5 mM EDTA, 0.5 mM EGTA) supplemented with 1 mM phenylmethansulfonylfluoride, 2 μg/ml leupeptin, 2 μg/ml aprotinin, 1 mM NaF, 100 μM sodium orthovanadate, and 1 μM cantharidin by sonication. The suspended lysate was cleared by centrifugation at 9000g for 20 min and the supernatant was incubated for 1 h with glutathione Sepharose beads (GE Healthcare). The beads were suspended in buffer-H (50 mM Tris-HCl, pH 7.5, 1 M NaCl, 1 mM DTT, 0.5 mM EDTA, 0.5 mM EGTA and 0.05% Brij35) and washed with buffer-H followed by buffer-L (50 mM Tris-HCl, pH 7.5, 150 mM NaCl, 1 mM DTT, 0.5 mM EDTA, 0.5 mM EGTA, 0.05% Brij35) in an Econo-pack column (BIO-RAD). The bound TNIK_N was eluted with elution buffer (50 mM Tris-HCl, pH 8.0, 150 mM NaCl, 1 mM DTT, 10% glycerol, 0.5 mM EDTA, 0.5 mM EGTA and 5 mM reduced glutathione). The eluted fractions were collected and determined the protein concentration by Bradford reagent (BIO-RAD). The TNIKN fractions were pooled and desalted using 10DG column (BIORAD) equilibrated with the storage buffer (50 mM Tris-HCl, pH 7.5, 150 mM NaCl, 1 mM DTT, 10% glycerol, 0.05% Brij35). The purified TNIKN was characterized by electrophoresis using 4-20% polyacrylamide gels and matrix-assisted laser desorption/ionization reflection time-of-flight (MALDI-TOF) mass spectrometry on a Voyager-DE RP MALDI/TOF (Applied Biosystems). TNIK_N was confirmed by the molecular weight and. MASCOT Peptide Mass Fingerprint.

Kinase assay:

The kinase assays were conducted in a 20 μl volume using 384-well plates (Greiner). The reaction mixture consists of compound or vehicle (1% DMSO), 0.08 ng/μl TNIK_N, 1 μM FITC-labeled substrate peptides, including E-aminocaproic acid and 7 amino acids (described as SEQ ID NO.3 in "Kinase assay of TEST EXAMPLE 1" of WO 2010/064111(P.31)), 20 mM Hepes, pH 7.5, 0.01% Triton X-100, 5 mM MgCl$_2$, 25 μM ATP and 2 mM DTT. As blank, TNIK N was excluded from the reaction mixture of vehicle (1% DMSO). The kinase reaction was carried out 1 h at room temperature and terminated by addition of 60 μl of the termination buffer (127 mM Hepes, pH 7.5, 26.7 mM EDTA, 0.01% Triton X-100, 1% DMSO and 0.13% Coating Reagent 3 (Caliper Life Sciences)). The amount of unphosphorylated and phosphorylated FITC-labeled substrate peptides was detected by Mobility Shift Micro Fluidic Technology (Caliper LC3000 System, Caliper Life Sciences). The kinase activity of TNIK_N was defined as P/(P+S) (P: peak height of the phosphorylated FITC-labeled substrate peptide; S: peak height of the FITC-labeled substrate peptide). Inhibition of the compounds was calculated as follows; inhibition (%)=(1−(A−C)/(B−C))×100 A: the mean P/(P+S) of compound wells; B: the mean P/(P+S) of vehicle wells; C: the mean P/(P+S) of blank wells. The IC50 values of the compound against the kinases were calculated from regression analysis of the log-concentration-inhibition curves.

Result:

The test results of illustrative compounds are shown in Table 2.

TABLE 2

| Example number | Test Compound | IC$_{50}$ (nM) |
|---|---|---|
| 1 | 5-(4-acetamidobenzamido)-2-(naphthalen-1-ylamino)thiazole-4-carboxamide | 24.7 |
| 2 | 5-(4-acetamidobenzamido)-2-(naphthalen-2-ylamino)thiazole-4-carboxamide | 19.8 |
| 4 | 5-(4-methoxybenzamido)-2-(quinolin-6-ylamino)thiazole-4-carboxamide | 21.5 |
| 9 | 5-(3-amino-4-methylbenzamido)-2-(naphthalen-2-ylamino)thiazole-4-carboxamide | 27.2 |
| 10 | 5-[4-(2-hydroxyethylamino)benzamido]-2-(naphthalen-2-ylamino)thiazole-4-carboxamide | 10.6 |
| 11 | 5-{4-[2-(dimethylamino)ethylamino]benzamido}-2-(naphthalen-2-ylamino)thiazole-4-carboxamide | 8.6 |
| 12 | 5-[4-(4-methylpiperazin-1-yl)benzamido]-2-(naphthalen-2-ylamino)thiazole-4-carboxamide | 10.2 |
| 13 | 2-(naphthalen-2-ylamino)-5-{4-[2-(piperidin-1-yl)ethylamino]benzamido}thiazole-4-carboxamide | 8.0 |
| 16 | 5-(4-aminobenzamido)-2-(naphthalen-2-ylamino)thiazole-4-carboxamide | 20.3 |
| 17 | 5-{4-[(4-methylpiperazin-1-yl)methyl]benzamido}-2-(naphthalen-2-ylamino)thiazole-4-carboxamide | 5.1 |
| 18 | 5-[4-(morpholinomethyl)benzamido]-2-(naphthalen-2-ylamino)thiazole-4-carboxamide | 8.6 |

TABLE 2-continued

| Example number | Test Compound | IC$_{50}$ (nM) |
|---|---|---|
| 23 | 5-(4-aminomethylbenzamido)-2-(naphthalen-2-yl-amino)thiazole-4-carboxamide | 5.3 |
| 24 | 5-[4-(4-methylpiperazin-1-yl)benzamido]-2-(quinolin-6-ylamino)thiazole-4-carboxamide | 4.1 |
| 26 | 5-[4-(4-methylpiperazin-1-yl)benzamido]-2-(quinolin-5-ylamino)thiazole-4-carboxamide | 15.6 |
| 27 | 5-[4-(4-methylpiperazin-1-yl)benzamido]-2-(quinolin-8-ylamino)thiazole-4-carboxamide | 19.1 |
| 28 | 2-[methyl(quinolin-6-yl)amino]-5-[4-(4-methylpiperazin-1-yl)benzamido]thiazole-4-carboxamide | 17.0 |
| 29 | 5-{4-[(2-hydroxyethyl)methylamino]benzamido}-2-(naphthalen-2-ylamino)thiazole-4-carboxamide | 27.4 |
| 30 | 5-{4-[(2-hydroxypropyl)amino]benzamido}-2-(naphthalen-2-ylamino)thiazole-4-carboxamide | 10.7 |
| 33 | 2-(naphthalen-2-ylamino)-5-(1H-pyrrole-2-carboxamido)thiazole-4-carboxamide | 7.5 |
| 35 | N-[4-carbamoyl-2-(naphthalen-2-ylamino)thiazol-5-yl]-4H-thieno[3,2-b]pyrrole-5-carboxamide | 22.7 |
| 40 | 2-(quinolin-5-ylamino)-5-(thiophene-3-carboxamido)thiazole-4-carboxamide | 9.4 |
| 46 | 2-(isoquinolin-6-ylamino)-5-(thiophene-3-carboxamido)thiazole-4-carboxamide | 12.0 |
| 51 | 2-[methyl(quinolin-6-yl)amino]-5-[5-(morpholinomethyl)thiophene-3-carboxamido]thiazole-4-carboxamide | 5.7 |
| 56 | 5-{5-[(4-methylpiperazin-1-yl)methyl]thiophene-3-carboxamido}-2-(quinolin-5-ylamino)thiazole-4-carboxamide | 8.2 |
| 65 | 2-[methyl(naphthalen-2-yL)amino]-5-[4-(4-methylpiperazin-1-yl)benzamido]thiazole-4-carboxamide | 36.3 |
| 70 | 2-{[6-(hydroxymethyl)naphthalen-2-yl]amino}-5-(thiophene-3-carboxamido)thiazole-4-carboxamide | 5.5 |
| 74 | 2-[(4-methoxynaphthalen-2-yl)amino]-5-(thiophene-3-carboxamido)thiazole-4-carboxamide | 51.3 |
| 80 | 2-[(7-fluoronaphthalen-2-yl)amino]-5-(thiophene-3-carboxamido)thiazole-4-carboxamide | 16.9 |
| 83 | 5-(3-methylbut-2-enamido)-2-(naphthalen-2-ylamino)thiazole-4-carboxamide | 12.7 |
| 92 | 5-(6-morpholinohexanamido)-2-(naphthalen-2-yl-amino)thiazole-4-carboxamide | 20.2 |
| 93 | 5-(cyclopropanecarboxamido)-2-(naphthalen-2-yl-amino)thiazole-4-carboxamide | 15.0 |
| 97 | 5-[4-(4-hydroxypiperidin-1-yl)benzamido]-2-(naphthalen-2-ylamino)thiazole-4-carboxamide | 12.7 |
| 112 | 2-[(6-fluoronaphthalen-2-yl)amino]-5-{4-[(2-hydroxyethyl)amino]benzamido}thiazole-4-carboxamide | 22.5 |
| 113 | 5-{4-[(2-hydroxyethyl)amino]benzamido}-2-[(6-methoxynaphthalen-2-yl)amino]thiazole-4-carboxamide | 14.8 |
| 116 | 5-[4-(2-hydroxyethyl)benzamido]-2-(naphthalen-2-yl-amino)thiazole-4-carboxamide | 5.8 |
| 121 | 5-{3-amino-4-[(2-hydroxyethyl)amino]benzamido}-2-(naphthalen-2-ylamino)thiazole-4-carboxamide | 24.4 |
| 122 | 5-(cyclopropanecarboxamido)-2-[(7-fluoronaphthalen-2-yl)amino]thiazole-4-carboxamide | 12.8 |
| 124 | 2-[(7-fluoronaphthalen-2-yl)amino]-5-{4-[(2-hydroxyethyl)amino]benzamido}thiazole-4-carboxamide | 12.9 |
| 128 | 2-[(7-fluoronaphthalen-2-yl)amino]-5-(3-methylbut-2-enamido)thiazole-4-carboxamide | 7.2 |
| 130 | 2-[(7-fluoronaphthalen-2-yl)amino]-5-(6-morpholinohexanamido)thiazole-4-carboxamide | 19.5 |
| 136 | 5-(4-aminobenzamido)-2-[(6-methoxynaphthalen-2-yl)amino]thiazole-4-carboxamide | 9.7 |
| 137 | 2-[(6-methoxynaphthalen-2-yl)amino]-5-(3-methylbut-2-enamido)thiazole-4-carboxamide | 15.2 |
| 138 | 5-(cyclopropanecarboxamido)-2-{[6-(hydroxymethyl)naphthalen-2-yl]amino}thiazole-4-carboxamide | 5.8 |
| 139 | 2-{[6-(hydroxymethyl)naphthalen-2-yl]amino}-5-(3-methylbut-2-enamido)thiazole-4-carboxamide | 1.6 |
| 146 | (S)-5-{4-[(2-hydroxypropyl)amino]benzamido}-2-(naphthalen-2-ylamino)thiazole-4-carboxamide | 15.1 |
| 147 | (R)-5-{4-[(2-hydroxypropyl)amino]benzamido}-2-(naphthalen-2-ylamino)thiazole-4-carboxamide | 16.8 |
| 151 | 2-{[6-(hydroxymethyl)naphthalen-2-yl]amino}-5-(5-methylthiophene-2-carboxamido)thiazole-4-carboxamide | 11.1 |
| 163 | 5-(4-{[(2-hydroxyethyl)amino]methyl}benzamido)-2-(naphthalen-2-ylamino)thiazole-4-carboxamide | 3.7 |
| 165 | 5-(but-2-ynamido)-2-(naphthalen-2-ylamino)thiazole-4-carboxamide | 4.4 |
| 173 | 5-{4-[(4-hydroxypiperidin-1-yl)methyl]benzamido}-2-(naphthalen-2-ylamino)thiazole-4-carboxamide | 3.4 |

TABLE 2-continued

| Example number | Test Compound | IC$_{50}$ (nM) |
|---|---|---|
| 174 | (E)-5-[4-(4-methylpiperazin-1-yl)but-2-enamido]-2-(naphthalen-2-ylamino)thiazole-4-carboxamide | 16.0 |
| 180 | 2-(naphthalen-2-ylamino)-5-{4-[(3-oxopiperazin-1-yl)methyl]benzamido}thiazole-4-carboxamide | 4.2 |
| 185 | 5-(4-{[4-(2-hydroxyethyl)piperazin-1-yl]methyl}benzamido)-2-(naphthalen-2-ylamino)thiazole-4-carboxamide | 2.7 |
| 187 | 5-{4-[4-(2-hydroxyethyl)piperazin-1-yl]benzamido}-2-(naphthalen-2-ylamino)thiazole-4-carboxamide | 7.2 |
| 188 | 5-{4-[(2-aminoethyl)amino]benzamido}-2-(naphthalen-2-ylamino)thiazole-4-carboxamide | 8.4 |
| 189 | 5-(4-{[2-(hydroxymethyl)piperidin-1-yl]methyl}benzamido)-2-(naphthalen-2-ylamino)thiazole-4-carboxamide | 6.8 |
| 190 | 5-{4-[(4-methyl-1,4-diazepan-1-yl)methyl]benzamido}-2-(naphthalen-2-ylamino)thiazole-4-carboxamide | 3.2 |
| 195 | 5-{4-[(1H-1,2,4-triazol-1-yl)methyl]benzamido}-2-(naphthalen-2-yl-amino)thiazole-4-carboxamide | 2.5 |
| 201 | 5-{4-[(3-hydroxyazetidin-1-yl)methyl]benzamido}-2-(naphthalen-2-ylamino)thiazole-4-carboxamide | 5.6 |
| 202 | (R)-5-{4-[(3-hydroxypyrrolidin-1-yl)methyl]benzamido}-2-(naphthalen-2-ylamino)thiazole-4-carboxamide | 5.5 |
| 203 | (S)-5-{4-[(3-hydroxypyrrolidin-1-yl)methyl]benzamido}-2-(naphthalen-2-ylamino)thiazole-4-carboxamide | 5.0 |
| 204 | 2-(naphthalen-2-ylamino)-5-propiolamidothiazole-4-carboxamide | 6.0 |
| 205 | 5-(4-[(1H tetrazol-1-yl)methyl]benzamido)-2-(naphthalen-2-ylamino)thiazole-4-carboxamide | 5.9 |
| 208 | 5-{4-[(1H-imidazol-1-yl)methyl]benzamido}-2-(naphthalen-2-ylamino)thiazole-4-carboxamide | 3.0 |
| 218 | 5-(4-hydroxybut-2-ynamido)-2-(naphthalen-2-ylamino)thiazole-4-carboxamide | 4.5 |
| 220 | (S)-5-{4-[(3-aminopyrrolidin-1-yl)methyl]benzamido}-2-(naphthalen-2-ylamino)thiazole-4-carboxamide | 3.0 |
| 221 | (S)-5-(4-{[3-(dimethylamino)pyrrolidin-1-yl]methyl}benzamido)-2-(naphthalen-2-ylamino)thiazole-4-carboxamide | 2.6 |
| 222 | 5-{4-[(4-aminopiperidin-1-yl)methyl]benzamido}-2-(naphthalen-2-ylamino)thiazole-4-carboxamide | 1.3 |
| 225 | 5-(5-hydroxypent-2-ynamido)-2-(naphthalen-2-ylamino)thiazole-4-carboxamide | 4.0 |
| 231 | 5-{4-[(2H-tetrazol-5-yl)methyl]benzamido}-2-(naphthalen-2-ylamino)thiazole-4-carboxamide | 2.9 |
| 232 | 5-{4-[(1H-pyrazol-1-yl)methyl]benzamido}-2-(naphthalen-2-ylamino)thiazole-4-carboxamide | 10.3 |
| 233 | 5-[6-(1H-1,2,4-triazol-1-yl)hex-2-ynamido]-2-(naphthalen-2-ylamino)thiazole-4-carboxamide | 10.7 |
| 234 | 5-[6-(1H-imidazol-1-yl)hex-2-ynamido]-2-(naphthalen-2-ylamino)thiazole-4-carboxamide | 9.7 |
| 235 | 2-(naphthalen-2-ylamino)-5-{4-[(2-nitro-1H-imidazol-1-yl)methyl]benzamido}thiazole-4-carboxamide | 9.5 |
| 237 | 5-{4-[(2-methyl-1H-imidazol-1-yl)methyl]benzamido}-2-(naphthalen-2-ylamino)thiazole-4-carboxamide | 2.3 |
| 238 | 5-{4-[(4-methyl-1H-imidazol-1-yl)methyl]benzamido}-2-(naphthalen-2-ylamino)thiazole-4-carboxamide | 3.1 |
| 239 | 2-(naphthalen-2-ylamino)-5-{4-[(4-nitro-1H-imidazol-1-yl)methyl]benzamido}thiazole-4-carboxamide | 5.9 |
| 243 | 2-(naphthalen-2-ylamino)-5-{4-[(3-nitro-1H-1,2,4-triazol-1-yl)methyl]benzamido}thiazole-4-carboxamide | 14.8 |
| 244 | 5-{4-[(5-methyl-1H-tetrazol-1-yl)methyl]benzamido}-2-(naphthalen-2-ylamino)thiazole-4-carboxamide | 7.1 |
| 246 | 5-{4-[(4-(hydroxymethyl)-1H-imidazol-1-yl)methyl]benzamido}-2-(naphthalen-2-ylamino)thiazole-4-carboxamide | 3.5 |
| 248 | 5-{4-[(1H-imidazol-1-yl)methyl]benzamido}-2-[(6-methoxynaphthalen-2-yl)amino]thiazole-4-carboxamide | 6.1 |
| 249 | 5-{4-[(1H-imidazol-1-yl)methyl]benzamido}-2-[(6-fluoronaphthalen-2-yl)amino]thiazole-4-carboxamide | 10.1 |
| 250 | 5-{4-[(1H-imidazol-1-yl)methyl]benzamido}-2-(quinolin-6-ylamino)thiazole-4-carboxamide | 3.0 |
| 251 | 5-{5-[(1H-imidazol-1-yl)methyl]thiophene-2-carboxamido}-2-(naphthalen-2-ylamino)thiazole-4-carboxamide | 7.7 |
| 252 | 5-{4-[(2,4-dioxothiazolidin-3-yl)methyl]benzamido}-2-(naphthalen-2-ylamino)thiazple-4-carboxamide | 15.9 |
| 254 | 5-{4-[(1H-imidazol-1-yl)methyl]benzamido}-2-(quinolin-5-ylamino)thiazole-4-carboxamide | 4.8 |
| 255 | 5-{4-[(1H-imidazol-1-yl)methyl]benzamido}-2-(quinolin-4-ylamino)thiazole-4-carboxamide | 26.5 |
| 256 | 5-{4-[(3-methyl-1,2,4-oxadiazol-5-yl)methyl]benzamido}-2-(naphthalen-2-ylamino)thiazole-4-carboxamide | 18.5 |
| 257 | 5-{4-[(5-methyl-1,3,4-oxadiazol-2-yl)methyl]benzamido}-2-(naphthalen-2-ylamino)thiazole-4-carboxamide | 6.2 |

TABLE 2-continued

| Example number | Test Compound | IC$_{50}$ (nM) |
|---|---|---|
| 258 | 5-{5-[(1H-imidazol-1-yl)methyl]thiophene-3-carboxamido}-2-(naphthalen-2-ylamino)thiazole-4-carboxamide | 8.7 |
| 259 | 5-{4-[(1H-imidazol-1-yl)methyl]benzamido}-2-(quinolin-8-ylamino)thiazole-4-carboxamide | 5.5 |
| 260 | 5-{4-[(4-(hydroxymethyl)-1H-1,2,3-triazol-1-yl)methyl]benzamido}-2-(naphthalen-2-ylamino)thiazole-4-carboxamide | 5.3 |
| 262 | 5-{4-[(1H-imidazol-1-yl)methyl]benzamido}-2-[(7-fluoronaphthalen-2-yl)amino]thiazole-4-carboxamide | 8.4 |

Test Example 2

In Vitro Cell Proliferation Assay

The human colon cancer cell line HCT-116 was seeded at 600 cells/well in 96 well-plate (ThermoFisher) using RPMI medium containing 2 mM L-glutamine (Invitrogen) supplemented with 10% FCS (Invitrogen) and 1% penicillin/streptomycin (Sigma) and maintained at 37° C., 5% $CO_2$ and 100% humidity. The following day, old medium was withdrawn and the fresh medium was added. Initial numbers of cells were counted before adding compounds. Then cells were treated in duplicates with compounds (a half-logarithmic serial dilution from 10 μM). Eight untreated control wells were incubated in each plate. After 72 hours of treatment, cells were fixed with 2% paraformaldehyde, and the nucleus were stained with Hoechst 33258 (Invitrogen). The numbers of cells were counted with ArrayScan™ VTI (ThermoFisher Scientific). Data were evaluated as percent of the control wells:

% Inhibition=(1−(Treated−Initial)/(Control−Initial))×100.

where Treated: mean cell number of wells after compound treatment for 72 h

Control: mean cell number of wells without compound treatment for 72 h

Initial: mean cell number of wells before compound treatment

IC$_{50}$ values were calculated by regression analysis of the log-concentration-inhibition curves.

Given the above assays, the compounds of formula (I) of the invention resulted to possess a remarkable antiproliferative activity, as shown in Table 3.

TABLE 3

Cell-based activity of representative compounds

| Example number | Test Compound | IC$_{50}$ (nM) |
|---|---|---|
| 2 | 5-(4-acetamidobenzamido)-2-(naphthalen-2-ylamino)thiazole-4-carboxamide | *** |
| 8 | 5-(4-fluorobenzamido)-2-(naphthalen-2-ylamino)thiazole-4-carboxamide | ** |
| 10 | 5-[4-(2-hydroxyethylamino)benzamido]-2-(naphthalen-2-ylamino)thiazole-4-carboxamide | *** |
| 11 | 5-{4-[2-(dimethylamino)ethylamino]benzamido}-2-(naphthalen-2-ylamino)thiazole-4-carboxamide | *** |
| 12 | 5-[4-(4-methylpiperazin-1-yl)benzamido]-2-(naphthalen-2-ylamino)thiazole-4-carboxamide | ** |
| 13 | 2-(naphthalen-2-ylamino)-5-{4-[2-(piperidin-1-yl)ethylamino]benzamido}thiazole-4-carboxamide | *** |
| 15 | 5-(4-morpholinobenzamido)-2-(naphthalen-2-ylamino)thiazole-4-carboxamide | *** |
| 16 | 5-(4-aminobenzamido)-2-(naphthalen-2-ylamino)thiazole-4-carboxamide | *** |
| 17 | 5-{4-[(4-methylpiperazin-1-yl)methyl]benzamido}-2-(naphthalen-2-ylamino)thiazole-4-carboxamide | *** |
| 18 | 5-[4-(morpholinomethyl)benzamido]-2-(naphthalen-2-ylamino)thiazole-4-carboxamide | *** |
| 19 | 2-(naphthalen-2-ylamino)-5-[4-(piperazin-1-ylmethyl)benzamido]thiazole-4-carboxamide | ** |
| 20 | 5-{4-[(dimethylamino)methyl]benzamido}-2-(naphthalen-2-ylamino)thiazole-4-carboxamide | *** |
| 21 | 5-[4-(2-hydroxyacetamido)benzamido]-2-(naphthalen-2-ylamino)thiazole-4-carboxamide | *** |
| 23 | 5-(4-aminomethylbenzamido)-2-(naphthalen-2-ylamino)thiazole-4-carboxamide | ** |
| 24 | 5-[4-(4-methylpiperazin-1-yl)benzamido]-2-(quinolin-6-ylamino)thiazole-4-carboxamide | * |
| 26 | 5-[4-(4-methylpiperazin-1-yl)benzamido]-2-(quinolin-5-ylamino)thiazole-4-carboxamide | * |
| 27 | 5-[4-(4-methylpiperazin-1-yl)benzamido]-2-(quinolin-8-ylamino)thiazole-4-carboxamide | * |
| 28 | 2-[methyl(quinolin-6-yl)amino]-5-[4-(4-methylpiperazin-1-yl)benzamido]thiazole-4-carboxamide | ** |

TABLE 3-continued

Cell-based activity of representative compounds

| Example number | Test Compound | IC$_{50}$ (nM) |
|---|---|---|
| 34 | 5-(5-methylthiophene-2-carboxamido)-2-(naphthalen-2-ylamino)thiazole-4-carboxamide | *** |
| 35 | N-[4-carbamoyl-2-(naphthalen-2-ylamino)thiazol-5-yl]-4H-thieno[3,2-b]pyrrole-5-carboxamide | ** |
| 46 | 2-(isoquinolin-6-ylamino)-5-(thiophene-3-carboxamido)thiazole-4-carboxamide | ** |
| 49 | 5-[5-(morpholinomethyl)thiophene-3-carboxamido]-2-(quinolin-5-ylamino)thiazole-4-carboxamide | * |
| 60 | 5-{5-[(4-methylpiperazin-1-yl)methyl]thiophene-3-carboxamido}-2-(naphthalen-2-ylamino)thiazole-4-carboxamide | *** |
| 65 | 2-[methyl(naphthalen-2-yl)amino]-5-[4-(4-methylpiperazin-1-yl)benzamido]thiazole-4-carboxamide | * |
| 67 | 5-[5-(morpholinomethyl)thiophene-3-carboxamido]-2-(quinolin-4-ylamino)thiazole-4-carboxamide | * |
| 73 | 2-[(6-methoxynaphthalen-2-yl)amino]-5-(thiophene-3-carboxamido)thiazole-4-carboxamide | * |
| 78 | 5-(4-{[2-(2-hydroxyethoxy)ethyl]amino}benzamido)-2-(naphthalen-2-ylamino)thiazole-4-carboxamide | *** |
| 83 | 5-(3-methylbut-2-enamido)-2-(naphthalen-2-ylamino)thiazole-4-carboxamide | * |
| 91 | 5-[6-(4-methylpiperazin-1-yl)hexanamido]-2-(naphthalen-2-ylamino)thiazole-4-carboxamide | ** |
| 97 | 5-[4-(4-hydroxypiperidin-1-yl)benzamido]-2-(naphthalen-2-ylamino)thiazole-4-carboxamide | *** |
| 195 | 5-{4-[(1H-1,2,4-triazol-1-yl)methyl]benzamido}-2-(naphthalen-2-ylamino)thiazole-4-carboxamide | *** |
| 205 | 5-(4-[(1H-tetrazol-1-yl)methyl)benzamido]-2-(naphthalen-2-ylamino)thiazole-4-carboxamide | *** |
| 208 | 5-{4-[(1H-imidazol-1-yl)methyl]benzamido}-2-(naphthalen-2-ylamino)thiazole-4-carboxamide | *** |

\*\*\* IC$_{50}$ < 100 nM
\*\* 100 ≤ IC$_{50}$ ≤ 1000 nM
\* 1000 < IC$_{50}$ ≤ 10000 nM

EXAMPLE

The following examples are illustrative only, and not intended to limit the scope of the limit the present invention.

Abbreviations and symbols used in the following descriptions mean as follows:

CDCl$_3$: chloroform-d
D$_2$O: deuterium oxide
DCM: dichloromethane
DMA: dimethylacetamide
DMAP: 4-dimethyl aminopyridine
DMF: dimethyl formamide
DMSO: dimethyl sulfoxide
EtOH: ethanol
EtOAc: ethyl acetate
HCl: hydrochloric acid
K$_2$CO$_3$: potassium carbonate
MeOH: methanol
MgSO$_4$: magnesium sulfate
NaHCO$_3$: sodium bicarbonate
Na$_2$SO$_4$: sodium sulfate
NH$_4$Cl: ammonium chloride
NH$_3$: ammonia
NMP: N-methylpyrrolidone
POCl$_3$: phosphorous oxychloride
Pd$_2$(dba)$_3$: Tris(dibenzylideneacetone)dipalladium(0)
THF: tetrahydrofuran
TFA: trifluoroacetic acid
Xantphos: 4,5-Bis(diphenylphosphino)-9,9-dimethylxanthene
EDC: 1-ethyl-3-(3-dimethylaminopropyl) carbodiimide hydrochloride
HOBT: hydroxybenzotriazole
min.: minute(s)
h or hr(s): hour(s)
RT or rt: room temperature
sat.: saturated
aq.: aqueous
TLC: thin layer chromatography
HPLC: high performance liquid chromatography
Prep HPLC: preparative HPLC
LCMS: high performance liquid chromatography/mass spectrometry
MS: mass spectrometry
NMR: nuclear magnetic resonance Example 1

5-(4-acetamidobenzamido)-2-(naphthalen-1-ylamino)thiazole-4-carboxamide

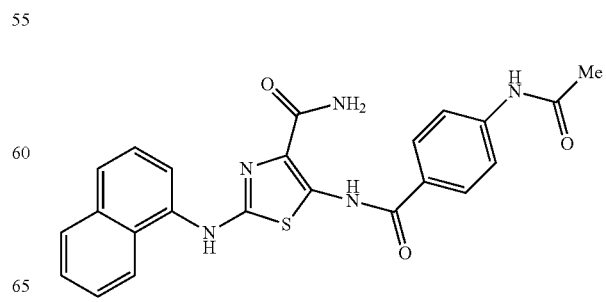

(a) 5-amino-2-(naphthalen-1-ylamino)thiazole-4-carboxamide

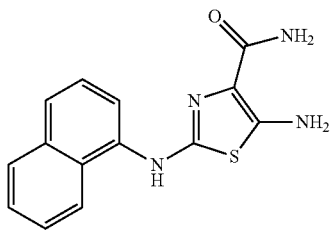 [SMILES: NC(=O)c1nc(Nc2cccc3ccccc23)sc1N]

To a suspension of 2-amino-2-cyanoacetamide (0.25 g, 2.53 mmol) in EtOAc (8 mL), was added 1-isothiocyanatonaphthalene (0.467 g, 2.53 mmol), and the mixture was refluxed for 30 min. The solvent was evaporated under reduced pressure, and the resulting crude residue was purified by silica gel column chromatography eluted with 2% MeOH in DCM to give 0.35 g (48% yield) of the titled compound.

$^1$H-NMR (400 MHz, DMSO-$d_6$) δ (ppm) 6.73 (br, 2H), 6.81 (br, 1H), 6.93 (br, 1H), 7.43 (t, 1H, J=7.9 Hz), 7.45-7.55 (m, 3H), 7.87 (m, 1H), 8.29 (d, 2H, J=7.3 Hz), 9.42 (s, 1H); LCMS: m/z [M+H]$^+$285.0

(b) 5-(4-acetamidobenzamido)-2-(naphthalen-1-ylamino)thiazole-4-carboxamide

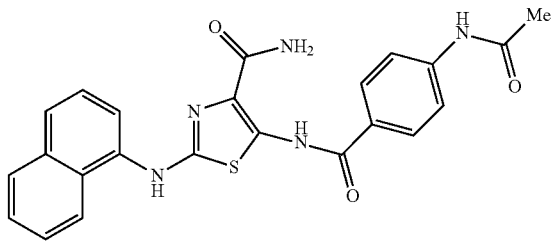 [SMILES: CC(=O)Nc1ccc(C(=O)Nc2sc(Nc3cccc4ccccc34)nc2C(N)=O)cc1]

To a mixture of 4-acetamidobenzoic acid (0.151 g, 0.845 mmol) and a catalytic amount of DMF in dry THF (8 mL) was added dropwise oxalyl chloride (0.12 mL, 1.40 mmol) at 0° C., and the mixture was stirred for 2 hrs at rt. The solvent was evaporated, and the residual oxalyl chloride was removed with azeotropic distillation using toluene under nitrogen atmosphere. The resulting acid chloride was then dissolved in pyridine (5 mL) and cooled to 0° C. To this solution, a solution of 5-amino-2-(naphthalene-1-ylamino)thiazole-4-carboxamide (0.2 g, 0.70 mmol) in pyridine (5 mL) was added at 0° C., and the mixture was stirred for 12 hrs at rt. The solvent was evaporated, and the residue was suspended into I M HCl, and the resulting solids were collected and dried. The crude solids were purified by silica gel column chromatography eluted with 3% MeOH in DCM to give 91 mg (29% yield) of the titled compound.

$^1$H-NMR (400 MHz, DMSO-$d_6$) δ (ppm) 2.10 (s, 3H), 7.45-7.65 (m, 5H), 7.75-7.89 (m, 5H), 7.92 (d, 1H, J=7.6 Hz), 8.34 (d, 1H, J=7.9 Hz), 8.49 (d, 1H, J=7.6 Hz), 9.92 (s, 1H), 10.34 (s, 1H), 12.53 (s, 1H); LCMS m/z [M+H]$^+$446.2.

Example 2

5-(4-acetamidobenzamido)-2-(naphthalen-2-ylamino)thiazole-4-carboxamide

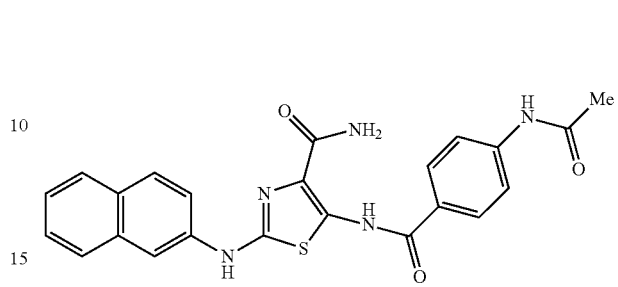

(a) 2-isothiocyanatonaphthalene

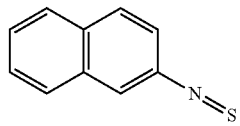 [SMILES: S=Nc1ccc2ccccc2c1]

To a mixture of naphthalen-2-amine (0.50 g, 3.49 mmol) in water (10 mL) was added CSCl$_2$ (0.3 mL, 4.19 mmol) at 0° C., and the mixture was stirred for 40 min at rt. Then the reaction mixture was diluted with water and extracted with ether (2×50 mL). The combined ether layer was dried over Na$_2$SO$_4$, and concentrated under reduced pressure to give 0.62 g (96% yield) of the titled compound which was used in the next step without further purification.

$^1$H-NMR (400 MHz, DMSO-$d_6$) δ (ppm) 7.50-7.61 (m, 3H), 7.91-8.02 (m, 4H).

(b) 5-amino-2-(naphthalen-2-ylamino)thiazole-4-carboxamide

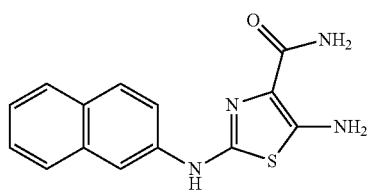 [SMILES: NC(=O)c1nc(Nc2ccc3ccccc3c2)sc1N]

To a suspension of 2-amino-2-cyanoacetamide (0.486 g, 2.70 mmol) in EtOAc (15 mL), was added 2-isothiocyanatonaphthalene (0.5 g, 2.70 mmol), and the mixture was refluxed for 30 min. The solvent was evaporated under reduced pressure, and the resulting crude residue was purified by silica gel column chromatography eluted with 2% MeOH in DCM to give 0.6 g (78% yield) of the titled compound.

$^1$H-NMR (400 MHz, DMSO-$d_6$) δ (ppm) 6.75 (s, 2H), 6.97 (s, 1H), 7.02 (s, 1H), 7.28 (t, 1H, J=7.3 Hz), 7.39 (d, 2H, J=8.2 Hz), 7.74-7.77 (m, 2H), 7.94 (d, 1H, J=8.2 Hz), 8.35 (s, 1H), 9.78 (s, 1H); LCMS: m/z [M+H]$^+$285.2.

(c) 5-(4-acetamidobenzamido)-2-(naphthalen-2-ylamino)thiazole-4-carboxamide

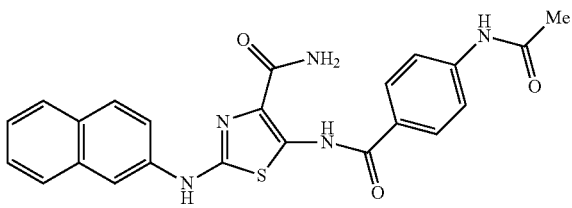 [SMILES: CC(=O)Nc1ccc(C(=O)Nc2sc(Nc3ccc4ccccc4c3)nc2C(N)=O)cc1]

To a mixture of 4-acetamidobenzoic acid (0.204 g, 1.14 mmol) and a catalytic amount of DMF in dry THF (15 mL) was added dropwise oxalyl chloride (0.2 mL, 2.30 mmol) at 0° C., and the mixture was stirred for 2 hrs at rt. The solvent was evaporated, and the residual oxalyl chloride was removed with azeotropic distillation using toluene under nitrogen atmosphere 4 times. The resulting acid chloride was then dissolved in pyridine (6 mL) and cooled to 0° C. To this solution, a solution of 5-amino-2-(naphthalene-2-ylamino)thiazole-4-carboxamide (0.27 g, 0.95 mmol) in pyridine (6 mL) was added at 0° C., and the mixture was stirred for 12 hrs at rt. The solvent was evaporated, and the residue was suspended into 1M HCl, and the resulting solids were collected and dried. The crude solids were purified by silica gel column chromatography eluted with 3% MeOH in DCM to give 16 mg (3.7% yield) of the titled compound.

$^1$H-NMR (400 MHz, DMSO-d$_6$) δ (ppm) 2.10 (s, 3H), 7.32 (t, 1H, J=7.34 Hz), 7.44 (t, 1H, J=7.42 Hz), 7.52 (d, 1H, J=8.5 Hz), 7.74-7.9 (m, 8H), 8.04 (d, 1H, J=8.0 Hz), 8.55 (s, 1H), 10.29 (s, 1H), 10.34 (s, 1H), 12.64 (s, 1H); LCMS m/z [M+H]$^+$446.2.

Example 3

2-(isoquinolin-3-ylamino)-5-(4-methoxybenzamido)thiazole-4-carboxamide

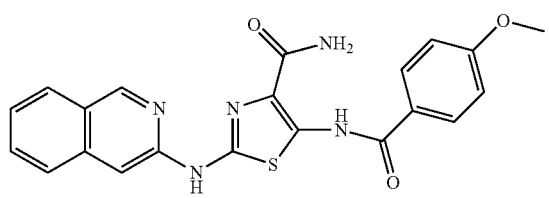 [SMILES: COc1ccc(C(=O)Nc2sc(Nc3cc4ccccc4cn3)nc2C(N)=O)cc1]

(a) 3-isothiocyanatoisoquinoline

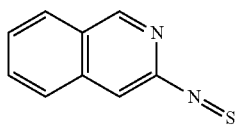

To a mixture of isoquinolin-3-amine (0.2 g, 1.38 mmol) in water (5 mL) was added CSCl$_2$ (0.1 mL, 1.52 mmol) slowly for a period of 5 min at 0° C., and the mixture was stirred for 40 min at rt. The reaction mixture was diluted with water and extracted with ether (2×50 mL). The combined ether layer was dried over Na$_2$SO$_4$ and concentrated under reduced pressure to give 0.158 g (62% yield) of the titled compound which was used in the next step without further purification.

$^1$H-NMR (400 MHz, DMSO-d$_6$) δ (ppm) 7.73 (t, 1H, J=7.5 Hz), 7.85 (t, 1H, J=7.56 Hz), 7.90 (s, 1H), 7.99 (d, 1H, J=8.24 Hz), 8.19 (t, 1H, J=8.12 Hz), 9.26 (s, 1H).

(b) 5-amino-2-(isoquinolin-3-ylamino)thiazole-4-carboxamide

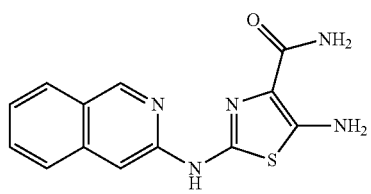 [SMILES: NC(=O)c1nc(Nc2cc3ccccc3cn2)sc1N]

To a suspension of 2-amino-2-cyanoacetamide (0.167 g, 1.69 mmol) in EtOAc (15 mL), was added isoquinolin-3-ylisocyanate (0.315 g, 1.69 mmol), and the mixture was refluxed for 2 hrs. The solvent was evaporated under reduced pressure, and the resulting crude residue was purified by silica gel column chromatography eluted with 2% MeOH in DCM to give 0.1 g (21% yield) of the titled compound.

$^1$H-NMR (400 MHz, DMSO-d$_6$) δ (ppm) 6.60-6.70 (br, 2H), 7.37 (t, 1H, J=7.5 Hz), 7.61 (t, 1H, J=8.0 Hz), 7.63 (s, 1H), 7.68-7.70 (m, 2H), 7.84 (d, 1H, J=8.2 Hz), 7.96 (d, 1H, J=8.03 Hz), 9.06 (s, 1H), 10.58 (s, 1H); LCMS m/z [M+H]$^+$ 286.2.

(c) 2-(isoquinolin-3-ylamino)-5-(4-methoxybenzamido)thiazole-4-carboxamide

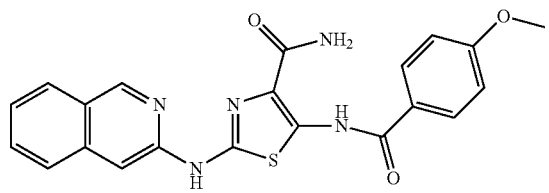 [SMILES: COc1ccc(C(=O)Nc2sc(Nc3cc4ccccc4cn3)nc2C(N)=O)cc1]

To a mixture of p-anisoyl chloride (0.4 mL, 3.0 mmol) in pyridine (2 mL) was added dropwise a solution of 5-amino-2-(isoquinolin-3-ylamino)-thiazole-4-carboxamide (0.20 g, 0.70 mmol) in pyridine (3 mL), and the mixture was stirred overnight at rt. The solvent was evaporated. The residue was triturated with MeOH, and the resulting solids were collected to give 42 mg (28% yield) of the titled compound.

$^1$H-NMR (400 MHz, DMSO-d$_6$) δ (ppm) 3.87 (s, 3H), 7.18 (d, 2H, J=8.5 Hz), 7.58-7.62 (m, 2H), 7.85-8.0 (m, 4H), 8.04 (s, 1H), 8.18-8.22 (m, 1H), 8.89 (s, 1H), 9.17 (s, 1H), 10.79 (s, 1H), 12.67 (s, 1H); LCMS m/z [M+H]$^+$420.4.

Example 9

5-(3-amino-4-methylbenzamido)-2-(naphthalen-2-ylamino)thiazole-4-carboxamide

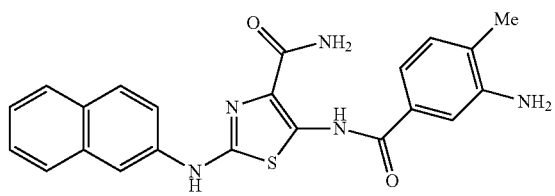 [SMILES: Cc1ccc(C(=O)Nc2sc(Nc3ccc4ccccc4c3)nc2C(N)=O)cc1N]

(a) 5-(4-methyl-3-nitrobenzamido)-2-(naphthalen-2-ylamino)thiazole-4-carboxamide

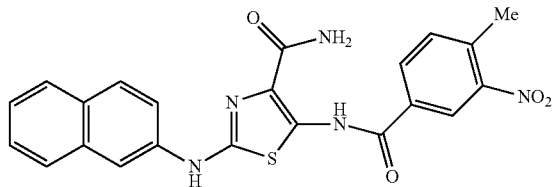 [SMILES: Cc1ccc(C(=O)Nc2sc(Nc3ccc4ccccc4c3)nc2C(N)=O)cc1[N+](=O)[O-]]

To a mixture of 5-amino-2-(naphthalen-2-ylamino)thiazole-4-carboxamide (0.2 g, 0.70 mmol) in pyridine (5 mL) was added a solution of 4-methyl-3-nitrobenzoyl chloride in pyridine (3 mL) at 0° C. under nitrogen atmosphere. The mixture was allowed to warm up to rt, and stirred for 16 hrs at rt. The solvent was evaporated, and the crude residue was suspended into EtOAc (20 mL). The resulting solids were collected by filtration and washed with MeOH (2×5 mL) to give 0.21 g (66% yield) of the titled compound.

$^1$H-NMR (400 MHz, DMSO-d$_6$) δ (ppm) 2.63 (s, 3H), 7.45-7.65 (m, 4H-1), 7.70 (br, 1H), 7.77 (d, 1H, J=8.1 Hz), 7.87-7.96 (m, 2H), 8.09 (d, 1H, J=8.2 Hz), 8.35 (d, 1H, J=7.7 Hz), 8.46 (s, 1H), 8.51 (d, 1H, J=7.7 Hz), 9.99 (s, 1H), 12.77 (s, 1H); LCMS m/z [M+H]$^+$448.2.

(b) 5-(3-amino-4-methylbenzamido)-2-(naphthalen-2-ylamino)thiazole-4-carboxamide

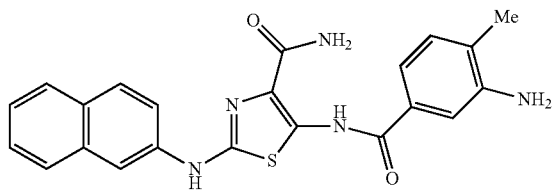 [SMILES: Cc1ccc(C(=O)Nc2sc(Nc3ccc4ccccc4c3)nc2C(N)=O)cc1N]

To a mixture of 5-(4-methyl-3-nitrobenzamido)-2-(naphthalen-2-ylamino)thiazole-4-carboxamide (0.07 g, 0.15 mmol) in MeOH-THF (10 mL, 1:1) was added 10% Pd/C (0.014 g) under N$_2$-atmosphere. The mixture was stirred for 16 hrs under hydrogen atmosphere. The insoluble material was then filtered off, and the filtrate was concentrated under reduced pressure to give 0.032 g (49% yield) of the titled compound.

$^1$H-NMR (400 MHz, DMSO-d$_6$) δ (ppm) 2.13 (s, 3H), 5.29 (br, 2H), 6.92-7.17 (m, 2H), 7.20 (s, 1H), 7.44-7.69 (m, 5H), 7.79 (br, 1H), 7.93 (d, 1H, J=6.9 Hz), 8.35 (d, 1H, J=7.3 Hz), 8.49 (d, 1H, J=7.3 Hz), 9.91 (s, 1H), 12.39 (s, 1H); LCMS m/z [M+H]$^+$418.2.

Example 10

5-[4-(2-hydroxyethylamino)benzamido]-2-(naphthalen-2-ylamino)thiazole-4-carboxamide

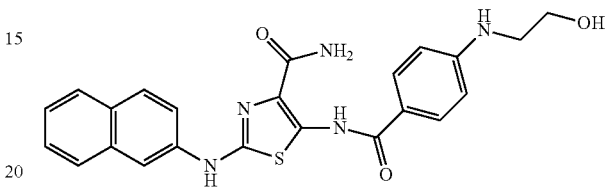

A solution of 5-(4-fluorobenzamido)-2-(naphthalen-2-ylamino)thiazole-4-carboxamide (0.10 g, 0.25 mmol) and 2-aminoethanol (0.15 g, 2.46 mmol) in NMP (1 mL) was treated using a microwave synthesizer for 1 hr (CEM Corp., 180° C.). The, reaction mixture was diluted with water (3 mL), and the resulting solids were collected by filtration. The solids were washed with water, and dried to give 0.035 g (31% yield) of the titled compound.

$^1$H-NMR (400 MHz, DMSO-d$_6$) δ (ppm) 3.20 (d, 2H, J=5.6 Hz), 3.58 (d, 2H, J=5.6 Hz), 4.77 (t, 1H, J=5.1 Hz), 6.61 (br, 1H), 6.72 (d, 2H, J=8.6 Hz), 7.26-7.37 (m, 1H), 7.44 (t, 1H, J=7.6 Hz), 7.51 (d, 1H, J=8.6 Hz), 7.65 (d, 2H, J=8.6 Hz), 7.74-7.92 (m, 4H), 8.04 (d, 1H, J=8.1 Hz), 8.6 (br, 1H), 10.23 (s, 1H), 12.42 (s, 1H); LCMS m/z [M+H]$^+$448.2.

Example 17

5-{4-[(4-methylpiperazin-1-yl)methyl]benzamido}-2-(naphthalen-2-ylamino)thiazole-4-carboxamide

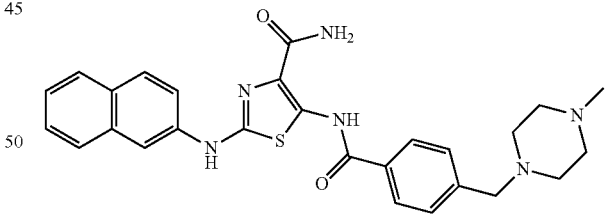

To a mixture of 5-amino-2-(naphthalen-2-ylamino)thiazole-4-carboxamide (0.50 g, 1.76 mmol) and. N,N-diisopropylethylamine (0.3 mL, 1.94 mmol) in DMA (30 mL) was added 4-chloromethylbenzoyl chloride (0.37g, 1.94 mmol) at 0° C. The mixture was stirred for 3 hrs at rt. Then 1-methylpiperazine (0.1 mL, 0.95 mmol) was added to the mixture (0.083 g in 5 mL DMA), and the mixture was stirred for 16 hrs at rt. The reaction mixture was diluted with ethyl acetate (150 mL), washed with water, and dried over Na$_2$SO$_4$. The solvent was evaporated under reduced pressure, and the crude residue was purified by silica gel column chromatograph eluted with 5% MeOH in DCM to give 0.010 g (11% yield) of the titled compound.

¹H-NMR (400 MHz, DMSO-d$_6$) δ (ppm) 2.25-2.6 (m, 11H), 3.61 (s, 2H), 7.29-7.38 (m, 1H), 7.40-7.48 (m, 1H), 7.56 (d, 3H, J=7.3 Hz), 7.76-7.85 (m, 2H), 7.85-7.95 (m, 4H), 8.04 (d, 1H, J=7.8 Hz), 8.56 (s, 1H), 10.34 (s, 1H), 12.71 (s, 1H); LCMS m/z [M+H]⁺501.4.

Example 19

2-(naphthalen-2-ylamino)-5-[4-(piperazin-1-ylmethyl)benzamido]thiazole-4-carboxamide

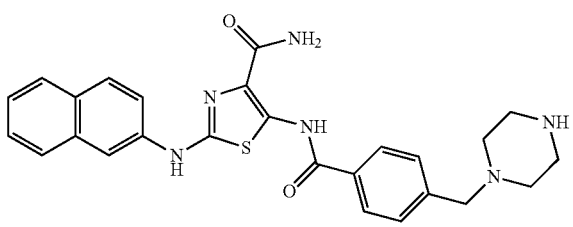 [SMILES: NC(=O)c1nc(Nc2ccc3ccccc3c2)sc1NC(=O)c1ccc(CN2CCNCC2)cc1]

(a) tert-butyl 4-(4-{[4-carbamoyl-2-(naphthalen-2-ylamino)thiazol-5-yl]carbamoyl}benzyl)piperazine-1-carboxylate

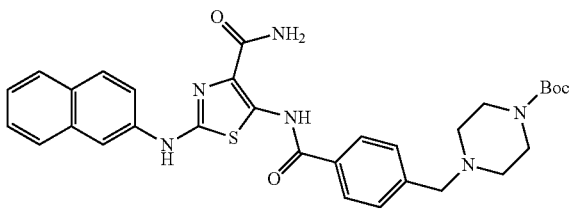 [SMILES: CC(C)(C)OC(=O)N1CCN(Cc2ccc(C(=O)Nc3sc(Nc4ccc5ccccc5c4)nc3C(N)=O)cc2)CC1]

To a mixture of 5-amino-2-(naphthalen-2-ylamino)thiazole-4-carboxamide (0.5 g, 1.76 mmol) and N,N-diisopropylethylamine (0.3 mL, 1.94 mmol) in DMA (30 mL) was added 4-chloromethylbenzoyl chloride (0.37g, 1.94 mmol) at 0° C. The mixture was stirred for 3 hrs at rt. Then 1-Boc-piperazine (0.18 g, 0.95 mmol) was added to the mixture (0.083 g in 5 mL DMA), and the mixture was stirred for 16 hrs at rt. The reaction mixture was diluted with ethyl acetate (150 mL), washed with water, and dried over Na$_2$SO$_4$. The solvent was evaporated under reduced pressure, and the crude residue was purified by silica gel column chromatography eluted with 5% MeOH in DCM to give 0.010 g (11% yield) of the titled compound.

¹H-NMR (400 MHz, DMSO-d$_6$) δ (ppm) 1.35-1.45 (m, 9H), 2.3-2.4 (m, 8H), 3.40 (br, 2H), 7.3-7.4 (m, 1H), 7.4-7.5 (m, 1H), 7.5-7,6 (m, 3H), 7.7-8.0 (m, 5H), 8.04 (d, 1H, J=8.3 Hz), 8.55 (s, 1H), 10.32 (s, 1H), 12.71 (s, 1H); LCMS m/z [M+H]⁺587.2.

(b) 2-(naphthalen-2-ylamino)-5-[4-(piperazin-1-ylmethyl)benzamido]thiazole-4-carboxamide

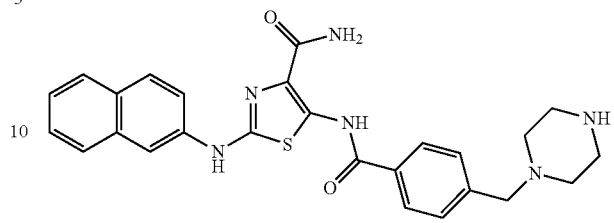

A solution of tert-butyl 4-(4-{[4-carbamoyl-2-(naphthalen-2-ylamino)thiazol-5-yl]carbamoyl}benzy)piperazine-1-carboxylate (0.025 g, 0.04 mmol) in 4N HCl-dioxane (5 mL) was stirred for 2 hrs at rt under N$_2$-atmosphere. The solvent was evaporated in vacuo, and the residue was washed with ether and purified by silica gel column chromatography eluted with 50% EtOAc in hexane to give 0.013 g (68% yield) of the titled compound.

¹H-NMR (400 MHz, DMSO-d$_6$) δ (ppm) 2.3-2.7 (m, 8H), 3.15 (s, 2 H), 7.26-7.39 (m, 1H), 7.44 (t, 1H, J=7.1 Hz), 7.47-7.60 (m, 3H), 7.74-8.00 (m, 6H), 8.05 (d, 1H, J=8.1 Hz), 8.57 (br, 1H), 9.0-9.5 (m, 1H), 10.43 (s, 1H), 12.76 (br, 1H); LCMS m/z [M+H]⁺487.4.

Example 21

5-[4-(2-hydroxyacetamido)benzamido]-2-(naphthalen-2-ylamino)thiazole-4-carboxamide

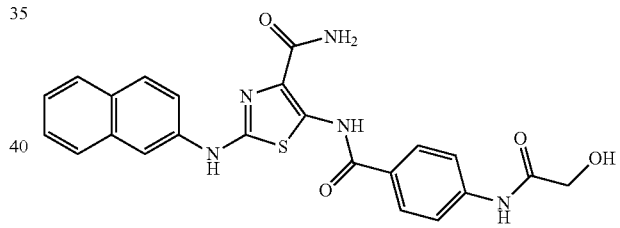

(a) 5-[4-(2-acetoxyacetamido)benzamido]-2-(naphthalen-2-ylamino)thiazole-4-carboxamide

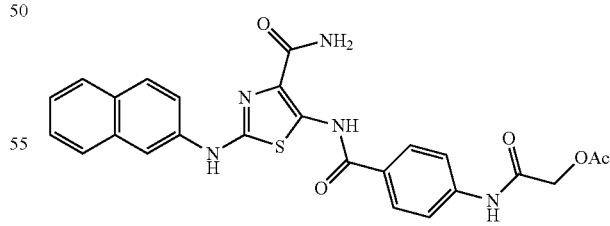

To a mixture of 5-(4-aminobenzamido)-2-(naphthalen-2-ylamino)thiazole-4-carboxamide (0.15 g, 0.37 mmol) and Et$_3$N (0.3 mL, 2.33 mmol) in THF (20 mL) was added acetoxyacetyl chloride (0.12 mL, 1.11 mmol) at 0° C. The mixture was stirred overnight at rt. The solvent was evaporated, and the residue was purified by silica gel column chromatography eluted with 50% EtOAc in hexane to give 0.15 g (80% yield) of the titled compound.

¹H-NMR (400 MHz, DMSO-d₆) δ (ppm) 2.14 (s, 3H), 4.70 (s, 2H), 7.3-7.4 (m, 1H), 7.42 (t, 1H, J=6.7 Hz), 7.53 (d, 1H, J=8.4 Hz), 7.7-7.95 (m, 8H), 8.04 (d, 1H, J=7.9 Hz), 8.55 (s, 1H), 10.29 (s, 1H), 10.49 (s, 1H), 12.66 (s, 1H); LCMS m/z [M+H]⁺504.2.

(b) 5-[4-(2-hydroxyacetamido)benzamido]-2-(naphthalen-2-ylamino)thiazole-4-carboxamide

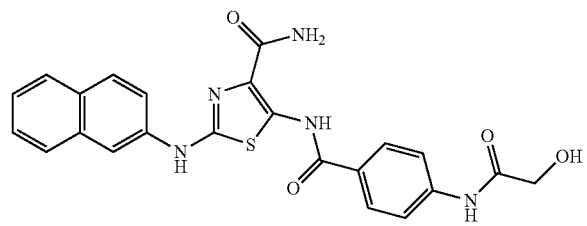 [SMILES: NC(=O)c1nc(Nc2ccc3ccccc3c2)sc1NC(=O)c1ccc(NC(=O)CO)cc1]

To a mixture of 5-[4-(2-acetoxyacetamido)benzamido]-2-(naphthalen-2-ylamino)thiazole-4-carboxamide (0.10 g, 0.20 mmol) in MeOH (10 mL) was added $K_2CO_3$ (0.14 g, 0.99 mmol) and 1 drop of water at rt. The mixture was stirred for 16 hrs at rt. The insoluble material was filtered off, and the filtrate was concentrated in vacuo. The resulting solids were collected and washed with $Et_2O$ to give 0.008 g (5% yield) of the titled compound.

¹H-NMR (400 MHz, DMSO-d₆) δ (ppm) 4.05 (s, 2H), 5.71 (br, 1H), 7.33 (t, 1H, J=7.3 Hz), 7.44 (t, 1H, J=7.2 Hz), 7.53 (d, 1H, J=8.2 Hz), 7.75-8.0 (m, 8H), 8.04 (d, 1H, J=7.9 Hz), 8.55 (s, 1H), 10.08 (s, 1H), 10.30 (s, 1H), 12.66 (s, 1H); LCMS m/z [M+H]⁺462.2.

Example 22

1-{4-[4-carbamoyl-2-(naphthalen-2-ylamino)thiazol-5-ylcarbamoyl]benzyl}pyridinium chloride

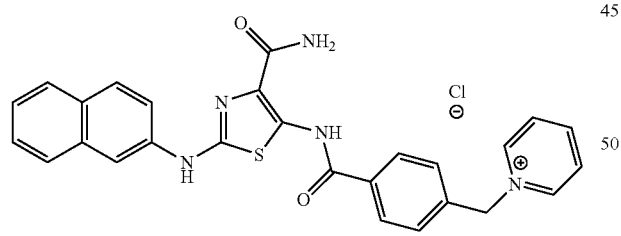

To a solution of 5-amino-2-(naphthalen-2-ylamino)thiazole-4-carboxamide (0.18 g, 0.62 mmol) and a catalytic amount of DMAP in pyridine (5 mL) was added 4-chloromethylbenzoyl chloride (0.13 g, 0.68 mmol) at 0° C. under $N_2$-atmosphere. The mixture was stirred for 16 hrs at rt under nitrogen atmosphere. The solvent was evaporated, and the residue was triturated with water. The resulting solids were collected by filtration and washed with MeOH to give 0.030 g (10% yield) of the titled compound.

¹H-NMR (400 MHz, DMSO-d₆) δ (ppm) 6.01 (s, 2H), 7.27-7.38 (m, 1H), 7.44 (t, 1H, J=7.3 Hz), 7.55 (d, 1H, J=8.3 Hz), 7.68-7.87 (m, 4H), 7.87-8.11 (m, 5H), 8.23 (d, 2H, J=6.4 Hz), 8.56 (br, 1H), 8.67 (t, 1H, J=7.6 Hz), 9.26 (d, 2H, J=5.4 Hz), 10.44 (s, 1H), 12.75 (s, 1H); LCMS m/z [M+H]⁺480.0.

Example 24

5-[4-(4-methylpiperazin-1-yl)benzamido]-2-(quinolin-6-ylamino)thiazole-4-carboxamide

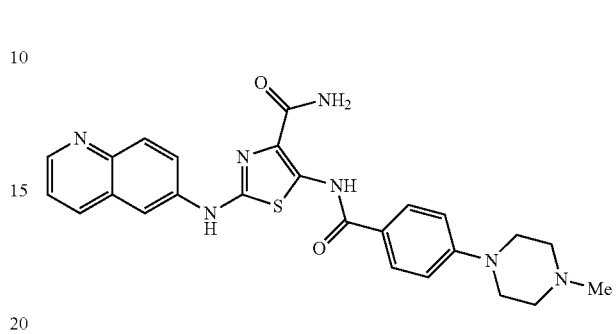

(a) 6-isothiocyanatoquinoline

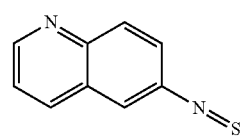 [SMILES: S=Nc1ccc2ncccc2c1]

1,1'-Thiocarbonyldiimidazole (740 mg, 4.16 mmol) was added portion-wise to a solution of quinolin-6-amine (0.50 g, 3.47 mmol) in DCM (15 mL) at 0° C., and the mixture was stirred at rt for 1.5 hrs. The reaction mixture was concentrated in vacuo, and the residue was purified by column chromatography eluted with DCM to give 0.60 g (93% yield) of the titled compound.

¹H-NMR (400 MHz, DMSO-d₆) δ (ppm) 7.61 (dd, 1H, J=8.3, 4.2 Hz), 7.77 (dd, 1H, J=8.9, 2.3 Hz), 8.07 (d, 1H, J=9.0 Hz), 8.10 (d, 1H, J=2.2 hz), 8.37 (d, 1H, J=8.2 Hz), 8.94 (dd, 1H, J=4.2, 1.6 Hz); LCMS m/z [M+H]⁺187.0.

(b) 5-amino-2-(quinolin-6-ylamino)thiazole-4-carboxamide

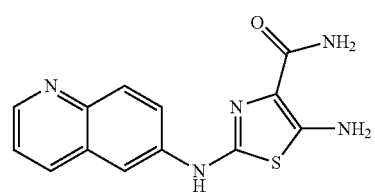 [SMILES: NC(=O)c1nc(Nc2ccc3ncccc3c2)sc1N]

A mixture of 6-isothiocyanatoquinoline (0.50 g, 2.7 mmol) and 2-amino-cyanoacetamide (0.26g, 2.68 mmol) in EtOAc (20 mL) was refluxed for 90 min. The reaction mixture was concentrated in vacuo, and the residue was purified by silica gel column chromatography eluted with 2% MeOH in DCM to give 0.50 g (65% yield) of the titled compound.

¹H-NMR (400 MHz, DMSO-d₆) δ (ppm) 6.79 (br, 2H), 7.00 (br, 1H), 7.13 (br, 1H), 7.42 (dd, 1H, 4.2 Hz, J=8.3), 7.58 (dd, 1H, J=9.1, 2.4 Hz), 7.87 (d, 1H, J=9.0 Hz), 8.42 (d, 1H, J=8.1 Hz), 8.48 (d, 1H, J=2.2 Hz), 8.66 (d, 1H, J=4.1, 1.4 Hz), 9.96 (s, 1H); LCMS m/z [M+H]$^+$286.2.

(c) 5-(4-fluorobenzamido)-2-(quinolin-6-ylamino)thiazole-4-carboxamide

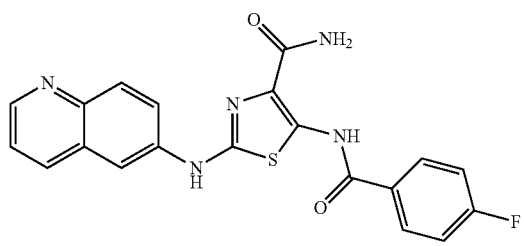 [SMILES: NC(=O)c1nc(Nc2ccc3ncccc3c2)sc1NC(=O)c1ccc(F)cc1]

To solution of 4-fluorobenzoyl chloride (0.16 g, 1.2 mmol) in pyridine (5 mL) was added dropwise a solution of 5-amino-2-(quinolin-6-ylamino)thiazole-4-carboxamide (0.30 g, 1.05 mmol) and a catalytic amount of DMAP in pyridine (5 mL) at 0° C., and the mixture was stirred for 16 hrs at rt. The reaction mixture was quenched with ice-water. The resulting solids were collected by filtration and washed successively with water, MeOH and ether to give 0.18 g (42% yield) of the titled compound.

$^1$H-NMR (400 MHz, DMSO-d$_6$) δ (ppm) 7.4-7.53 (m, 3H), 7.72 (d, 1H, J=9.0 Hz), 7.85-8.05 (m, 5H), 8.50 (d, 1H, J=8.2 Hz), 8.67 (s, 1H), 8.71 (d, 1H, J=3.2 Hz), 10.49 (s, 1H), 12.74 (s, 1H); LCMS m/z [M+H]$^+$408.0.

(d) 5-[4-(4-methylpiperazin-1-yl)benzamido]-2-(quinolin-6-ylamino)thiazole-4-carboxamide

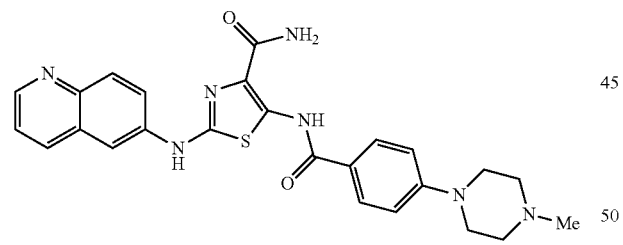

A mixture of 5-(4-fluorobenzamido)-2-(quinolin-6-ylamino)thiazole-4-carboxamide (90 mg, 0.22 mmol) and 1-methyl-piperazine (110 mg, 1.10 mmol) in NMP (3 mL) was heated at 150° C. for 1.5 h. The reaction mixture was diluted with ice-water (5 mL), and the resulting solids were collected by filtration and washed successively with water, ether and dried to give 0.049 g (45% yield) of the titled compound.

$^1$H-NMR (400 MHz, DMSO-d$_6$) δ (ppm) 2.23 (s, 3H), 2.4-2.6 (m, 4H), 3.25-3.4 (m, 4H), 7.10 (d, 2H, J=8.3 Hz), 7.45 (d, 1H, J=4.4 Hz), 7.62-7.8 (m, 3H), 7.85-7.95 (m, 3H), 8.49 (d, 1H, J=8.3 Hz), 8.61-8.75 (m, 2H), 10.42 (s, 1H), 12.55 (s, 1H); LCMS m/z [M+H]$^+$488.4.

Example 28

2-[methyl(quinolin-6-yl)amino]-5-[4-(4-methylpiperazin-1-yl]benzamido)thiazole-4-carboxamide

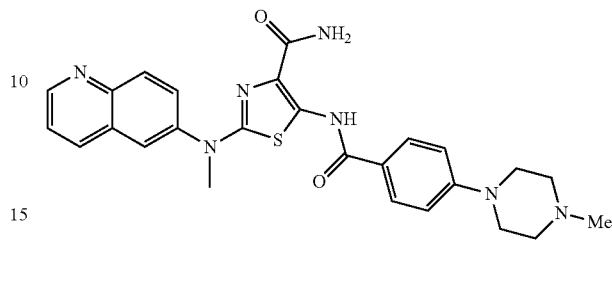

(a) ethyl 5-amino-2-bromothiazole-4-carboxylate

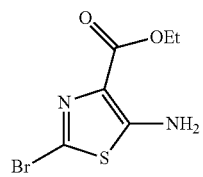 [SMILES: CCOC(=O)c1nc(Br)sc1N]

N-Bromosuccinimide (0.54 g, 3.03 mmol) was added to a solution of 5-aminothiazole-4-carboxylic acid ethyl ester (0.44 g, 2.53 mmol) [prepared according to the procedure described by Golankiewicz et al. (Tetrahedron, 41 (24), 5989-5994 (1985))] in acetonitrile (10 mL), and the mixture was stirred for 30 min. The reaction mixture was diluted with EtOAc (50 mL) and washed with 5% K$_2$CO$_3$ aq. solution (25 mL) followed by brine (25mL). The organic layer was dried over Na$_2$SO$_4$ and concentrated. The residue was purified by silica gel column chromatography eluted with 15% EtOAc in hexane to give 0.37 g (58% yield) of the titled compound.

$^1$H-NMR (400 MHz, CDCl$_3$) δ (ppm) 1.38 (t, 3H, J=7.1 Hz), 4.37 (q, 2H, J=7.1 Hz), 6.02 (s, 2H); LCMS m/z [M+H]$^+$ 253.1.

(b) ethyl 2-bromo-5-(4-fluorobenzamido)-thiazole-4-carboxylate

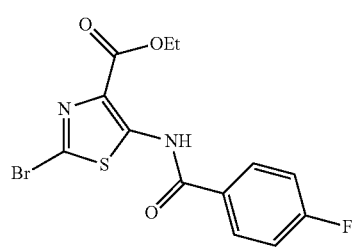 [SMILES: CCOC(=O)c1nc(Br)sc1NC(=O)c1ccc(F)cc1]

To a mixture of ethyl 5-amino-2-bromothiazole-4-caboxylate (0.50 g, 1.99 mmol) and a catalytic amount of DMAP in pyridine (5 mL) was added a solution of 4-fluorobenzoyl chloride (0.377 g, 2.39 mmol) in pyridine (5 mL) at 0° C. The mixture was allowed to warm to rt, and stirred for 16 hrs. The reaction mixture was quenched with ice-water, and the resulting solids were collected. The solids were purified by silica gel column chromatography eluted with 20% EtOAc in hexane to give 0.70 g (93% yield) of the title compound.

$^1$H-NMR (400 MHz, DMSO-d$_6$) δ (ppm) 1.36 (t, 3H, J=7.1 Hz), 4.40 (q, 2H, J=7.1 Hz), 7.49 (t, 2H, J=4.7 Hz), 8.0-8.1 (m, 2H), 11.58 (s, 1H); LCMS m/z [M+H]$^+$373.0.

(c) ethyl 5-(4-fluorobenzamido)-2-[methyl(quinolin-6-yl)amino]thiazole-4-carboxylate

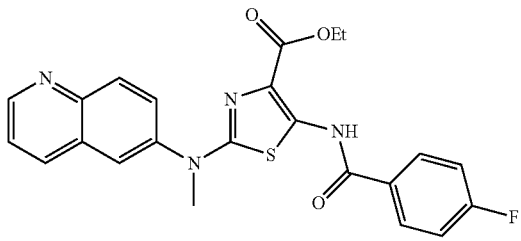 [SMILES: CCOC(=O)c1nc(N(C)c2ccc3ncccc3c2)sc1NC(=O)c1ccc(F)cc1]

To a solution of ethyl 2-bromo-5-(4-fluorobenzamido)-thiazole-4-carboxylate (0.2 g, 0.50 mmol) in toluene (10 mL) was added Xantphos (0.061 g, 0.10 mmol) and Pd$_2$(dba)$_3$ (0.048 g, 0.040 mmol) under argon gas. To this suspension, cesium carbonate (0.344 g, 0.90 mmol) and N-methylquinolin-6-amine (0.084 g, 0.53 mmol) were added, and the mixture was heated at 110° C. for 16 h. The reaction mixture was filtered through a bed of Celite, and the celite pad was washed with ethyl acetate (3×5 mL). The filtrate was concentrated, and the crude residue was purified by silica gel column chromatography eluted with 50% EtOAc in hexane to give 0.14 g (58% yiled) of the titled compound.

$^1$H-NMR (400 MHz, DMSO-d$_6$) δ (ppm) 1.36 (t, 3H, J=7.1 Hz), 3.58 (s, 3H), 4.39 (q, 2H, J=7.1 Hz), 7.45 (t, 2H, J=8.7 Hz), 7.58 (dd, 1H, J=8.3, 4.2 Hz), 7.85-8.0 (m, 3H), 8.05-8.15 (m, 2H), 8.38 (d, 1H, J=8.1 Hz), 8.92 (d, 1H, J=3.4 Hz), 11.36 (s, 1H); LCMS m/z [M+H]$^+$451.0.

(d) 5-(4-fluorobenzamido)-2-[methyl(quinolin-6-yl)amino]thiazole-4-carboxamide

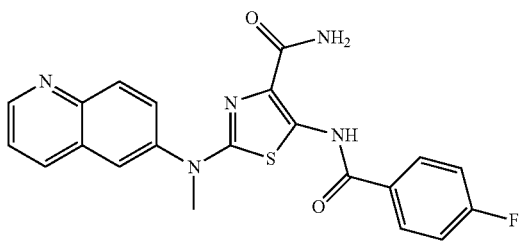 [SMILES: CN(c1ccc2ncccc2c1)c1nc(C(N)=O)c(NC(=O)c2ccc(F)cc2)s1]

To a solution of ethyl 5-(4-fluorobenzamido)-2-[methyl(quinolin-6-yl)-amino]thiazole-4-carboxylate (0.14 g, 0.31 mmol) in THF (5 mL) was added 7N NH$_3$-MeOH (5mL), and the mixture was heated at 80° C. for 16 hrs in a sealed tube. The solvent was evaporated in vacuo, and the resulting solids were purified by silica gel chromatography eluted with EtOAc to give 110 mg (84% yield) of the titled compound.

$^1$H-NMR (400 MHz, DMSO-d$_6$) δ (ppm) 3.58 (s, 3H), 7.25-7.4 (m, 2H), 7.53 (dd, 1H, J=8.2, 3.8 Hz), 7.8-8.1 (m, 5H), 8.34 (d, 1H, J=7.9 Hz), 8.85 (s, 1H); LCMS m/z [M+H]$^+$ 422.0.

(e) 2-[methyl(quinolin-6-yl)amino]-5-[4-(4-methylpiperazin-1-yl]benzamido)thiazole-4-carboxamide

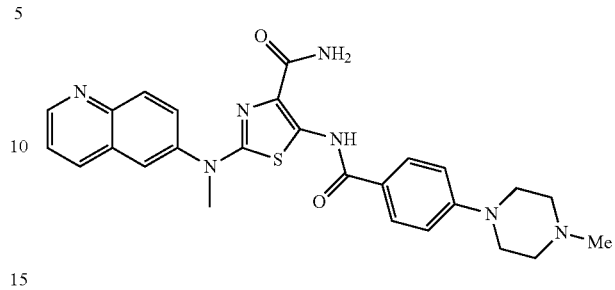

A mixture of 5-(4-fluorobenzamido)-2-[methyl(quinolin-6-yl)amino]thiazole-4-carboxamide (100 mg, 0.24 mmol) and 1-methyl-piperazine (110 mg, 1.10 mmol) in NMP (3 mL) was heated at 150° C. for 1.5 hrs. The reaction mixture was diluted with ice-water (5 mL), and the resulting solids were collected by filtration and washed successively with water and ether to give 0.065 g (54% yield) of the titled compound.

$^1$H-NMR (400 MHz, DMSO-d$_6$) δ (ppm) 2.22 (s, 3H), 2.4-2.5 (m, 4H), 3.25-3.4 (m, 4H), 3.62 (s, 3H), 7.06 (d, 2H, J=8.8 Hz), 7.56 (dd, 1H, J=7.8, 3.9 Hz), 7.61 (br, 1H), 7.67 (d, 2H, J=8.3 Hz), 7.79 (br, 1H), 7.95 (d, 1H, J=8.8 Hz), 8.04-8.13 (m, 2H), 8.38 (d, 1H, J=7.8 Hz), 8.90 (s, 1H), 12.27 (s, 1H); LCMS m/z [M+H]$^+$502.4.

Example 32

5-[4-(4-methylpiperazin-1-yl)benzamido]-2-(quinolin-4-ylamino)thiazole-4-carboxamide

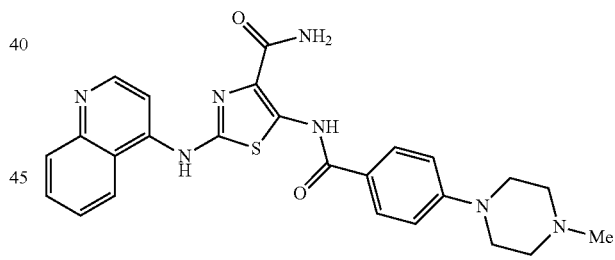

(a) 4-isothiocyanatoquinoline

A mixture of 4-chloroquinoline (300 mg, 1.84 mmol) and silver (1) thiocyanate (607 mg, 3.68 mmol) in anhydrous toluene (15 mL) was stirred at 110° C. for 12 hrs. The reaction mixture was filtered and washed three times with chloroform. The filtrate was concentrated in vacuo to give 0.31 g (90% yield) of the titled compound.

¹H-NMR (400 MHz, DMSO-d₆) δ (ppm) 7.64 (d, 1H, J=8.7 Hz), 7.78 (t, 1H, J=7.3 Hz), 7.89 (td, 1H, J=8.2, 1.2 Hz), 8.09 (d, 1H, J=8.2 Hz), 8.12 (d, 1H, J=8.4 Hz), 8.93 (d, 1H, J=4.6 Hz).

(b) 5-amino-2-(quinolin-4-ylamino)thiazole-4-carboxamide

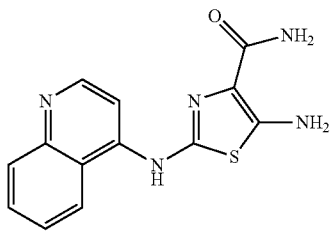 [SMILES: NC(=O)c1nc(Nc2ccnc3ccccc23)sc1N]

A mixture of 4-isothiocyanatoquinoline (0.3 g, 1.6 mmol) and 2-amino-cyanoacetamide (0.26g, 2.68 mmol) in EtOAc (20 mL) was refluxed for 90 min. The reaction mixture was concentrated in vacuo, and the resulting solids were collected and washed with EtOAc to give 0.33 g (contained impurities) of the titled compound which was used in the next step without further purification.
LCMS m/z [M+H]⁺286.0.

(c) 5-(4-fluorobenzamido)-2-(quinolin-4-ylamino)thiazole-4-carboxamide

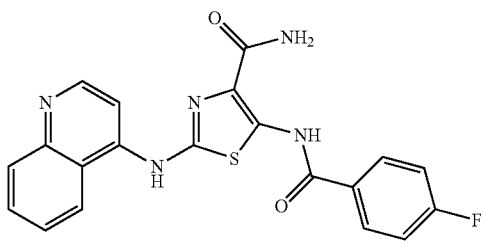 [SMILES: NC(=O)c1nc(Nc2ccnc3ccccc23)sc1NC(=O)c1ccc(F)cc1]

To a mixture of 4-fluorobenzoylchloride (0.16 g, 1 mmol) and a catalytic amount of DMAP in pyridine (5 mL) was added dropwise a solution of 5-amino-2-(quinolin-4-ylamino)thiazole-4-carboxamide (0.25 g, 0.87 mmol) in pyridine (5 mL), and the mixture was stirred for 16 hrs at rt. The reaction mixture was quenched with ice-water. The resulting solids were collected by filteration and washed successively with water, ether, and MeOH to give 0.12 g (33% yield) of the titled compound. LCMS m/z [M+H]⁺408.2 .

(d) 5-[4-(4-methylpiperazin-1-yl)benzamido]-2-(quinolin-4-ylamino)thiazole-4-carboxamide

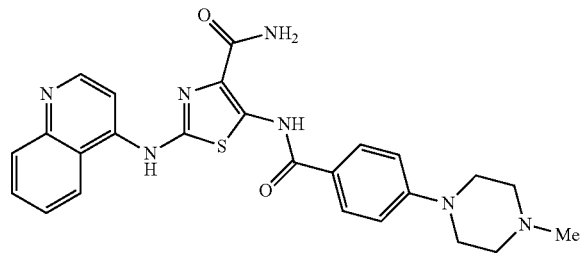 [SMILES: CN1CCN(c2ccc(C(=O)Nc3sc(Nc4ccnc5ccccc45)nc3C(N)=O)cc2)CC1]

A mixture of 5-(4-fluorobenzamido)-2-(quinolin-4-ylamino)thiazole-4-carboxamide (110 mg, 0.27 mmol) and 1-methyl-piperazine (1.5 mL) in NMP (1.5 mL) was heated at 150° C. for 4 hrs. The reaction mixture was diluted with ice water (1 mL). The resulting solids were collected by filtration and washed successively with water and ether, and dried to give 0.090 g (69% yield) of the titled compound.
¹H-NMR (400 MHz, DMSO-d₆) δ (ppm) 2.23 (s, 31-1), 2.4-2.5 (m, 4H), 3.2-3.4 (m, 4H), 7.10 (d, 2H, J=8.3 Hz), 7.57-7.68 (m, 1H), 7.7-7.85 (m,3 H), 7.85-8.06 (m, 3 H), 8.52 (d, 1H, J=7.3 Hz), 8.59-8.87 (m, 2H), 10.42 (s, 1H), 12.54 (s, 1H); LCMS m/z [M+H]⁺488.2.

Example 38

N-methyl-2-(naphthalen-2-ylamino)-5-(thiophene-3-carboxamido)thiazole-4-carboxamide

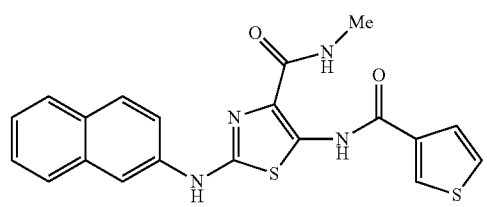 [SMILES: CNC(=O)c1nc(Nc2ccc3ccccc3c2)sc1NC(=O)c1ccsc1]

(a) ethyl 5-amino-2-(naphthalen-2-ylamino)thiazole-4-carboxylate

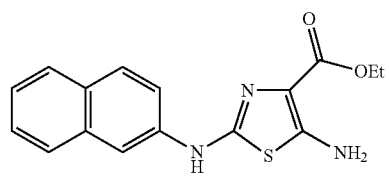 [SMILES: CCOC(=O)c1nc(Nc2ccc3ccccc3c2)sc1N]

A mixture of 2-naphthalenyl isothiocyanate (0.5 g, 2.7 mmol) and ethyl 2-amino-2-cyanoacetate (0.38 g, 2.97 mmol) in EtOH (16 mL) was heated at 80° C. for 3 h. The reaction mixture was cooled to rt, and the solvent was concentrated in vacuo. The resulting solids were collected and washed with n-Hexane-EtOAc (1:1) to give 565 mg (67% yield) of the titled compound.
¹H-NMR (400 MHz, DMSO-d₆) δ (ppm) 1.32 (t, J=7.0 Hz, 3H), 4.23 (q, J=7.0 Hz, 2H), 6.97 (br, 2H), 7.31 (ddd, J=8.0, 6.9, 1.1 Hz, 1H), 7.38-7.46 (m, 2H), 7.67 (d, J=8.3 Hz, 1H), 7.75-7.82 (m, 2H), 8.24 (d, J=2.0 Hz, 1H), 9.83 (s, 1H).

(b) ethyl 2-(naphthalen-2-ylamino)-5-(thiophene-3-carboxamido)thiazole-4-carboxylate

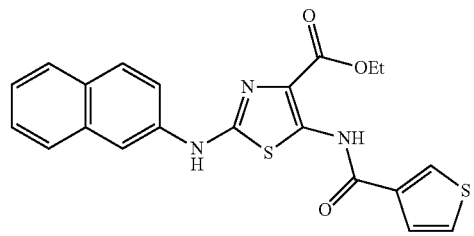 [SMILES: CCOC(=O)c1nc(Nc2ccc3ccccc3c2)sc1NC(=O)c1ccsc1]

To a solution of ethyl 5-amino-2-(naphthalen-2-ylamino) thiazole-4-carboxylate (100 mg, 0.32 mmol) in pyridine (3 mL) was added 3-thiophene carbonyl chloride (61 mg, 0.42 mmol) at 0° C. The mixture was allowed to warm to rt and stirred overnight. The reaction was quenched with ice-water, and the mixture was extracted with EtOAc. The organic layer was washed with water, and dried over Na$_2$SO$_4$. The solvent was evaporated, and the resulting solids were collected and washed with EtOAc to give 55 mg (40% yield) of the titled compound.

$^1$H-NMR (400 MHz, DMSO-d$_6$) δ (ppm) 1.41 (t, J=7.0 Hz, 3 H), 4.42 (q, J=7.1 Hz, 2H), 7.36 (td, J=7.5, 1.3 Hz, 1H), 7.47 (td, J=7.5, 1.3 Hz, 1H), 7.51-7.57 (m, 2H), 7.74 (d, J=8.0 Hz, 1H), 7.79 (dd, J=5.1, 2.9 Hz, 1H), 7.82 (d, J=8.0 Hz, 1H), 7.87 (d, J=8.8 Hz, 1H), 8.39 (d, J=2.3 Hz, 1H), 8.43 (dd, J=3.0, 1.3 Hz, 1H), 10.38 (s, 1H), 11.19 (s, 1H).

(c) N-methyl-2-(naphthalen-2-ylamino)-5-(thiophene-3-carboxamido)thiazole-4-carboxamide

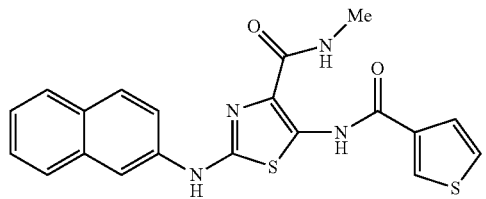 [SMILES: CNC(=O)c1nc(Nc2ccc3ccccc3c2)sc1NC(=O)c1ccsc1]

To a solution of ethyl 2-(naphthalen-2-ylamino)-5-(thiophene-3-carboxamido)thiazole-4-carboxylate (50 mg, 0.118 mmol) in THF (5 mL) was added 40% methylamine in water (0.5 mL) at rt, and the mixture was stirred overnight at rt. To complete the reaction, an additional 40% methylamine in water (0.5 mL) was added to the mixture, and stirring was continued at rt overnight. The solvent was removed, and the residue was triturated with water. The resulting solids were collected by filtration, and the solids were washed successively with water and EtOAc to give 28 mg (58% yield) of the titled compound.

$^1$H-NMR (400 MHz, DMSO-d$_6$) δ (ppm) 2.93 (d, J=4.8 Hz, 3H), 7.34 (t, J=7.4 Hz, 1H), 7.46 (t, J=7.5 Hz, 1H), 7.51 (dd, J=5.1, 1.4 Hz, 1H), 7.54 (dd, J=8.8, 2.3 Hz, 1H), 7.74-7.88 (m, 3H), 8.03 (d, J=8.0 Hz, 1H), 8.34 (dd, J=3.0, 1.3 Hz, 2H), 8.56 (d, J=1.8 Hz, 1H), 10.31 (s, 1H), 12.42 (s, 1H); LCMS m/z [M+H]$^+$408.8.

Example 44

6-{[4-carbamoyl-5-(thiophene-3-carboxamido)thiazol-2-yl]amino}-1-methylquinolin-1-ium iodide

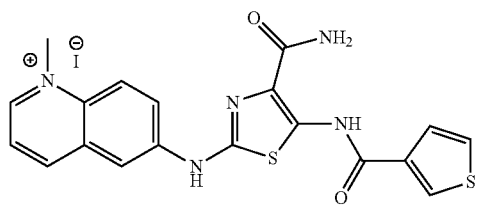 [SMILES: C[n+]1cccc2cc(Nc3nc(C(N)=O)c(NC(=O)c4ccsc4)s3)ccc21 ; [I-]]

To a solution of 2-(quinolin-6-ylamino)-5-(thiophene-3-carboxamido)thiazole-4-carboxamide (50 mg, 0.126 mmol) in DMF (1 mL) was added K$_2$CO$_3$ (50 mg, 0.152 mmol) and. MeI (27 mg, 0.190 mmol) at rt. The mixture was stirred overnight at rt. The reaction was quenched by adding cold-water, and the reaction mixture was diluted with EtOAc. The resulting precipitates were collected by filtration and washed successively with EtOAc and water to afford 10 mg (15% yield) of the titled compound.

$^1$H-NMR (400 MHz, DMSO-d$_6$) δ (ppm) 4.58 (s, 3H), 7.50 (d, 1H, J=5.0 Hz), 7.74-7.86 (m, 1H), 7.96-8.14 (m, 4H), 8.36 (s, 1H), 8.42 (d, 1H, J=9.2 Hz), 9.14 (s, 1H), 9.23 (d, 1H, J=5.6 Hz), 9.34 (d, 1H, J=8.4 Hz), 11.01 (s, 1H), 12.51 (s, 1H); LCMS m/z [M+H]$^+$410.0.

Example 68

2-[(5-methoxynaphthalen-2-yl)amino]-5-(thiophene-3-carboxamido)thiazole-4-carboxamide

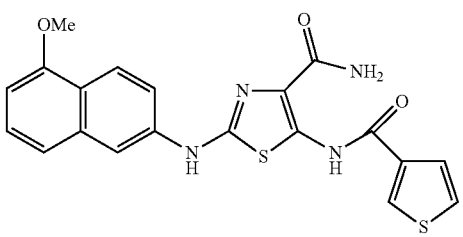 [SMILES: COc1cccc2cc(Nc3nc(C(N)=O)c(NC(=O)c4ccsc4)s3)ccc12]

(a) ethyl 2-bromo-5-(thiophene-3-carboxamide)thiazole-4-carboxylate

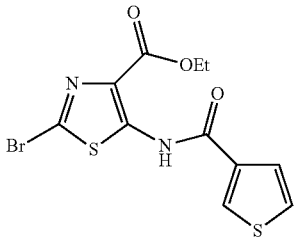 [SMILES: CCOC(=O)c1nc(Br)sc1NC(=O)c1ccsc1]

To a solution of ethyl 5-amino-2-bromothiazole-4-caboxylate in pyridine (0.86 g, 3.42 mmol) in pyridine (16 mL) was added 3-thiophene carbonyl chloride (0.65 g, 4.45 mmol) at 0° C. The mixture was allowed to warm to rt, and stirred overnight. To complete the reaction, 3-thiophene carbonyl chloride (100 mg, 0.68 mmol) was added to the mixture, and the stirring was continued for 6 h. The reaction was quenched by adding ice-water, and the reaction mixture was diluted with EtOAc. The resulting precipitates were collected and washed with successively water and EtOAc to give 0.55 g (45% yield) of the title compound.

$^1$H-NMR (400 MHz, DMSO-d$_6$) δ (ppm) 1.36 (t, 3H, J=7.2 Hz), 4.40 (q, 2H, J=7.2 Hz), 7.56 (dd, 1H, J=5.2, 1.6 Hz), 7.80 (dd, 1H, J=5.2, 2.8 Hz), 8.49 (dd, 1H, J=2.8, 1.6 Hz), 11.34 (s, 1H).

(b) ethyl 2-[(5-methoxynaphthalen-2-yl)amino]-5-(thiophene-3-carboxamido)thiazole-4-carboxylate

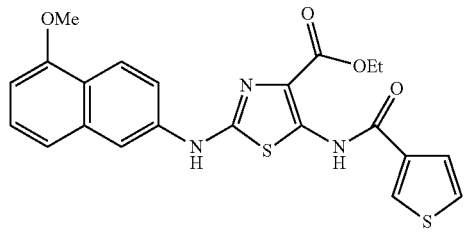 [SMILES: CCOC(=O)c1nc(Nc2ccc3c(OC)cccc3c2)sc1NC(=O)c1ccsc1]

To a mixture of ethyl 2-bromo-5-(thiophene-3-carboxamide)thiazole-4-carboxylate (0.2 g, 0.55 mmol) and 5-methoxynaphthalen-2-ylamine (95 mg, 0.55 mmol) in toluene (10 mL) was added Pd$_2$(dba)$_3$ (50 mg, 0.055 mmol), Xantphos (64 mg, 0.110 mmol) and Cs$_2$CO$_3$ (357 mg, 1.10 mmol), and the mixture was refluxed for 16 h at 110° C. under argon atmosphere. The reaction mixture was filtered through a bed of Celite. The filtrate was concentrated in vacuo. The resulting solids were purified by silica gel chromatography eluted with 50% EtOAc in Hexane to give 110 mg (44% yield) of the titled compound.

$^1$H-NMR (400 MHz, DMSO-d$_6$) δ (ppm) 1.38 (t, 3H, J=7.1 Hz), 3.93 (s, 3H), 4.38 (q, 2H, J=7.1 Hz), 6.80 (d, 1H, J=7.5 Hz), 7.27 (d, 1H, J=8.2 Hz), 7.36 (dd, 1H, J=8.0, 7.9 Hz), 7.46 (dd, 1H, J=9.1, 2.1 Hz), 7.52 (d, 1H, J=4.0 Hz), 7.7-7.8 (m, 1H), 8.05 (d, 1H, J=9.0 Hz), 8.33 (d, 1H, J=2.0 Hz), 8.40 (d, 1H, J=1.6 Hz), 10.36 (s, 1H), 11.16 (s, 1H); LCMS m/z [M+H]$^+$454.2.

(c) 2-[(5-methoxynaphthalen-2-yl)amino]-5-(thiophene-3-carboxamido)thiazole-4-carboxamide

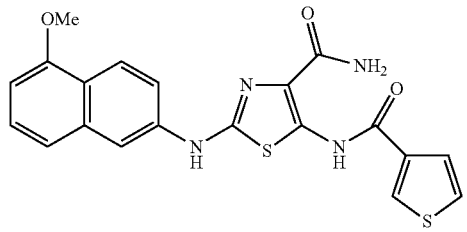 [SMILES: COc1cccc2cc(Nc3nc(C(N)=O)c(NC(=O)c4ccsc4)s3)ccc12]

To a solution of ethyl 2-[(5-methoxynaphthalen-2-yl)amino]-5-(thiophene-3-carboxamido)-thiazole-4-carboxylate (0.105 g, 0.23 mmol) in THF (5 mL) was added 7N NH$_3$—MeOH (5 mL), and the mixture was heated at 80° C. for 16 hrs in a sealed tube. The solvent was evaporated in vacuo, and the resulting solids were collected by filtration and washed with MeOH to give 90 mg (92% yield) of the titled compound.

$^1$H-NMR (400 MHz, DMSO-d$_6$) δ (ppm) 3.94 (s, 31-1), 6.79 (d, 1H, J=7.8 Hz), 7.35 (t, 1H, J=7.8 Hz), 7.45-7.55 (m, 2H), 7.60 (d, 1H, J=7.8 Hz), 7.75-7.93 (m, 3H), 8.06 (d, 1H, J=9.3 Hz), 8.33 (br, 1H), 8.47 (s, 1H), 10.29 (s, 1H), 12.45 (br, 1H); LCMS m/z [M+H]$^+$425.2.

Example 81

5-(2-cyclopentylacetamido)-2-(naphthalen-2-ylamino)thiazole-4-carboxamide

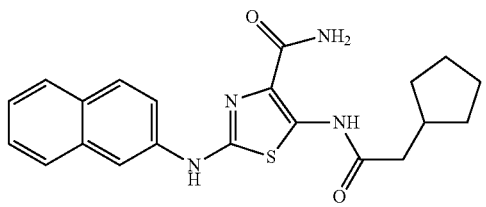 [SMILES: NC(=O)c1nc(Nc2ccc3ccccc3c2)sc1NC(=O)CC1CCCC1]

A solution of 2-cyclopentylacetyl chloride (0.35 mL, 2.64 mmol) in THF (2 mL) was added dropwise to a mixture of 5-amino-2-(naphthalen-2-ylamino) thiazole-4-carboxamide (0.15 g, 0.53 mmol) and pyridine (2 mL) in THF (10 mL) at 0° C., and the mixture was stirred for 16 hrs at rt. The reaction mixture was quenched with ice-water. The resulting solids were collected by filtration and washed successively with ether and EtOAc to give 0.12 g (58% yield) of the titled compound.

$^1$H-NMR (400 MHz, DMSO-d$_6$) δ (ppm) 1.11-1.27 (m, 2H), 1.44-1.56 (m, 2H), 1.61 (d, 2H, J=6.4 Hz), 1.79 (d, 2H, J=6.8 Hz), 2.1-2.3 (m, 2H), 2.4-2.6 (m, 2H), 7.32 (t, 1H, J=7.3 Hz), 7.39-7.46 (m, 1H), 7.50 (d, 1H, J=8.8 Hz), 7.68-7.86 (m, 4H), 8.02 (d, 1H, J=8.3 Hz), 8.51 (s, 1H), 10.22 (s, 1H), 11.48 (s, 1H); LCMS m/z [M+H]$^+$394.8.

Example 92

5-(6-morpholinohexanamido)-2-(naphthalen-2-ylamino)thiazole-4- carboxamide

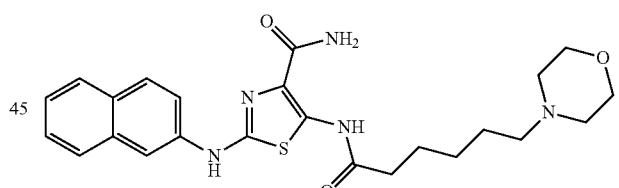

(a) 5-(6-bromohexanamido)-2-(naphthalen-2-ylamino)thiazole-4-carboxamide

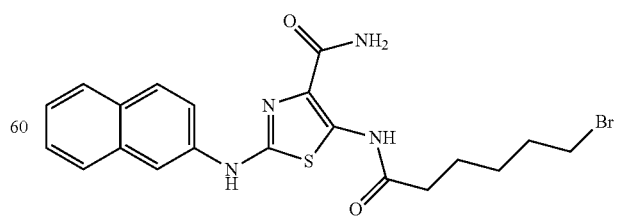

A solution of 6-bromohexanoyl chloride (0.82 mL, 5.28 mmol) in THF (4 mL) was added dropwise to a mixture of 5-amino-2-(naphthalen-2-ylamino)thiazole-4-carboxamide (0.30 g, 1.06 mmol) and pyridine (4 mL) in THF (20 mL) at 0° C., and the mixture was stirred for 16 hrs at rt. The reaction mixture was quenched with ice-water. The resulting solids were collected by filtration and washed with ether and EtOAc to give 0.45 g (92% yield) of the titled compound.

$^1$H-NMR (400 MHz, DMSO-$d_6$) δ (ppm) 1.35-1.5 (m, 2H), 1.55-1.7 (m, 2H), 1.75-1.9 (m, 2H), 2.45-2.6 (m, 2H), 3.54 (t, 2H, J=6.6 Hz), 7.32 (dd, 1H, J=7.7, 7.2 Hz), 7.45 (t, 1H, J=7.4 Hz), 7.50 (dd, 1H, J=8.8, 1.8 Hz), 7.71 (br, 1H), 7.75 (br, 1H), 7.80 (t, 2H, J=9.4 Hz), 8.02 (d, 1H, J=8.3 Hz), 8.50 (b, 1H), 10.19 (s, 1H), 11.46 (s, 1H).

(b) 5-(6-morpholinohexanamido)-2-(naphthalen-2-ylamino)thiazole-4-carboxamide

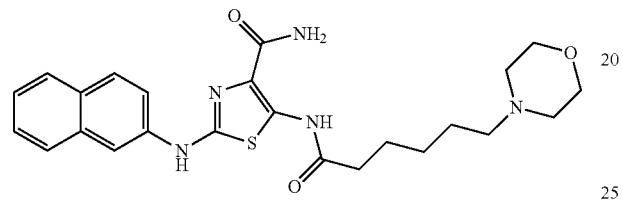

A mixture of 5-(6-bromohexanamido)-2-(naphthalen-2-ylamino)thiazole-4-carboxamide (150 mg, 0.32 mmol) and morpholine (0.06 mL, 0.69 mmol) in DMA (0.5 ml) was heated at 120° C. for 1.5 hrs in a sealed tube. The reaction mixture was then diluted with ice-water. The resulting solids were collected by filtration and washed successively with ether and MeOH to give 135 mg (90% yield) of the titled compound.

$^1$H-NMR (400 MHz, DMSO-$d_6$) δ (ppm) 1.25-1.38 (m, 2H), 1.39-1.50 (m, 2H), 1.55-1.68 (m, 2H), 2.25 (t, 2H, J=7.1 Hz), 2.29-2.37 (m, 4H), 3.2-3.35 (m, 2H), 3.47-3.59 (m, 4H), 7.28-7.36 (m, 1H), 7.43 (t, 1H, J=7.6 Hz), 7.50 (d, 1H, J=8.8 Hz), 7.68-7.76 (m, 2H), 7.80 (t, 2H, J=9.3 Hz), 8.02 (d, 1H, J=7.8 Hz), 8.50 (s, 1H), 10.19 (s, 1H), 11.47 (s, 1H); LCMS m/z [M+H]$^+$468.2.

Example 103

5-(4-aminobutanamido)-2-(naphthalen-2-ylamino)thiazole-4-carboxamide

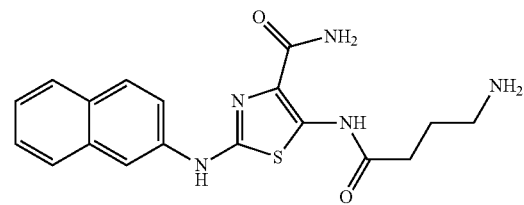 [SMILES: NCCCC(=O)Nc1sc(Nc2ccc3ccccc3c2)nc1C(N)=O]

A mixture of 2-(naphthalen-2-ylamino)-5-(4-phthalimidobutanamido)thiazole-4-carboxamide (180 mg, 0.36 mmol) and 33% methylamine in EtOH (5 mL) was heated at 70° C. for 4 hrs. The solvent was removed, and water was added to the residual oil. The resulting solids were collected by filtration and washed successively with ether, DCM and MeOH to give 38 mg (29% yield) of the titled compound.

$^1$H-NMR (400 MHz, DMSO-$d_6$) δ (ppm) 1.67-1.84 (m, 2H), 2.55-2.62 (m, 2H), 2.72 (t, 2H, J=6.8 Hz), 7.32 (t, 1H, J=7.3 Hz), 7.43 (t, 1H, J=7.3 Hz), 7.50 (d, 1H, J=8.3 Hz), 7.68-7.84 (m, 4H), 8.01 (d, 1H, J=7.8 Hz), 8.50 (s, 1H), 10.20 (br, 1H); LCMS m/z [M+H]$^+$370.4.

Example 106

N-(2-hydroxyethyl)-5-{4-[(2-hydroxyethyl)amino]benzamido}-2-(naphthalen-2-ylamino)thiazole-4-carboxamide

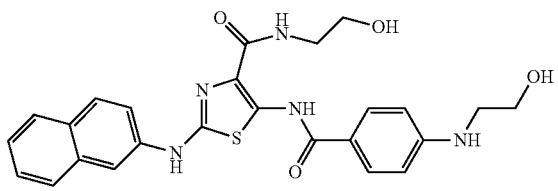 [SMILES: O=C(Nc1sc(Nc2ccc3ccccc3c2)nc1C(=O)NCCO)c1ccc(NCCO)cc1]

(a) Ethyl 5-(4-fluorobenzamido)-2-(naphthalen-2-ylamino)thiazole-4-carboxylate

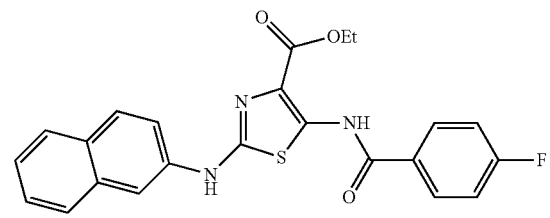 [SMILES: CCOC(=O)c1nc(Nc2ccc3ccccc3c2)sc1NC(=O)c1ccc(F)cc1]

To a solution of ethyl 5-amino-2-(naphthalen-2-ylamino)thiazole-4-carboxylate (170 mg, 0.54 mmol) in pyridine (3 mL) was added 4-fluorobenzoyl chloride (0.09 mL, 0.81 mmol) at 0° C. The mixture was allowed to warm to rt, and stirred overnight. The reaction mixture was diluted with EtOAc, and washed with water. The organic layer was dried over Na$_2$SO$_4$ and concentrated in vacuo. The residue was triturated with EtOAc, and the resulting solids were collected by filtration to give 140 mg (59% Yield) of the titled compound.

$^1$H-NMR (400 MHz, DMSO-$d_6$) δ (ppm) 1.42 (t, 3H, J=7.0 Hz), 4.42 (q, 2H, J=7.0 Hz), 7.33-7.40 (m, 1H), 7.45-7.52 (m, 3H), 7.54 (dd, 1H, J=8.8, 2.0 Hz), 7.74 (d, 1H, J=8.0 Hz), 7.83 (d, 1H, J=8.0 Hz), 7.87 (d, 1H, J=9.0 Hz), 8.03 (dd, 2H, J=8.8, 5.3 Hz), 8.39 (d, 1H, J=1.8 Hz), 10.41 (s, 1H), 11.43 (s, 1H).

(b) N-(2-hydroxyethyl)-5-{4-[(2-hydroxyethyl)amino]benzamido}-2-(naphthalen-2-yl-amino)thiazole-4-carboxamide

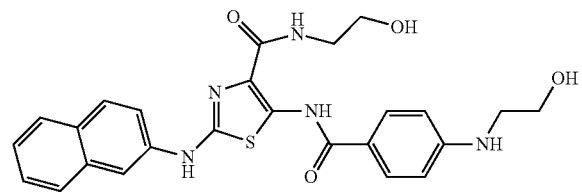 [SMILES: O=C(Nc1sc(Nc2ccc3ccccc3c2)nc1C(=O)NCCO)c1ccc(NCCO)cc1]

A solution of Ethyl 5-(4-fluorobenzamido)-2-(naphthalen-2-ylamino)thiazole-4-carboxylate (25 mg, 0.06 mmol) and 2-aminoethanol (0.024 mL, 0.40 mmol) in NMP (0.5 mL)

was treated using a microwave synthesizer for 70 min (Biotage, 150° C.). The reaction mixture was diluted with EtOAc. The organic layer was washed with H2O, dried over Na$_2$SO$_4$ and concentrated in vacuo. The resulting residue was purified by silica gel chromatography eluted with 2.5% MeOH in DCM to give 7 mg (25% yield) of the titled compound.

$^1$H-NMR (400 MHz, DMSO-d$_6$) δ (ppm) 3.20 (q, 2H, J=5.8 Hz), 3.48 (q, 2H, J=6.1 Hz), 3.54-3.66 (m, 4H), 4.76 (t, 1H, J=5.5 Hz), 4.91 (t, 1H, J=5.4 Hz), 6.60 (t, 1H, J=5.5 Hz), 6.73 (d, 2H, J=8.8 Hz), 7.28-7.38 (m, 1H), 7.46 (t, 1H, J=7.2 Hz), 7.52 (dd, 1H, J=8.9, 2.1 Hz), 7.66 (d, 2H, J=8.5 Hz), 7.81 (d, 1H, J=8.5 Hz), 7.84 (d, 1H, J=8.5 Hz), 7.94 (d, 1H, J=8.3 Hz), 8.14 (t, 1H, J=5.9 Hz), 8.52 (s, 1H), 10.29 (s, 1H), 12.29 (s, 1H); LCMS m/z [M+H]$^+$492.0.

Example 110

5-(4-hydroxybenzamido)-2-(naphthalen-2-ylamino)thiazole-4-carboxamide

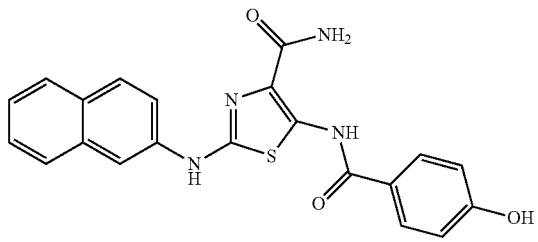 [SMILES: NC(=O)c1nc(Nc2ccc3ccccc3c2)sc1NC(=O)c1ccc(O)cc1]

To a mixture of 4-{[4-carbamoyl-2-(naphthalen-2-ylamino)thiazol-5-yl]carbamoyl}phenyl acetate (100 mg, 0.22 mmol) in MeOH (10 mL) was added K$_2$CO$_3$ (93 mg, 0.67 mmol) at rt, and the mixture was stirred for 1 h. The reaction mixture was concentrated, and the residue was diluted with water and extracted with EtOAc. The organic layer was dried over Na$_2$SO$_4$ and concentrated in vacuo. The resulting solids were collected by filtration and washed with MeOH to give 60 mg (68% yield) of the titled compound.

$^1$H-NMR (400 MHz, DMSO-d$_6$) δ (ppm) 6.96 (d, 2H, J=8.8 Hz), 7.28-7.37 (m, 1H), 7.44 (t, 1H, J=7.3 Hz), 7.53 (d, 1H, J=7.3 Hz), 7.71-7.91 (m, 6H), 8.04 (d, 1H, J=8.3 Hz), 8.55 (s, 1H), 10.27 (s, 1H), 10.41 (s, 1H), 12.56 (s, 1H); LCMS m/z [M−H]403.0.

Example 111

5-[4-(2-hydroxyethoxy)benzamido]-2-(naphthalen-2-ylamino)thiazole-4-carboxamide

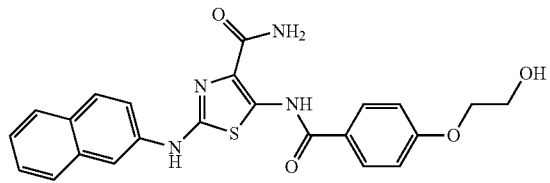 [SMILES: NC(=O)c1nc(Nc2ccc3ccccc3c2)sc1NC(=O)c1ccc(OCCO)cc1]

To a mixture of 5-(4-hydroxybenzamido)-2-(naphthalen-2-ylamino)thiazole-4-carboxamide (200 mg, 0.5 mmol) and 2-bromoethanol (123 mg, 1.0 mmol) in DMF (10 mL) was added K$_2$CO$_3$ (136 mg, 1.0 mmol), and the mixture was stirred at 80° C. for 16 hrs. The reaction mixture was diluted with water and extracted with EtOAc. The organic layer was dried over Na$_2$SO$_4$ and concentrated in vacuo. The residue was purified by column chromatography eluted with 3.5% MeOH in DCM to give 40 mg (18% yield) of the titled compound.

$^1$H-NMR (400 MHz, DMSO-d$_6$) δ (ppm) 3.65-3.84 (m, 2H), 4.01-4.17 (m, 2H,), 4.92 (t, 1H, J=8.0 Hz), 7.17 (d, 2H, J=8.3 Hz), 7.33 (t, 1H, J=7.3 Hz), 7.44 (t, 1H, J=7.8 Hz), 7.53 (d, 1H, J=8.8 Hz), 7.75-7.93 (m, 6H), 8.04 (d, 1H, J=7.8 Hz), 8.55 (s, 1H), 10.28 (s, 1H), 12.63 (br, 1H); LCMS m/z [M+H]$^+$449.0.

The following compounds in Table 4 are additional representative examples of formula (I), as provided by the present invention, and were prepared according to the examples indicated or by processes analogous thereto using the appropriate reagents, starting materials and methods well known to those skill in the art.

TABLE 4

| Example No. | $^1$H-NMR (400 MHz) δ (ppm) | LCMS m/z [M + H]$^+$ | Synthetic Method |
|---|---|---|---|
| 4 | (DMSO-d$_6$): 3.87 (s, 3H), 7.18 (d, 2H, J = 8.5 Hz), 7.77 (br, 1H), 7.85-8.0 (m, 5H,), 8.09 (d, 1H, J = 8.0 Hz), 8.83-8.95 (m, 3H), 10.74 (s, 1H), 12.66 (s, 1H). | 420.2 | Similar to Example 3 |
| 5 | (DMSO-d$_6$): 3.87 (s, 3H), 7.18 (d, 2H, J = 8.5 Hz), 7.58-7.62 (m, 2H), 7.85-8.0 (m, 4H), 8.04 (s, 1H), 8.18-8.22 (m, 1H), 8.89 (s, 1H), 9.17 (s, 1H), 10.79 (s, 1H), 12.67 (s, 1H). | 420.2 | Similar to Example 3 |
| 6 | (DMSO-d$_6$): 3.87 (s, 3H), 7.17 (d, 2H, J = 8.5 Hz), 7.69 (br, 1H), 7.85-7.95 (m, 3H), 8.00 (d, 1H, J = 9.1), 8.15 (d, 1H, J = 9.2 Hz), 8.39 (s, 1H), 8.74 (s, 1H), 8.83 (s, 1H), 10.68 (s, 1H), 12.56 (s, 1H). | 421.2 | Similar to Example 3 |
| 7 | (DMSO-d$_6$): 3.88 (s, 3H), 7.18 (d, 2H, J = 8.7 Hz), 7.26 (br, 1H), 7.29 (d, 1H, J = 9.0 Hz), 7.42 (t, 1H, J = 7.4 Hz), 7.72 (t, 1H, J = 7.6 Hz), 7.82-7.9 (m, 3H), 7.92 (d, 2H, J = 8.6 Hz), 8.22 (d, 1H, J = 8.9 Hz), 11.45 (s, 1H), 12.42 (s, 1H). | 420.4 | Similar to Example 3 |
| 8 | (DMSO-d$_6$): 7.26-7.38 (m, 1H) 7.39-7.58 (m, 4H) 7.72-8.11 (m, 7H) 8.55 (s, 1H) 10.32 (s, 1H) 12.72 (s, 1H) | 407.0 | Similar to Example 3 |

TABLE 4-continued

| Example No. | ¹H-NMR (400 MHz) δ (ppm) | LCMS m/z [M + H]⁺ | Synthetic Method |
|---|---|---|---|
| 11 | (DMSO-d$_6$): 2.20 (s, 6H), 2.42-2.47 (m, 2H), 3.16-3.23 (m, 2H), 6.44 (br, 1H), 6.73 (d, 2H, J = 7.8 Hz), 7.28-7.37 (m, 1H), 7.44 (t, 1H, J = 7.1 Hz) 7.52 (d, 1H, J = 8.3 Hz) 7.66 (d, 2H, J = 7.8 Hz) 7.75-7.88 (m, 4H) 8.03 (d, 1H, J = 7.8 Hz) 8.54 (br, 1H) 10.23 (s, 1H) 12.42 (s, 1H). | 475.2 | Similar to Example 10 |
| 12 | (DMSO-d$_6$): 2.23 (s, 3H), 2.41-2.47 (m, 4H), 3.25-3.5 (m, 4H), 7.10 (d, 2H, J = 8.6 Hz), 7.27-7.38 (m, 1H), 7.44 (t, 1H, J = 7.3 Hz), 7.52 (d, 1H, J = 7.6 Hz), 7.67-7.91 (m, 6H), 8.04 (d, 1H, J = 8.1 Hz), 8.56 (br, 1H), 10.26 (s, 1H), 12.54 (s, 1H). | 487.4 | Similar to Example 10 |
| 13 | (DMSO-d$_6$): 1.3-1.45 (m, 2H), 1.45-1.6 (m, 4H), 2.3-2.5 (m, 6H), 3.15-3.3 (m, 2H), 6.42 (t, 1H, J = 5.5 Hz), 6.72 (d, 2H, J = 8.7 Hz), 7.32 (t, 1H, J = 6.9 Hz), 7.44 (t, 1H, J = 6.8 Hz), 7.52 (t, 1H, J = 8.7 Hz), 7.65 (d, 2H, J = 8.2 Hz), 7.75-7.9 (m, 4H), 8.03 (d, 1H, J = 8.3 Hz), 8.54 (s, 1H), 10.22 (s, 1H), 12.42 (s, 1H). | 515.4 | Similar to Example 10 |
| 14 | (DMSO-d$_6$): 2.89 (t, 2H, J = 7.1 Hz), 3.38-3.47 (m, 2H), 6.75 (d, 3H, J = 8.1 Hz), 7.33 (d, 3H, J = 5.6 Hz), 7.44 (t, 1H, J = 7.6 Hz), 7.52 (d, 1H, J = 8.6 Hz), 7.67 (d, 2H, J = 8.6 Hz), 7.75-7.86 (m, 4H), 8.04 (d, 1H, J = 8.1 Hz), 8.48 (d, 2H, J = 5.6 Hz), 8.55 (s, 1H), 10.24 (s, 1H), 12.44 (s, 1H). | 509.2 | Similar to Example 10 |
| 15 | (DMSO-d$_6$): 3.2-3.35 (m, 4H), 3.68-3.83 (m, 4H), 7.11 (d, 2H, J = 8.3 Hz), 7.28-7.38 (m, 1H), 7.44 (t, 1H, J = 7.3 Hz), 7.53 (d, 1H, J = 8.8 Hz), 7.7-7.9 (m, 6H), 8.04 (d, 1H, J = 8.3 Hz), 8.55 (br, 1H), 10.26 (s, 1H), 12.55 (s, 1H). | 474.2 | Similar to Example 10 |
| 16 | (DMSO-d$_6$): 6.06 (s, 2H), 6.67 (d, 2H, J = 7.6 Hz), 7.33 (d, 2H, J = 7.1 Hz), 7.39-7.48 (m, 1H), 7.52 (d, 1H, J = 7.6 Hz), 7.61 (d, 2H, J = 8.1 Hz), 7.73-7.88 (m, 4H), 8.03 (d, 1H, J = 7.6 Hz), 8.54 (br, 1H), 10.22 (s, 1H), 12.40 (s, 1H). | 404.2 | Similar to Example 9 |
| 18 | (DMSO-d$_6$): 2.3-2.45 (m, 4H), 3.5-3.65 (m, 6H), 7.33 (t, 1H, J = 7.2 Hz), 7.44 (t, 1H, J = 7.2 Hz), 7.5-7.6 (m, 3H), 7.75-7.85 (m, 2H), 7.85-7.95 (m, 4H), 8.05 (d, 1H, J = 8.3 Hz), 8.56 (s, 1H), 10.32 (s, 1H), 12.71 (s, 1H). | 488.0 | Similar to Example 17 |
| 20 | (DMSO-d$_6$): 2.19 (s, 6H), 3.52 (s, 2H), 7.28-7.37 (m, 1H), 7.44 (t, 1H, J = 7.1 Hz), 7.55 (d, 3H, J = 7.6 Hz), 7.81 (dd, 2H, J = 11.9, 8.8 Hz), 7.85-7.98 (m, 4H), 8.05 (d, 1 H, J = 8.1 Hz), 8.56 (br, 1H), 10.33 (s, 1H), 12.72 (s, 1H). | 446.4 | Similar to Example 17 |
| 23 | (DMSO-d$_6$): 3.93 (s, 2H), 7.33 (t, 1H, J = 7.2 Hz), 7.44 (t, 1H, J = 7.4 Hz), 7.53 (d, 1H, J = 8.6 Hz), 7.61 (d, 2H, J = 7.8 Hz), 7.75-7.85 (m, 2H), 7.85-7.95 (m, 3H), 8.04 (d, 1H, J = 7.8 Hz), 8.28 (s, 1H), 8.55 (s, 1H), 10.31 (s, 1H). | 418.0 | Similar to Example 17 |
| 25 | (DMSO-d$_6$): 2.23 (s, 3H), 2.35-2.5 (m, 4H), 3.3-3.4 (m, 4H), 7.10 (d, 2H, J = 8.8 Hz), 7.59 (d, 1H, J = 8.8 Hz), 7.76 (d, 2H, J = 8.8 Hz), 7.86-8.04 (m, 4H), 8.38 (d, 1H, J = 5.4 Hz), 8.60-8.67 (m, 1H), 9.09 (s, 1H), 10.55 (s, 1H), 12.56 (s, 1H). | 488.2 | Similar to Example 24 |
| 26 | (DMSO-d$_6$): 2.23 (s, 3H), 2.4-2.5 (m, 4 H), 3.25-3.5 (m, 4H), 7.09 (d, 2H, J = 8.3 Hz), 7.58 (dd, 1H, J = 8.6, 4.2 Hz), 7.62-7.82 (m, 5H), 8.18 (s, 1H), 8.65 (d, 1H, J = 7.3 Hz), 8.81 (d, 1H, J = 8.8 Hz), 8.91 (d, 1H, J = 2.9 Hz), 10.05 (s, 1H), 12.45 (s, 1H). | 488.2 | Similar to Example 24 |
| 27 | (DMSO-d$_6$): 2.23 (s, 3H), 2.4-2.5 (m, 4H), 3.25-3.4 (m, 4H), 7.10 (d, 2H, J = 7.8 Hz), 7.44-7.70 (m, 3H), 7.68-7.90 (m, 3H), 8.38 (d, 1H, J = 8.3 Hz), 8.82-9.06 (m, 2H), 10.60 (s, 1H), 12.50 (s, 1H). | 488.2 | Similar to Example 24 |
| 29 | (DMSO-d$_6$): 3.05 (s, 3H), 3.52 (d, 2H, J = 5.5 Hz), 3.58 (t, 2H, J = 5.6 Hz), 4.77 (t, 1H, J = 5.4 Hz), 6.85 (d 2H, J = 9.0 Hz,), 7.30-7.36 (m, 1H), 7.44 (t, 1H, J = 7.2 Hz), 7.51 (dd, 1H, J = 8.8, 2.0 Hz), 7.72 (d, 2H, J = 8.8 Hz), 7.77-7.87 (m, 4H), 8.05 (d, 1H, J = 8.0 Hz), 8.57 (s, 1H), 10.26 (s, 1H), 12.48 (s, 1H). | 462.0 | Similar to Example 10 |
| 30 | (DMSO-d$_6$): 1.13 (d, 3H, J = 6.3 Hz), 2.97-3.11 (m, 2H), 3.77-3.89 (m, 1H), 4.77 (d, 1H, J = 4.8 Hz), 6.58 (t, 1H, J = 5.6 Hz), 6.74 (d, 2H, J = 8.8 Hz), 7.27-7.36 (m, 1H), 7.44 (t, 1H, J = 7.5 Hz), 7.52 (dd, 1H, J = 8.9, 2.1 Hz), 7.65 (d, 2H, J = 8.5 Hz), 7.75-7.85 (m, 4H), 8.04 (d, 1H, J = 8.3 Hz), 8.55 (s, 1H), 10.23 (s, 1H), 12.42 (s, 1H). | 462.0 | Similar to Example 10 |

TABLE 4-continued

| Example No. | ¹H-NMR (400 MHz) δ (ppm) | LCMS m/z [M + H]⁺ | Synthetic Method |
|---|---|---|---|
| 31 | (DMSO-d₆): 2.21 (s, 3H), 2.35-2.5 (m, 4H), 3.25-3.45 (m, 4H), 3.60 (s, 3H), 7.02 (d, 2H, J = 9.3 Hz), 7.51-7.67 (m, 4H), 7.75 (t, 2H, J = 7.6 Hz), 7.95 (d, 1H, J = 7.3 Hz), 8.12 (d, 1H, J = 8.3 Hz), 8.22 (s, 1H), 8.52 (d, 1H, J = 8.3 Hz), 8.93 (d, 1H, J = 3.9 Hz), 12.15 (s, 1H). (as a formate salt) | 502.4 | Similar to Example 28 |
| 33 | (DMSO-d₆): 6.28 (s, 1H), 6.75 (s, 1H), 7.11 (s, 1H), 7.32 (s, 1H), 7.4-7.6 (m, 2H), 7.6-8.0 (m, 4H), 8.04 (d, J = 7.4 Hz, 1H), 8.56 (s, 1H), 10.25 (s, 1H), 12.09 (s, 1H), 12.22 (s, 1H). | 378.4 | Similar to Example 2 |
| 34 | (DMSO-d₆): 2.55 (s, 3H), 7.02 (d, J = 2.7 Hz, 1H), 7.02 (d, 1H, J = 2.7 Hz), 7.33 (dd, J = 7.7, 7.1 Hz, 1H), 7.44 (dd, J = 7.4, 7.0 Hz, 1H), 7.51 (dd, J = 8.0, 1.6 Hz, 1H), 7.56 (d, J = 3.6 Hz, 1H), 7.75-7.95 (m, 4H), 8.04 (d, J = 8.3 Hz, 1H), 8.54 (s, 1H), 10.30 (s, 1H), 12.49 (s, 1H). | 409 | Similar to Example 2 |
| 35 | (DMSO-d₆): 7.03 (d, J = 5.3 Hz, 1H), 7.08 (s, 1H), 7.33 (t, J = 6.8 Hz, 1H), 7.44 (t, J = 7.3 Hz, 1H), 7.46-7.6 (m, 2H), 7.74-7.95 (m, 4H), 8.05 (d, J = 8.4 Hz, 1H), 8.56 (s, 1H), 10.28 (s, 1H), 12.26 (s, 1H), 12.39 (s, 1H). | 434 | Similar to Example 2 |
| 36 | (DMSO-d₆): 3.93 (s, 3H), 6.21 (s, 1H), 6.79 (s, 1H), 7.16 (s, 1H), 7.3-7.4 (m, 1H), 7.42 (t, J = 7.4 Hz, 1H), 7.52 (d, J = 8.5 Hz, 1H), 7.7-7.9 (m, 4H), 8.03 (d, J = 7.9 Hz, 1H), 8.53 (s, 1H), 10.24 (s, 1H), 12.28 (s, 1H). | 392.2 | Similar to Example 2 |
| 37 | (DMSO-d₆): 7.33 (t, J = 7.1 Hz, 1H), 7.44 (t, J = 7.2 Hz, 1H), 7.46-7.55 (m, 2H), 7.7-7.85 (m, 3H), 7.85-8.0 (m, 2H), 8.05 (d, J = 8.0 Hz, 1H), 8.31 (s, 1H), 8.56 (s, 1H), 10.31 (s, 1H), 12.47 (s, 1H). | 394.8 | Similar to Example 3 |
| 39 | (DMSO-d₆): 7.50 (d, 1H, J = 4.9 Hz), 7.61-7.70 (m, 1H), 7.71-7.84 (m, 3H), 7.87 (s, 1H), 8.28 (d, 1H, J = 5.9 Hz), 8.34 (s, 1H), 8.56 (d, 1H, J = 5.9 Hz), 8.93 (d, 1 H, J = 7.8 Hz), 9.29 (s, 1H), 10.10 (s, 1H), 12.40 (s, 1H). | 396.4 | Similar to Example 3 |
| 40 | (DMSO-d₆): 7.49 (d, 1H, J = 4.9 Hz), 7.63 (dd, 1H, J = 8.8, 3.9 Hz), 7.68-7.82 (m, 4H), 7.86 (br, 1H), 8.34 (br, 1H), 8.71 (d, 1H, J = 7.8 Hz), 8.89 (d, 1H, J = 8.8 Hz), 8.95 (d, 1H, J = 3.4 Hz), 10.16 (s, 1H), 12.39 (s, 1H). | 396.4 | Similar to Example 3 |
| 41 | (DMSO-d₆): 7.37-7.55 (m, 2H), 7.70 (d, J = 9.3 Hz, 1H), 7.76-7.84 (m, 1H), 7.87-7.99 (m, 3H), 8.33 (br, 1H), 8.49 (d, 1H, J = 7.8 Hz), 8.61-8.74 (m, 2H), 10.47 (s, 1H), 12.48 (s, 1H). | 396.2 | Similar to Example 3 |
| 42 | (DMSO-d₆): 7.35 (dd, 1H, J = 7.3, 3.9 Hz), 7.50 (d, 1H, J = 4.4 Hz), 7.62 (br, 1H), 7.79 (br, 1H), 7.85-8.02 (m, 3H), 8.19-8.30 (m, 2H), 8.34 (s, 1H), 8.80 (s, 1H), 10.52 (s, 1H), 12.36 (s, 1H). | 396.2 | Similar to Example 3 |
| 43 | (DMSO-d₆): 7.44-7.69 (m, 4H), 7.79 (dd, 1H, J = 4.6, 2.7 Hz), 7.88 (br, 2H), 8.33 (br, 1H), 8.38 (d, 1H, J = 8.3 Hz), 8.93 (d, 1H, J = 2.9 Hz), 9.01 (d, 1H, J = 7.3 Hz), 10.71 (s, 1H), 12.45 (s, 1H). | 396.2 | Similar to Example 3 |
| 45 | (DMSO-d₆): 7.50 (d, 1H, J = 4.9 Hz), 7.63-7.73 (m, 2H), 7.75-7.82 (m, 1H), 7.88 (d, 1H, J = 8.8 Hz), 7.94 (br, 1H), 7.99 (br, 1H), 8.30-8.39 (m, 2H), 8.82 (s, 1H), 9.44 (s, 1H), 10.53 (s, 1H), 12.50 (s, 1H). | 396.2 | Similar to Example 3 |
| 46 | (DMSO-d₆): 7.50 (d, 1H, J = 4.9 Hz), 7.59 (d, 1H, J = 8.8 Hz), 7.76-7.84 (m, 1H), 7.88-8.04 (m, 4H), 8.34 (br, 1H), 8.38 (d, 1H, J = 5.9 Hz), 8.63 (s, 1H), 9.10 (s, 1H), 10.59 (s, 1H), 12.49 (s, 1H). | 396.2 | Similar to Example 3 |
| 47 | (DMSO-d₆): 7.49 (d, 1H, J = 4.9 Hz), 7.57 (d, 1H, J = 7.3 Hz), 7.69-7.87 (m, 5H), 8.37 (br, 1H), 8.52 (d, 1H, J = 5.4 Hz), 8.71-8.80 (m, 1H), 9.77 (s, 1H). | 396 | Similar to Example 3 |
| 48 | (DMSO-d₆): 7.51 (d, 1H, J = 4.4 Hz), 7.58 (br, 1H), 7.73 (t, 1H, J = 7.1 Hz), 7.80 (d, 1H, J = 2.9 Hz), 7.85-8.0 (m, 3H), 8.35 (s, 1H), 8.46-8.90 (m, 3H), 10.51 (br, 1H), 12.48 (s, 1H). | 396.2 | Similar to Example 32 |
| 49 | (DMSO-d₆): 2.38-2.45 (m, 4H), 3.55-3.64 (m, 4H), 3.73 (s, 2H), 7.33 (s, 1H), 7.58 (dd, 1H, J = 8.8, 3.9 Hz), 7.64-7.79 (m, 3H), 7.81 (br, 1H), 8.21 (s, 1H), 8.65 (d, 1H, J = 7.3 Hz), 8.81 (d, 1H, J = 8.3 Hz), 8.91 (d, 1H, J = 2.9 Hz), 10.10 (br, 1H), 12.30 (br, 1H). | 495 | Similar to Example 3 |
| 50 | (DMSO-d₆): 2.35-2.42 (m, 4H), 3.52-3.58 (m, 4H), 3.61 (s, 3H), 3.67 (s, 2H), 7.18 (s, 1H), 7.54-7.68 (m, 2H), 7.70-7.80 (m, 2H), 7.96 (d, 1H, J = 6.8 Hz), 8.05 (s, 1H), 8.12 (d, 1H, J = 8.3 Hz), 8.52 (d, 1H, J = 8.3 Hz), 8.92 (br, 1H), 12.04 (br, 1H). | 509.2 | Similar to Example 68 |

TABLE 4-continued

| Example No. | ¹H-NMR (400 MHz) δ (ppm) | LCMS m/z [M + H]⁺ | Synthetic Method |
|---|---|---|---|
| 51 | (DMSO-d₆): 2.37-2.44 (m, 4H), 3.53-3.60 (m, 4H), 3.62 (s, 3H), 3.70 (s, 2H), 7.25 (s, 1H), 7.57 (dd, 1H, J = 8.3, 3.9 Hz), 7.65 (s, 1H), 7.82 (br, 1H), 7.91-7.97 (m, 1H), 8.06-8.12 (m, 2H), 8.15 (s, 1H), 8.38 (d, 1H, J = 8.3 Hz), 8.90 (d, 1H, J = 2.4 Hz), 12.14 (s, 1H). | 509.2 | Similar to Example 68 |
| 52 | (DMSO-d₆): 2.38-2.46 (m, 4H), 3.53-3.64 (m, 4H), 3.73 (s, 2H), 7.33 (s, 1H), 7.45 (br, 1H), 7.73 (br, 1H), 7.8-7.95 (m, 3H), 8.15-8.27 (m, 1H), 8.48 (br, 1H), 8.6-8.7 (m, 2H), 10.47 (br, 1H), 12.42 (br, 1H). | 495.2 | Similar to Example 3 |
| 53 | (DMSO-d₆): 2.40-2.46 (m, 4H), 3.53-3.65 (m, 4H), 3.74 (s, 2H), 7.34 (s, 1H), 7.48-7.68 (m, 3H), 7.8-7.9 (m, 2H), 8.22 (s, 1H), 8.38 (d, 1H, J = 8.3 Hz), 8.93 (br, 1H), 8.99 (d, 1H, J = 7.3 Hz), 10.67 (s, 1H), 12.39 (s, 1H). | 495.4 | Similar to Example 3 |
| 54 | (DMSO-d₆): 2.40-2.46 (m, 4H), 3.55-3.63 (m, 4H), 3.74 (s, 2H), 7.34 (s, 1H), 7.59 (d, 1H, J = 8.8 Hz), 7.8-8.05 (m, 4H), 8.23 (br, 1H), 8.34-8.42 (m, 1H), 8.62 (br, 1H), 9.09 (s, 1H), 10.57 (br, 1H), 12.44 (br, 1H). | 494.8 | Similar to Example 3 |
| 55 | (DMSO-d₆): 2.79 (s, 3H), 3.07-3.40 (m, 4H), 3.43-3.60 (m, 4H), 4.32 (br, 2H), 7.62 (br, 1H), 7.91-8.03 (m, 2H), 8.08 (br, 1H), 8.14 (d, 1H, J = 8.8 Hz), 8.30 (d, 1H, J = 9.3 Hz), 8.38 (br, 1H), 8.98-9.10 (m, 2H), 9.24 (d, 1H, J = 7.8 Hz), 11.24 (s, 1H), 12.49 (s, 1H). | 508.2 | Similar to Example 3 |
| 56 | (DMSO-d₆): 2.79 (s, 3H), 3.0-3.2 (m, 4H), 3.3-3.5 (m, 4H), 4.01 (br, 2H), 7.46 (s, 1H), 7.70-8.02 (m, 5H), 8.32 (s, 1H), 8.93 (br, 1H), 9.15 (br, 1H), 9.31 (br, 1H), 9.95 (br, 1H), 10.47 (s, 1H), 12.38 (s, 1H). (as a HCl salt) | 508.4 | Similar to Example 3 |
| 57 | (DMSO-d₆): 2.74 (s, 3H), 2.98-3.17 (m, 4H), 3.31-3.45 (m, 4H), 3.97 (br, 2H), 7.45 (br, 1H), 7.91 (d, 1H, J = 8.8 Hz), 8.00 (br, 1H), 8.12 (br, 1H), 8.32 (s, 1H), 8.38 (d, 1H, J = 8.8 Hz), 8.45-8.54 (m, 2H), 8.95 (br, 1H), 9.56 (s, 1H), 10.40 (br, 1H), 11.58 (s, 1H), 12.50 (s, 1H). (as a HCl salt) | 508.2 | Similar to Example 3 |
| 58 | (DMSO-d₆): 2.16 (s, 3H), 2.25-2.5 (m, 8H), 3.62 (s, 3H), 3.69 (s, 2H), 7.23 (s, 1H), 7.57 (dd, 1H, J = 8.1, 4.2 Hz), 7.64 (br, 1H), 7.81 (br, 1H), 7.95 (d, 1H, J = 9.3 Hz), 8.04-8.17 (m, 3H), 8.38 (d, 1H, J = 8.3 Hz), 8.90 (s, 1H), 12.13 (s, 1H). | 522.2 | Similar to Example 68 |
| 59 | (DMSO-d₆): 2.14 (s, 3H), 2.26-2.43 (m, 8H), 3.61 (s, 3H), 3.66 (s, 2H), 7.16 (s, 1H), 7.49-7.69 (m, 2H), 7.70-7.84 (m, 2H), 7.96 (d, 1H, J = 6.8 Hz), 8.03 (s, 1H), 8.11 (d, 1H, J = 7.8 Hz), 8.24 (br, 1H), 8.52 (d, 1H, J = 7.3 Hz), 8.93 (d, 1H, J = 2.4 Hz), 12.03 (br, 1H). (as a formate salt) | 522.2 | Similar to Example 68 |
| 60 | (DMSO-d₆): 2.16 (s, 3H), 2.25-2.5 (m, 8H), 3.71 (s, 2H), 7.26-7.37 (m, 2H), 7.44 (t, 1H, J = 7.6 Hz), 7.53 (d, 1H, J = 8.8 Hz), 7.72-7.92 (m, 4H), 8.04 (d, 1H, J = 8.3 Hz), 8.12-8.26 (m, 1H), 8.55 (s, 1H), 10.33 (s, 1H), 12.40 (br, 1H). | 507.2 | Similar to Example 2 |
| 61 | (DMSO-d₆): 2.39-2.46 (m, 4H), 3.55-3.8 (m, 4H), 3.73 (s, 2H), 7.27-7.35 (m, 2H), 7.44 (t, 1H, J = 7.3 Hz), 7.54 (d, 1H, J = 8.3 Hz), 7.80 (t, 2H, J = 9.3 Hz), 7.85-8.05 (m, 2H), 8.17 (br, 1H), 8.47 (s, 1H), 8.50 (br, 1H), 10.35 (br, 1H), 12.40 (br, 1H). | 494.2 | Similar to Example 2 |
| 62 | (DMSO-d₆): 2.35-2.45 (m, 4H), 3.5-3.6 (m, 4H), 3.60 (s, 3H), 3.70 (s, 2H), 7.24 (s, 1H), 7.51-7.59 (m, 2H), 7.62 (br, 1H), 7.66 (d, 1H, J = 8.8 Hz), 7.79 (br, 1H), 7.95 (t, 2H, J = 7.8 Hz), 8.0-8.1 (m, 2H), 8.12 (s, 1H), 12.11 (s, 1H). | 508.2 | Similar to Example 68 |
| 63 | (DMSO-d₆): 2.78 (s, 3H), 2.98-3.24 (m, 4H), 3.35-3.8 (m, 6H), 7.52 (br, 1H), 7.93 (t, 1H, J = 7.6 Hz), 8.00-8.26 (m, 4H), 8.39 (br, 1H), 8.77 (d, 1 H, J = 6.8 Hz), 8.98 (d, 1H, J = 8.8 Hz), 9.21 (d, 1H, J = 6.4 Hz), 11.89 (br, 1H), 12.49 (s, 1H). | 508.4 | Similar to Example 32 |
| 64 | (DMSO-d₆): 2.14 (s, 3H), 2.23-2.35 (m, 4H), 2.36-2.46 (m, 4H), 3.58 (s, 3H), 3.67 (s, 2H), 7.22 (s, 1H), 7.45-7.6 (m, 2H), 7.65 (d, 1H, J = 7.8 Hz), 7.68-7.8 (m, 1H), 7.88-8.12 (m, 5H), 8.42 (br, 1H), 12.10 (br, 1H). | 521.2 | Similar to Example 68 |
| 65 | (DMSO-d₆): 2.21 (s, 3H), 2.36-2.47 (m, 4H), 3.2-3.25 (m, 4H), 3.59 (s, 3H), 7.05 (d, 2H, J = 8.8 Hz), 7.50-7.61 (m, 3H), 7.62-7.69 (m, 3H), 7.77 (br, 1H), 7.95 (t, 2H, J = 8.1 Hz), 8.0-8.1 (m, 2H), 12.23 (s, 1H). | 501.4 | Similar to Example 28 |
| 66 | (DMSO-d₆): 2.16 (s, 3H), 2.25-2.5 (m, 8H), 3.72 (s, 2H), 7.31 (s, 1H), 7.48-7.67 (m, 3H), 8.18 (br, 1H), 8.35-8.46 (m, 1H), 8.9-9.0 (m, 2H), 10.60 (br, 1H). | 508.4 | Similar to Example 3 |

TABLE 4-continued

| Example No. | $^1$H-NMR (400 MHz) δ (ppm) | LCMS m/z [M + H]$^+$ | Synthetic Method |
|---|---|---|---|
| 67 | (DMSO-d$_6$): 2.39-2.45 (m, 4H), 3.5-3.65 (m, 4H), 3.73 (s, 2H), 7.34 (s, 1H), 7.55 (br, 1H), 7.71 (t, 1H, J = 7.6 Hz), 7.8-8.0 (m, 2H), 8.16 (br, 1H), 8.3-8.4 (m, 2H), 8.52 (d, 1H, J = 7.8 Hz) 8.52-8.7 (m, 1H). | 495.2 | Similar to Example 32 |
| 69 | (DMSO-d$_6$): 2.22 (s, 3H), 2.3-2.45 (m, 4H), 3.3-3.5 (m, 4H), 3.64 (s, 3H), 7.07 (d, 2H, J = 7.8 Hz), 7.6-7.75 (m, 3H), 7.81 (br, 2H), 7.88 (d, 1H, J = 7.8 Hz), 7.98 (br, 1H), 8.17 (d, 1H, J = 8.8 Hz), 8.48 (d, 1H, J = 5.4 Hz), 9.27 (br, 1H), 12.32 (br, 1H). | 502.4 | Similar to Example 28 |
| 70 | (DMSO-d$_6$): 4.62 (d, 2H, J = 5.4 Hz), 5.23 (t, 1H, J = 5.6 Hz), 7.40 (d, 1H, J = 8.3 Hz), 7.46-7.57 (m, 2H), 7.70 (s, 1H), 7.79 (d, 2H, J = 8.3 Hz), 7.82-7.92 (m, 2H), 8.00 (d, 1H, J = 8.3 Hz), 8.33 (br, 1H), 8.53 (br, 1H), 10.27 (br, 1H), 12.40-12.56 (m, 1H). | 425 | Similar to Example 68 |
| 71 | (DMSO-d$_6$): 3.90 (s, 3H), 7.50 (d, 1H, J = 4.9 Hz), 7.58 (d, 1H, J = 8.8 Hz), 7.79 (dd, 1 H, J = 4.6, 2.7 Hz), 7.87-7.99 (m, 3H), 8.03 (d, 1H, J = 9.3 Hz), 8.16 (d, 1H, J = 8.8 Hz), 8.34 (br, 1H), 8.51 (s, 1H), 8.68 (s, 1H), 10.53 (s, 1H), 12.49 (s, 1H). | 453.2 | Similar to Example 68 |
| 72 | (DMSO-d$_6$): 7.29-7.41 (m, 1H), 7.44-7.65 (m, 3H), 7.72-7.85 (m, 2H), 7.88-7.92 (m, 2H), 8.14 (dd, 1H, J = 9.3, 5.9 Hz), 8.32 (s, 1H), 8.63 (s, 1H), 10.31 (s, 1H), 12.47 (s, 1H). | 411.2 (M − H) | Similar to Example 68 |
| 73 | (DMSO-d$_6$): 3.85 (s, 3H), 7.11 (d, 1H, J = 8.8 Hz), 7.23 (s, 1H), 7.49 (d, 2H, J = 5.9 Hz), 7.67-7.91 (m, 4H), 7.97 (d, 1H, J = 9.3 Hz), 8.32 (br, 1H), 8.49 (s, 1H), 10.18 (s, 1H), 12.45 (s, 1H). | 424.8 | Similar to Example 68 |
| 74 | (DMSO-d$_6$): 3.98 (s, 3H), 6.91 (s, 1H), 7.30 (t, 1H, J = 7.3 Hz), 7.34-7.54 (m, 2H), 7.78 (br, 2H), 7.88 (br, 1H), 8.00 (t, 2H, J = 7.1 Hz), 8.16 (s, 1H), 8.33 (br, 1H), 10.25 (s, 1H), 12.44 (s, 1H). | 425 | Similar to Example 68 |
| 75 | (DMSO-d$_6$): 3.88 (s, 3H), 6.92-7.02 (m, 1H), 7.35 (d, 1H, J = 8.8 Hz), 7.43-7.55 (m, 2H), 7.71 (dd, 2H, J = 14.2, 8.8 Hz), 7.76-7.83 (m, 1H), 7.83-7.95 (m, 2H), 8.33 (br, 1H), 8.46 (s, 1H), 10.24 (s, 1H), 12.45 (s, 1H). | 425 | Similar to Example 68 |
| 76 | (DMSO-d$_6$): 1.15 (d, 3H, J = 6.3 Hz), 3.17 (d, 1H, J = 5.0 Hz), 3.42-3.50 (m, 1H), 3.51-3.61 (m, 1H), 4.76 (t, 1H, J = 5.5 Hz), 6.38 (d, 1H, J = 7.8 Hz), 6.72 (d, 2H, J = 8.8 Hz), 7.27-7.36 (m, 1H), 7.44 (t, 1H, J = 7.5 Hz), 7.52 (dd, 1H, J = 8.9, 2.1 Hz), 7.64 (d, 2H, J = 8.8 Hz), 7.73-7.86 (m, 4H), 8.03 (d, 1 H, J = 8.3 Hz), 8.54 (s, 1H), 10.22 (s, 1H), 12.41 (s, 1H). | 461.9 | Similar to Example 10 |
| 77 | (DMSO-d$_6$): 1.66-1.77 (m, 2H), 3.12-3.20 (m, 2H), 3.52 (q, 2H, J = 5.8 Hz), 4.52 (t, 1 H, J = 5.0 Hz), 6.60 (t, 1H, J = 5.0 Hz), 6.69 (d, 2H, J = 8.8 Hz), 7.24-7.37 (m, 1H), 7.44 (t, 1 H, J = 7.3 Hz), 7.52 (dd, 1 H, J = 8.8, 2.0 Hz), 7.66 (d, 2H, J = 8.5 Hz), 7.72-7.87 (m, 4H), 8.03 (d, 1H, J = 8.0 Hz), 8.54 (s, 1H), 10.22 (br, 1H), 12.42 (br, 1H). | 462 | Similar to Example 10 |
| 78 | (DMSO-d$_6$): 3.25-3.35 (m, 2H), 3.43-3.50 (m, 2H), 3.52 (t, 2H, J = 4.9 Hz), 3.60 (t, 2H, J = 5.6 Hz), 4.61 (s, 1H), 6.62 (s, 1H), 6.74 (d, 2H, J = 8.8 Hz), 7.33 (d, 1H, J = 7.0 Hz), 7.44 (s, 1H), 7.52 (dd, 1H, J = 8.9, 2.1 Hz), 7.67 (d, 2H, J = 8.8 Hz), 7.74-7.87 (m, 4H), 8.03 (d, 1H, J = 8.3 Hz), 8.54 (s, 1H), 10.23 (s, 1H), 12.41 (br, 1H). | 492 | Similar to Example 10 |
| 79 | (DMSO-d$_6$): 5.25 (s, 2H), 6.68-6.81 (m, 1H), 6.88 (s, 1H), 7.14-7.25 (m, 1H), 7.42-7.5 (m, 2H), 7.51-7.58 (m, 1H), 7.65-7.72 (m, 1H), 7.76-7.81 (m, 1H), 7.84-7.91 (m, 1H), 8.01 (s, 1H), 8.32 (s, 1H), 10.05 (s, 1H), 12.37 (s, 1H). | 410.2 | Similar to Example 68 |
| 80 | (DMSO-d$_6$): 7.13-7.30 (m, 1H), 7.40 (d, 1H, J = 9.3 Hz), 7.49 (d, 1H, J = 4.9 Hz), 7.74-8.0 (m, 6H), 8.33 (br, 1H), 8.66 (s, 1H), 10.38 (s, 1H), 12.49 (s, 1H). | 413.2 | Similar to Example 68 |
| 82 | (DMSO-d$_6$): 0.94 (s, 3H), 0.96 (s, 3H), 2.06 (dt, 1H, J = 13.3, 6.8 Hz), 2.37 (d, 2H, J = 7.3 Hz), 7.32 (t, 1H, J = 7.1 Hz), 7.43 (t, 1H, J = 7.6 Hz), 7.50 (dd, 1H, J = 8.8, 1.5 Hz), 7.69-7.84 (m, 4H), 8.02 (d, 1H, J = 8.3 Hz), 8.50 (s, 1H), 10.20 (s, 1H), 11.46 (s, 1H). | 369.2 | Similar to Example 81 |
| 83 | (DMSO-d$_6$): 1.93 (s, 3H), 2.19 (s, 3H), 6.01 (br, 1H), 7.32 (t, 1H, J = 7.1 Hz), 7.38-7.47 (m, 1H), 7.51 (d, 1H, J = 8.3 Hz), 7.65-7.85 (m, 4H), 8.02 (d, 1H, J = 8.3 Hz), 8.51 (s, 1H), 10.21 (s, 1H), 11.42 (s, 1H). | 367.4 | Similar to Example 81 |
| 84 | (DMSO-d$_6$): 4.14 (s, 2H), 7.01-7.06 (m, 1H), 7.09 (s, 1H), 7.26-7.36 (m, 1H), 7.39-7.53 (m, 3H), 7.71 (d, 2H, J = 8.8 Hz), 7.79 (t, 2H, J = 9.0 Hz), 8.01 (d, 1H, J = 8.3 Hz), 8.50 (s, 1H), 10.21 (s, 1H), 11.56 (s, 1H). | 409.2 | Similar to Example 81 |

TABLE 4-continued

| Example No. | ¹H-NMR (400 MHz) δ (ppm) | LCMS m/z [M + H]⁺ | Synthetic Method |
|---|---|---|---|
| 85 | (DMSO-d₆): 3.97 (s, 2H), 7.32 (t, 1H, J = 7.3 Hz), 7.36-7.45 (m, 3H), 7.49 (d, 1H, J = 8.8 Hz), 7.68-7.83 (m, 4H), 8.02 (d, 1H, J = 8.3 Hz), 8.50 (br, 1H), 8.55 (d, 2H, J = 4.4 Hz), 10.22 (s, 1H), 11.55 (s, 1H). | 404.1 | Similar to Example 81 |
| 86 | (DMSO-d₆): 0.93 (t, 3H, J = 6.6 Hz), 1.63 (d, 2H, J = 6.8 Hz), 3.2-3.45 (m, 2H), 7.27-7.37 (m, 1H), 7.43 (br, 1H), 7.50 (d, 1H, J = 8.3 Hz), 7.65-7.88 (m, 4H), 8.02 (d, 1H, J = 7.8 Hz), 8.50 (s, 1H), 10.19 (s, 1H), 11.47 (s, 1H). | 355.2 | Similar to Example 81 |
| 87 | (DMSO-d₆): 2.21 (s, 3H), 4.81 (s, 2H), 7.29-7.36 (m, 1H), 7.44 (t, 1H, J = 7.3 Hz), 7.50 (dd, 1H, J = 8.6, 1.7 Hz), 7.76-7.86 (m, 3H), 7.89 (br, 1H), 8.04 (d, 1H, J = 7.8 Hz), 8.53 (s, 1H), 10.28 (s, 1H), 12.06 (s, 1H). | 385.4 | Similar to Example 81 |
| 88 | (DMSO-d₆): 4.11 (s, 2H), 6.16 (br, 1H), 7.32 (t, 1H, J = 7.1 Hz), 7.43 (t, 1H, J = 7.3 Hz), 7.52 (br, 1H), 7.65-7.75 (m, 2H), 7.75-7.84 (m, 2H), 8.02 (d, 1H, J = 7.8 Hz), 8.50 (s, 1H), 10.21 (br, 1H), 12.04 (s, 1H). | 343.4 | Similar to Example 21 |
| 89 | (DMSO-d₆): 1.76 (t, 2H, J = 6.8 Hz), 2.09 (s, 3H), 2.17-2.4 (m, 8H), 2.4-2.6 (m, 4H), 7.33 (t, 1H, J = 7.3 Hz), 7.42 (t, 1H, J = 7.8 Hz), 7.50 (d, 1H, J = 8.3 Hz), 7.6-7.75 (m, 2H), 7.79 (t, 2H, J = 9.3 Hz), 8.01 (d, 1H, J = 8.3 Hz), 8.50 (s, 1H), 10.17 (s, 1H), 11.44 (s, 1H). | 453.6 | Similar to Example 92 |
| 90 | (DMSO-d₆): 1.78 (t, 2H, J = 6.6 Hz), 2.20-2.38 (m, 6H), 2.4-2.5 (m, 2H), 3.45-3.55 (m, 4H), 7.33 (t, 1H, J = 7.3 Hz), 7.42 (t, 1H, J = 7.3 Hz), 7.50 (d, 1H, J = 8.3 Hz), 7.65-7.75 (m, 2H), 7.80 (t, 2H, J = 9.3 Hz), 8.01 (d, 1H, J = 7.8 Hz), 8.50 (s, 1H), 10.18 (s, 1H), 11.45 (s, 1H). | 440.2 | Similar to Example 92 |
| 91 | (DMSO-d₆): 1.31 (d, 2H, J = 6.4 Hz), 1.37-1.48 (m, 2H), 1.54-1.67 (m, 2H), 2.12 (s, 3H), 2.23 (t, 2H, J = 7.1 Hz), 2.25-2.4 (m, 8H), 2.4-2.5 (m, 2H), 7.32 (t, 1H, J = 7.3 Hz), 7.43 (t, 1H, J = 7.3 Hz), 7.50 (d, 1H, J = 8.8 Hz), 7.66-7.76 (m, 2H), 7.76-7.85 (m, 2H), 8.02 (d, 1H, J = 8.3 Hz), 8.50 (s, 1H), 10.19 (s, 1H), 11.46 (s, 1H). | 481.2 | Similar to Example 92 |
| 93 | (DMSO-d₆): 0.75-1.05 (m, 4H), 1.87-2.10 (m, 1H), 7.32 (t, 1H, J = 7.1 Hz), 7.43 (t, 1H, J = 7.1 Hz), 7.49 (d, 1H, J = 7.3 Hz), 7.65-7.84 (m, 4H), 8.02 (d, 1H, J = 8.3 Hz), 8.50 (s, 1H), 10.19 (s, 1H), 11.68 (s, 1H). | 353.2 | Similar to Example 81 |
| 94 | (DMSO-d₆): 1.33-1.49 (m, 1H), 1.50-1.64 (m, 1H), 1.90 (t, 2H, J = 11.7 Hz), 2.01 (s, 3H), 2.65 (t, 1H, J = 11.5 Hz), 2.79 (t, 1H, J = 11.0 Hz), 3.12 (t, 1H, J = 12.0 Hz), 3.86 (d, 1H, J = 13.2 Hz), 4.38 (d, 1H, J = 12.7 Hz), 7.28-7.36 (m, 1H), 7.43 (t, 1H, J = 7.1 Hz), 7.50 (d, 1H, J = 8.8 Hz), 7.70-7.87 (m, 4H), 8.02 (d, 1H, J = 8.3 Hz), 8.51 (s, 1H), 10.22 (s, 1H), 11.66 (s, 1H). | 438.4 | Similar to Example 81 |
| 95 | (DMSO-d₆): 3.25-3.4 (m, 1H), 3.4-3.57 (m, 4H), 4.72 (t, 2H, J = 5.4 Hz), 6.32 (d, 1H, J = 7.3 Hz), 6.77 (d, 2H, J = 8.8 Hz), 7.29-7.36 (m, 1H), 7.44 (t, 1H, J = 7.4 Hz), 7.52 (dd, 1H, J = 8.9, 2.1 Hz), 7.64 (d, 2H, J = 8.5 Hz), 7.76-7.86 (m, 4H), 8.04 (d, 1H, J = 8.0 Hz), 8.54 (s, 1H), 10.23 (s, 1H), 12.42 (s, 1H). | 478 | Similar to Example 10 |
| 96 | (DMSO-d₆): 2.13 (s, 3H), 2.65-2.71 (m, 2H), 3.27-3.38 (m, 2H), 6.69-6.80 (m, 3H), 7.29-7.36 (m, 1H), 7.44 (t, 1H, J = 7.4 Hz), 7.52 (dd, 1H, J = 8.9, 2.1 Hz), 7.67 (d, 2H, J = 8.5 Hz), 7.76-7.86 (m, 4H), 8.04 (d, 1H, J = 8.0 Hz), 8.55 (d, 1H, J = 1.5 Hz), 10.24 (s, 1H), 12.44 (s, 1H). | 477.9 | Similar to Example 10 |
| 97 | (DMSO-d₆): 1.32-1.52 (m, 2H), 1.73-1.88 (m, 2H), 3.00-3.14 (m, 2H), 3.62-3.83 (m, 3H), 4.75 (d, 1H, J = 4.3 Hz), 7.09 (d, 2H, J = 9.0 Hz), 7.28-7.37 (m, 1H), 7.44 (t, 1H, J = 7.2 Hz), 7.52 (dd, 1H, J = 8.8, 2.0 Hz), 7.74 (d, 2H, J = 8.8 Hz), 7.77-7.89 (m, 4H), 8.05 (d, 1H, J = 8.0 Hz), 8.57 (d, 1H, J = 1.3 Hz), 10.27 (s, 1H), 12.52 (s, 1H). | 488 | Similar to Example 10 |
| 98 | (DMSO-d₆): 3.88 (s, 2H), 7.21-7.39 (m, 6H), 7.39-7.45 (m, 1H), 7.48 (d, 1H, J = 8.3 Hz), 7.65-7.73 (m, 2H), 7.79 (t, 2H, J = 8.8 Hz), 8.01 (d, 1H, J = 8.3 Hz), 8.49 (s, 1H), 10.19 (s, 1H), 11.48 (s, 1H). | 403.2 | Similar to Example 81 |
| 99 | (DMSO-d₆): 4.11 (s, 2H), 7.31 (br, 1H), 7.35-7.55 (m, 2H), 7.6-7.85 (m, 6H), 7.95-8.05 (m, 1H), 8.2-8.3 (m, 2H), 8.49 (br, 1H), 10.21 (s, 1H), 11.53 (br, 1H). | 446.2 (M − H) | Similar to Example 81 |
| 100 | (DMSO-d₆): 3.68 (s, 2H), 6.60-6.78 (m, 2H), 6.99-7.17 (m, 2H), 7.25-7.35 (m, 1H), 7.37-7.44 (m, 1H), 7.48 (d, 1H, J = 8.3 Hz), 7.62-7.72 (m, 2H), 7.75-7.88 (m, 2H), 8.01 (d, 1H, J = 7.8 Hz), 8.50 (s, 1H), 10.18 (s, 1H), 11.42 (s, 1H). | 418.2 | Similar to Example 9 |

TABLE 4-continued

| Example No. | $^1$H-NMR (400 MHz) δ (ppm) | LCMS m/z [M + H]$^+$ | Synthetic Method |
|---|---|---|---|
| 101 | (DMSO-d$_6$): 1.44-1.80 (m, 6H), 1.86-2.02 (m, 2H), 2.80-3.01 (m, 1H), 7.28-7.37 (m, 1H), 7.39-7.46 (m, 1H), 7.50 (d, 1H, J = 8.3 Hz), 7.64-7.86 (m, 4H), 8.02 (d, 1H, J = 6.8 Hz), 8.50 (s, 1H), 10.19 (s, 1H), 11.57 (s, 1H). | 381 | Similar to Example 81 |
| 102 | (DMSO-d$_6$): 1.84-2.06 (m, 2H), 2.53-2.64 (m, 2H), 3.66 (t, 2H, J = 6.1 Hz), 7.28-7.35 (m, 1H), 7.43 (t, 1H, J = 7.3 Hz), 7.49 (d, 1H, J = 8.3 Hz), 7.65-7.75 (m, 2H), 7.76-7.88 (m, 6H), 8.01 (d, 1H, J = 7.8 Hz), 8.48 (s, 1H), 10.15 (s, 1H), 11.37 (s, 1H). | 500.4 | Similar to Example 81 |
| 104 | (DMSO-d$_6$): 3.27-3.31 (m, 5H), 3.51 (t, 2H, J = 5.5 Hz), 6.66 (t, 1H, J = 5.5 Hz), 6.74 (d, 2H, J = 8.8 Hz), 7.29-7.36 (m, 1H), 7.44 (t, 1H, J = 7.2 Hz), 7.52 (dd, 1H, J = 8.9, 2.1 Hz), 7.66 (d, 2H, J = 8.8 Hz), 7.76-7.85 (m, 4H), 8.04 (d, 1H, J = 8.3 Hz), 8.55 (d, 1H, J = 1.8 Hz), 10.23 (s, 1H), 12.43 (s, 1H). | 461.9 | Similar to Example 10 |
| 105 | (DMSO-d$_6$): 3.11-3.23 (m, 2H), 3.48-3.64 (m, 2H), 4.77 (br, 1H), 6.62 (br, 1H), 6.73 (d, 2H, J = 7.8 Hz), 7.58 (d, 1H, J = 8.3 Hz), 7.66 (d, 2H, J = 7.8 Hz), 7.78-8.08 (m, 4H), 8.37 (d, 1H, J = 5.4 Hz), 8.63 (s, 1H), 9.09 (s, 1H), 10.54 (br, 1H), 12.46 (br, 1H). | 449.4 | Similar to Example 28 |
| 107 | (DMSO-d$_6$): 3.14-3.22 (m, 2H), 3.58 (t, 2H, J = 5.6 Hz), 4.62 (br, 2H), 4.76 (br, 1H), 5.21 (br, 1H), 6.52-6.63 (m, 1H), 6.72 (d, 2H, J = 8.3 Hz), 7.40 (d, 1H, J = 8.8 Hz), 7.51 (d, 1H, J = 8.8 Hz), 7.65 (d, 2H, J = 8.8 Hz), 7.70 (s, 1H), 7.74-7.82 (m, 2H), 7.99 (d, 1H, J = 8.3 Hz), 8.42 (br, 1H), 8.51 (s, 1H), 10.19 (br, 1H), 12.41 (br, 1H). | 478.2 | Similar to Example 28 |
| 108 | (DMSO-d$_6$): 3.18 (dd, 2H, J = 13.7, 5.4 Hz), 3.58 (d, 2H, J = 5.4 Hz), 4.59-4.87 (m, 1H), 6.62 (br, 1H), 6.73 (d, 2H, J = 7.8 Hz), 7.55-7.7 (m, 3H), 7.7-8.0 (m, 4H), 8.52 (d, 1H, J = 7.8 Hz), 8.71 (br, 1H), 8.76 (br, 1H), 10.40 (br, 1H), 12.43 (br, 1H). | 449.2 | Similar to Example 32 |
| 109 | (DMSO-d$_6$): 2.33 (s, 3H), 7.29-7.37 (m, 1H), 7.38-7.48 (m, 3H), 7.53 (d, 1H, J = 8.8 Hz), 7.80 (d, 1H, J = 8.3 Hz), 7.83 (d, 1H, J = 9.3 Hz), 7.91 (d, 2H, J = 8.3 Hz), 7.97 (d, 2H, J = 8.8 Hz), 8.05 (d, 1H, J = 8.3 Hz), 8.56 (s, 1H), 10.33 (s, 1H), 12.73 (s, 1H). | 447 | Similar to Example 2 |

The following compounds in Table 5 are additional representative examples of formula (1), as provided by the present invention, and were synthesized following the methods described for example 1-111, or by processes analogous thereto using the appropriate reagents, starting materials and methods well known to those skill in the art.

TABLE 5

| Example No. | $^1$H-NMR (400 MHz) δ (ppm) | LCMS m/z [M + H]$^+$ |
|---|---|---|
| 112 | (DMSO-d6): 3.20 (d, 2H, J = 5.3 Hz), 3.5-3.65 (m, 2H), 4.77 (br, 1H), 6.60 (s, 1H), 6.72 (d, 2H, J = 7.4 Hz), 7.35 (t, 1H, J = 7.6 Hz), 7.54 (d, 1H, J = 9.2 Hz), 7.58 (d, 1H, J = 9.2 Hz), 7.65 (d, 2H, J = 8.0 Hz), 7.75-7.85 (m, 3H), 8.14 (s, 1H), 8.63 (s, 1H), 10.24 (s, 1H), 12.43 (s, 1H) | 446.0 |
| 113 | (DMSO-d6): 3.20 (dd, 2H, J = 11.4, 5.7 Hz), 3.58 (dd, 2H, J = 11.4, 5.8 Hz), 3.85 (s, 3H), 4.76 (t, 1H, J = 5.5 Hz), 6.59 (t, 1H, J = 5.4 Hz), 6.72 (d, 2H, J = 8.8 Hz), 7.11 (dd, 1H, J = 8.9, 2.4 Hz), 7.23 (s, 1H), 7.48 (d, 2H, J = 6.9 Hz), 7.65 (d, 2H, J = 8.7 Hz), 7.73 (d, 1H, J = 8.8 Hz), 7.76 (s, 1H), 7.78 (s, 1H), 7.96 (d, 1H, J = 9.0 Hz), 8.48 (s, 1H), 10.11 (s, 1H), 12.40 (s, 1H) | 478.4 |
| 114 | (DMSO-d6): 1.22 (t, 3H, J = 7.1 Hz), 3.17 (t, 2H, J = 5.8 Hz), 3.55 (q, 2H, J = 5.8 Hz), 4.11 (q, 2H, J = 6.9 Hz), 4.73 (t, 1H, J = 5.5 Hz), 6.54 (t, 1H, J = 5.6 Hz), 6.67 (d, 2H, J = 8.5 Hz), 7.26-7.45 (m, 1H), 7.45-7.65 (m, 5H), 7.71 (s, 1H), 7.84-8.29 (m, 4H), 12.11 (s, 1H) | 476.2 |
| 115 | (DMSO-d6): 1.99 (s, 3H), 3.01 (t, 2H, J = 6.8 Hz), 4.28 (t, 2H, J = 6.5 Hz), 7.33 (t, 1H, J = 7.6 Hz), 7.45-7.55 (m, 4H), 7.75-7.98 (m, 6H), 8.05 (d, 1H, J = 7.9 Hz), 8.55 (s, 1H), 10.31 (s, 1H), 12.70 (s, 1H) | 475.2 |
| 116 | (DMSO-d6): 2.83 (t, 2H, J = 6.8 Hz), 3.67 (q, 2H, J = 6.4 Hz), 4.72 (t, 1H, J = 5.1 Hz), 7.33 (t, 1H, J = 7.4 Hz), 7.37-7.64 (m, 4H), 7.70-7.97 (m, 6H), 8.05 (d, 1H, J = 8.3 Hz), 8.56 (d, 1H, J = 2.2 Hz), 10.32 (s, 1H), 12.70 (s, 1H) | 433.2 |

TABLE 5-continued

| Example No. | ¹H-NMR (400 MHz) δ (ppm) | LCMS m/z [M + H]⁺ |
|---|---|---|
| 117 | (DMSO-d6): 1.94 (t, 2H, J = 7.6 Hz), 2.01 (s, 3H), 2.76 (t, 2H, J = 7.8 Hz), 4.02 (t, 2H, J = 6.5 Hz), 7.33 (t, 1H, J = 7.4 Hz), 7.4-7.6 (m, 4H), 7.75-7.9 (m, 6H), 8.05 (d, 1H, J = 8.2 Hz), 8.56 (s, 1H), 10.31 (s, 1H), 12.70 (s, 1H) | 489.4 |
| 118 | (DMSO-d6): 1.76 (quintet, 2H, J = 7.9Hz), 2.73 (t, 2H, J = 7.9 Hz), 3.43 (q, 2H, J = 6.1 Hz), 4.52 (t, 1H, J = 5.1 Hz), 7.33 (t, 1H, J = 7.5 Hz), 7.4-7.5 (m, 3H), 7.53 (dd, 1H, J = 8.8, 2.3 Hz), 7.69-7.97 (m, 6H), 8.04 (d, 1H, J = 8.2 Hz), 8.55 (d, 1H, J = 1.8 Hz), 10.30 (s, 1H), 12.68 (s, 1H) | 447.0 |
| 119 | (DMSO-d6): 2.12 (s, 3H), 5.19 (s, 2H), 7.33 (t, 1H, J = 7.4 Hz), 7.44 (t, 1H, J = 7.7 Hz), 7.49-7.56 (m, 1H), 7.61 (d, 2H, J = 7.9 Hz), 7.81 (dd, 2H, J = 12.5, 8.5 Hz), 7.88-8.0 (m, 4H), 8.05 (d, 1H, J = 8.3 Hz), 8.56 (s, 1H), 10.32 (s, 1H), 12.74 (s, 1H) | 461.2 |
| 120 | (DMSO-d6): 4.61 (d, 2H, J = 5.9 Hz), 5.41 (t, 1H, J = 5.8 Hz), 7.33 (t, 1H, J = 7.6 Hz), 7.44 (t, 1H, J = 7.6 Hz), 7.5-7.65 (m, 3H), 7.7-8.0 (m, 6H), 8.04 (d, 1H, J = 8.2 Hz), 8.56 (s, 1H), 10.31 (s, 1H), 12.72 (s, 1H) | 419.1 |
| 121 | (DMSO-d6): 3.1-3.4 (m, 2H), 3.63 (d, 2H, J = 6.5 Hz), 4.75 (d, 1H, J = 6.0 Hz), 4.90 (s, 1H), 5.29 (s, 1H), 6.57 (d, 1H, J = 8.2 Hz), 7.1-7.2 (m, 2H), 7.32 (t, 1H, J = 7.4 Hz), 7.43 (t, 1H, J = 7.8 Hz), 7.51 (d, 1H, J = 9.0 Hz), 7.65-7.9 (m, 5H), 8.03 (d, 1H, J = 8.2 Hz), 8.54 (s, 1H), 10.20 (s, 1H), 12.32 (s, 1H) | 463.2 |
| 122 | (DMSO-d6): 0.85-1.0 (m, 4H), 1.82-2.12 (m, 1H), 7.10-7.28 (m, 1H), 7.27-7.44 (m, 1H), 7.62-8.06 (m, 5H), 8.60 (d, 1H, J = 2.3 Hz), 10.27 (s, 1H), 11.71 (s, 1H) | 371.2 |
| 123 | (DMSO-d6): 1.22 (s, 3H), 2.21 (s, 3H), 2.35-2.55(m, 8H), 4.11 (s, 2H), 7.04 (s, 2H), 7.45-7.82 (m, 7H), 7.85-8.18 (m, 4H), 12.22 (s, 1H) | 515.2 |
| 124 | (DMSO-d6): 3.20 (q, 2H, J = 6.1 Hz), 3.58 (q, 2H, J = 5.8 Hz), 4.76 (t, 1H, J = 5.5 Hz), 6.60 (t, 1H, J = 5.6 Hz), 6.72 (d, 2H, J = 8.6 Hz), 7.14-7.25 (m, 1H), 7.32-7.48 (m, 1H), 7.65 (d, 2H, J = 8.5 Hz), 7.75-7.97 (m, 5H), 8.65 (d, 1H, J = 2.2 Hz), 10.31 (s, 1H), 12.45 (s, 1H) | 466.2 |
| 125 | (DMSO-d6): 2.55 (s, 3H), 7.02 (d, 1H, J = 3.7 Hz), 7.21 (td, 1H, J = 8.8, 2.7 Hz), 7.39 (dd, 1H, J = 8.9, 2.3 Hz), 7.57 (d, 1H, J = 3.8 Hz), 7.79-7.98 (m, 5H), 8.61-8.68 (m, 1H), 10.38 (s, 1H), 12.53 (s, 1H) | 425.2 (M − H) |
| 126 | (DMSO-d6): 6.07 (s, 2H), 6.67 (d, 2H, J = 8.5 Hz), 7.20 (td, 1H, J = 8.8, 2.7 Hz), 7.40 (dd, 1H, J = 8.9, 2.3 Hz), 7.61 (d, 2H, J = 8.4 Hz), 7.76-7.94 (m, 5H), 8.64 (d, 1H, J = 2.2 Hz), 10.30 (s, 1H), 12.42 (s, 1H) | 422.2 |
| 127 | (DMSO-d6): 2.35-2.45 (m, 4H), 3.5-3.65 (m, 6H), 7.21 (td, 1H, J = 8.9, 2.8 Hz), 7.41 (dd, 1H, J = 9.1, 2.1 Hz), 7.57 (d, 2H, J = 7.9 Hz), 7.8-8.0 (m, 7H), 8.66 (s, 1H), 10.39 (s, 1H), 12.74 (s, 1H) | 506.4 |
| 128 | (DMSO-d6): 1.93 (s, 3H), 2.19 (s, 3H), 6.01 (s, 1H), 7.02-7.29 (m, 1H), 7.39 (dd, 1H, J = 8.6, 2.3 Hz), 7.63-7.94 (m, 5H), 8.61 (d, 1H, J = 2.2 Hz), 10.28 (s, 1H), 11.45 (s, 1H) | 385.4 |
| 129 | (Methanol-d4): 1.45 (q, 2H, J = 7.8 Hz), 1.64 (quintet, 2H, J = 7.7 Hz), 1.76 (quintet, 2H, J = 7.4 Hz), 2.53 (t, 2H, J = 7.4 Hz), 2.58 (s, 3H), 2.69 (t, 2H, J = 7.7 Hz), 2.8-3.1 (m, 8H), 7.11 (td, 1H, J = 8.8, 2.6 Hz), 7.44 (dd, 1H, J = 8.9, 2.3 Hz), 7.51 (dd, 1H, J = 10.6, 2.6 Hz), 7.72-7.82 (m, 2H), 8.30 (d, 1H, J = 2.2 Hz), 8.38 (br, 1H) | 499.4 |
| 130 | (DMSO-d6): 1.32 (quintet, 2H, J = 7.34 Hz), 1.45 (quintet, 2H, J = 7.4 Hz), 1.62 (quintet, 2H, J = 7.5 Hz), 2.25 (t, 2H, J = 7.2 Hz), 2.28-2.35 (m, 4H), 2.46-2.54 (m, 2H), 3.5-3.6 (m, 4H), 7.19 (td, 1H, J = 8.8, 2.7 Hz), 7.37 (dd, 1H, J = 8.9, 2.3 Hz), 7.73-7.92 (m, 4H), 8.16 (s, 1H), 8.61 (d, 1H, J = 2.3 Hz), 10.28 (s, 1H), 11.50 (s, 1H) | 486.4 |
| 131 | (DMSO-d6): 2.55 (s, 3H), 7.02 (d, 1H, J = 3.7 Hz), 7.36 (td, 1H, J = 8.9, 2.7 Hz), 7.49-7.67 (m, 3H), 7.82 (d, 1H, J = 8.9 Hz), 7.89 (s, 2H), 8.14 (dd, 1H, J = 9.1, 5.8 Hz), 8.63 (d, 1H, J = 2.2 Hz), 10.31 (s, 1H), 12.50 (s, 1H) | 425.0 |
| 132 | (DMSO-d6): 6.06 (s, 2H), 6.67 (d, 2H, J = 8.3 Hz), 7.35 (t, 1H, J = 8.9 Hz), 7.47-7.67 (m, 4H), 7.71-7.88 (m, 3H), 8.13 (dd, 1H, J = 9.0, 5.7 Hz), 8.62 (s, 1H), 10.23 (s, 1H), 12.40 (s, 1H) | 422.2 |
| 133 | (DMSO-d6): 1.93 (s, 3H), 2.19 (s, 3H), 6.00 (s, 1H), 7.35 (td, 1H, J = 8.8, 2.8 Hz), 7.51-7.55 (m, 1H), 7.58 (dd, 1H, J = 10.3, 2.7 Hz), 7.75 (s, 2H), 7.81 (d, 1H, J = 8.9 Hz), 8.12 (dd, 1H, J = 9.2, 5.8 Hz), 8.59 (d, 1H, J = 2.2 Hz), 10.21 (s, 1H), 11.43 (s, 1H) | 385.0 |
| 134 | (DMSO-d6): 0.8-0.95 (m, 4H), 1.9-2.05 (m, 1H), 3.84 (s, 3H), 7.10 (dd, 1H, J = 9.0, 2.7 Hz), 7.22 (d, 1H, J = 2.7 Hz), 7.46 (dd, 1H, J = 8.8, 2.3 Hz), 7.6-7.8 (m, 3H), 7.94 (d, 1H, J = 9.0 Hz), 8.43 (d, 1H, J = 2.4 Hz), 10.07 (s, 1H), 11.66 (s, 1H) | 383.2 |
| 135 | (DMSO-d6): 2.55 (s, 3H), 3.85 (s, 3H), 6.96-7.07 (m, 1H), 7.11 (dd, 1H, J = 8.9, 2.6 Hz), 7.23 (d, 1H, J = 2.6 Hz), 7.48 (dd, 1H, J = 8.9, 2.3 Hz), 7.56 (d, 1H, J = 3.7 Hz), 7.73 (d, 1H, J = 8.9 Hz), 7.8-7.92 (m, 2H), 7.97 (d, 1H, J = 9.0 Hz), 8.48 (d, 1H, J = 2.2 Hz), 10.19 (s, 1H), 12.49 (s, 1H) | 439.2 |

TABLE 5-continued

| Example No. | ¹H-NMR (400 MHz) δ (ppm) | LCMS m/z [M + H]⁺ |
|---|---|---|
| 136 | (DMSO-d6): 3.85 (s, 3H), 6.06 (s, 2H), 6.67 (d, 2H, J = 8.3 Hz), 7.11 (dd, 1H, J = 9.0, 2.6 Hz), 7.23 (d, 1H, J = 2.7 Hz), 7.48 (dd, 1H, J = 8.8, 2.3 Hz), 7.60 (d, 2H, J = 8.4 Hz), 7.7-7.85 (m, 3H), 7.96 (d, 1H, J = 9.1 Hz), 8.48 (d, 1H, J = 2.0 Hz), 10.11 (s, 1H), 12.39 (s, 1H) | 434.0 |
| 137 | (DMSO-d6): 1.92 (s, 3H), 2.19 (s, 3H), 3.84 (s, 3H), 5.99 (s, 1H), 6.97-7.14 (m, 1H), 7.22 (s, 1H), 7.48 (d, 1H, J = 9.2 Hz), 7.59-7.82 (m, 3H), 7.94 (d, 1H, J = 9.0 Hz), 8.43 (s, 1H), 10.07 (s, 1H), 11.40 (s, 1H) | 397.4 |
| 138 | (DMSO-d6): 0.66-1.05 (m, 4H), 1.83-2.10 (m, 1H), 4.61 (d, 2H, J = 5.7 Hz), 5.22 (t, 1H, J = 5.7 Hz), 7.39 (d, 1H, J = 8.5 Hz), 7.48 (dd, 1H, J = 8.8, 2.3 Hz), 7.70 (d, 2H, J = 8.3 Hz), 7.73-7.81 (m, 2H), 7.98 (d, 1H, J = 8.5 Hz), 8.48 (d, 1H, J = 2.2 Hz), 10.16 (s, 1H), 11.68 (s, 1H) | 383.2 |
| 139 | (DMSO-d6): 1.93 (s, 3H), 2.19 (s, 3H), 4.62 (d, 2H, J = 5.8 Hz), 5.22 (t, 1H, J = 5.7 Hz), 6.00 (s, 1H), 7.29-7.43 (m, 1H), 7.50 (dd, 1H, J = 8.9, 2.3 Hz), 7.56-7.91 (m, 4H), 7.98 (d, 1H, J = 8.5 Hz), 8.48 (s, 1H), 10.17 (s, 1H), 11.42 (s, 1H) | 397.2 |
| 140 | (DMSO-d6): 2.4-2.55 (m, 4H), 3.45-3.75 (m, 4H), 3.8-4.1 (m, 2H), 7.37 (td, 1H, J = 8.9, 2.7 Hz), 7.48-7.87 (m, 5H), 7.87-8.1(m, 4H), 8.15 (dd, 1H, J = 9.1, 5.8 Hz), 8.64 (d, 1H, J = 2.3 Hz), 10.35 (s, 1H), 12.76 (s, 1H) | 505.8 |
| 141 | (DMSO-d6): 0.85-0.97 (m, 4H), 1.89-2.03 (m, 1H), 7.35 (td, 1H, J = 8.9, 2.7 Hz), 7.46-7.55 (m, 1H), 7.58 (dd, 1H, J = 10.5, 2.6 Hz), 7.7-7.85 (m, 3H), 8.12 (dd, 1H, J = 9.1, 5.8 Hz), 8.59 (d, 1H, J = 2.2 Hz), 10.20 (s, 1H), 11.69 (s, 1H) | 371.2 |
| 142 | (DMSO-d6): 2.32-2.43 (m, 4H), 3.5-3.65 (m, 6H), 3.85 (s, 3H), 7.11 (dd, 1H, J = 8.9, 2.6 Hz), 7.24 (d, 1H, J = 2.6 Hz), 7.42-7.62 (m, 3H), 7.74 (d, 1H, J = 8.8 Hz), 7.8-7.92 (m, 4H), 7.96 (d, 1H, J = 9.0 Hz), 8.48 (s, 1H), 10.19 (s, 1H), 12.69 (s, 1H) | 518.2 |
| 143 | (DMSO-d6): 1.20-1.41 (m, 2H), 1.49 (t, 2H, J = 7.7 Hz), 1.62 (quintet, 2H, J = 7.4 Hz), 2.41 (s, 3H), 2.45-2.9 (m, 12H), 3.84 (s, 3H), 7.10 (dd, 1H, J = 8.9, 2.6 Hz), 7.22 (d, 1H, J = 2.6 Hz), 7.47 (dd, 1H, J = 8.9, 2.4 Hz), 7.65-7.80 (m, 3H), 7.94 (d, 1H, J = 9.1 Hz), 8.43 (d, 1H, J = 2.2 Hz), 10.07 (s, 1H), 11.45 (s, 1H) | 511.2 |
| 144 | (DMSO-d6): 1.36 (t, 2H, J = 7.7 Hz), 1.6-1.75 (m, 4H), 2.45-2.6 (m, 2H), 2.95-3.2 (s, 4H), 3.35-3.5 (m, 2H), 3.64 (t, 2H, J = 11.9 Hz), 3.84 (s, 3H), 3.9-4.05 (m, 2H), 7.10 (dd, 1H, J = 8.9, 2.6 Hz), 7.22 (d, 1H, J = 2.6 Hz), 7.47 (dd, 1H, J = 8.9, 2.3 Hz), 7.62-7.81 (m, 3H), 7.94 (d, 1H, J = 9.0 Hz), 8.43 (d, 1H, J = 2.2 Hz), 9.58 (s, 1H), 10.08 (s, 1H), 11.46 (s, 1H) | 498.2 |
| 145 | (DMSO-d6): 1.18 (d, 6H, J = 6.2 Hz), 2.42 (dd, 2H, J = 12.4, 10.5 Hz), 3.65-3.73 (m, 2H), 3.73-3.93 (m, 2H), 7.03-7.17 (m, 2H), 7.33 (ddd, 1H, J = 8.1, 6.8, 1.3 Hz), 7.44 (ddd, 1H, J = 8.2, 6.8, 1.3 Hz), 7.52 (dd, 1H, J = 8.9, 2.3 Hz), 7.76 (d, 2H, J = 9.1 Hz), 7.79-7.90 (m, 4H), 8.04 (dd, 1H, J = 8.3, 1.1 Hz), 8.56 (d, 1H, J = 2.2 Hz), 10.26 (s, 1H), 12.54 (s, 1H) | 502.0 |
| 146 | (DMSO-d6): 1.13 (d, 3H, J = 6.2 Hz), 2.97-3.11 (m, 2H), 3.69-3.95 (m, 1H), 4.77 (d, 1H, J = 4.7 Hz), 6.58 (t, 1H, J = 5.7 Hz), 6.65-6.80 (m, 2H), 7.32 (ddd, 1H, J = 8.1, 6.8, 1.2 Hz), 7.44 (ddd, 1H, J = 8.2, 6.8, 1.3 Hz), 7.52 (dd, 1H, J = 8.9, 2.3 Hz), 7.59-7.70 (m, 2H), 7.71-7.89 (m, 4H), 8.04 (d, 1H, J = 8.1 Hz), 8.55 (d, 1H, J = 2.2 Hz), 10.23 (s, 1H), 12.42 (s, 1H) | 461.9 |
| 147 | (DMSO-d6): 1.13 (d, 3H, J = 6.2 Hz), 2.95-3.15 (m, 2H), 3.68-3.90 (m, 1H), 4.77 (d, 1H, J = 4.7 Hz), 6.58 (t, 1H, J = 5.7 Hz), 6.74 (d, 2H, J = 8.9 Hz), 7.32 (ddd, 1H, J = 8.1, 6.8, 1.2 Hz), 7.44 (ddd, 1H, J = 8.2, 6.8, 1.3 Hz), 7.52 (dd, 1H, J = 8.8, 2.2 Hz), 7.65 (d, 2H, J = 8.8 Hz), 7.75-7.9 (m, 4H), 8.04 (d, 1H, J = 8.1 Hz), 8.55 (d, 1H, J = 2.2 Hz), 10.23 (s, 1H), 12.42 (s, 1H) | 462.0 |
| 148 | (DMSO-d6): 7.50 (d, 1H, J = 5.2 Hz), 7.58 (dd, 1H, J = 8.9, 2.3 Hz), 7.79 (dd, 1H, J = 5.1, 2.9 Hz), 7.87-7.97 (m, 3H), 8.00 (d, 1H, J = 9.0 Hz), 8.13 (d, 1H, J = 8.7 Hz), 8.34 (dd, 1H, J = 2.9, 1.4 Hz), 8.47 (d, 1H, J = 1.7 Hz), 8.67 (d, 1H, J = 2.2 Hz), 10.56 (s, 1H), 12.49 (s, 1H) | 439.4 |
| 149 | (DMSO-d6): 1.22-1.36 (m, 2H), 1.44 (q, 2H, J = 7.4 Hz), 1.62 (quintet, 2H, J = 7.5 Hz), 2.20 (s, 3H), 2.30 (t, 2H, J = 7.3 Hz), 2.35-2.5 (m, 10H), 7.35 (td, 1H, J = 8.9, 2.7 Hz), 7.52 (dd, 1H, J = 8.8, 2.3 Hz), 7.58 (dd, 1H, J = 10.2, 2.7 Hz), 7.75 (s, 2H), 7.80 (d, 1H, J = 8.9 Hz), 8.12 (dd, 1H, J = 9.2, 5.8 Hz), 8.15 (s, 1H), 8.59 (d, 1H, J = 2.1 Hz), 10.21 (s, 1H), 11.47 (s, 1H) | 499.2 |
| 150 | (DMSO-d6): 1.32 (quintet, 2H, J = 7.8 Hz), 1.45 (quintet, 2H, J = 7.3 Hz), 1.62 (quintet, 2H, J = 7.5 Hz), 2.25 (t, 2H, J = 7.2 Hz), 2.27-2.4 (m, 4H), 2.4-2.5 (m, 2H), 3.5-3.6 (m, 4H), 7.35 (td, 1H, J = 8.9, 2.8 Hz), 7.52 (dd, 1H, J = 9.0, 2.2 Hz), 7.58 (dd, 1H, J = 10.3, 2.7 Hz), 7.74 (s, 2H), 7.80 (d, 1H, J = 8.9 Hz), 8.12 (dd, 1H, J = 9.1, 5.8 Hz), 8.20 (s, 1H), 8.59 (d, 1H, J = 2.2 Hz), 10.20 (s, 1H), 11.47 (s, 1H) | 485.8 |

TABLE 5-continued

| Example No. | ¹H-NMR (400 MHz) δ (ppm) | LCMS m/z [M + H]⁺ |
|---|---|---|
| 151 | (DMSO-d6): 2.55 (s, 3H), 4.62 (d, 2H, J = 5.7 Hz), 5.23 (t, 1H, J = 5.7 Hz), 6.96-7.07 (m, 1H), 7.40 (dd, 1H, J = 8.4, 1.7 Hz), 7.50 (dd, 1H, J = 8.8, 2.4 Hz), 7.56 (d, 1H, J = 3.8 Hz), 7.70 (s, 1H), 7.79 (d, 1H, J = 8.9 Hz), 7.82-7.92 (m, 2H), 8.00 (d, 1H, J = 8.4 Hz), 8.53 (d, 1H, J = 2.2 Hz), 10.27 (s, 1H), 12.50 (s, 1H) | 439.2 |
| 152 | (DMSO-d6): 4.62 (d, 2H, J = 5.0 Hz), 5.22 (t, 1H, J = 5.7 Hz), 6.06 (s, 2H), 6.67 (d, 2H, J = 8.2 Hz), 7.40 (d, 1H, J = 8.6 Hz), 7.50 (d, 1H, J = 9.0 Hz), 7.61 (d, 2H, J = 8.3 Hz), 7.69 (s, 1H), 7.75-7.82 (m, 3H), 7.99 (d, 1H, J = 8.4 Hz), 8.52 (s, 1H), 10.20 (s, 1H), 12.39 (s, 1H) | 434.2 |
| 153 | (DMSO-d6): 2.35-2.45 (m, 4H), 3.55-3.65 (m, 6H), 4.62 (d, 2H, J = 5.7 Hz), 5.22 (t, 1H, J = 5.8 Hz), 7.41 (d, 1H, J = 8.5 Hz), 7.52 (d, 1H, J = 9.4 Hz), 7.57 (d, 2H, J = 8.0 Hz), 7.71 (s, 1H), 7.80 (d, 1H, J = 9.0 Hz), 7.85-7.95 (m, 4H), 8.00 (d, 1H, J = 8.6 Hz), 8.53 (s, 1H), 10.28 (s, 1H), 12.70 (s, 1H) | 518.0 |
| 154 | (DMSO-d6): 1.25-1.35 (m, 2H), 1.35-1.5 (m, 2H), 1.55-1.65 (m, 2H), 2.12 (s, 3H), 2.15-2.7 (m, 12H), 4.61 (s, 2H), 7.39 (d, 1H, J = 8.2 Hz), 7.49 (d, 1H, J = 8.8 Hz), 7.65-7.83 (m, 4H), 7.97 (d, 1H, J = 8.4 Hz), 8.48 (s, 1H), 10.2 (br, 1H) | 510.8 |
| 155 | (DMSO-d6): 1.33 (q, 2H, J = 7.7 Hz), 1.44 (q, 2H, J = 7.4 Hz), 1.63 (q, 2H, J = 7.4 Hz), 2.25 (t, 2H, J = 7.2 Hz), 2.27-2.35 (m, 4H), 2.4-2.6 (m, 2H), 3.5-3.6 (m, 4H), 4.61 (d, 2H, J = 5.7 Hz), 5.22 (t, 1H, J = 5.7 Hz), 7.33-7.43 (m, 1H), 7.48 (dd, 1H, J = 8.9, 2.3 Hz), 7.63-7.82 (m, 4H), 7.98 (d, 1H, J = 8.6 Hz), 8.48 (d, 1H, J = 2.0 Hz), 10.16 (s, 1H), 11.46 (s, 1H) | 498.2 |
| 156 | (DMSO-d6): 0.72-0.8 (m, 1H), 1.05-1.15 (m, 4H), 1.25-1.4 (m, 1H), 1.73 (dd, 1H, J = 8.0, 4.1 Hz), 7.32 (t, 1H, J = 7.4 Hz), 7.43 (t, 1H, J = 7.5 Hz), 7.50 (dd, 1H, J = 8.8, 2.4 Hz), 7.65-7.87 (m, 4H), 8.01 (d, 1H, J = 8.2 Hz), 8.50 (d, 1H, J = 1.9 Hz), 10.18 (s, 1H), 11.63 (s, 1H) | 367.2 |
| 157 | (DMSO-d6): 1.73 (quintet, 2H, J = 7.3 Hz), 1.87 (quintet, 2H, J = 6.7 Hz), 2.56 (t, 2H, J = 7.4 Hz), 3.58 (t, 2H, J = 6.6 Hz), 7.32 (t, 1H, J = 7.6 Hz), 7.43 (t, 1H, J = 7.7 Hz), 7.50 (dd, 1H, J = 8.9, 2.3 Hz), 7.66-7.83 (m, 4H), 8.02 (d, 1H, J = 8.3 Hz), 8.44-8.53 (m, 1H), 10.20 (s, 1H), 11.46 (s, 1H) | 447.2 |
| 158 | (DMSO-d6): 2.32 (s, 3H), 6.65 (s, 1H), 7.33 (t, 1H, J = 7.4 Hz), 7.43 (t, 1H, J = 7.5 Hz), 7.52 (dd, 1H, J = 8.9, 2.3 Hz), 7.68-7.87 (m, 4H), 8.02 (d, 1H, J = 8.2 Hz), 8.51 (d, 1H, J = 2.2 Hz), 10.25 (s, 1H), 11.79 (s, 1H) | 387.2 |
| 159 | (DMSO-d6): 1.98 (s, 3H), 3.92 (d, 2H, J = 5.9 Hz), 7.32 (t, 1H, J = 7.5 Hz), 7.43 (t, 1H, J = 7.6 Hz), 7.49 (dd, 1H, J = 8.8, 2.3 Hz), 7.70-7.88 (m, 4H), 8.03 (d, 1H, J = 8.3 Hz), 8.52 (s, 1H), 8.69 (t, 1H, J = 5.7 Hz), 10.23 (s, 1H), 11.92 (s, 1H) | 383.9 |
| 160 | (DMSO-d6): 3.17 (t, 2H, J = 6.3 Hz), 3.73 (t, 2H, J = 6.3 Hz), 7.32 (t, 1H, J = 7.5 Hz), 7.43 (t, 1H, J = 7.5 Hz), 7.50 (dd, 1H, J = 8.8, 2.3 Hz), 7.63-7.90 (m, 4H), 8.02 (d, 1H, J = 8.3 Hz), 8.51 (d, 1H, J = 2.2 Hz), 10.23 (s, 1H), 11.53 (s, 1H) | 420.9 |
| 161 | (DMSO-d6): 2.00-2.19 (m, 2H), 3.75 (t, 2H, J = 6.4 Hz), 4.29 (t, 2H, J = 6.2 Hz), 7.32 (t, 1H, J = 7.5 Hz), 7.43 (t, 1H, J = 7.5 Hz), 7.48 (dd, 1H, J = 8.9, 2.3 Hz), 7.68-7.85 (m, 4H), 8.02 (d, 1H, J = 8.3 Hz), 8.50 (d, 1H, J = 2.2 Hz), 10.23 (s, 1H), 10.83 (s, 1H) | 405.2 |
| 162 | (DMSO-d6): 2.6-2.7 (m, 4H), 3.75-3.85 (m, 4H), 7.08 (d, 2H, J = 9.1 Hz), 7.33 (ddd, 1H, J = 8.1, 6.8, 1.2 Hz), 7.44 (ddd, 1H, J = 8.2, 6.8, 1.3 Hz), 7.52 (dd, 1H, J = 8.8, 2.3 Hz), 7.68-7.91 (m, 6H), 8.04 (d, 1H, J = 8.2 Hz), 8.55 (d, 1H, J = 2.2 Hz), 10.25 (s, 1H), 12.52 (s, 1H) | 489.9 |
| 163 | (DMSO-d6): 2.59 (t, 2H, J = 5.8 Hz), 3.49 (q, 2H, J = 5.6 Hz), 3.83 (s, 2H), 4.50 (t, 1H, J = 5.3 Hz), 7.33 (ddd, 1H, J = 8.1, 6.8, 1.2 Hz), 7.45 (ddd, 1H, J = 8.2, 6.8, 1.3 Hz), 7.49-7.62 (m, 3H), 7.75-7.94 (m, 6H), 8.05 (d, 1H, J = 8.3 Hz), 8.56 (d, 1H, J = 2.1 Hz), 10.31 (s, 1H), 12.70 (br, 1H) | 462.2 |
| 164 | (DMSO-d6): 2.4-2.5 (m, 2H), 2.61-2.79 (m, 2H), 2.84 (t, 1H, J = 2.7 Hz), 7.32 (t, 1H, J = 7.5 Hz), 7.43 (t, 1H, J = 7.6 Hz), 7.50 (dd, 1H, J = 8.8, 2.2 Hz), 7.68-7.85 (m, 4H), 8.02 (d, 1H, J = 8.4 Hz), 8.50 (d, 1H, J = 2.2 Hz), 10.21 (s, 1H), 11.49 (s, 1H) | 365.4 |
| 165 | (DMSO-d6): 2.11 (s, 3H), 7.33 (t, 1H, J = 7.5 Hz), 7.44 (t, 1H, J = 7.5 Hz), 7.50 (dd, 1H, J = 8.8, 2.3 Hz), 7.68-7.96 (m, 4H), 8.03 (d, 1H, J = 8.3 Hz), 8.51 (d, 1H, J = 2.0 Hz), 10.30 (s, 1H), 11.82 (s, 1H) | 349.2 (M − H) |
| 166 | (DMSO-d6): 0.82 (q, 2H, J = 3.9 Hz), 1.14 (q, 2H, J = 3.9 Hz), 1.44 (s, 3H), 7.32 (t, 1H, J = 7.5 Hz), 7.43 (t, 1H, J = 7.4 Hz), 7.49 (dd, 1H, J = 8.8, 2.2 Hz), 7.7-7.85 (m, 4H), 8.03 (d, 1H, J = 8.3 Hz), 8.53 (d, 1H, J = 2.1 Hz), 10.22 (s, 1H), 12.13 (s, 1H) | 367.2 |
| 167 | (DMSO-d6): 4.45 (d, 2H, J = 6.8 Hz), 6.63 (d, 1H, J = 15.1 Hz), 6.83-6.95 (m, 1H), 7.33 (t, 1H, J = 7.3 Hz), 7.43 (d, 1H, J = 7.5 Hz), 7.51 (dd, 1H, J = 8.9, 2.1 Hz), 7.7-7.9 (m, 4H), 8.02 (d, 1H, J = 8.3 Hz), 8.51 (s, 1H), 110.26 (s, 1H), 11.69 (s, 1H) | 387.2 |

TABLE 5-continued

| Example No. | ¹H-NMR (400 MHz) δ (ppm) | LCMS m/z [M + H]⁺ |
|---|---|---|
| 168 | (DMSO-d6): 2.35-2.55 (m, 4H), 2.55-2.7 (m, 4H), 3.65-3.8 (m, 4H), 7.32 (t, 1H, J = 7.4 Hz), 7.43 (t, 1H, J = 7.5 Hz), 7.50 (dd, 1H, J = 8.8, 2.2 Hz), 7.6-7.7 (m, 2H), 7.79 (t, 2H, J = 9.4 Hz), 8.01 (d, 1H, J = 8.3 Hz), 8.48 (d, 1H, J = 2.2 Hz), 10.15 (s, 1H), 12.03 (s, 1H) | 426.0 |
| 169 | (DMSO-d6): 1.47 (quintet, 2H, J = 7.3 Hz), 1.63 (quintet, 2H, J = 7.4 Hz), 2.21-2.37 (m, 8H), 3.5-3.6 (m, 4H), 7.32 (t, 1H, J = 7.5 Hz), 7.43 (t, 1H, J = 7.5 Hz), 7.50 (dd, 1H, J = 8.9, 2.3 Hz), 7.67-7.86 (m, 4H), 8.02 (d, 1H, J = 8.3 Hz), 8.50 (d, 1H, J = 2.2 Hz), 10.19 (s, 1H), 11.46 (s, 1H) | 454.1 |
| 170 | (DMSO-d6): 1.81 (t, 2H, J = 6.8 Hz), 2.25-2.45 (m, 6H), 3.5-3.6 (m, 4H), 4.21 (t, 2H, J = 6.6 Hz), 7.32 (t, 1H, J = 7.5 Hz), 7.43 (t, 1H, J = 7.5 Hz), 7.48 (d, 1H, J = 9.0 Hz), 7.67-7.86 (m, 4H), 8.02 (d, 1H, J = 8.2 Hz), 8.49 (s, 1H), 10.23 (s, 1H), 10.79 (s, 1H) | 456.0 |
| 171 | (DMSO-d6): 1.03 (d, 6H, J = 6.3 Hz), 1.60-1.74 (m, 2H), 2.64-2.73 (m, 2H), 3.46-3.66 (m, 4H), 7.33 (ddd, 1H, J = 8.1, 6.8, 1.2 Hz), 7.45 (ddd, 1H, J = 8.2, 6.8, 1.3 Hz), 7.5-7.6 (m, 3H), 7.80 (d, 1H, J = 8.1 Hz), 7.83 (d, 1H, J = 8.9 Hz), 7.85-7.95 (m, 4H), 8.05 (d, 1H, J = 8.0 Hz), 8.56 (d, 1H, J = 2.2 Hz), 10.32 (s, 1H), 12.71 (s, 1H) | 516.2 |
| 172 | (DMSO-d6): 1.62-1.79 (m, 2H), 1.8-1.95 (m, 2H), 2.23-2.38 (m, 2H), 2.45-2.6 (m, 2H), 3.58 (s, 2H), 4.6-4.8 (m, 1H), 7.33 (ddd, 1H, J = 8.1, 6.8, 1.3 Hz), 7.45 (ddd, 1H, J = 8.2, 6.8, 1.3 Hz), 7.49-7.61 (m, 3H), 7.72-7.95 (m, 6H), 8.05 (d, 1H, J = 8.0 Hz), 8.56 (d, 1H, J = 2.2 Hz), 10.31 (s, 1H), 12.71 (s, 1H) | 504.2 |
| 173 | (DMSO-d6): 1.30-1.51 (m, 2H), 1.60-1.79 (m, 2H), 1.97-2.14 (m, 2H), 2.59-2.74 (m, 2H), 3.40-3.62 (m, 3H), 4.55 (d, 1H, J = 4.1 Hz), 7.33 (ddd, 1H, J = 8.1, 6.8, 1.2 Hz), 7.45 (ddd, 1H, J = 8.2, 6.8, 1.3 Hz), 7.5-7.6 (m, 3H), 7.74-7.95 (m, 6H), 8.05 (d, 1H, J = 8.2 Hz), 8.56 (d, 1H, J = 2.1 Hz), 10.31 (s, 1H), 12.70 (s, 1H) | 502.3 |
| 174 | (DMSO-d6): 2.16 (s, 3H), 2.25-2.45 (m, 8H), 3.15 (d, 2H, J = 6.0 Hz), 6.41 (d, 1H, J = 15.3 Hz), 6.78 (dd, 1H, J = 13.8, 7.6 Hz), 7.32 (t, 1H, J = 7.4 Hz), 7.43 (t, 1H, J = 7.6 Hz), 7.51 (dd, 1H, J = 8.8, 2.3 Hz), 7.69-7.87 (m, 4H), 8.01 (d, 1H, J = 8.2 Hz), 8.49 (s, 1H), 10.20 (s, 1H) | 451.2 |
| 175 | (DMSO-d6): 2.35-2.45 (m, 4H), 3.1-3.2 (m, 2H), 3.55-3.65 (m, 4H), 6.4-6.5 (m, 1H), 6.75-6.85 (m, 1H), 7.32 (t, 1H, J = 7.6 Hz), 7.39-7.47 (m, 1H), 7.52 (d, 1H, J = 9.0 Hz), 7.7-7.85 (m, 4H), 7.95-8.05 (m, 1H), 8.50 (s, 1H), 10.23 (s, 1H), 11.60 (s, 1H) | 438.2 |
| 176 | (DMSO-d6): 3.36-3.44 (m, 4H), 3.62-3.7 (m, 4H), 7.31 (t, 1H, J = 7.5 Hz), 7.42 (t, 1H, J = 7.6 Hz), 7.48 (dd, 1H, J = 8.9, 2.2 Hz), 7.66 (d, 2H, J = 9.3 Hz), 7.78 (t, 2H, J = 8.6 Hz), 8.01 (d, 1H, J = 8.2 Hz), 8.50 (d, 1H, J = 2.2 Hz), 10.10 (s, 1H), 11.43 (s, 1H) | 398.0 |
| 177 | (DMSO-d6): 1.89 (t, 2H, J = 6.5 Hz), 3.2-3.35 (m, 2H), 3.69 (t, 2H, J = 6.5 Hz), 7.30 (t, 1H, J = 7.5 Hz), 7.41 (t, 1H, J = 7.3 Hz), 7.45-7.55 (m, 3H), 7.78 (t, 2H, J = 8.3 Hz), 7.87-8.04 (m, 2H), 8.46 (d, 1H, J = 2.2 Hz), 10.02 (s, 1H), 10.46 (s, 1H) | 404.4 |
| 178 | (DMSO-d6): 1.60 (q, 2H, J = 6.9 Hz), 2.20-2.39 (m, 6H), 3.13 (q, 2H, J = 6.4 Hz), 3.5-3.6 (m, 4H), 7.30 (t, 1H, J = 7.5 Hz), 7.41 (t, 1H, J = 7.5 Hz), 7.44-7.5 (m, 3H), 7.77 (t, 2H, J = 8.3 Hz), 7.84 (br, 1H), 7.98 (d, 1H, J = 8.3 Hz), 8.46 (d, 1H, J = 2.2 Hz), 10.00 (s, 1H), 10.41 (s, 1H) | 455.2 |
| 179 | (DMSO-d6): 2.52-2.63 (m, 4H), 3.47 (q, 4H, J = 6.1 Hz), 3.76 (s, 2H), 4.39 (t, 2H, J = 5.4 Hz), 7.33 (ddd, 1H, J = 8.0, 6.8, 1.2 Hz), 7.44 (ddd, 1H, J = 8.2, 6.8, 1.3 Hz), 7.53 (dd, 1H, J = 8.9, 2.3 Hz), 7.60 (d, 2H, J = 8.3 Hz), 7.71-7.96 (m, 6H), 7.99-8.09 (m, 1H), 8.56 (d, 1H, J = 2.2 Hz), 10.31 (s, 1H), 12.70 (s, 1H) | 506.2 |
| 180 | (DMSO-d6): 2.52-2.63 (m, 2H), 2.95 (d, 2H, J = 3.6 Hz), 3.10-3.23 (m, 2H), 3.66 (s, 2H), 7.33 (ddd, 1H, J = 8.1, 6.8, 1.2 Hz), 7.45 (ddd, 1H, J = 8.2, 6.8, 1.3 Hz), 7.47-7.64 (m, 3H), 7.73-7.86 (m, 5H), 7.90 (d, 2H, J = 8.3 Hz), 8.05 (d, 1H, J = 8.1 Hz), 8.56 (d, 1H, J = 2.2 Hz), 10.31 (s, 1H), 12.72 (s, 1H) | 501.2 |
| 181 | (DMSO-d6): 1.83-2.10 (m, 4H), 2.4-2.6 (m, 4H), 3.66 (s, 2H), 7.33 (ddd, 1H, J = 8.1, 6.8, 1.2 Hz), 7.44 (ddd, 1H, J = 8.2, 6.8, 1.3 Hz), 7.48-7.62 (m, 3H), 7.80 (d, 1H, J = 8.0 Hz), 7.83 (d, 1H, J = 8.9 Hz), 7.85-7.95 (m, 4H), 8.01-8.08 (m, 1H), 8.55 (d, 1H, J = 2.2 Hz), 10.31 (s, 1H), 12.71 (s, 1H) | 522.2 |
| 182 | (DMSO-d6): 2.80-2.99 (m, 4H), 3.07-3.23 (m, 4H), 3.79 (s, 2H), 7.33 (ddd, 1H, J = 8.1, 6.8, 1.2 Hz), 7.44 (ddd, 1H, J = 8.2, 6.8, 1.3 Hz), 7.53 (dd, 1H, J = 8.9, 2.3 Hz), 7.60 (d, 2H, J = 8.3 Hz), 7.76-7.85 (m, 2H), 7.85-7.94 (m, 4H), 8.04 (d, 1H, J = 8.0 Hz), 8.55 (d, 1H, J = 2.2 Hz), 10.31 (s, 1H), 12.72 (s, 1H) | 536.1 |
| 183 | (DMSO-d6): 1.39 (s, 9H), 2.95-3.25 (m, 4H), 6.62 (t, 1H, J = 5.5 Hz), 6.71 (d, 2H, J = 8.8 Hz), 6.91 (t, 1H, J = 5.5 Hz), 7.32 (ddd, 1H, J = 8.1, 6.8, 1.2 Hz), 7.44 (ddd, 1H, J = 8.2, 6.8, 1.3 Hz), 7.52 (dd, 1H J = 8.9, 2.2 Hz), 7.66 (d, 2H, J = 8.7 Hz), 7.72-7.86 (m, 4H), 8.03 (d, 1H, J = 8.2 Hz), 8.54 (d, 1H, J = 2.1 Hz), 10.22 (s, 1H), 12.43 (s, 1H) | 547.2 |

TABLE 5-continued

| Example No. | $^1$H-NMR (400 MHz) δ (ppm) | LCMS m/z [M + H]$^+$ |
|---|---|---|
| 184 | (DMSO-d6): 2.56-2.76 (m, 8H), 3.61 (s, 2H), 7.33 (ddd, 1H, J = 8.1, 6.8, 1.2 Hz), 7.44 (ddd, 1H, J = 8.2, 6.8, 1.3 Hz), 7.47-7.61 (m, 3H), 7.72-7.98 (m, 6H), 7.98-8.13 (m, 1H), 8.55 (d, 1H, J = 2.2 Hz), 10.31 (s, 1H), 12.71 (s, 1H) | 504.2 |
| 185 | (DMSO-d6): 2.27-2.5 (m, 10H), 3.48 (td, 2H, J = 6.3, 5.3 Hz), 3.56 (s, 2H), 4.35 (t, 1H, J = 5.3 Hz), 7.33 (ddd, 1H, J = 8.1, 6.8, 1.2 Hz), 7.44 (ddd, 1H, J = 8.2, 6.8, 1.3 Hz), 7.50-7.58 (m, 3H), 7.73-7.94 (m, 6H), 8.04 (d, 1H, J = 8.1 Hz), 8.55 (d, 1H, J = 2.2 Hz), 10.30 (s, 1H), 12.70 (s, 1H) | 531.3 |
| 186 | (DMSO-d6): 0.97-1.07 (m, 2H), 1.17 (t, 2H, J = 7.3 Hz), 1.21-1.28 (m, 2H), 7.31 (t, 1H, J = 7.5 Hz), 7.43 (t, 1H, J = 7.5 Hz), 7.51 (dd, 1H, J = 8.8, 2.3 Hz), 7.61 (br, 2H), 7.79 (t, 2H, J = 9.2 Hz), 8.01 (d, 1H, J = 8.3 Hz), 8.50 (d, 1H, J = 2.2 Hz), 10.18 (s, 1H) | 368.2 |
| 187 | (DMSO-d6): 2.31-2.62 (m, 6H), 3.17-3.40 (m, 4H), 3.55 (q, 2H, J = 6.0 Hz), 4.44 (t, 1H, J = 5.4 Hz), 7.09 (d, 2H, J = 9.0 Hz), 7.33 (ddd, 1H, J = 8.1, 6.8, 1.3 Hz), 7.44 (ddd, 1H, J = 8.2, 6.8, 1.3 Hz), 7.52 (dd, 1H, J = 8.9, 2.3 Hz), 7.69-7.87 (m, 6H), 8.00-8.09 (m, 1H), 8.54 (d, 1H, J = 2.2 Hz), 10.25 (s, 1H), 12.52 (s, 1H) | 517.3 |
| 188 | (DMSO-d6): 3.00 (q, 2H, J = 6.0 Hz), 3.41 (t, 2H, J = 6.5 Hz), 3.58-4.08 (m, 2H), 6.78 (d, 2H, J = 8.7 Hz), 7.33 (ddd, 1H, J = 8.1, 6.8, 1.2 Hz), 7.44 (ddd, 1H, J = 8.2, 6.8, 1.3 Hz), 7.54 (dd, 1H, J = 9.0, 2.2 Hz), 7.61-7.86 (m, 6H), 7.9-8.1 (m, 3H), 8.55 (d, 1H, J = 2.1 Hz), 10.30 (d, 1H, J = 6.1 Hz), 12.47 (s, 1H) | 447.2 |
| 189 | (DMSO-d6): 1.2-1.52 (m, 4H), 1.57-1.77 (m, 2H), 2.0-2.1 (m, 1H), 2.25-2.39 (m, 1H), 2.58-2.72 (m, 1H), 3.3-3.4 (m, 1H), 3.4-3.5 (m, 1H), 3.64 (dt, 1H, J = 10.6, 5.1 Hz), 4.18 (d, 1H, J = 14.6 Hz), 4.50 (t, 1H, J = 5.3 Hz), 7.33 (ddd, 1H, J = 8.1, 6.8, 1.3 Hz), 7.44 (ddd, 1H, J = 8.2, 6.8, 1.3 Hz), 7.50-7.62 (m, 3H), 7.74-7.94 (m, 6H), 8.05 (d, 1H, J = 8.1 Hz), 8.56 (d, 1H, J = 2.2 Hz), 10.31 (s, 1H), 12.69 (s, 1H) | 516.3 |
| 190 | (DMSO-d6): 1.68-1.8 (m, 2H), 2.26 (s, 3H), 2.52-2.74 (m, 8H), 3.71 (s, 2H), 7.26-7.37 (m, 1H), 7.44 (ddd, 1H, J = 8.1, 6.8, 1.2 Hz), 7.51-7.64 (m, 3H), 7.7-7.97 (m, 6H), 8.05 (d, 1H, J = 8.2 Hz), 8.55 (s, 1H), 10.31 (s, 1H), 12.70 (s, 1H) | 515.3 |
| 191 | (DMSO-d6): 2.07 (t, 2H, J = 7.5 Hz), 2.83 (t, 2H, J = 7.7 Hz), 3.66 (t, 2H, J = 6.5 Hz), 7.33 (t, 1H, J = 7.5 Hz), 7.39-7.56 (m, 4H), 7.75-7.95 (m, 6H), 8.05 (d, 1H, J = 8.3 Hz), 8.56 (d, 1H, J = 2.2 Hz), 10.31 (s, 1H), 12.70 (s, 1H) | 463.2 (M − H) |
| 192 | (DMSO-d6): 3.15 (t, 2H, J = 7.0 Hz), 3.93 (t, 2H, J = 6.9 Hz), 7.33 (t, 1H, J = 7.5 Hz), 7.44 (t, 1H, J = 7.3 Hz), 7.5-7.6 (m, 3H), 7.73-7.96 (m, 6H), 8.05 (d, 1H, J = 8.2 Hz), 8.56 (s, 1H), 10.31 (s, 1H), 12.71 (s, 1H) | 451.2 |
| 193 | (DMSO-d6): 4.35 (d, 2H, J = 6.1 Hz), 5.43 (t, 1H, J = 6.0 Hz), 7.33 (t, 1H, J = 7.6 Hz), 7.44 (t, 1H, J = 7.5 Hz), 7.53 (d, 1H, J = 8.9 Hz), 7.67 (d, 2H, J = 7.9 Hz), 7.72-8.13 (m, 7H), 8.56 (s, 1H), 10.33 (s, 1H), 12.77 (s, 1H) | 443.0 |
| 194 | (DMSO-d6): 3.36-3.51 (m, 6H), 3.88 (s, 2H), 4.35 (s, 3H), 7.33 (ddd, 1H, J = 8.1, 6.8, 1.3 Hz), 7.44 (ddd, 1H, J = 8.2, 6.8, 1.3 Hz), 7.53 (dd, 1H, J = 8.8, 2.3 Hz), 7.61 (d, 2H, J = 8.3 Hz), 7.71-7.95 (m, 6H), 7.98-8.16 (m, 1H), 8.56 (d, 1H, J = 2.1 Hz), 10.32 (s, 1H), 12.71 (s, 1H) | 522.3 |
| 195 | (DMSO-d6): 5.56 (s, 2H), 7.33 (ddd, 1H, J = 8.1, 6.8, 1.3 Hz), 7.4-7.57 (m, 4H), 7.77-7.81 (m, 1H), 7.83 (d 1H, J = 8.9 Hz,), 7.87-7.96 (m, 4H), 8.0-8.08 (m, 2H), 8.56 (d, 1H, J = 2.2 Hz), 8.72 (s, 1H), 10.32 (s, 1H), 12.72 (s, 1H) | 470.2 |
| 196 | (DMSO-d6): 1.76 (quintet, 2H, J = 7.3 Hz), 2.15 (s, 3H), 2.2-2.4 (m, 10H), 2.65-2.75 (m, 2H), 7.33 (t, 1H, J = 7.5 Hz), 7.4-7.5 (m, 3H), 7.54 (dd, 1H, J = 8.9, 2.2 Hz), 7.71-7.96 (m, 6H), 8.04 (d, 1H, J = 8.3 Hz), 8.55 (s, 1H), 10.33 (s, 1H), 12.68 (s, 1H) | 528.8 |
| 197 | (DMSO-d6): 1.77 (quintet, 2H, J = 7.4 Hz), 2.2-2.4 (m, 6H), 2.71 (t, 2H, J = 8.2 Hz), 3.5-3.65 (m, 4H), 7.33 (t, 1H, J = 7.3 Hz), 7.4-7.5 (m, 3H), 7.53 (d, 1H, J = 8.9 Hz), 7.66-7.95 (m, 6H), 8.04 (d, 1H, J = 8.3 Hz), 8.56 (s, 1H), 10.31 (s, 1H), 12.69 (s, 1H) | 516.2 |
| 198 | (DMSO-d6): 2.15 (s, 3H), 2.4-2.6 (m, 10H), 2.83 (t, 2H, J = 7.7 Hz), 7.33 (t, 1H, J = 7.5 Hz), 7.39-7.56 (m, 4H), 7.74-7.95 (m, 5H), 8.05 (d, 1H, J = 8.3 Hz), 8.21 (s, 1H), 8.56 (d, 1H, J = 2.3 Hz), 10.31 (s, 1H), 12.69 (s, 1H) | 515.2 |
| 199 | (DMSO-d6): 2.35-2.6 (m, 6H), 2.85 (t, 2H, J = 7.7 Hz), 3.5-3.65 (m, 4H), 7.33 (t, 1H, J = 7.5 Hz), 7.4-7.6 (m, 4H), 7.67-7.93 (m, 6H), 8.04 (d, 1H, J = 7.7 Hz), 8.55 (s, 1H), 10.31 (s, 1H), 12.69 (s, 1H) | 502.4 |
| 200 | (DMSO-d6): 5.46 (d, 1H, J = 10.8 Hz), 6.04 (d, 1H, J = 17.7 Hz), 6.86 (dd, 1H, J = 17.6, 10.9 Hz), 7.33 (t, 1H, J = 7.5 Hz), 7.44 (t, 1H, J = 7.5 Hz), 7.49-7.59 (m, 1H), 7.73 (d, 2H, J = 7.9 Hz), 7.75-7.85 (m, 2H), 7.85-7.95 (m, 4H), 8.05 (d, 1H, J = 8.0 Hz), 8.56 (s, 1H), 10.32 (s, 1H), 12.75 (s, 1H) | 413.0 (M − H) |

TABLE 5-continued

| Example No. | ¹H-NMR (400 MHz) δ (ppm) | LCMS m/z [M + H]⁺ |
|---|---|---|
| 201 | (DMSO-d6): 2.80 (t, 2H, J = 6.9 Hz), 3.53 (td, 2H, J = 6.0, 2.1 Hz), 3.66 (s, 2H), 4.21 (q, 1H, J = 6.1 Hz), 5.33 (d, 1H, J = 6.4 Hz), 7.33 (ddd, 1H, J = 8.1, 6.8, 1.2 Hz), 7.44 (ddd, 1H, J = 8.2, 6.8, 1.3 Hz), 7.47-7.56 (m, 3H), 7.69-7.98 (m, 6H), 8.05 (d, 1H, J = 8.3 Hz), 8.56 (d, 1H, J = 2.2 Hz), 10.31 (s, 1H), 12.70 (s, 1H) | 474.2 |
| 202 | (DMSO-d6): 1.46-1.65 (m, 1H), 1.91-2.11 (m, 1H), 2.26-2.39 (m, 1H), 2.45 (dd, 1H, J = 8.1, 5.7 Hz), 2.51-2.65 (m, 1H), 2.62-2.74 (m, 1H), 3.63 (d, 1H, J = 13.6 Hz), 3.69 (d, 1H, J = 13.6 Hz), 4.21 (dd, 1H, J = 6.0, 3.4 Hz), 4.70 (d, 1H, J = 4.5 Hz), 7.33 (ddd, 1H, J = 8.1, 6.8, 1.2 Hz), 7.44 (ddd, 1H, J = 8.2, 6.8, 1.3 Hz), 7.48-7.62 (m, 3H), 7.67-7.96 (m, 6H), 8.05 (d, 1H, J = 8.3 Hz), 8.49-8.59 (m, 1H), 10.31 (s, 1H), 12.71 (s, 1H) | 488.3 |
| 203 | (DMSO-d6): 1.48-1.64 (m, 1H), 1.94-2.07 (m, 1H), 2.26-2.37 (m, 1H), 2.45 (dd, 1H, J = 8.1, 5.8 Hz), 2.51-2.64 (m, 1H), 2.65-2.74 (m, 1H), 3.64 (d, 1H, J = 13.8 Hz), 3.69 (d, 1H, J = 13.8 Hz), 4.14-4.26 (m, 1H), 4.71 (d, 1H, J = 4.5 Hz), 7.33 (ddd, 1H, J = 8.1, 6.8, 1.2 Hz), 7.45 (ddd, 1H, J = 8.2, 6.8, 1.3 Hz), 7.48-7.60 (m, 3H), 7.70-7.97 (m, 6H), 8.05 (d, 1H, J = 8.2 Hz), 8.56 (d, 1H, J = 2.2 Hz), 10.31 (s, 1H), 12.71 (s, 1H) | 488.3 |
| 204 | (DMSO-d6): 4.74 (s, 1H), 7.33 (t, 1H, J = 7.5 Hz), 7.44 (t, 1H, J = 7.6 Hz), 7.46-7.55 (m, 1H), 7.75-7.85 (m, 2H), 7.91 (br, 1H), 7.97 (br, 1H), 8.04 (d, 1H, J = 8.3 Hz), 8.52 (s, 1H), 10.34 (s, 1H), 12.05 (s, 1H) | 337.2 |
| 205 | (DMSO-d6): 5.86 (s, 2H), 7.33 (ddd, 1H, J = 8.1, 6.8, 1.3 Hz), 7.44 (ddd, 1H, J = 8.2, 6.8, 1.3 Hz), 7.5-7.65 (m, 3H), 7.75-7.85 (m, 2H), 7.87-7.98 (m, 4H), 8.05 (d, 1H, J = 8.0 Hz), 8.56 (d, 1H, J = 2.2 Hz), 9.58 (s, 1H), 10.33 (s, 1H), 12.74 (s, 1H) | 471.1 |
| 206 | (DMSO-d6): 4.78 (s, 2H), 7.33 (t, 1H, J = 7.2 Hz), 7.44 (t, 1H, J = 7.2 Hz), 7.51 (dd, 1H, J = 8.9, 2.4 Hz), 7.75-7.85 (m, 2H), 7.92 (br, 1H), 7.96 (br, 1H), 8.04 (d, 1H, J = 8.2 Hz), 8.52 (d, 1H, J = 2.2 Hz), 10.38 (s, 1H), 12.03 (s, 1H) | 385.2 |
| 207 | (DMSO-d6): 2.02 (quintet, 2H, J = 6.7 Hz), 2.64 (t, 2H, J = 7.0 Hz), 3.75 (t, 2H, J = 6.4 Hz), 7.33 (t, 1H, J = 7.5 Hz), 7.44 (t, 1H, J = 7.6 Hz), 7.51 (dd, 1H, J = 8.9, 2.3 Hz), 7.75-7.83 (m, 2H), 7.86 (s, 1H), 7.91 (s, 1H), 8.03 (d, 1H, J = 8.3 Hz), 8.47-8.54 (m, 1H), 10.30 (s, 1H), 11.86 (s, 1H) | 412.8 |
| 208 | (DMSO-d6): 5.34 (s, 2H), 6.95 (t, 1H, J = 1.1 Hz), 7.24 (t, 1H, J = 1.3 Hz), 7.33 (ddd, 1H, J = 8.1, 6.8, 1.3 Hz), 7.40-7.47 (m, 3H), 7.52 (dd, 1H, J = 8.9, 2.3 Hz), 7.75-7.95 (m, 7H), 8.05 (d, 1H, J = 8.0 Hz), 8.56 (d, 1H, J = 2.2 Hz), 10.32 (s, 1H), 12.71 (s, 1H) | 469.2 |
| 209 | (DMSO-d6): 1.02 (s, 6H), 3.26 (d, 2H, J = 5.3 Hz), 3.76 (s, 2H), 4.59 (br, 1H), 7.33 (ddd, 1H, J = 8.1, 6.8, 1.3 Hz), 7.44 (ddd, 1H, J = 8.2, 6.8, 1.3 Hz), 7.53 (dd, 1H, J = 8.8, 2.3 Hz), 7.60 (d, 2H, J = 8.1 Hz), 7.72-7.97 (m, 6H), 8.05 (d, 1H, J = 8.1 Hz), 8.56 (d, 1H, J = 2.2 Hz), 10.31 (s, 1H), 12.71 (s, 1H) | 490.3 |
| 210 | (DMSO-d6): 2.45-2.6 (m, 4H), 3.47-3.70 (m, 6H), 7.33 (t, 1H, J = 7.5 Hz), 7.44 (t, 1H, J = 7.6 Hz), 7.54 (d, 1H, J = 9.1 Hz), 7.68 (d, 2H, J = 7.9 Hz), 7.75-7.95 (m, 6H), 8.04 (d, 1H, J = 8.4 Hz), 8.55 (s, 1H), 10.32 (s, 1H), 12.77 (s, 1H) | 512.3 |
| 211 | (DMSO-d6): 2.17 (s, 3H), 2.45-2.6 (m, 8H), 3.56 (s, 2H), 7.33 (t, 1H, J = 7.4 Hz), 7.44 (t, 1H, J = 7.4 Hz), 7.53 (dd, 1H, J = 8.8, 2.2 Hz), 7.67 (d, 2H, J = 8.0 Hz), 7.75-7.95 (m, 6H), 8.05 (d, 1H, J = 8.4 Hz), 8.55 (s, 1H), 10.32 (s, 1H), 12.77 (s, 1H) | 525.0 |
| 212 | (DMSO-d6): 1.68 (quintet, 2H, J = 6.7 Hz), 3.2-3.4 (m, 2H), 3.49 (q, 2H, J = 5.7 Hz), 4.59 (s, 1H), 7.32 (t, 1H, J = 7.4 Hz), 7.43 (t, 1H, J = 7.5 Hz), 7.51 (dd, 1H, J = 8.6, 2.2 Hz), 7.65-8.1 (m, 5H), 8.47 (br, 1H), 10.27 (br, 1H), 11.82 (br, 1H) | 394.8 |
| 213 | (DMSO-d6): 1.89 (quintet, 2H, J = 7.5 Hz), 3.11 (t, 2H, J = 7.8 Hz), 3.25-3.4 (m, 2H), 3.48 (t, 2H, J = 7.1 Hz), 3.59 (q, 2H, J = 5.8 Hz), 4.78 (s, 1H), 4.81 (t, 1H, J = 5.5 Hz), 7.30 (t, 1H, J = 7.5 Hz), 7.41 (t, 1H, J = 7.6 Hz), 7.45-7.53 (m, 3H), 7.78 (t, 2H, J = 8.7 Hz), 7.98 (d, 1H, J = 8.3 Hz), 8.47 (d, 1H, J = 2.1 Hz), 10.00 (s, 1H), 10.76 (s, 1H) | 438.0 |
| 214 | (DMSO-d6): 7.33 (ddd, 1H, J = 8.1, 6.8, 1.2 Hz), 7.4-7.47 (m, 1H), 7.51 (dd, 1H, J = 8.8, 2.3 Hz), 7.69 (s, 2H), 7.75-7.85 (m, 2H), 8.02 (d, 1H, J = 8.0 Hz), 8.50 (d, 1H, J = 2.2 Hz), 8.54-8.62 (m, 1H), 10.23 (s, 1H), 12.42 (s, 1H) | 473.9 |
| 215 | (DMSO-d6): 6.97 (br, 2H), 7.30 (ddd, 1H, J = 8.1, 6.8, 1.2 Hz), 7.41 (ddd, 1H, J = 8.2, 6.8, 1.3 Hz), 7.43-7.53 (m, 3H), 7.78 (t, 2H, J = 8.4 Hz), 7.99 (d, 1H, J = 8.1 Hz), 8.46 (d, 1H, J = 2.2 Hz), 9.97 (s, 1H), 10.36 (s, 1H) | 328.1 |
| 216 | (DMSO-d6): 3.1-3.3 (m, 2H), 3.5-3.6 (m, 2H), 5.0-5.15 (m, 3H), 7.20 (br, 1H), 7.31 (t, 1H, J = 7.5 Hz), 7.37-7.50 (m, 1H), 7.57 (dd, 1H, J = 8.9, 2.2 Hz), 7.64-7.92 (m, 4H), 8.25 (s, 1H), 8.69 (s, 1H), 10.05 (s, 1H) | 410.3 |
| 217 | (DMSO-d6): 3.2-3.4 (m, 4H), 3.6-3.75 (m, 4H), 5.2-5.3 (m, 3H), 7.31 (t, 1H, J = 7.1 Hz), 7.42 (dd, 1H, J = 8.2, 6.7 Hz), 7.51 (dd, 1H, J = 8.8, 2.3 Hz), 7.59 (s, 1H), 7.63 (s, 1H), 7.7-7.85 (m, 2H), 8.00 (d, 1H, J = 7.8 Hz), 8.49 (d, 1H, J = 2.2 Hz), 10.13 (s, 1H), 11.12 (s, 1H) | 472.3 |

TABLE 5-continued

| Example No. | ¹H-NMR (400 MHz) δ (ppm) | LCMS m/z [M + H]⁺ |
|---|---|---|
| 218 | (DMSO-d6): 4.31 (s, 2H), 5.61 (br, 1H), 7.32 (t, 1H, J = 7.4 Hz), 7.43 (t, 1H, J = 7.5 Hz), 7.53 (d, 1H, J = 9.2 Hz), 7.7-8.15 (m, 5H), 8.48 (br, 1H), 10.31 (br, 1H), 11.5-12.0 (m, 1H) | 367.0 |
| 219 | (DMSO-d6): 1.37 (s, 9H), 1.52-1.65 (m, 1H), 2.00-2.10 (m, 1H), 2.23-2.35 (m, 1H), 2.4-2.6 (m, 2H), 2.73 (dd, 1H, J = 9.1, 7.2 Hz), 3.63 (d, 1H, J = 13.9 Hz), 3.68 (d, 1H, J = 13.9 Hz), 3.92 (br, 1H), 7.00 (d, 1H, J = 7.1 Hz), 7.33 (ddd, 1H, J = 8.0, 6.8, 1.2 Hz), 7.45 (ddd, 1H, J = 8.2, 6.8, 1.3 Hz), 7.48-7.61 (m, 3H), 7.73-7.94 (m, 6H), 8.05 (d, 1H, J = 8.2 Hz), 8.56 (d, 1H, J = 2.2 Hz), 10.31 (s, 1H), 12.71 (s, 1H) | 587.1 |
| 220 | (DMSO-d6): 2.0-2.39 (m, 2H), 2.50-2.59 (m, 2H), 3.23 (br, 2H), 3.72-3.85 (m, 1H), 3.85-4.15 (m, 2H), 4.5-4.7 (m, 2H), 7.34 (ddd, 1H, J = 8.1, 6.8, 1.3 Hz), 7.45 (ddd, 1H, J = 8.2, 6.8, 1.3 Hz), 7.56 (dd, 1H, J = 8.9, 2.3 Hz), 7.71-8.12 (m, 6H), 8.46 (s, 2H), 8.51-8.68 (m, 2H), 10.44 (s, 1H), 11.4-11.9 (m, 1H), 12.78 (s, 1H) | 487.2 |
| 221 | (DMSO-d6): 1.51-1.75 (m, 1H), 1.78-1.95 (m, 1H), 2.11 (s, 6H), 2.25-2.37 (m, 1H), 2.45-2.55 (m, 1H), 2.55-2.64 (m, 1H), 2.62-2.72 (m, 1H), 2.75 (s, 1H), 3.61 (d, 1H, J = 13.7 Hz), 3.71 (d, 1H, J = 13.7 Hz), 7.33 (ddd, 1H, J = 8.0, 6.8, 1.2 Hz), 7.45 (ddd, 1H, J = 8.2, 6.8, 1.3 Hz), 7.49-7.60 (m, 3H), 7.73-7.97 (m, 6H), 8.05 (d, 1H J = 8.2 Hz), 8.56 (d, 1H, J = 2.2 Hz), 10.32 (s, 1H), 12.71 (s, 1H) | 515.2 |
| 222 | (DMSO-d6): 1.87-2.05 (m, 2H), 2.04-2.16 (m, 2H), 3.03 (q, 2H, J = 11.9 Hz), 3.18- 3.31 (m, 1H), 3.38-3.5 (m, 2H), 4.37 (d, 2H, J = 5.1 Hz), 7.34 (ddd, 1H, J = 8.1, 6.8, 1.3 Hz), 7.45 (ddd, 1H, J = 8.2, 6.8, 1.3 Hz), 7.55 (dd, 1H, J = 8.8, 2.3 Hz), 7.69-8.10 (m, 7H), 8.13-8.37 (m, 3H), 8.56 (d, 1H, J = 2.2 Hz), 10.33-10.46 (m, 1H), 11.02 (br, 1H), 12.77 (s, 1H) | 501.2 |
| 223 | (DMSO-d6): 3.01 (t, 2H, J = 6.3 Hz), 3.82 (t, 2H, J = 6.3 Hz), 7.33 (t, 1H, J = 7.4 Hz), 7.44 (t, 1H, J = 7.5 Hz), 7.52 (d, 1H, J = 8.8 Hz), 7.80 (t, 2H, J = 9.6 Hz), 7.84-7.96 (m, 2H), 8.02 (d, 1H, J = 8.2 Hz), 8.51 (s, 1H), 10.37 (s, 1H), 11.90 (br, 1H) | 398.8 |
| 224 | (DMSO-d6): 2.5-2.7 (m, 2H), 3.16 (d, 2H, J = 5.7 Hz), 3.56 (d, 2H, J = 5.9 Hz), 4.38 (t, 2H, J = 6.1 Hz), 4.83 (s, 1H), 4.95 (s, 1H), 7.01-7.19 (m, 1H), 7.25-7.38 (m, 2H), 7.43 (t, 1H, J = 7.5 Hz), 7.58 (dd, 1H, J = 8.8, 2.2 Hz), 7.71 (d, 1H, J = 8.2 Hz), 7.75-7.9 (m, 2H), 8.27 (s, 1H), 8.91 (d, 1H, J = 4.1 Hz), 10.01 (s, 1H) | 424.2 |
| 225 | (DMSO-d6): 2.61 (t, 2H, J = 6.3 Hz), 3.60 (q, 2H, J = 6.1 Hz), 5.04 (t, 1H, J = 5.5 Hz), 7.33 (t, 1H, J = 7.5 Hz), 7.44 (t, 1H, J = 7.5 Hz), 7.46-7.55 (m, 1H), 7.70-7.96 (m, 4H), 8.03 (d, 1H, J = 8.3 Hz), 8.50 (s, 1H), 10.29 (s, 1H), 11.81 (s, 1H) | 381.0 |
| 226 | (DMSO-d6): 3.57 (t, 2H, J = 6.2 Hz), 3.66 (t, 2H, J = 6.0 Hz), 6.32 (t, 1H, J = 6.0 Hz), 7.30 (td, 1H, J = 7.4, 6.8, 1.2 Hz), 7.35-7.43 (m, 1H), 7.43-7.55 (m, 3H), 7.78 (t, 2H, J = 8.4 Hz), 7.99 (d, 1H, J = 8.3 Hz), 8.46 (d, 1H, J = 2.2 Hz), 10.03 (s, 1H), 10.53 (s, 1H) | 390.2 |
| 227 | (DMSO-d6): 1.7-2.0 (m, 4H), 2.5-2.65 (m, 2H), 3.4-3.6 (m, 2H), 6.98-7.62 (m, 5H), 7.7-7.85 (m, 2H), 7.99 (d, 1H, J = 8.2 Hz), 8.4-8.55 (m, 1H), 10.08 (s, 1H), 10.81 (s, 1H) | 394.4 |
| 228 | (DMSO-d6): 1.06 (t, 3H, J = 7.2 Hz), 3.05-3.17 (m, 2H), 7.30 (t, 1H, J = 7.5 Hz), 7.35-7.58 (m, 4H), 7.7-7.85 (m, 3H), 7.98 (d, 1H, J = 8.2 Hz), 8.46 (d, 1H, J = 2.2 Hz), 10.00 (s, 1H), 10.40 (s, 1H) | 356.0 |
| 229 | (DMSO-d6): 2.97 (s, 6H), 7.31 (t, 1H, J = 7.4 Hz), 7.42 (t, 1H, J = 7.5 Hz), 7.48 (dd, 1H, J = 8.9, 2.2 Hz), 7.57-7.65 (m, 2H), 7.78 (t, 2H, J = 8.4 Hz), 8.00 (d, 1H, J = 8.2 Hz), 8.50 (s, 1H), 10.07 (s, 1H), 11.29 (s, 1H) | 356.2 |
| 230 | (DMSO-d6): 4.21 (s, 2H), 7.33 (ddd, 1H, J = 8.1, 6.8, 1.2 Hz), 7.45 (ddd, 1H, J = 8.2, 6.8, 1.3 Hz), 7.53 (dd, 1H, J = 8.8, 2.3 Hz), 7.61 (d, 2H, J = 8.4 Hz), 7.77-7.81 (m, 1H), 7.83 (d, 1H, J = 8.9 Hz), 7.87-7.99 (m, 4H), 8.05 (d, 1H, J = 8.2 Hz), 8.56 (d, 1H, J = 2.3 Hz), 10.33 (s, 1H), 12.75 (s, 1H) | 428.1 |
| 231 | (DMSO-d6): 4.13 (s, 2H), 7.33 (ddd, 1H, J = 8.1, 6.8, 1.2 Hz), 7.40-7.49 (m, 3H), 7.53 (dd, 1H, J = 8.8, 2.3 Hz), 7.75-7.85 (m, 5H), 7.87 (br, 1H), 7.91 (br, 1H), 8.00-8.10 (m, 1H), 8.56 (d, 1H, J = 2.2 Hz), 10.32 (s, 1H), 12.68 (s, 1H) | 471.1 |
| 232 | (DMSO-d6): 5.47 (s, 2H), 6.23-6.38 (m, 1H), 7.33 (ddd, 1H, J = 8.1, 6.8, 1.2 Hz), 7.40 (d, 2H, J = 8.4 Hz), 7.44 (ddd, 1H, J = 8.2, 6.8, 1.3 Hz), 7.50-7.55 (m, 2H), 7.77-7.81 (m, 1H), 7.82 (d, 1H, J = 9.0 Hz), 7.85-7.95 (m, 5H), 8.04 (dd, 1H, J = 8.4, 1.1 Hz), 8.55 (d, 1H, J = 2.2 Hz), 10.31 (s, 1H), 12.70 (s, 1H) | 469.2 |
| 233 | (DMSO-d6): 2.02-2.21 (m, 2H), 2.4-2.6 (m, 2H), 4.30 (t, 2H, J = 6.9 Hz), 7.33 (t, 1H, J = 7.3 Hz), 7.44 (t, 1H, J = 7.6 Hz), 7.48-7.56 (m, 1H), 7.73-7.94 (m, 4H), 7.94-8.08 (m, 2H), 8.50 (s, 1H), 8.55 (s, 1H), 10.29 (s, 1H), 11.82 (s, 1H) | 446.2 |
| 234 | (DMSO-d6): 1.9-2.05 (m, 2H), 2.3-2.45 (m, 2H), 4.06 (t, 2H, J = 7.1 Hz), 6.91 (s, 1H), 7.21 (s, 1H), 7.32 (t, 1H, J = 7.6 Hz), 7.38-7.55 (m, 2H), 7.64 (s, 1H), 7.71-8.03 (m, 6H), 10.26 (s, 1H), 11.5-12.0 (m, 1H) | 445.4 |

TABLE 5-continued

| Example No. | ¹H-NMR (400 MHz) δ (ppm) | LCMS m/z [M + H]⁺ |
|---|---|---|
| 235 | (DMSO-d6): 5.34 (s, 2H), 6.97 (d, 1H, J = 1.5 Hz), 7.33 (ddd, 1H, J = 8.2, 6.8, 1.2 Hz), 7.37-7.47 (m, 3H), 7.48 (d, 1H, J = 1.5 Hz), 7.53 (dd, 1H, J = 8.9, 2.2 Hz), 7.79 (d, 1H, J = 8.1 Hz), 7.82 (d, 1H, J = 9.0 Hz), 7.86-7.95 (m, 4H), 8.02-8.07 (m, 1H), 8.55 (d, 1H, J = 2.2 Hz), 10.31 (s, 1H), 12.71 (s, 1H) | 512.0 (M − H) |
| 236 | (DMSO-d6): 1.90-2.09 (m, 2H), 3.48 (t, 2H, J = 7.8 Hz), 3.72 (t, 2H, J = 6.5 Hz), 7.23 (s, 1H), 7.33 (t, 1H, J = 7.4 Hz), 7.44 (t, 1H, J = 7.5 Hz), 7.48-7.58 (m, 1H), 7.73-7.89 (m, 4H), 8.03 (d, 1H, J = 8.3 Hz), 8.51 (d, 1H, J = 2.0 Hz), 10.04 (s, 1H), 10.27 (s, 1H), 11.80 (s, 1H) | 438.2 |
| 237 | (DMSO-d6): 2.23 (s, 3H), 5.28 (s, 2H), 6.81 (d, 1H, J = 1.3 Hz), 7.17 (d, 1H, J = 1.3 Hz), 7.3-7.4 (m, 3H), 7.44 (ddd, 1H, J = 8.1, 6.8, 1.3 Hz), 7.53 (dd, 1H, J = 8.9, 2.3 Hz), 7.81 (dd, 2H, J = 12.1, 8.4 Hz), 7.85-7.95 (m, 4H), 8.04 (d, 1H, J = 8.1 Hz), 8.55 (d, 1H, J = 2.1 Hz), 10.31 (s, 1H), 12.71 (s, 1H) | 483.2 |
| 238 | (DMSO-d6): 2.08 (d, 3H, J = 1.0 Hz), 5.24 (s, 2H), 6.89 (t, 1H, J = 1.3 Hz), 7.33 (ddd, 1H, J = 8.1, 6.8, 1.3 Hz), 7.4-7.47 (m, 3H), 7.53 (dd, 1H, J = 8.9, 2.3 Hz), 7.65 (d, 1H, J = 1.4 Hz), 7.74-7.86 (m, 2H), 7.86-7.95 (m, 4H), 8.00-8.09 (m, 1H), 8.56 (d, 1H, J = 2.2 Hz), 10.32 (s, 1H), 12.71 (s, 1H) | 483.2 |
| 239 | (DMSO-d6): 5.45 (s, 2H), 7.33 (ddd, 1H, J = 8.1, 6.8, 1.3 Hz), 7.44 (ddd, 1H, J = 8.2, 6.8, 1.3 Hz), 7.53 (dd, 1H, J = 8.9, 2.3 Hz), 7.59 (d, 2H, J = 8.4 Hz), 7.80 (d, 1H, J = 8.2 Hz), 7.83 (d, 1H, J = 9.0 Hz), 7.87-7.97 (m, 4H), 8.01-8.08 (m, 2H), 8.55 (dd, 2H, J = 3.3, 1.8 Hz), 10.33 (s, 1H), 12.73 (s, 1H) | 514.0 |
| 240 | (DMSO-d6): 4.88 (d, 2H, J = 5.4 Hz), 6.14 (d, 1H, J = 15.2 Hz), 6.7-7.05 (m, 2H), 7.20 (s, 1H), 7.32 (t, 1H, J = 7.4 Hz), 7.38-7.46 (m, 1H), 7.48-7.57 (m, 1H), 7.68 (s, 1H), 7.80 (t, 2H, J = 9.3 Hz), 7.89-8.07 (m, 4H), 8.48 (s, 1H), 10.23 (s, 1H) | 419.2 |
| 241 | (DMSO-d6): 5.35-5.47 (m, 2H), 6.38 (d, 1H, J = 15.4 Hz), 7.00 (dt, 1H, J = 15.6, 5.4 Hz), 7.32 (t, 1H, J = 7.5 Hz), 7.43 (t, 1H, J = 7.4 Hz), 7.51 (dd, 1H, J = 8.8, 2.3 Hz), 7.63-7.85 (m, 4H), 8.01 (d, 1H, J = 8.4 Hz), 8.49 (d, 1H, J = 1.7 Hz), 9.48 (s, 1H), 10.24 (s, 1H), 11.57 (s, 1H) | 421.2 |
| 242 | (DMSO-d6): 5.66 (d, 2H, J = 5.7 Hz), 6.46 (d, 1H, J = 15.3 Hz), 7.02 (d, 1H, J = 15.4 Hz), 7.32 (t, 1H, J = 7.4 Hz), 7.43 (t, 1H, J = 7.5 Hz), 7.50 (t, 1H, J = 8.1 Hz), 7.72-7.84 (m, 4H), 8.02 (d, 1H, J = 8.2 Hz), 8.50 (d, 1H, J = 2.0 Hz), 9.07 (s, 1H), 10.25 (s, 1H), 11.62 (s, 1H) | 421.2 |
| 243 | (DMSO-d6): 5.72 (s, 2H), 7.33 (ddd, 1H, J = 8.1, 6.8, 1.2 Hz), 7.44 (ddd, 1H, J = 8.2, 6.8, 1.3 Hz), 7.53 (dd, 1H, J = 8.9, 2.3 Hz), 7.61 (d, 2H, J = 8.4 Hz), 7.78-7.81 (m, 1H), 7.83 (d, 1H, J = 9.0 Hz), 7.87-7.98 (m, 4H), 8.05 (d, 1H, J = 8.1 Hz), 8.55 (d, 1H, J = 2.2 Hz), 9.06 (s, 1H), 10.32 (s, 1H), 12.74 (s, 1H) | 515.0 |
| 244 | (DMSO-d6): 2.54 (s, 3H), 5.78 (s, 2H), 7.33 (ddd, 1H, J = 8.1, 6.8, 1.2 Hz), 7.44 (ddd, 1H, J = 8.2, 6.8, 1.3 Hz), 7.49 (d, 2H, J = 8.4 Hz), 7.53 (dd, 1H, J = 8.9, 2.3 Hz), 7.80 (d, 1H, J = 8.0 Hz), 7.83 (d, 1H, J = 8.9 Hz), 7.87-7.97 (m, 4H), 8.05 (d, 1H, J = 8.3 Hz), 8.56 (d, 1H, J = 2.2 Hz), 10.32 (s, 1H), 12.73 (s, 1H) | 485.1 |
| 245 | (DMSO-d6): 2.46 (s, 3H), 6.01 (s, 2H), 7.33 (ddd, 1H, J = 8.0, 6.8, 1.2 Hz), 7.44 (ddd, 1H, J = 8.2, 6.8, 1.3 Hz), 7.53 (dd, 1H, J = 8.9, 2.3 Hz), 7.57 (d, 2H, J = 8.4 Hz), 7.77-7.81 (m, 2H), 7.83 (d, 1H, J = 9.0 Hz), 7.86-7.98 (m, 4H), 8.05 (d, 1H, J = 8.2 Hz), 8.56 (d, 1H, J = 2.2 Hz), 10.32 (s, 1H), 12.73 (s, 1H) | 485.0 |
| 246 | (DMSO-d6): 4.23-4.41 (m, 2H), 4.69-5.17 (m, 1H), 5.19-5.45 (m, 2H), 6.77-7.13 (m, 1H), 7.22-7.58 (m, 5H), 7.67-7.85 (m, 3H), 7.87-.98 (m, 4H), 8.05 (d, 1H, J = 8.1 Hz), 8.56 (d, 1H, J = 2.2 Hz), 10.32 (s, 1H), 12.71 (s, 1H) | 499.2 |
| 247 | (DMSO-d6): 4.62 (s, 2H), 7.33 (ddd, 1H, J = 8.1, 6.8, 1.2 Hz), 7.45 (ddd, 1H, J = 8.2, 6.8, 1.3 Hz), 7.53 (dd, 1H, J = 8.9, 2.3 Hz), 7.62 (d, 2H, J = 8.3 Hz), 7.77-7.82 (m, 1H), 7.83 (d, 1H, J = 9.0 Hz), 7.86-8.01 (m, 4H), 8.05 (d, 1H, J = 8.1 Hz), 8.56 (d, 1H, J = 2.3 Hz), 10.32 (s, 1H), 12.75 (s, 1H) | 444.1 |
| 248 | (DMSO-d6): 3.85 (s, 3H), 5.34 (s, 2H), 7.11 (d, 1H, J = 8.9 Hz), 7.16-7.33 (m, 2H), 7.33-7.59 (m, 3H), 7.59-8.11 (m, 6H), 8.49 (s, 1H), 10.21 (s, 1H), 12.69 (s, 1H) | 499.2 |
| 249 | (DMSO-d6): 5.12-5.53 (m, 2H), 6.94 (s, 1H), 7.23 (s, 1H), 7.27-7.51 (m, 2H), 7.49-7.71 (m, 2H), 7.71-8.01 (m, 7H), 8.03-8.43 (m, 1H), 8.64 (br, 1H), 10.35 (br, 1H), 12.72 (br, 1H) | 487.2 |
| 250 | (DMSO-d6): 5.27-5.41 (m, 2H), 6.84-7.05 (m, 1H), 7.13-7.33 (m, 1H), 7.34-7.51 (m, 3H), 7.61-8.21 (m, 6H), 8.31-8.60 (m, 1H), 8.63-8.83 (m, 2H), 10.48 (br, 1H), 12.70 (br, 1H) | 470.2 |
| 251 | (DMSO-d6): 5.52 (s, 2H), 6.94 (s, 1H), 7.23 (d, 1H, J = 3.8 Hz), 7.27 (s, 1H), 7.33 (t, 1H, J = 7.5 Hz), 7.44 (t, 1H, J = 7.5 Hz), 7.51 (dd, 1H, J = 8.9, 2.2 Hz), 7.63 (d, 1H, J = 3.8 Hz), 7.75-7.85 (m, 3H), 7.87 (br, 1H), 7.90 (br, 1H), 8.04 (d, 1H, J = 8.3 Hz), 8.54 (d, 1H, J = 2.2 Hz), 10.30 (s, 1H), 12.56 (s, 1H) | 475.4 |

TABLE 5-continued

| Example No. | ¹H-NMR (400 MHz) δ (ppm) | LCMS m/z [M + H]⁺ |
|---|---|---|
| 252 | (DMSO-d6): 4.31 (s, 2H), 4.79 (s, 2H), 7.33 (ddd, 1H, J = 8.1, 6.8, 1.2 Hz), 7.44 (ddd, 1H, J = 8.2, 6.8, 1.3 Hz), 7.48-7.56 (m, 3H), 7.80 (d, 1H, J = 8.2 Hz), 7.83 (d, 1H, J = 9.0 Hz), 7.85-7.96 (m, 4H), 8.02-8.07 (m, 1H), 8.55 (d, 1H, J = 2.2 Hz), 10.32 (s, 1H), 12.71 (s, 1H) | 518.1 |
| 253 | (DMSO-d6): 5.31-5.42 (m, 2H), 7.04-7.20 (m, 1H), 7.36 (s, 1H), 7.47 (d, 2H, J = 8.1 Hz), 7.58 (dd, 1H, J = 9.0, 2.2 Hz), 7.83-8.06 (m, 6H), 8.06-8.25 (m, 1H), 8.29-8.50 (m, 1H), 8.64 (d, 1H, J = 2.1 Hz), 9.10 (s, 1H), 10.65 (s, 1H), 12.73 (s, 1H) | 470.2 |
| 254 | (DMSO-d6): 5.28 (s, 2H), 6.93 (s, 1H), 7.06-7.41 (m, 3H), 7.41-8.16 (m, 6H), 8.57-9.19 (m, 3H), 9.7-10.3 (m, 1H) | 469.9 |
| 255 | (DMSO-d6): 5.15-5.42 (m, 2H), 6.77-7.11 (m, 1H), 7.25 (s, 1H), 7.45 (d, 2H, J = 7.7 Hz), 7.51-8.21 (m, 8H), 8.51 (d, 1H, J = 8.5 Hz), 8.54-8.97 (m, 2H), 10.3-10.7 (m, 1H), 12.69 (br, 1H) | 470.2 |
| 256 | (DMSO-d6): 2.32 (s, 3H), 4.46 (s, 2H), 7.33 (ddd, 1H, J = 8.1, 6.8, 1.2 Hz), 7.44 (ddd, 1H, J = 8.2, 6.8, 1.2 Hz), 7.53 (dd, 1H, J = 8.9, 2.3 Hz), 7.60 (d, 2H, J = 8.4 Hz), 7.77-7.81 (m, 1H), 7.83 (d, 1H, J = 9.0 Hz), 7.86-7.97 (m, 4H), 8.05 (d, 1H, J = 8.2 Hz), 8.56 (d, 1H, J = 2.2 Hz), 10.32 (s, 1H), 12.72 (s, 1H) | 485.2 |
| 257 | (DMSO-d6): 2.46 (s, 3H), 4.37 (s, 2H), 7.33 (ddd, 1H, J = 8.1, 6.8, 1.2 Hz), 7.44 (ddd, 1H, J = 8.2, 6.8, 1.3 Hz), 7.53 (dd, 1H, J = 8.9, 2.3 Hz), 7.57 (d, 2H, J = 8.3 Hz), 7.76-7.81 (m, 1H), 7.83 (d, 1H, J = 9.0 Hz), 7.87-7.96 (m, 4H), 8.03-8.07 (m, 1H), 8.56 (d, 1H, J = 2.2 Hz), 10.32 (s, 1H), 12.72 (s, 1H) | 485.2 |
| 258 | (DMSO-d6): 5.49 (s, 2H), 6.93 (s, 1H), 7.27 (s, 1H), 7.33 (t, 1H, J = 7.2 Hz), 7.40-7.49 (m, 2H), 7.51 (dd, 1H, J = 8.8, 2.3 Hz), 7.75-7.84 (m, 3H), 7.87 (br, 1H), 7.89 (br, 1H), 8.04 (d, 1H, J = 8.3 Hz), 8.24 (s, 1H), 8.55 (d, 1H, J = 2.1 Hz), 10.29 (s, 1H), 12.42 (s, 1H) | 475.2 |
| 259 | (DMSO-d6): 5.34 (s, 2H), 6.94 (s, 1H), 7.23 (s, 1H), 7.45 (d, 2H, J = 7.9 Hz), 7.48-7.70 (m, 3H), 7.80 (s, 1H), 7.81-7.94 (m, 4H), 8.28-8.44 (m, 1H), 8.93 (d, 1H, J = 4.1 Hz), 9.00 (d, 1H, J = 7.6 Hz), 10.70 (s, 1H), 12.68 (s, 1H) | 470.4 |
| 260 | (DMSO-d6): 4.52 (d, 2H, J = 5.7 Hz), 5.18 (t, 1H, J = 5.7 Hz), 5.72 (s, 2H), 7.33 (ddd, 1H, J = 8.1, 6.9, 1.3 Hz), 7.44 (ddd, 1H, J = 8.2, 6.8, 1.2 Hz), 7.49-7.55 (m, 3H), 7.80 (d, 1H, J = 8.2 Hz), 7.83 (d, 1H, J = 8.9 Hz), 7.88-7.97 (m, 4H), 8.05 (d, 1H, J = 8.0 Hz), 8.09 (s, 1H), 8.56 (d, 1H, J = 2.2 Hz), 10.33 (s, 1H), 12.72 (s, 1H) | 500.2 |
| 261 | (DMSO-d6): 2.65 (s, 3H), 6.05 (s, 2H), 7.33 (ddd, 1H, J = 8.1, 6.8, 1.2 Hz), 7.44 (ddd, 1H, J = 8.2, 6.8, 1.3 Hz), 7.53 (dd, 1H, J = 8.9, 2.3 Hz), 7.59 (d, 2H, J = 8.3 Hz), 7.80 (dd, 1H, J = 8.3, 1.2 Hz), 7.83 (d, 1H, J = 8.9 Hz), 7.87-7.98 (m, 4H), 8.01-8.07 (m, 1H), 8.56 (d, 1H, J = 2.2 Hz), 10.33 (s, 1H), 12.74 (s, 1H) | 517.2 |
| 262 | (DMSO-d6): 5.34 (s, 2H), 6.95 (s, 1H), 7.14-7.30 (m, 2H), 7.35-7.52 (m, 3H), 7.74-8.00 (m, 7H), 8.65 (d, 1H, J = 2.1 Hz), 10.40 (s, 1H), 12.73 (s, 1H) | 487.0 |
| 263 | (DMSO-d6): 3.56 (s, 3H), 6.26 (s, 2H), 7.33 (ddd, 1H, J = 8.1, 6.8, 1.2 Hz), 7.44 (ddd, 1H, J = 8.2, 6.8, 1.3 Hz), 7.53 (dd, 1H, J = 8.9, 2.3 Hz), 7.68 (d, 2H, J = 8.4 Hz), 7.80 (d, 1H, J = 8.2 Hz), 7.83 (d, 1H, J = 8.9 Hz), 7.90 (br, 1H), 7.92 (br, 1H), 7.97 (d, 2H, J = 8.4 Hz), 8.05 (d, 1H, J = 8.0 Hz), 8.56 (d, 1H, J = 2.2 Hz), 10.33 (s, 1H), 12.75 (s, 1H) | 549.2 |
| 264 | (DMSO-d6): 4.18 (s, 3H), 5.52 (s, 2H), 7.33 (ddd, 1H, J = 8.1, 6.8, 1.2 Hz), 7.44 (ddd, 1H, J = 8.2, 6.8, 1.3 Hz), 7.47-7.58 (m, 3H), 7.80 (d, 1H, J = 8.1 Hz), 7.83 (d, 1H, J = 8.9 Hz), 7.87-7.97 (m, 4H), 8.05 (d, 1H, J = 8.1 Hz), 8.56 (d, 1H, J = 2.2 Hz), 10.32 (s, 1H), 12.73 (s, 1H) | 549.3 |
| 265 | (DMSO-d6): 2.74 (s, 3H), 5.71 (s, 2H), 7.33 (ddd, 1H, J = 8.1, 6.8, 1.3 Hz), 7.40-7.51 (m, 3H), 7.53 (dd, 1H, J = 8.9, 2.3 Hz), 7.77-7.81 (m, 1H), 7.83 (d, 1H, J = 9.0 Hz), 7.88-7.97 (m, 4H), 8.05 (d, 1H, J = 8.1 Hz), 8.56 (d, 1H, J = 2.2 Hz), 10.32 (s, 1H), 12.73 (s, 1H) | 517.2 |

Referential Example 1

Preparation of Tablets:

Tablets each containing 100 mg of 5-(4-acetamidobenzamido)-2-(naphthalen-2-ylamino)thiazole-4-carboxamide (Example 2) are obtained by the following procedure.

TABLE 6

| Formulation: | |
|---|---|
| Ingredients | Amount |
| Compound of example 2 | 100 parts by weight |
| Cornstarch | 46 parts by weight |
| Microcrystalline cellulose | 98 parts by weight |
| Hydroxypropyl cellulose | 2 parts by weight |
| Magnesium stearate | 4 parts by weight |

Procedure:

The compound of example 2, cornstarch and microcrystalline cellulose are mixed and the mixture is added to hydroxypropyl cellulose dissolved in 50 parts by weight of water, followed by sufficient kneading. The kneaded mixture is passed through a sieve to granulate, dried mixed with magnesium stearate and then compressed into tablets of 250 mg each.

Referential Example 2

Preparation of Granules:

Granules containing 5-(4-acetamidobenzamido)-2-(naphthalen-2-ylamino)thiazole-4-carboxamide (Example 2) are obtained by the following procedure.

TABLE 7

| Formulation: | |
|---|---|
| Ingredients | Amount |
| Compound of example 2 | 200 parts by weight |
| Lactose | 185 parts by weight |
| Cornstarch | 109 parts by weight |
| Hydroxypropyl cellulose | 6 parts by weight |

Procedure:

The compound of example 2, lactose and cornstarch are mixed and the mixture is added to hydroxypropyl cellulose dissolved in 120 parts by weight of water, followed by sufficient kneading. The kneaded mixture is passed through a 20 mesh sieve to granulate, dried and then size-adjusted to obtain granules containing 200 mg of Compound of example 2 per 500 mg of granule.

Referential Example 3

Preparation of Capsules:

Capsules each containing 100 mg of 5-(4-acetamidobenzamido)-2-(naphthalen-2-ylamino)thiazole-4-carboxamide (Example 2) are obtained by the following procedure.

TABLE 8

| Formulation: | |
|---|---|
| Ingredients | Amount |
| Compound of example 2 | 100 parts by weight |
| Lactose | 35 parts by weight |
| Cornstarch | 60 parts by weight |
| Magnesium stearate | 5 parts by weight |

Procedure:

The compound of example 2, lactose, cornstarch and magnesium stearate are well mixed and 200 mg each of the powder mixture is encapsulated to obtain capsules.

The invention claimed is:

1. A compound represented by the following general formula:

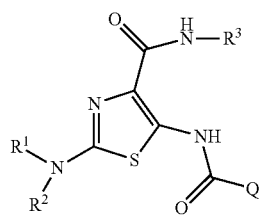

(wherein, $R^1$ is

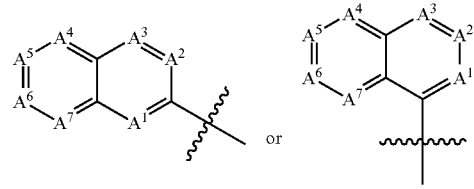

wherein each of $A^1, A^2, A^3, A^4, A^5, A^6, A^7$ is, independently C—Z or N, $R^2$ is a hydrogen atom, a substituted or unsubstituted alkyl group, $R^3$ is a hydrogen atom, a substituted or unsubstituted alkyl group, a hydroxyl group, a substituted or unsubstituted alkoxy group, Q is

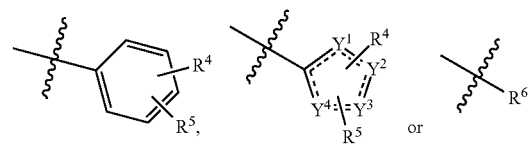

wherein each of $Y^1, Y^2, Y^3$ and $Y^4$ is, independently represent a nitrogen atom optionally substituted with hydrogen atom or lower alkyl group, sulfur atom, oxygen atom or carbon atom, Z, $R^4$ and $R^5$ independently represent a hydrogen atom, a halogen atom, a substituted or unsubstituted alkyl group, a substituted or unsubstituted alkenyl group, a substituted or unsubstituted alkynyl group, a hydroxyl group, a substituted or unsubstituted alkoxy group, a substituted or unsubstituted amino group, a carboxyl group, a ester group, a formyl group, a substituted carbonyl group, a substituted carbamoyl group, a substituted or unsubstituted urea group, a substituted or unsubstituted aromatic group, a substituted or unsubstituted heterocyclic group, a substituted or unsubstituted heteroaromatic group, a substituted or unsubstituted acylamino group, a substituted or unsubstituted arylcarbonylamino group, a thiol group, a substituted or unsubstituted thioalkyl group, a sulfonic acid group, a substituted sulfone group, a substituted or unsubstituted sulfonamide group, a cyano group, a nitro group, or neighboring $R^4$ and $R^5$ may be combined to form a 5- to 7-membered ring forming an alicyclic or heterocyclic bicyclic fused ring respectively, wherein the 5- to 7-membered ring may optionally have a substituent, $R^6$ is a substituted or unsubstituted alkyl group, a substituted or unsubstituted alkenyl group, a substituted or unsubstituted alkynyl group, a substituted or unsubstituted alkoxy group, a substituted or unsubstituted amino group, a substituted or unsubstituted heterocyclic group)

or a pharmaceutically acceptable salt thereof.

2. The compound according to claim 1 or a pharmaceutically acceptable salt thereof, wherein Q is

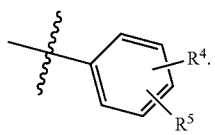
3. The compound according to claim 1 or a pharmaceutically acceptable salt thereof, wherein Q is
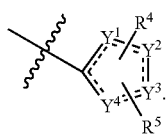
4. The compound according to claim 1 or a pharmaceutically acceptable salt thereof, wherein Q is
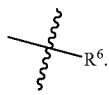
* * * * *